US012629357B2

(12) United States Patent
Burke et al.

(10) Patent No.: US 12,629,357 B2
(45) Date of Patent: May 19, 2026

(54) TREATMENT OF VIRAL INFECTIONS, OF ORGAN INJURY, AND OF RELATED CONDITIONS USING A HIF PROLYL HYDROXYLASE INHIBITOR OR A HIF-ALPHA STABILIZER

(71) Applicant: Akebia Therapeutics, Inc., Cambridge, MA (US)

(72) Inventors: Steven Burke, Cambridge, MA (US); Michael Rabinowitz, Cambridge, MA (US)

(73) Assignee: Akebia Therapeutics, Inc., Cambridge, MA (US)

( * ) Notice: Subject to any disclaimer, the term of this patent is extended or adjusted under 35 U.S.C. 154(b) by 840 days.

(21) Appl. No.: 17/996,575

(22) PCT Filed: Apr. 20, 2021

(86) PCT No.: PCT/US2021/028126
§ 371 (c)(1),
(2) Date: Oct. 19, 2022

(87) PCT Pub. No.: WO2021/216530
PCT Pub. Date: Oct. 28, 2021

(65) Prior Publication Data

US 2023/0218592 A1 Jul. 13, 2023

Related U.S. Application Data

(60) Provisional application No. 63/047,501, filed on Jul. 2, 2020, provisional application No. 63/022,890, filed on May 11, 2020, provisional application No. 63/012,839, filed on Apr. 20, 2020.

(51) Int. Cl.

| | |
|---|---|
| ***A61K 31/4418*** | (2006.01) |
| ***A61K 45/06*** | (2006.01) |
| ***A61P 1/16*** | (2006.01) |
| ***A61P 9/02*** | (2006.01) |
| ***A61P 11/00*** | (2006.01) |
| ***A61P 13/12*** | (2006.01) |
| ***A61P 25/00*** | (2006.01) |
| ***A61P 31/14*** | (2006.01) |

(52) U.S. Cl.
CPC .......... *A61K 31/4418* (2013.01); *A61K 45/06* (2013.01); *A61P 1/16* (2018.01); *A61P 9/02* (2018.01); *A61P 11/00* (2018.01); *A61P 13/12* (2018.01); *A61P 25/00* (2018.01); *A61P 31/14* (2018.01)

(58) Field of Classification Search
CPC .. A61K 31/4418; A61K 45/06; A61K 31/437; A61K 31/4375; A61K 31/47; A61K 31/4704; A61K 31/506; A61K 31/515; A61K 31/44; A61P 1/16; A61P 9/02; A61P 11/00; A61P 13/12; A61P 25/00; A61P 31/14; A61P 31/12; A61P 31/16
See application file for complete search history.

(56) References Cited

U.S. PATENT DOCUMENTS

| | | | |
|---|---|---|---|
| 3,655,679 | A | 4/1972 | Shen et al. |
| 3,703,582 | A | 11/1972 | Shen et al. |
| 3,894,920 | A | 7/1975 | Kondo et al. |
| 4,016,287 | A | 4/1977 | Eberhardt et al. |
| 4,764,522 | A | 8/1988 | Imhof et al. |
| 5,397,799 | A | 3/1995 | Kress et al. |
| 5,405,613 | A | 4/1995 | Rowland |
| 5,607,954 | A | 3/1997 | Weidmann et al. |
| 5,610,172 | A | 3/1997 | Weidmann et al. |
| 5,620,995 | A | 4/1997 | Weidmann et al. |
| 5,620,996 | A | 4/1997 | Weidmann et al. |
| 5,658,933 | A | 8/1997 | Weidmann et al. |
| 5,719,164 | A | 2/1998 | Weidmann et al. |
| 5,726,305 | A | 3/1998 | Weidmann et al. |
| 6,020,350 | A | 2/2000 | Weidmann et al. |

(Continued)

FOREIGN PATENT DOCUMENTS

| | | |
|---|---|---|
| AU | 2007265460 B2 | 3/2011 |
| AU | 2016243700 B2 | 8/2020 |

(Continued)

OTHER PUBLICATIONS

"42-Day Repeat Oral Dose Study of AKB-6548 in Participants With Chronic Kidney Disease and Anemia", ClinicalTrials.gov, U.S. National Institutes of Health, Jul. 27, 2011, NCT01381094 (116 pages).

(Continued)

*Primary Examiner* — Jeffrey S Lundgren
*Assistant Examiner* — Paul Randall Gauger
(74) *Attorney, Agent, or Firm* — Proskauer Rose LLP

(57) ABSTRACT

Disclosed herein are new therapeutic methods comprising administering compounds that can stabilize HIF and inhibit HIF prolyl hydroxylase (HIF-PH). In particular, methods described herein can be useful for treating/preventing a disease or condition in patients in need thereof, such as a patient having a viral infection such as a respiratory and/or pulmonary viral infection (e.g., an infection such as COVID-19 or a coronavirus infection). Methods described herein can also be useful for treating/preventing organ injury (e.g. organ injury that occurs concurrently or as a result of an infection). For example, methods described herein can be useful for treating or preventing acute lung injury, acute respiratory distress syndrome (ARDS), cardiovascular injury, injury to the liver, kidney diseases, and/or multi-organ failure.

21 Claims, No Drawings

(56) References Cited

U.S. PATENT DOCUMENTS

| | | | |
|---|---|---|---|
| 6,093,730 | A | 7/2000 | Weidmann et al. |
| 6,159,379 | A | 12/2000 | Means et al. |
| 6,420,427 | B1 | 7/2002 | Takahashi et al. |
| 6,566,088 | B1 | 5/2003 | McKnight et al. |
| 6,589,758 | B1 | 7/2003 | Zhu |
| 6,855,510 | B2 | 2/2005 | Kaelin et al. |
| 7,183,287 | B2 | 2/2007 | Durley |
| 7,307,060 | B2 | 12/2007 | Compernolle et al. |
| 7,323,475 | B2 | 1/2008 | Arend et al. |
| 7,402,696 | B2 | 7/2008 | Suzuki et al. |
| 7,588,924 | B2 | 9/2009 | Evdokimov et al. |
| 7,618,940 | B2 | 11/2009 | Fourney et al. |
| 7,625,927 | B2 | 12/2009 | Klimko et al. |
| 7,629,357 | B2 | 12/2009 | Arend et al. |
| 7,662,854 | B2 | 2/2010 | Schofield et al. |
| 7,696,223 | B2 | 4/2010 | Deng et al. |
| 7,811,595 | B2 | 10/2010 | Kawamoto et al. |
| 7,897,612 | B2 | 3/2011 | Fitch et al. |
| 7,928,120 | B2 | 4/2011 | Arend et al. |
| 8,050,873 | B2 | 11/2011 | Evdokimov et al. |
| 8,124,582 | B2 | 2/2012 | Guenzler-Pukall et al. |
| 8,217,043 | B2 | 7/2012 | Deng et al. |
| 8,269,008 | B2 | 9/2012 | Arend et al. |
| 8,273,773 | B2 | 9/2012 | Brameld et al. |
| 8,283,465 | B2 | 10/2012 | Mitani et al. |
| 8,309,537 | B2 | 11/2012 | Gardner et al. |
| 8,314,103 | B2 | 11/2012 | Kumar et al. |
| 8,323,671 | B2 | 12/2012 | Wu et al. |
| 8,324,208 | B2 | 12/2012 | Duffy et al. |
| 8,324,405 | B2 | 12/2012 | Ho et al. |
| 8,343,952 | B2 | 1/2013 | Kawamoto et al. |
| 8,389,520 | B2 | 3/2013 | Thede et al. |
| 8,512,972 | B2 | 8/2013 | Evdokimov et al. |
| 8,530,404 | B2 | 9/2013 | Seeley et al. |
| 8,598,210 | B2 | 12/2013 | Kawamoto et al. |
| 8,703,795 | B2 | 4/2014 | Turtle et al. |
| 8,722,895 | B2 | 5/2014 | Kawamoto et al. |
| 8,759,345 | B2 | 6/2014 | Hocutt et al. |
| 8,796,263 | B2 | 8/2014 | Rabinowitz et al. |
| 8,865,748 | B2 | 10/2014 | Shalwitz et al. |
| 8,883,823 | B2 | 11/2014 | Witschi et al. |
| 8,916,585 | B2 | 12/2014 | Arend et al. |
| 8,921,389 | B2 | 12/2014 | Ng et al. |
| 8,927,591 | B2 | 1/2015 | Ho et al. |
| 8,937,078 | B2 | 1/2015 | Bembenek et al. |
| 8,940,773 | B2 | 1/2015 | Kawamoto et al. |
| 8,952,160 | B2 | 2/2015 | Zhou et al. |
| 9,040,522 | B2 | 5/2015 | Brown et al. |
| 9,115,085 | B2 | 8/2015 | Witschi et al. |
| 9,145,366 | B2 | 9/2015 | Lanthier et al. |
| 9,273,034 | B2 | 3/2016 | Sepassi et al. |
| 9,394,300 | B2 | 7/2016 | Desai et al. |
| 9,598,370 | B2 | 3/2017 | Kawamoto et al. |
| 9,701,636 | B2 | 7/2017 | Copp et al. |
| 9,776,969 | B2 | 10/2017 | Lanthier et al. |
| 9,918,977 | B2 | 3/2018 | Witschi et al. |
| 9,987,262 | B2 | 6/2018 | Copp et al. |
| 10,149,842 | B2 | 12/2018 | Copp et al. |
| 10,246,416 | B2 | 4/2019 | Lanthier et al. |
| 10,278,942 | B2 | 5/2019 | Josey et al. |
| RE47,437 | E | 6/2019 | Kawamoto et al. |
| 10,596,158 | B2 | 3/2020 | Copp et al. |
| 10,729,681 | B2 | 8/2020 | Kawamoto et al. |
| 10,738,010 | B2 | 8/2020 | Lanthier et al. |
| 10,766,855 | B2 | 9/2020 | Blanco et al. |
| 10,899,713 | B2 | 1/2021 | Desai et al. |
| 10,919,843 | B2 | 2/2021 | Muñoz Blanco et al. |
| 11,065,237 | B2 | 7/2021 | Copp et al. |
| 11,267,785 | B2 | 3/2022 | Lanthier et al. |
| 11,324,734 | B2 | 5/2022 | Smith et al. |
| 11,426,393 | B2 | 8/2022 | Kawamoto et al. |
| 11,844,756 | B2 | 12/2023 | Smith et al. |
| 11,883,386 | B2 | 1/2024 | Kawamoto et al. |
| 2002/0049161 | A1 | 4/2002 | Lehmann |
| 2002/0192737 | A1 | 12/2002 | Kaelin, Jr. et al. |
| 2003/0153503 | A1 | 8/2003 | Klaus et al. |
| 2003/0176317 | A1 | 9/2003 | Guenzler-Pukall et al. |
| 2004/0235082 | A1 | 11/2004 | Fourney et al. |
| 2004/0254215 | A1 | 12/2004 | Arend et al. |
| 2005/0043227 | A1 | 2/2005 | Compernolle et al. |
| 2006/0142389 | A1 | 6/2006 | Aurell et al. |
| 2006/0276477 | A1 | 12/2006 | Klaus et al. |
| 2007/0105899 | A1 | 5/2007 | Suzuki et al. |
| 2007/0154482 | A1 | 7/2007 | Sukhatme et al. |
| 2007/0203174 | A1 | 8/2007 | Klimko et al. |
| 2007/0213335 | A1 | 9/2007 | Fitch et al. |
| 2007/0298104 | A1 | 12/2007 | Arend et al. |
| 2007/0299086 | A1 | 12/2007 | Kawamoto et al. |
| 2008/0004309 | A1 | 1/2008 | Deng et al. |
| 2008/0124740 | A1 | 5/2008 | Evdokimov et al. |
| 2008/0213404 | A1 | 9/2008 | Johnson et al. |
| 2009/0011051 | A1 | 1/2009 | Roth et al. |
| 2009/0023666 | A1 | 1/2009 | Gardiner et al. |
| 2009/0082357 | A1 | 3/2009 | Fitch et al. |
| 2009/0176726 | A1 | 7/2009 | Fisher et al. |
| 2010/0021423 | A1 | 1/2010 | Brameld et al. |
| 2010/0330199 | A1 | 12/2010 | Zhou et al. |
| 2010/0331400 | A1 | 12/2010 | Ho et al. |
| 2011/0028507 | A1 | 2/2011 | Kim et al. |
| 2011/0077267 | A1 | 3/2011 | Mitani et al. |
| 2011/0305776 | A1 | 12/2011 | Ho et al. |
| 2012/0028950 | A1 | 2/2012 | Haerter et al. |
| 2012/0070369 | A1 | 3/2012 | Iliopoulos et al. |
| 2012/0282627 | A1 | 11/2012 | Evdokimov et al. |
| 2012/0309977 | A1 | 12/2012 | Lanthier et al. |
| 2012/0316204 | A1 | 12/2012 | Shalwitz et al. |
| 2012/0329836 | A1 | 12/2012 | Marsh et al. |
| 2013/0022974 | A1 | 1/2013 | Chinnaiyan et al. |
| 2013/0085121 | A1 | 4/2013 | Wang et al. |
| 2013/0123345 | A1 | 5/2013 | Davis |
| 2013/0150325 | A1 | 6/2013 | Haerter et al. |
| 2013/0196964 | A1 | 8/2013 | Haerter et al. |
| 2014/0024675 | A1 | 1/2014 | Witschi et al. |
| 2014/0024676 | A1 | 1/2014 | Witschi et al. |
| 2014/0045899 | A1 | 2/2014 | Kawamoto et al. |
| 2014/0057892 | A1 | 2/2014 | Kawamoto et al. |
| 2014/0088101 | A1 | 3/2014 | Ng et al. |
| 2014/0171465 | A1 | 6/2014 | Yu |
| 2014/0329797 | A1 | 11/2014 | Härter et al. |
| 2015/0119425 | A1 | 4/2015 | Kawamoto et al. |
| 2015/0141467 | A1 | 5/2015 | Copp et al. |
| 2015/0361043 | A1 | 12/2015 | Lanthier et al. |
| 2016/0009648 | A1 | 1/2016 | Kawamoto et al. |
| 2016/0143891 | A1 | 5/2016 | Shalwitz et al. |
| 2016/0145254 | A1 | 5/2016 | Mitani et al. |
| 2016/0199434 | A1 | 7/2016 | Eubank et al. |
| 2016/0214939 | A1 | 7/2016 | Hanselmann et al. |
| 2016/0339005 | A1 | 11/2016 | Shalwitz et al. |
| 2017/0189387 | A1 | 7/2017 | Kawamoto et al. |
| 2017/0260226 | A1 | 9/2017 | Bothe et al. |
| 2017/0362178 | A1 | 12/2017 | Lanthier et al. |
| 2018/0065933 | A1 | 3/2018 | Hanselmann et al. |
| 2018/0092892 | A1 | 4/2018 | Smith et al. |
| 2019/0192494 | A1 | 6/2019 | Kawamoto et al. |
| 2019/0359574 | A1 | 11/2019 | Desai et al. |
| 2019/0367447 | A1 | 12/2019 | Blanco et al. |
| 2020/0017492 | A1 | 1/2020 | Mitani et al. |
| 2020/0087247 | A1 | 3/2020 | Blanco et al. |
| 2020/0368223 | A1 | 11/2020 | King |
| 2021/0070709 | A1 | 3/2021 | Gorin et al. |
| 2021/0206721 | A1 | 7/2021 | Ranjan et al. |
| 2022/0040159 | A1 | 2/2022 | Copp et al. |
| 2023/0002323 | A1 | 1/2023 | Lanthier et al. |
| 2023/0071553 | A1 | 3/2023 | Smith et al. |
| 2023/0144457 | A1 | 5/2023 | Burke et al. |
| 2023/0159462 | A1 | 5/2023 | Ootsuki et al. |
| 2023/0201178 | A1 | 6/2023 | Kawamoto et al. |

FOREIGN PATENT DOCUMENTS

| | | | |
|---|---|---|---|
| CA | 2098158 | A1 | 12/1993 |
| CA | 2253282 | A1 | 11/1997 |
| CA | 2659682 | A1 | 1/2008 |
| CN | 101506149 | A | 8/2009 |

(56) References Cited

FOREIGN PATENT DOCUMENTS

| | | | |
|---|---|---|---|
| CN | 103429239 | A | 12/2013 |
| CN | 111662389 | A | 9/2020 |
| EP | 0650960 | A1 | 5/1995 |
| EP | 0650961 | A1 | 5/1995 |
| EP | 2044005 | B1 | 10/2010 |
| EP | 1738751 | B1 | 5/2011 |
| EP | 2455381 | A1 | 5/2012 |
| EP | 2951159 | B1 | 8/2018 |
| EP | 3613742 | A1 | 2/2020 |
| EP | 3277270 | B1 | 10/2021 |
| ES | 8800158 | A1 | 11/1987 |
| GB | 2163746 | A | 3/1986 |
| GB | 2444904 | A | 6/2008 |
| JP | S6160657 | A | 3/1986 |
| JP | H09221476 | | 8/1997 |
| JP | H11512414 | | 10/1999 |
| JP | 2001-048786 | A | 2/2001 |
| JP | 2003-527424 | A | 9/2003 |
| JP | 2007-194072 | A | 8/2007 |
| JP | 2008-201711 | A | 9/2008 |
| JP | 2010-527378 | A | 8/2010 |
| KR | 10-2010-0020893 | A | 2/2010 |
| WO | WO 1996/022021 | A1 | 7/1996 |
| WO | WO 1997/041103 | A1 | 11/1997 |
| WO | WO 1997/044333 | A1 | 11/1997 |
| WO | WO 1999/048870 | A1 | 9/1999 |
| WO | WO 1999/063970 | A1 | 12/1999 |
| WO | WO 2001/070225 | A2 | 9/2001 |
| WO | WO 2002/074980 | A2 | 9/2002 |
| WO | WO 2002/074981 | A2 | 9/2002 |
| WO | WO 2002/083688 | A1 | 10/2002 |
| WO | WO 2003/028663 | A2 | 4/2003 |
| WO | WO 2003/032972 | A1 | 4/2003 |
| WO | WO 2003/049686 | A2 | 6/2003 |
| WO | WO 2003/053997 | A2 | 7/2003 |
| WO | WO 2003/097040 | A1 | 11/2003 |
| WO | WO 2004/019868 | A2 | 3/2004 |
| WO | WO 2004/035812 | A2 | 4/2004 |
| WO | WO 2004/048383 | A1 | 6/2004 |
| WO | WO 2004/108121 | A1 | 12/2004 |
| WO | WO 2005/007192 | A2 | 1/2005 |
| WO | WO 2005/115984 | A2 | 12/2005 |
| WO | WO 2005/118836 | A2 | 12/2005 |
| WO | WO 2006/019831 | A1 | 2/2006 |
| WO | WO 2006/030977 | A2 | 3/2006 |
| WO | WO 2006/114213 | A1 | 11/2006 |
| WO | WO 2006/138511 | A2 | 12/2006 |
| WO | WO 2007/031933 | A2 | 3/2007 |
| WO | WO 2007/038571 | A2 | 4/2007 |
| WO | WO 2007/047194 | A2 | 4/2007 |
| WO | WO 2007/070359 | A2 | 6/2007 |
| WO | WO 2007/082899 | A1 | 7/2007 |
| WO | WO 2007/084667 | A2 | 7/2007 |
| WO | WO 2007/088571 | A2 | 8/2007 |
| WO | WO 2007/103905 | A2 | 9/2007 |
| WO | WO 2007/128495 | A2 | 11/2007 |
| WO | WO 2007/136990 | A2 | 11/2007 |
| WO | WO 2007/150011 | A2 | 12/2007 |
| WO | WO 2008/002576 | A2 | 1/2008 |
| WO | WO 2008/043167 | A1 | 4/2008 |
| WO | WO 2008/089051 | A1 | 7/2008 |
| WO | WO 2008/089052 | A2 | 7/2008 |
| WO | WO 2008/130508 | A1 | 10/2008 |
| WO | WO 2008/130527 | A1 | 10/2008 |
| WO | WO 2008/137060 | A1 | 11/2008 |
| WO | WO 2008/141731 | A2 | 11/2008 |
| WO | WO 2008/144266 | A1 | 11/2008 |
| WO | WO 2009/019656 | A1 | 2/2009 |
| WO | WO 2009/020119 | A1 | 2/2009 |
| WO | WO 2009/035534 | A2 | 3/2009 |
| WO | WO 2009/037570 | A2 | 3/2009 |
| WO | WO 2009/039321 | A1 | 3/2009 |
| WO | WO 2009/039323 | A1 | 3/2009 |
| WO | WO 2009/043093 | A1 | 4/2009 |
| WO | WO 2009/049112 | A1 | 4/2009 |
| WO | WO 2009/067790 | A1 | 6/2009 |
| WO | WO 2009/070644 | A1 | 6/2009 |
| WO | WO 2009/073497 | A2 | 6/2009 |
| WO | WO 2009/073669 | A1 | 6/2009 |
| WO | WO 2009/086044 | A1 | 7/2009 |
| WO | WO 2009/086592 | A1 | 7/2009 |
| WO | WO 2009/089547 | A1 | 7/2009 |
| WO | WO 2009/111337 | A1 | 9/2009 |
| WO | WO 2010/006189 | A2 | 1/2010 |
| WO | WO 2010/018458 | A2 | 2/2010 |
| WO | WO 2010/029577 | A2 | 3/2010 |
| WO | WO 2010/113942 | A1 | 10/2010 |
| WO | WO 2011/056725 | A1 | 5/2011 |
| WO | WO 2011/057112 | A1 | 5/2011 |
| WO | WO 2011/084437 | A1 | 7/2011 |
| WO | WO 2012/058325 | A1 | 5/2012 |
| WO | WO 2012/170377 | A1 | 12/2012 |
| WO | WO 2012/170439 | A1 | 12/2012 |
| WO | WO 2012/170442 | A1 | 12/2012 |
| WO | WO 2013/013609 | A1 | 1/2013 |
| WO | WO 2013/070908 | A1 | 5/2013 |
| WO | WO 2014/075692 | A1 | 5/2014 |
| WO | WO 2014/168986 | A1 | 10/2014 |
| WO | WO 2014/197660 | A1 | 12/2014 |
| WO | WO 2014/200773 | A2 | 12/2014 |
| WO | WO 2015/023967 | A2 | 2/2015 |
| WO | WO 2015/073779 | A1 | 5/2015 |
| WO | WO 2015/112831 | A1 | 7/2015 |
| WO | WO 2016/118858 | A1 | 7/2016 |
| WO | WO 2016/153996 | A1 | 9/2016 |
| WO | WO 2016/160668 | A1 | 10/2016 |
| WO | WO 2016/161094 | A1 | 10/2016 |
| WO | WO 2018/031680 | A1 | 2/2018 |
| WO | WO 2018/232227 | A1 | 12/2018 |
| WO | WO 2019/028150 | A1 | 2/2019 |
| WO | WO 2019/060850 | A1 | 3/2019 |
| WO | WO 2020/055687 | A1 | 3/2020 |
| WO | WO 2020/072645 | A1 | 4/2020 |
| WO | WO 2021/087144 | A1 | 5/2021 |
| WO | WO 2021/216530 | A1 | 10/2021 |
| WO | 2021263281 | A2 | 12/2021 |
| WO | WO 2021/257800 | A1 | 12/2021 |
| WO | WO 2022/006427 | A1 | 1/2022 |
| WO | WO 2022/150621 | A1 | 7/2022 |
| WO | WO 2022/150623 | A1 | 7/2022 |
| WO | 2022179967 | A1 | 9/2022 |
| WO | WO 2022/187142 | A1 | 9/2022 |

OTHER PUBLICATIONS

"Akebia closes $41 million series C", Triathlon Medical Ventures, Jun. 4, 2013, retrieved Dec. 1, 2014 from URL: http://www.tmvp.com/news_Akebia_06042013.html, (2 pages).

"Assessment of Thromboembolic Events with Vadadustat vs. Darbepoetin Alfa for Treatment of Anemia in Patients with Non-Dialysis-Dependent CKD", Abstract: PO0462, Nov. 4, 2021 (2 pages).

"BPT closes $12 million in Series B financing", Membrane Technology, Oct. 2009, pp. 1,16, retrieved from URL: httpps:/ /www.sciencedirect.com/science/article/11ii/S0958211809701983, (3 pages).

"Comprehensive Safety Profile of Vadadustat from Global Phase 3 Clinical Trials", Abstract: PO0460, Nov. 2, 2021 (2 pages).

"Handbook of Pharmaceutical Excipients", Sixth Edition 2009, Edited by Rowe et al., pp. 129-133, 663-666 (9 pages).

"Hippuric Acid Sodium Salt", Science Lab.com: Chemicals & Laboratory Equipment, retrieved Mar. 11, 2010 from URL: http://web.archive.org/web/20041107121553/http://sciencelab.com/page/S/PVAR/10415/SLH2620, (1 page).

"Iron-Related Outcomes in Patients with Dialysis-Dependent CKD Randomized to Vadadustal vs. Darbepoetin Alfa", Abstract: PO0457, Nov. 4, 2021 (2 pages).

"Iron-Related Outcomes in Patients with Non-Dialysis-Dependent CKD Randomized to Vadadustat vs Darbepoetin Alfa", Abstract: PO0482, Nov. 4, 2022 (2 pages).

"SCHEMBL3484399", PubChem, National Center for Biotechnology Information, CID 49848485, Jan. 31, 2011, retrieved Mar. 15,

(56) References Cited

OTHER PUBLICATIONS 2016 from URL: https://pubchem.ncbi.nlm.nih.gov/compound/49848485, (13 pages).
"Thromboembolic Events with Vadadustat vs Darbepoetin Alfa for Anemia Treatment in Patients with Dialysis-Dependent CKD", Abstract: PO0463, Nov. 4, 2022 (2 pages).
"Vadadustat for Treatment of Anemia in Patients with Dialysis-Dependent CKD Receiving Peritoneal Dialysis", Abstract: PO0464, Nov. 4, 2021 (2 pages).
"Vadadustat", Wikipedia, Nov. 2, 2018, retrieved Jun. 4, 2019 from URL: https://en.wikipedia.org/wiki/Vadadustat (2 pages).
"Vadadustat, an Oral HIF-PHI, Is Not Associated with Increased Risk of Neoplasm in Patients with Anemia due to CKD", Abstract: PO0461, Nov. 4, 2021 (2 pages).
"Vadadustat", PubChem Compound Summary for CID 23634441, National Center for Biotechnology Information, 2022, retrieved Sep. 14, 2022 from URL: https://pubchemncbi.nirn.nih.aov/comooundVadadustat (1 page).
"XEADCOHJERWFOI-UHFFFAOYSA-M", PubChem, National Center for Biotechnology Information, CID 71491828, Jun. 10, 2013, retrieved Mar. 21, 2016 from URL: https://pubchem.ncbi.nlm.nih.gov/compound/71491828, (12 pages).
"Akebia Announces Positive Top-Line Results from its Phase 2 Study of Vadadustat in Dialysis Patients with Anemia Related Chronic Kidney Disease", Press Release, Akebia Therapeutics, Inc., Sep. 8, 2015 (4 pages).
"Akebia Announces Presentation of Results from its Phase 2b Study of AKB-6548 in Non-Dialysis Patients with Anemia Related to Chronic Kidney Disease at the International Society of Nephrology's World Congress of Nephrology", Press Release, Akebia Therapeutics, Inc., Mar. 15, 2015 (4 pages).
"Akebia Annual Report 2014", Akebia Annual Report for the fiscal year ended Dec. 31, 2014 (136 pages).
"Akebia Therapeutics Announces Presentation of Clinical Data at Kidney Week 2011", Press Release, Akebia Therapeutics, Inc., Nov. 15, 2011 (2 pages).
"International Nonproprietary Names for Pharmaceutical Substances (INN)", WHO Drug Information, vol. 29, No. 4, 2015, (100 pages).
Acker et al., "Genetic evidence for a tumor suppressor role of HIF-2α", Cancer Cell, vol. 8, No. 2, Aug. 2005, pp. 131-141, DOI: 10.1016/j.ccr.2005.07.003, (11 page).
Alesso et al., "Improving resins for solid phase synthesis: incorporation of 1-[2-(2-methoxyethoxy)ethoxy]-4-vinyl-benzene", Tetrahedron, vol. 59, No. 36, Sep. 1, 2003, pp. 7163-7169, DOI: 10.1016/S0040-4020(03)01100-1, (7 pages).
Altschul et al., "Gapped BLAST and PSI-BLAST: a new generation of protein database search programs", Nucleic Acids Research, vol. 25, No. 17, Sep. 1, 1997, pp. 3389-3402, DOI: 10.1093/nar/25.17.3389, (14 pages).
American Diabetes Association, "Standards of Medical Care in Diabetes-2006", Diabetes Care, vol. 29, Suppl. 1, Jan. 2006, pp. S4-S42, (39 pages).
Anderson et al., "Antileukemic Activity of Derivatives of 1,2-dimethyl-3,4-bis(hydroxymethyl)-5-phenylpyrrole Bis(N-methylcarbamate)", Journal of Medicinal Chemistry, vol. 22, No. 8, 1979, pp. 977-980, DOI: 10.1021/jm00194a018, (4 pages).
Anderson, Neal, "Chapter 12—Crystallization and Purification", Practical Process Research and Development (Second Edition), 2012, pp. 329-364, DOI: 10.1016/B978-0-12-386537-3.00012-5, (38 pages).
Annex et al., "Growth factor-induced therapeutic angiogenesis in the heart: protein therapy", Cardiovascular Research, vol. 65, No. 3, Feb. 2005, pp. 649-655, DOI: 10.1016/j.cardiores.2004.09.004, (7 pages).
Appelhoff et al., "Differential Function of the Prolyl Hydroxylases PHD1, PHD2, and PHD3 in the Regulation of Hypoxia-inducible Factor", Journal of Biological Chemistry, vol. 279, No. 37, Sep. 2004, DOI: 10.1074/jbc.M406026200, (8 pages).
Ardelt et al., "Estradiol Regulates Angiopoietin-1 mRNA Expression Through Estrogen Receptor-α in a Rodent Experimental Stroke Model", Stroke, vol. 36, No. 2, Feb. 2005, pp. 337-341, DOI: 10.1161/01.STR.0000153795.38388.72, (6 pages).
Aspden et al., "Preventing Medical Errors", Institute of Medicine of the National Academies, 2007, (481 pages).
Auerbach et al., "Angiogenesis Assays: A Critical Overview", Clinical Chemistry, vol. 49, No. 1, 2003, pp. 32-40, DOI: 10.1373/49.1.32, (9 pages).
Bao et al., "Chronic Inhibition of Hypoxia-inducible Factor Prolyl 4-hydroxylase Improves Ventricular Performance, Remodeling, and Vascularity After Myocardial Infarction in the Rat", Journal of Cardiovascular Pharmacology, vol. 56, No. 2, Aug. 2010, pp. 147-155, Exhibit C (9 pages).
Barany et al., "Solid-phase peptide synthesis: a silver anniversary report", Chemical Biology & Drug Design, vol. 30, No. 6, 1987, pp. 705-739, DOI: 10.1111/j.1399-3011.1987.tb03385.x, (35 pages).
Bartlett et al., "CAVEAT: a program to facilitate the design of organic molecules", Molecular Recognition in Chemical and Biological Problems, Special Pub., Royal Society of Chemistry, 1989, pp. 182-196 (15 pages).
Berge et al., "Pharmaceutical Salts", Journal of Pharmaceutical Sciences, vol. 66, No. 1, Jan. 1977, pp. 1-19, DOI: 10.1002/jps.2600660104, (19 pages).
Besarab et al., "Evaluation of hypoxia-inducible factor prolyl hydroxylase inhibitor FG-4592 for hemoglobin correction and maintenance in nondialysis chronic kidney disease patients for 16 and 24 weeks", Nephrology Dialysis Transplantation, 2012, (2 pages).
Beuck et al., "Hypoxia-inducible factor stabilizers and other small-molecule erythropoiesis-stimulating agents in current and preventive doping analysis", Drug Testing and Analysis, vol. 4, 2012, pp. 830-845, DOI: 10.1002/dta.390 (16 pages).
Böhm, Hans-Joachim, "The computer program LUDI: A new method for the de novo design of enzyme inhibitors", Journal of Computer-Aided Molecular Design, vol. 6, No. 1, 1992, pp. 61-78, DOI: 10.1007/BF00124387, (18 pages).
Bolhuis et al., "Polyols as filler-binders for disintegrating tablets prepared by direct compaction", Drug Development and Industrial Pharmacy, vol. 35, No. 6, 2009, pp. 671-677, DOI: 10.1080/03639040802587799 (7 pages).
Branden et al., Introduction to Protein Structure, Second Edition, Garland Science, 1998, pp. 374-375, (4 pages).
Brittain et al., Polymorphism in Pharmaceutical Solids, Second Edition, Drugs and Pharmaceutical Sciences, vol. 192, 2009, pp. 333-335, (7 pages).
Buch et al., "Dose Exposure Relationship of AKB-6548 Is Independent of the Level of Renal Function", Journal of the American Society of Nephrology, vol. 26, Abstract Edition, Nov. 2015, Exhibit D (3 pages).
Buch et al., "Dose Exposure Relationship of Vadadustat is Independent of the Level of Renal Function", Akebia Therapeutics, SA-PO537, Exhibit E, Nov. 2015 (1 page).
Buch et al., "Hemodialysis Has Minimal Impact on the Pharmacokinetics of AKB-6548, a Once-Daily Oral Inhibitor of Hypoxia Inducible Factor Prolyl-Hydroxylases (HIFPHs) for the Treatment of Anemia Related to Chronic Kidney Disease (CKD)", Journal of the American Society of Nephrology, vol. 25, 2014, Abstract FR-PO952 (1 page).
Burger, Alfred, "Isosterism and bioisosterism in drug design", Progress in Drug Research, vol. 37, 1991, pp. 287-371, DOI: 10.1007/978-3-0348-7139-6_7, (85 pages).
Bussolino et al., "Molecular mechanisms of blood vessel formation", Trends in Biochemical Sciences, vol. 22, No. 7, Jul. 1997, pp. 251-256, DOI: 10.1016/s0968-0004(97)01074-8, (6 pages).
Byrn et al., "Pharmaceutical Solids: A Strategic Approach to Regulatory Considerations", Pharmaceutical Research, vol. 12, No. 7, 1995, pp. 945-954, DOI: 10.1023/a:1016241927429, (10 pages).
Carey, Francis A., Organic Chemistry, Sixth Edition, McGraw Hill, 2006, Chapter 1, p. 9, Chapter 19, pp. 839-840, and Chapter 27, pp. 1182-1183, (12 pages).

(56) References Cited

OTHER PUBLICATIONS

Carrasco, Mercedes "Akebia Announces Vadadustat Efficacy and Safety Data to be Presented at American Society of Nephrology Kidney Week 2021", Press Release, Akebia Therapeutics, Inc., Oct. 18, 2021 (2 pages).
CAS Registry Nos. 1261813-98-2, 1261613-86-8, and 1261518-21-1, Chemcats, 2011, (2 pages).
Catrina et al., "Hyperglycemia Regulates Hypoxia-Inducible Factor-1α Protein Stability and Function", Diabetes, vol. 53, No. 12, 2004, pp. 3226-3232, DOI: 10.2337/diabetes.53.12.3226, (7 pages).
Chavan et al., "Pharmacokinetic Evaluation of Drug Interactions Between Vadadustat and HMG-COA Reductase Inhibitors (Statins)", EMBASE / Elsevier, Jan. 1, 2020, Database Accession No. EMB-633697266, Conference Abstract (2 pages).
Cheeseright, Tim, "The Identification of Bioisosteres as Drug Development Candidates", Innovations in Pharmaceutical Technology, 2009, (4 pages).
Cherng, Yie-Jia, "Synthesis of substituted pyridines by the reactions of halopyridines with sulfur, oxygen and carbon nucleophiles under focused microwave irradiation", Tetrahedron, vol. 58, No. 24, Jun. 10, 2002, pp. 4931-4935, DOI: 10.1016/S0040-4020(02)00424-6,(5 pages).
Chertow et al., "Vadadustat in Patients with Anemia and Non-Dialysis-Dependent CKD", The New England Journal of Medicine, vol. 384, No. 17, Apr. 29, 2021, pp. 1589-1600, DOI: 10.1056/NEJMoa2035938 (12 pages).
ClinicalTrials.gov, Archive No. NCT01235936, Aug. 30, 2012, retrieved Dec. 1, 2014 from URL: http://clinicaltrials.gov/archive/NCT01235936/2012_09_30, (3 pages).
Cortellis Vadadustat Change History created Mar. 2, 2022 (36 pages).
Costello et al., "Evidence for Changes in RREB-1, ZIP3, and Zinc in the Early Development of Pancreatic Adenocarcinoma", Journal of Gastrointestinal Cancer, vol. 43, No. 4, 2012, pp. 570-578, DOI: 10.1007/s12029-012-9378-1, (9 pages).
Cousins, Scott W., "Intravitreal Anti-VEGF and Anti-PDGF Combination Therapy", Retina Today, Oct. 2009, Retrieved from URL: http://retinatoday.com/2009/10/1009_12.php, (2 pages).
Crowley et al., "Drug-Excipient Interactions", Pharmaceutical Technology Europe, vol. 4, Mar. 2001, pp. 7-12 (6 pages).
Cunliffe et al., "Novel inhibitors of prolyl 4-hydroxylase. 3. Inhibition by the substrate analog N-oxaloglycine and its derivatives", Journal of Medicinal Chemistry, vol. 35, No. 14, 1992, pp. 2652-2658, DOI: 10.1021/jm00092a016, (7 pages).
Decision of the Technical Board of Appeal of the European Patent Office for Case No. T0777/08 dated May 24, 2011, Retrieved Dec. 19, 2017 from URL: https://www.epo.org/boards-of-appeal/decisions/pdf/t080777ex1.pdf, (17 pages).
Demetriades et al., "Dynamic Combinatorial Chemistry Employing Boronic Acids/Boronate Esters Leads to Potent Oxygenase Inhibitors" Angewandte Chemie, International Edition , vol. 51, No. 27, Jul. 2, 2012, pp. 6672-6675, DOI: 10.1002/anie.201202000, (4 pages).
Designation of Inventor for EP Pat. No. 2044005 dated Jan. 21, 2009 (2 pages).
Donkin et al., "A Substance P Antagonist Reduces Axonal Injury and Improves Neurologic Outcome When Administered Up to 12 Hours after Traumatic Brain Injury", Journal of Neurotrauma, vol. 28, Feb. 2011, pp. 217-224, DOI: 10.1089/neu.2010.1632 (8 pages).
Donkin et al., "Substance P is associated with the development of brain edema and functional deficits after traumatic brain injury", Journal of Cerebral Blood Flow & Metabolism, 2009, pp. 1-11, DOI: 10.1038/jcbfm.2009.63 (11 pages).
Dranoff, Glenn, "GM-CSF-secreting melanoma vaccines", Oncogene, vol. 22, 2003, pp. 3188-3192, DOI: 10.1038/sj.onc.1206459, (5 pages).
Eckardt et al., "Safety and Efficacy of Vadadustat for Anemia in Patients Undergoing Dialysis", The New England Journal of Medicine, vol. 384, 2021, pp. 1601-1612, DOI: 10.1056/NEJMoa2025956, (12 pages).
Eckle et al., "HIF1A Reduces Acute Lung Injury by Optimizing Carbohydrate Metabolism in the Alveolar Epithelium", PLOS Biology, vol. 11, No. 9, 2013, pp. e1001665, DOI: 10.1371/journal.pbio.1001665, (25 pages).
Elson et al., "Induction of hypervascularity without leakage or inflammation in transgenic mice overexpressing hypoxia-inducible factor-1α", Genes & Development, vol. 15, 2001, pp. 2520-2532, DOI: 10.1101/gad.914801, (13 pages).
Elvidge et al., "Concordant Regulation of Gene Expression by Hypoxia and 2-Oxoglutarate-dependent Dioxygenase Inhibition", Journal of Biological Chemistry, vol. 281, No. 22, Jun. 2006, pp. 15215-15226, DOI: 10.1074/jbc.M511408200, (13 pages).
Enoch et al., "ABC of wound healing: Non-surgical and drug treatments", BMJ, vol. 332, No. 7546, 2006, pp. 900-903, DOI: 10.1074/jbc.M511408200, (4 pages).
Exhibit A, "2009 Pat. App. LEXIS 10905", Board of Patent Appeals and Interferences, Mar. 11, 2009, Decided, Ex parte Thomas G. Xydis (5 pages).
Exhibit B, "2015 Pat. App. LEXIS 435", Patent Trial and Appeal Board, Jan. 27, 2015, Decided, Ex parte Christine Esau and Eric E. Swayze (9 pages).
Exhibit C: Lee et al., "6.1 Pharmaceutical Preformulation: Physicochemical Properties of Excipients and Powders and Tablet Characterization", Pharmaceutical Manufacturing Handbook: Production and Processes, 2008, pp. 881-931, (53 pages).
Exhibit D: Perumal et al., "6.2 Role of Preformulation in Development of Solid Dosage Forms", Pharmaceutical Manufacturing Handbook: Production and Processes, 2008, pp. 933-975, (45 pages).
Exhibit E: Cavatur et al., "Chapter 14—Preformulation Studies for Tablet Formulation Development", Pharmaceutical Dosage Forms—Tablets: Unit Operation and Mechanical Properties, 2008, pp. 465-483, (20 pages).
Exhibit F: *Endo Pharms. Sols., Inc.* v. *Custopharm Inc.*, United States Court of Appeals for the Federal Circuit, Case No. 2017-1719, Jul. 13, 2018 (10 pages).
Exhibit G: *Genetics Institute, LLC* v. *Novartis Vaccines and Diagnostics, Inc.*, United States Court of Appeals for the Federal Circuit, Case No. 2010-1264, Aug. 23, 2011 (23 pages).
Extended European Search Report for EP Application No. 11000872.9 dated Apr. 28, 2011 (8 pages).
Extract from USPTO Patent Assignment Database for U.S. Appl. No. 11/821,936, retrieved on Feb. 4, 2013 (1 page).
Favier et al., "HIF2α reduces growth rate but promotes angiogenesis in a mouse model of neuroblastoma", BMC Cancer, vol. 7, Article No. 139, 2007, DOI: 10.1186/1471-2407-7-139, (10 pages).
Felton et al., "An update on pharmaceutical film coating for drug delivery", Expert Opinion on Drug Delivery, vol. 10, No. 4, 2013, pp. 421-435, DOI: 10.1517/17425247.2013.763792, (15 pages).
Felton, "Film Coating of Oral Solid Dosage Forms", Encyclopedia of Pharmaceutical Technology, 2007, pp. 1729-1747, (18 pages).
Fiedler Lexikon de Hilfsstoffe für Pharmazie, Kosmetik und angrenzende Gebiete, Fifth Edition, 2002, vol. 9, pp. 1248, (3 pages).
Flower et al., "Modelling G-protein-coupled receptors for drug design", Biochimica et Biophysica Acta (BBA)—Reviews on Biomembranes, vol. 1422, No. 3, Nov. 16, 1999, pp. 207-234, DOI: 10.1016/s0304-4157(99)00006-4, (28 pages).
Folkman, Judah, "Chapter 10—Tumor Angiogenesis", The Molecular Basis of Cancer, 1995, pp. 206-232, (29 pages).
Franklin et al., "Approaches to the design of anti-fibrotic drugs", Biochemical Society Transactions, vol. 19, No. 4, Nov. 1991, pp. 812-815, DOI: 10.1042/bst0190812, (4 pages).
Gaunt et al., "Rational Design of Benzyl-Type Protecting Groups Allows Sequential Deprotection of Hydroxyl Groups by Catalytic Hydrogenolysis", Journal of Organic Chemistry, vol. 63, No. 13, 1998, pp. 4172-4173, DOI: 10.1021/JO980823V, (2 pages).
Gaunt et al., "Rational Design of Benzyl-Type Protecting Groups Allows Sequential Deprotection of Hydroxyl Groups by Catalytic Hydrogenolysis", Journal of Organic Chemistry, vol. 63, No. 13, 1998, pp. 4172-4173, DOI: 10.1021/JO980823V, Supplementary Materials (14 pages).

(56) References Cited

OTHER PUBLICATIONS

Gavhane et al., "Solid Tumors: Facts, Challenges and Solutions", International Journal of Pharma Sciences and Research, vol. 2, No. 1, 2011, pp. 1-12, (12 pages).
Goodford, P. J., "A computational procedure for determining energetically favorable binding sites on biologically important macromolecules", Journal of Medicinal Chemistry, vol. 28, No. 7, 1985, pp. 849-857, DOI: 10.1021/jm00145a002m (9 pages).
Goodsell et al., "Automated docking of substrates to proteins by simulated annealing", Proteins, vol. 8, No. 3, 1990, pp. 195-202, DOI: 10.1002/prot.340080302, (8 pages).
Greer et al., "The updated biology of hypoxia-inducible factor", The EMBO Journal, vol. 31, No. 11, May 30, 2012, pp. 2448-2460, DOI: 10.1038/emboj.2012.125, (13 pages).
Guillory et al., "Generation of Polymorphs, Hydrates, Solvates, and Amorphous Solids", Polymorphism in Pharmaceutical Solids, vol. 95, 1999, pp. 183-226, (46 pages).
Haase et al., "Effects of vadadustat on hemoglobin concentrations in patients receiving hemodialysis previously treated with erythropoiesis-stimulating agents", Nephrology Dialysis Transplantation, vol. 34, No. 1, Jan. 2019, pp. 90-99, DOI: 10.1093/ndt/gfy055, (10 pages).
Hardcastle et al., "Discovery of Potent Chromen-4-one Inhibitors of the DNA-Dependent Protein Kinase (DNA-PK) Using a Small-Molecule Library Approach", Journal of Medicinal Chemistry, vol. 48, No. 24, 2005, pp. 7829-7846, DOI: 10.1021/jm050444b, (18 pages).
Hartman et al., "Controlled Hemoglobin Response in a Double-Blind, Placebo-Controlled Trial of AKB-6548 in Subjects with Chronic Kidney Disease", Nephrology Dialysis Transplantation, vol. 29, Supplement No. 3, May 2014, pp. iii21-iii22, DOI: 10.1093/ndt/gfu117, Abstract SO051 (2 pages).
Haywood et al., "Pharmaceutical excipients—where do we begin?", Australian Prescriber, vol. 34, Aug. 2011, pp. 112-114 (3 pages).
Hoeksema et al., "Structure of rubradirin", Journal of the American Chemical Society, vol. 104, No. 19, 1982, pp. 5173-5181, DOI: 10.1021/ja00383a030, (9 pages).
Hu et al., "Differential Roles of Hypoxia-Inducible Factor 1α (HIF-1α) and HIF-2α in Hypoxic Gene Regulation", Molecular and Cellular Biology, vol. 23, No. 24, 2003, pp. 9361-9374, DOI: 10.1128/MCB.23.24.9361-9374.2003, (14 pages).
Ingersoll et al., "Hippuric Acid", Organic Synthesis, CV 2, 328, Retrieved on Mar. 11, 2010 from the Internet at <http://web.archive.org/web/20020724135719/http://www.orgsyn.org/orgsyn/orgsyn/prepContent.asp?prep=cv2p0328>, (4 pages).
Interlocutory Decision in Opposition Proceedings for EP Pat. No. 2044005 dated May 3, 2013 (76 pages).
International Preliminary Report on Patentability, Ch. I, for PCT/US2012/040833 dated Dec. 27, 2013 (7 pages).
International Preliminary Report on Patentability, Ch. I, for PCT/US2021/028126 dated Nov. 3, 2022 (14 pages).
International Search Report and Written Opinion for PCT/US2007/014832 dated May 8, 2008 (9 pages).
International Search Report and Written Opinion for PCT/US2012/040833 dated Aug. 29, 2012 (9 pages).
International Search Report and Written Opinion for PCT/US2014/040889 dated Dec. 31, 2014 (20 pages).
International Search Report and Written Opinion for PCT/US2015/012634 dated Apr. 20, 2015 (9 pages).
International Search Report and Written Opinion for PCT/US2016/025235 dated Jun. 20, 2016 (31 pages).
International Search Report and Written Opinion for PCT/US2020/058007 dated Jan. 25, 2021 (7 pages).
International Search Report and Written Opinion for PCT/US2021/028126 dated Jul. 16, 2021 (18 pages).
International Search Report and Written Opinion for PCT/US2021/037781 dated Oct. 15, 2021 (17 pages).
International Search Report and Written Opinion for PCT/US2022/011666 dated Apr. 8, 2022 (12 pages).
International Search Report and Written Opinion for PCT/US2022/018152 dated Jun. 14, 2022 (15 pages).
Ivan et al., "Biochemical purification and pharmacological inhibition of a mammalian prolyl hydroxylase acting on hypoxia-inducible factor", PNAS, vol. 99, No. 21, Sep. 26, 2002, pp. 13459-13464, DOI: 10.1073/pnas.192342099, (6 pages).
Ivan et al., "HIFα Targeted for VHL-Mediated Destruction by Proline Hydroxylation: Implications for O2 Sensing", Science, vol. 292, No. 5516, Apr. 5, 2001, pp. 464-468, DOI: 10.1126/science.1059817, (5 pages).
Ivanisevic et al., "Uses of X-Ray Powder Diffraction In the Pharmaceutical Industry", Pharmaceutical Formulation and Quality, 2010, DOI: 10.1002/9780470571224.pse414, (4 pages).
Iyoda et al., "Homocoupling of Aryl Halides Using Nickel(II) Complex and Zinc in the Presence of Et4NI. An Efficient Method for the Synthesis of Biaryls and Bipyridines", Bulletin of the Chemical Society of Japan, vol. 63, No. 1, 1990, pp. 80-87.
Jaakkola et al., "Targeting of HIF-α to the von Hippel-Lindau Ubiquitylation Complex by O2-Regulated Prolyl Hydroxylation", Science, vol. 292, No. 5516, Apr. 5, 2001, pp. 468-472, DOI: 10.1126/science.1059796, (5 pages).
Jones et al., "Molecular recognition of receptor sites using a genetic algorithm with a description of desolvation", Journal of Molecular Biology, vol. 245, No. 1, 1995, pp. 43-53, DOI: 10.1016/s0022-2836(95)80037-9, (11 pages).
Jones, David, "FASTtrack: Pharmaceutics—Dosage Form and Design", Pharmaceutical Press, 2008, (297 pages).
Kaelin, William G., "Proline hydroxylation and gene expression", Annual Review of Biochemistry, vol. 74, 2005, pp. 115-128, DOI: 10.1146/annurev.biochem.74.082803.133142, (14 pages).
Karuppagounder et al., "Hypoxia-Inducible Factor Prolyl Hydroxylase Inhibition: Robust New Target or Another Big Bust for Stroke Therapeutics?", Journal of Cerebral Blood Flow & Metabolism, vol. 32, No. 7, 2012, pp. 1347-1361, DOI: 10.1038/jcbfm.2012.28, (14 pages).
Kawashima et al., "Suppressive Effect of Quinolinic Acid and Hippuric Acid on Bone Marrow Erythroid Growth and Lymphocyte Blast Formation in Uremia", Advances in Experimental Medicine and Biology, vol. 223, 1987, pp. 69-72, DOI: 10.1007/978-1-4684-5445-1_9, (5 pages).
Ke et al., "Hypoxia-Inducible Factor-1 (HIF-1)", Molecular Pharmacology, vol. 70, No. 5, Nov. 2006, pp. 1469-1480, DOI: 10.1124/mol.106.027029, (12 pages).
Khandhadia et al., "Chapter 2—Age-Related Macular Degeneration", Neurodegenerative Diseases, Landes Bioscience and Springer Science+Business Media, 2012, pp. 15-36, (22 pages).
Kietzmann et al., "Perivenous expression of the mRNA of the three hypoxia-inducible factor α-subunits, HIF1α, HIF2α and HIF3α, in rat liver", Biochemical Journal, vol. 354, No. 3, Mar. 2001, pp. 531-537, DOI: 10.1042/bj3540531, (7 pages).
Kim et al., "Recent Advances in Developing Inhibitors for Hypoxia-Inducible Factor Prolyl Hydroxylases and Their Therapeutic Implications", Molecules, vol. 20, No. 11, 2015, pp. 20551-20568, DOI: 10.3390/molecules201119717, (18 pages).
Kirwan et al., "11-Crystallization in the pharmaceutical and bioprocessing industries", Handbook of Industrial Crystallization (Second Edition), 2002, pp. 249-266, DOI: 10.1016/B978-075067012-8/50013-6, (20 pages).
Krantz, Sanford B., "Erythropoietin", Blood, vol. 77, No. 3, Feb. 1, 1991, pp. 419-434, DOI: 10.1182/blood.V77.3.419.419, (16 pages).
Krapf et al., "Arterial Hypertension Induced by Erythropoietin and Erythropoiesis-Stimulating Agents (ESA)", Clin J Am Soc Nephrol, vol. 4, 2009, pp. 470-480, DOI: 10.2215/CJN.05040908 (11 pages).
Kuntz et al., "A geometric approach to macromolecule-ligand interactions", Journal of Molecular Biology, vol. 161, No. 2, Oct. 25, 1982, pp. 269-288, DOI: 10.1016/0022-2836(82)90153-x, (20 pages).
Kurti et al., "Strategic Applications of Named Reactions in Organic Synthesis", Elsevier, 2005, pp. 448-449, (4 pages).
Langsetmo et al., "Inhibition of HIF-Prolyl Hydroxylases with FG-4539 Is Neuroprotective in a Mouse Model of Permanent Focal Ischemia", International Stroke Conference, Kissimmee, Florida, Presentation No. 427, 2006, Abstract (1 page).

(56) References Cited

OTHER PUBLICATIONS

Lee et al., "Hypoxia signaling in human diseases and therapeutic targets", Experimental & Molecular Medicine, vol. 51, Jun. 20, 2019, pp. 1-13, DOI: 10.1038/s12276-019-0235-1, (13 pages).
Lee et al., "Structure of Human FIH-1 Reveals a Unique Active Site Pocket and Interaction Sites for HIF-1 and von Hippel-Lindau", Enzyme Catalysis and Regulation, vol. 278, No. 9, Feb. 2003, pp. 7558-7563, DOI: 10.1074/jbc.M210385200, (7 pages).
Leuenberger et al., "Pharmaceutical powder technology—from art to science: the challenge of the FDA's Process Analytical Technology initiative", Advanced Powder Technology, vol. 16, No. 1, 2005, pp. 3-25 (23 pages).
Li et al., "PR39, a peptide regulator of angiogenesis", Nature Medicine, vol. 6, No. 1, 2000, pp. 49-55, DOI: 10.1038/71527, (7 pages).
Lim, Chun Soo, "Clinical Practice Guidelines and Clinical Practice Recommendations for Anemia in Chronic Kidney Disease in Adults", Kidney Research and Clinical Practice, vol. 25, Appendix No. 2, 2006, pp. S551-S558 (8 pages).
Lima et al., "Bioisosterism: A Useful Strategy for Molecular Modification and Drug Design", Current Medicinal Chemistry, vol. 12, No. 1, 2005, pp. 23-49, DOI: 10.2174/0929867053363540, (27 pages).
Liu et al., "Hypoxia induces genomic DNA demethylation through the activation of HIF-1α and transcriptional upregulation of MAT2A in hepatoma cells", Molecular Cancer Therapeutics, vol. 10, No. 6, Jun. 1, 2011, pp. 1113-1123, DOI: 10.1158/1535-7163.MCT-10-1010, (12 pages).
Mancini et al., "Effect of Erythropoietin on Exercise Capacity in Patients With Moderate to Severe Chronic Heart Failure", Circulation, vol. 107, No. 2, 2002, pp. 294-299, DOI: 10.1161/01.CIR.0000044914.42696.6A, (7 pages).
Mcdonough et al., "Cellular oxygen sensing: Crystal structure of hypoxia-inducible factor prolyl hydroxylase (PHD2)", PNAS, vol. 103, No. 26, Jun. 27, 2006, pp. 9814-9819, DOI: 10.1073/pnas.0601283103, (6 pages).
Mcdonough et al., "Cellular oxygen sensing: Crystal structure of hypoxia-inducible factor prolyl hydroxylase (PHD2)", PNAS, vol. 103, No. 26, Jun. 27, 2006, pp. 9814-9819, DOI: 10.1073/pnas.0601283103, Online Abstract Showing Online Publication Date as Jun. 16, 2006 (4 pages).
Minutes of the Oral Proceedings Before the Opposition Division for EP Pat. No. 2044005 dated May 3, 2013 (6 pages).
Miranker et al., "Functionality maps of binding sites: A multiple copy simultaneous search method," Proteins: Structure, Function and Genetics, vol. 11, No. 1, Sep. 1991, pp. 29-34, DOI: 10.1002/prot.340110104, (6 pages).
Morissette et al., "High-throughput crystallization: polymorphs, salts, co-crystals and solvates of pharmaceutical solids", Advanced Drug Delivery Reviews, vol. 56, No. 3, Feb. 23, 2004, pp. 275-300, DOI: 10.1016/j.addr.2003.10.020, (26 pages).
Moss et al., "Glossary of class names of organic compounds and reactivity intermediates based on structure (IUPAC Recommendations 1995)", Pure and Applied Chemistry, vol. 67, Nos. 8/9, 1995, pp. 1307-1375, DOI: 10.1351/pac199567081307, (69 pages).
Myllyharju, J., "Prolyl 4-hydroxylases, master regulators of the hypoxia response", Acta Physiologica, vol. 208, No. 2, Jun. 2013, pp. 148-165, DOI: 10.1111/apha.12096, (18 pages).
Nangaku et al., "Vadadustat, an oral hypoxia-inducible factor prolyl hydroxylase inhibitor, for treatment of anemia of chronic kidney disease: two randomized Phase 2 trials in Japanese patients", Nephrology Dialysis Transplantation, vol. 36, No. 7, Jul. 2021, pp. 1244-1252, DOI: 10.1093/ndt/gfaa060, (9 pages).
Nangaku et al., "Efficacy and safety of vadadustat compared with darbepoetin alfa in Japanese anemic patients on hemodialysis: a Phase 3, multicenter, randomized, double-blind study", Nephrology Dialysis Transplantation, vol. 36, No. 9, Sep. 2021, pp. 1731-1741, DOI: 10.1093/ndt/gfab055, (11 pages).
Nangaku et al., "Phase 3 Randomized Study Comparing Vadadustat with Darbepoetin Alfa for Anemia in Japanese Patients with Nondialysis-Dependent CKD", Journal of the American Society Society of Nephrology, vol. 32, No. 7, Jul. 2021, pp. 1779-1790, (36 pages).
Nguyen et al., "Cellular interactions in vascular growth and differentiation", International Review of Cytology, vol. 204, 2001, pp. 1-48, DOI: 10.1016/s0074-7696(01)04002-5, (48 pages).
Nielsen et al., "Antiangiogenic therapy for breast cancer", Breast Cancer Research, vol. 12, Article No. 209, 2010, DOI: 10.1186/bcr2642, (16 pages).
Nishibata et al., "Automatic creation of drug candidate structures based on receptor structure. Starting point for artificial lead generation.", Tetrahedron, vol. 47, No. 43, Nov. 4, 1991, pp. 8985-8990, DOI: 10.1016/S0040-4020(01)86503-0, (6 pages).
Notice of Opposition to a European Patent for EP 3277270 dated Aug. 3, 2022 (29 pages).
Nowak, Jerzy, "Age-related macular degeneration (AMD): pathogenesis and therapy", Pharmacological Reports, vol. 58, 2006, pp. 353-363, (11 pages).
O'Reilly et al., "Angiostatin: A novel angiogenesis inhibitor that mediates the suppression of metastases by a lewis lung carcinoma", Cell, vol. 79, No. 2, 1994, pp. 315-328, DOI: 10.1016/0092-8674(94)90200-3, (14 pages).
O'Reilly et al., "Endostatin: An Endogenous Inhibitor of Angiogenesis and Tumor Growth", Cell, vol. 88, No. 2, 1997, pp. 277-285, DOI: 10.1016/S0092-8674(00)81848-6, (9 pages).
Pasqualetti et al., "Circadian rhythm of serum erythropoietin in myelodysplastic syndromes", European Review for Medical and Pharmacological Sciences, vol. 4, 2000, pp. 111-115 (5 pages).
PCT Request Form dated Jun. 26, 2007 for PCT/US2007/014832 (5 pages).
Pergola et al., "Vadadustat, a novel oral HIF stabilizer, provides effective anemia treatment in nondialysis-dependent chronic kidney disease", Kidney International, vol. 90, No. 5, Nov. 2016, pp. 1115-1122, DOI: 10.1016/j.kint.2016.07.019, (8 pages).
Perrie et al., "Chapter 1: Controlling Drug Delivery", Pharmaceutics—Drug Delivery and Targeting, Second Edition, Pharmaceutical Press, 2007, pp. 1-24 (24 pages).
Peyssonnaux et al., "HIF-1α expression regulates the bactericidal capacity of phagocytes", The Journal of Clinical Investigation, vol. 115, No. 7, Jul. 2005, pp. 1806-1815, DOI: 10.1172/JCI23865, (10 pages).
Piyamongkol et al., "Amido-3-hydroxypyridin-4-ones as Iron(III) Ligands", Chemistry A European Journal, vol. 16, No. 21, Jun. 1, 2010, pp. 6374-6381, DOI: 10.1002/chem.200902455, (8 pages).
Piyamongkol et al., "Amido-3-hydroxypyridin-4-ones as Iron(III) Ligands", Chemistry A European Journal, vol. 16, No. 21, Jun. 1, 2010, pp. 6374-6381, DOI: 10.1002/chem.200902455, Supporting Information (53 pages).
Poloznikov et al., "HIF Prolyl Hydroxylase Inhibitors for COVID-19 Treatment: Pros and Cons", Frontiers in Pharmacology, vol. 11, Article No. 621054, Jan. 2021, DOI: 10.3389/fphar.2020.621054, (11 pages).
Prabhakar et al., "Adaptive and Maladaptive Cardiorespiratory Responses to Continuous and Intermittent Hypoxia Mediated by Hypoxia-Inducible Factors 1 and 2", Physiological Reviews, vol. 92, No. 3, Jul. 2012, pp. 967-1003, DOI: 10.1152/physrev.00030.2011, Author Manuscript (6 pages).
Qian et al., "A Randomized, Double-Bind, Placebo Controlled Trial FG-4592 for Correction of Anemia in Subjects with Chronic Kidney Disease in China", Journal of the American Society of Nephrology, vol. 24, 2013, Oral Abstract FR-OR011 (1 page).
Qunibi et al., "A randomized controlled trial comparing intravenous ferric carboxymaltose with oral iron for treatment of iron deficiency anaemia of non-dialysis-dependent chronic kidney disease patients", Nephrology Dialysis Transplantation, vol. 26, No. 5, May 2011, pp. 1599-1607, DOI: 10.1093/ndt/gfq613, (9 pages).
Rahtu-Korpela et al., "HIF Prolyl 4-Hydroxylase-2 Inhibition Improves Glucose and Lipid Metabolism and Protects Against Obesity and Metabolic Dysfunction", Diabetes, vol. 63, No. 10, 2014, pp. 3324-3333, DOI: 10.2337/db14-0472, (10 pages).
Rankin et al., "Hypoxia-inducible factor-2 (HIF-2) regulates hepatic erythropoietin in vivo", The Journal of Clinical Investigation, vol. 117, No. 4, Apr. 2007, pp. 1068-1077, DOI: 10.1172/JCI30117, (10 pages).

(56) References Cited

OTHER PUBLICATIONS

Ratcliffe, Peter J., "HIF-1 and HIF-2: working alone or together in hypoxia?", The Journal of Clinical Investigation, vol. 117, No. 4, Apr. 2007, 862-865, Doi: 10.1172/JCI31750, (4 pages).
Redondo et al., "Vascular endothelial growth factor (VEGF) and melanoma. N-acetylcysteine downregulates VEGF production in vitro", Cytokine, vol. 12, No. 4, Apr. 2000, pp. 374-378, DOI: 10.1006/cyto. 1999.0566, (5 pages).
Ren et al., "Influenza A virus (H1N1) triggers a hypoxic response by stabilizing hypoxia-inducible factor-1α via inhibition of proteasome", Virology, vol. 530, Apr. 2019, pp. 51-58, DOI: 10.1016/j.virol.2019.02.010, (8 pages).
Request for Correction of Inventorship for U.S. Appl. No. 11/821,939 dated Jan. 16, 2009 (1 page).
Response to the Communication pursuant to Rules 70(2) and 70a(2) EPC for European Patent Application No. 16774184.2 dated Apr. 29, 2019 (7 pages).
Roda et al., "Stabilization of HIF-2α Induces sVEGFR-1 Production from Tumor-Associated Macrophages and Decreases Tumor Growth in a Murine Melanoma Model", The Journal of Immunology, vol. 189, No. 6, Sep. 15, 2012, pp. 3168-3177, DOI: 10.4049/jimmunol. 1103817, Author Manuscript (23 pages).
Schelhaas et al., "Protecting Group Strategies in Organic Synthesis", Angewandte Chemie, International Edition, vol. 35, No. 18, Oct. 1, 1996, pp. 2056-2083, DOI: 10.1002/anie.199620561, (27 pages).
Schöneberg et al., "Structural basis of G protein-coupled receptor function", Molecular and Cellular Endocrinology, vol. 151, No. 1-2, May 25, 1999, pp. 181-193, 10.1016/S0303-7207(99)00017-9, (13 pages).
Semenza et al., "Transcriptional regulation of genes encoding glycolytic enzymes by hypoxia-inducible factor", The Journal of Biological Chemistry, vol. 269, No. 38, Sep. 23, 1994, pp. 23757-23763, (7 pages).
Semenza, Gregg L, "Regulation of erythropoietin production. New insights into molecular mechanisms of oxygen homeostasis", Hematology/Oncology Clinic of North America, vol. 8, No. 5, Oct. 1994, pp. 863-884, (22 pages).
Semenza, Gregg L., "HIF-1 and human disease: one highly involved factor", Genes & Development, vol. 14, No. 16, 2000, pp. 1983-1991, DOI: 10.1101/gad.14.16.1983, (10 pages).
Semenza, Gregg L., "Signal transduction to hypoxia-inducible factor 1", Biochemical Pharmacology, vol. 64, No. 5-6, Sep. 2002, pp. 993-998, DOI: 10.1016/s0006-2952(02)01168-1, (6 pages).
Serebrovska et al., "Hypoxia, HIF-1α, and COVID-19: from pathogenic factors to potential therapeutic targets", Acta Pharmacologica Sinica, vol. 41, 2020, pp. 1539-1546, (8 pages).
Sexton, Patrick M, "Recent advances in our understanding of peptide hormone receptors and RAMPS", Current Opinions in Drug Discovery & Development, vol. 2, No. 5, 1999, pp. 440-448, (9 pages).
Shalwitz, Robert, "JASN Abstract Supplement", J Am Soc Nephrol, vol. 23, Oct. 30, 2012, Kidney Week (1175 pages).
Sheehan, John T., "3-Hydroxypicolinic Acid and Some of Its Derivatives", The Journal of Organic Chemistry, vol. 31, No. 2, 1966, pp. 636-638, DOI; 10.1021/jo01340a533, (5 pages).
Siddiq et al., "Hypoxia-inducible Factor Prolyl 4-Hydroxylase Inhibition. A target for neuroprotection in the central nervous system", Journal of Biological Chemistry, vol. 280, No. 50, Dec. 2005, pp. 41732-41743, DOI: 10.1074/jbc.M504963200, (13 pages).
Sowter et al., "Predominant Role of Hypoxia-Inducible Transcription Factor (Hif)-1α versus Hif-2α in Regulation of the Transcriptional Response to Hypoxia", Cancer Research, vol. 63, No. 19, Oct. 1, 2003, pp. 6130-6134, (8 pages).
Sporn et al., "Chemoprevention of cancer", Carcinogenesis, vol. 21, No. 3, Mar. 2000, pp. 525-530, DOI: 10.1093/carcin/21.3.525, (6 pages).
Steinmetz et al., "The basics of preclinical drug development for neurodegenerative disease indications", BMC Neurology, vol. 9, Suppl. 1, Article No. S2, 2009, DOI: 10.1186/1471-2377-9-SI-S2, (13 pages).
Stern et al., "Long-term Consequences of Repetitive Brain Trauma: Chronic Traumatic Encephalopathy", Physical Medicine and Rehabilitation, vol. 3, No. 10S2, Oct. 2011, pp. S460-S467, DOI: 10.1016/j.pmrj.2011.08.008 (8 pages).
Stille, John K., "The Palladium-Catalyzed Cross-Coupling Reactions of Organotin Reagents with Organic Electrophiles", Angewandte Chemie, International Edition, vol. 25, No. 6, Jun. 1986, pp. 508-524, DOI: 10.1002/anie.198605081, (18 pages).
Stohlawetz et al., "Effects of erythropoietin on platelet reactivity and thrombopoiesis in humans", Blood, vol. 95, No. 9, May 1, 2000, pp. 2983-2989 (7 pages).
Sun et al., "Development of a High Drug Load Tablet Formulation Based on Assessment of Powder Manufacturability: Moving Towards Quality by Design", Journal of Pharmaceutical Sciences, vol. 98, No. 1, Jan. 2009, pp. 239-247, DOI: 10.1002/jps.21422, Exhibit B (9 pages).
Sutter et al., "Hypoxia-inducible factor 1α protein expression is controlled by oxygen-regulated ubiquitination that is disrupted by deletions and missense mutations", PNAS, vol. 97, No. 9, Apr. 11, 2000, pp. 4748-4753, DOI: 10.1073/pnas.080072497, (6 pages).
Teicher et al., "Potentiation of cytotoxic cancer therapies by TNP-470 alone and with other anti-angiogenic agents", International Journal of Cancer, vol. 57, No. 6, Jun. 15, 1994, pp. 920-925, DOI: 10.1002/ijc.2910570624, (6 pages).
Tekin et al., "Hypoxia inducible factor 1 (HIF-1) and cardioprotection", Acta Pharmacologica Sinica, vol. 31, 2010, pp. 1085-1094, DOI: 10.1038/aps.2010.132 (10 pages).
Thoppil et al., "Terpenoids as potential chemopreventive and therapeutic agents in liver cancer", World Journal of Hepatology, vol. 3, No. 9, 2011, pp. 228-249, DOI: 10.4254/wjh.v3.i9.228, (22 pages).
Thornber, C. W., "Isosterism and molecular modification in drug design", Chemical Society Reviews, No. 8, 1979, 563-580, DOI: 10.1039/CS9790800563, (18 pages).
Tzschucke et al., "Fluorous-Silica-Supported Perfluoro-Tagged Palladium Complexes Catalyze Suzuki Couplings in Water", Helvetica Chima Acta, vol. 87, No. 11, Nov. 2004, pp. 2882-2889, DOI: 10.1002/hlca.200490260, (8 pages).
Ullman et al., "Ueber Synthesen in der Biphenyireihe", Ber. Deutsch. Chem. Ges., 1901, pp. 2174, (12 pages).
Variankaval et al., "From form to function: Crystallization of active pharmaceutical ingredients", AIChE Journal, vol. 54, No. 7, Jul. 2008, pp. 1682-1688, DOI: 10.1002/aic.11555, (7 pages).
Vickerstaffe et al., "Fully Automated Polymer-Assisted Synthesis of 1,5-Biaryl Pyrazoles", Journal of Combinatorial Chemistry, vol. 6, 2004, pp. 332-339, DOI: 10.1021/cc04997g, (8 pages).
Vincent et al., "Angiogenesis Is Induced in a Rabbit Model of Hindlimb Ischemia by Naked DNA Encoding an HIF-1α/VP16 Hybrid Transcription Factor", Circulation, vol. 102, No. 18, Oct. 31, 2000, pp. 2255-2261, DOI: 10.1161/01.cir.102.18.2255, (7 pages).
Vippagunta et al., "Crystalline solids", Advanced Drug Delivery Reviews, vol. 48, No. 1, May 16, 2001, pp. 3-26, DOI: 10.1016/S0169-409X(01)00097-7, (23 pages).
Wade et al., Organic Chemistry, Sixth Edition, 2005, pp. 780-781, (5 pages).
Waknine, Yael, "Black Box Warning for Erythropoiesis-Stimulating Agents", Medscape, Mar. 12, 2007, retrieved from URL: https://www.medscape.com/viewarticle/553499_print (1 pages).
Warnecke et al., "Activation of the hypoxia-inducible factor-pathway and stimulation of angiogenesis by application of prolyl hydroxylase inhibitors", The FASEB Journal, vol. 17, No. 9, 2003, pp. 1186-1188, DOI: 10.1096/fj.02-1062fje, (23 pages).
Warshakoon et al., "Design and synthesis of substituted pyridine derivatives as HIF-1α prolyl hydroxylase inhibitors", Bioorganic & Medicinal Chemistry Letters, vol. 16, No. 21, Nov. 1, 2006, pp. 5616-5620, DOI: 10.1016/j.bmcl.2006.08.026, (5 pages).
Wax et al., "SM-20 is a novel 40-kd protein whose expression in the arterial wall is restricted to smooth muscle", Laboratory Investigation, vol. 74, No. 4, 1996, pp. 797-808, (12 pages).

(56) References Cited

OTHER PUBLICATIONS

Weidner et al., "Tumor Angiogenesis and Metastasis—Correlation in Invasive Breast Carcinoma", The New England Journal of Medicine, vol. 324, No. 1, pp. 1-8, DOI: 10.1056/NEJM199101033240101, (111 pages).
Wiesener et al., "Widespread hypoxia-inducible expression of HIF-2alpha in distinct cell populations of different organs", The FASEB Journal, vol. 17, No. 2, 2003, pp. 271-273, DOI: 10.1096/fj.02-0445fje, (22 pages).
Wilson et al., "Opadry II / Opadry / Opaglos 2", Reprint of poster presented at American Association of Pharmaceutical Scientists Meeting, 2003, (6 pages).
Wing et al., "Hypoxic and pharmacological activation of HIF inhibits SARS-CoV-2 infection of lung epithelial cells", Cell Reports, vol. 35, No. 3, Apr. 5, 2021, pp. 109020, DOI: 10.1016/j.celrep.2021.109020, (15 pages).
Wing et al., "Hypoxic and pharmacological activation of HIF inhibits SARS-CoV-2 infection of lung epithelial cells", Cell Reports, vol. 35, No. 3, Apr. 5, 2021, pp. 109020, DOI: 10.1016/j.celrep.2021.109020, Abstract Only (1 page).
Wright et al., "Activation of the Prolyl Hydroxylase Oxygen-sensor Results in Induction of GLUT1, Heme Oxygenase-1, and Nitric-oxide Synthase Proteins and Confers Protection from Metabolic Inhibition to Cardiomyocytes", Journal of Biological Chemistry, vol. 278, No. 22, May 2003, pp. 20235-20239, DOI: 10.1074/jbc.M301391200, (5 pages).
Wu et al., "A systems biology perspective on sVEGFR1: its biological function, pathogenic role and therapeutic use", Journal of Cellular and Molecular Medicine, vol. 14, No. 3, Apr. 21, 2010, pp. 528-552, DOI: 10.1111/j.1582-4934.2009.00941.x, (25 pages).
Yang et al., "Desmoplakin acts as a tumor suppressor by inhibition of the Wnt/β-catenin signaling pathway in human lung cancer", Carcinogenesis, vol. 33, No. 10, Oct. 2012, pp. 1863-1870, DOI: 10.1093/carcin/bgs226, (8 pages).
Yapa, S. W. S. et al., "Steady-state pharmacokinetics of GSK 1278863 and metabolites with normal and impaired renal function", Clinical Pharmacology & Therapeutics, vol. 97, Supplement No. 1, Feb. 2015, pp. S92, Abstract PII-106 (37 pages).
Yuan et al., "Targeting Hypoxia Signaling for Perioperative Organ Injury", Anesthesia & Analgesia, vol. 126, No. 1, Jan. 2018, pp. 308-321, DOI: 10.1213/ANE.0000000000002288, (31 pages).
Zhao et al., "Deficiency of HIF-1α enhances influenza A virus replication by promoting autophagy in alveolar type II epithelial cells", Emerging Microbes & Infections, vol. 2, No. 1, 2020, pp. 691-706, DOI: 10.1080/22221751.2020.1742585, (17 pages).
Akebia Therapeutics, "Study to Evaluate the Pharmacokinetics, Pharmacodynamics, and Safety of Vadadustat in Hemodialysis Subjects With Anemia Associated with Chronic Kidney Disease" Sep. 2020 (9 pages).
Laukka, Amy, "Researchers study whether vadadustat, an investigational therapy, could mitigate acute lung injury in COVID-19 patients", Stories from UTHealth Houston, Jul. 2020 (4 pages).
Li, Xiangyun, et al., "Adenosine at the Interphase of Hypoxia and Inflammation in Lung Injury", Frontiers in Immunology, vol. 11, Jan. 15, 2021 (15 pages).
Meduri, G. Umberto, et al., "Inflammatory Cytokines in the BAL of Patients with ARDS: Persistent Elevation Over Time Predicts Poor Outcome", Clinical investigations in critical care, Nov. 1995, pp. 1303-1314 (12 pages).

TREATMENT OF VIRAL INFECTIONS, OF ORGAN INJURY, AND OF RELATED CONDITIONS USING A HIF PROLYL HYDROXYLASE INHIBITOR OR A HIF-ALPHA STABILIZER

CROSS-REFERENCE TO RELATED APPLICATIONS

The present application is a 35 U.S.C. § 371 National Stage Application of International Application No. PCT/US2021/028126, filed on Apr. 20, 2021, which claims the benefit of U.S. Provisional Application No. 63/012,839, filed Apr. 20, 2020, U.S. Provisional Application No. 63/022,890, filed May 11, 2020, and U.S. Provisional Application No. 63/047,501, filed Jul. 2, 2020, each of which is incorporated by reference in its entirety.

BACKGROUND OF THE INVENTION

Hypoxia is a condition or state in which the supply of oxygen is insufficient for normal life function, for example, where there is low arterial oxygen supply. Hypoxia can lead to functional impairment of cells and tissue damage. The activation of cellular defense mechanisms during hypoxia is mediated by HIF (Hypoxia-inducible factor) protein. In fact, many studies demonstrate that stabilization of HIF can dampen tissue inflammation and promote its repair (Lee et al. (2019) Exp. Mol. Med. 51:68).

Coronaviruses such as the human CoV isolates 229E and OC43 cause mild and self-limiting infections of the respiratory tract such as the common cold. Novel isolates HCoV-NL63 and HCoV-HKU1 have also been associated with the common cold. Some novel emerging coronaviruses have resulted in serious global outbreaks such as Severe Acute Respiratory Syndrome (SARS) in 2003, Middle East Respiratory Syndrome (MERS) in 2012 and Coronavirus Disease 2019 (COVID-19). There is a need for new therapeutic methods for treating viral infections caused by novel coronaviruses and related conditions or in treating conditions in patients having such viral infections.

Acute lung injury (ALI) and acute respiratory distress syndrome (ARDS) are examples of clinical syndromes of acute respiratory failure with substantial morbidity and mortality. ALI and ARDS are seen in many critically ill patients infected with coronavirus. There is a need for new therapeutic methods to improve clinical outcomes and reduce mortality and morbidity from ALI and ARDS.

Described herein are new therapeutic methods comprising administering compounds that can stabilize HIF and inhibit HIF prolyl hydroxylase (HIF-PH). In particular, methods described herein can be useful for treating/preventing a disease or condition in patients in need thereof, such as a patient having a viral infection such as a respiratory and/or pulmonary viral infection (e.g., an infection such as COVID-19 or a coronavirus infection). Methods described herein can also be useful for treating/preventing organ injury (e.g. organ injury that occurs concurrently or as a result of an infection). For example, methods described herein can be useful for treating or preventing acute lung injury, acute respiratory distress syndrome (ARDS), cardiovascular injury, injury to the liver, kidney diseases and/or multi-organ failure. Exemplary embodiments are described herein.

SUMMARY OF THE INVENTION

Described herein are therapeutic methods comprising administering to a patient in need thereof a compound that is a HIF prolyl hydroxylase inhibitor or a HIF-alpha stabilizer, or a pharmaceutically acceptable salt thereof. For example, methods described herein can be beneficial for the prevention and/or treatment of Acute Respiratory Distress Syndrome (ARDS), including ARDS in hospitalized patients with coronavirus disease 2019 (COVID-19).

In one aspect, the invention features a method of treating a respiratory viral infection, comprising administering to a patient in need thereof a compound that is a HIF prolyl hydroxylase inhibitor or a HIF-alpha stabilizer, or a pharmaceutically acceptable salt thereof.

In embodiments, a respiratory viral infection is induced by or associated with a virus that could lead to viral pneumonia.

In embodiments, a respiratory viral infection is induced by or associated with a coronavirus, an influenza A, an influenza B, a Rhinovirus, a respiratory syncytial virus (RSV), an adenovirus, a human parainfluenza virus (HPIV) or an enterovirus.

In embodiments, a respiratory viral infection is induced by or associated with a coronavirus.

In embodiments, a coronavirus is the SARS-CoV, MERS-CoV, or SARS-CoV-2.

In embodiments, a respiratory viral infection is lower respiratory infection.

In embodiments, a respiratory viral infection is pulmonary viral infection.

In embodiments, a respiratory viral infection is upper respiratory infection.

In embodiments, a respiratory viral infection is COVID-19.

In embodiments, a respiratory viral infection induces a lung disease.

In embodiments, a lung disease is selected from acute lung injury (ALI), bronchitis, pneumonia, pulmonary fibrosis, asthma, or acute respiratory distress syndrome (ARDS).

In embodiments, a patient develops pulmonary hypertension.

In embodiments, a patient develops multi-organ failure.

In embodiments, multi-organ failure comprises heart failure, liver failure, lung failure, kidney failure, and gastrointestinal (GI) system failure.

In another aspect, the invention features a method of treating a pulmonary viral infection, comprising administering to a patient in need thereof a compound that is a HIF prolyl hydroxylase inhibitor or a HIF-alpha stabilizer, or a pharmaceutically acceptable salt thereof.

In embodiments, a pulmonary viral infection is induced by or associated with a coronavirus, an influenza A, an influenza B, a Rhinovirus, a respiratory syncytial virus (RSV), an adenovirus, a human parainfluenza virus (HPIV) or an enterovirus.

In embodiments, a pulmonary viral infection is induced by or associated with a coronavirus.

In embodiments, a coronavirus is the SARS-CoV, MERS-CoV, or SARS-CoV-2.

In embodiments, a pulmonary viral infection is COVID-19.

In embodiments, a pulmonary viral infection induces a lung disease or acute respiratory failure. In embodiments, a lung disease or acute respiratory failure is selected from acute lung injury (ALI), bronchitis, pneumonia, pulmonary fibrosis, asthma, or acute respiratory distress syndrome (ARDS).

In embodiments, a patient develops pulmonary hypertension.

In embodiments, a patient develops multi-organ failure.

In embodiments, multi-organ failure comprises heart failure, liver failure, lung failure kidney failure, and gastrointestinal (GI) system failure.

In another aspect, the invention features a method of treating a coronavirus infection, comprising administering to a patient in need thereof a compound that is a HIF prolyl hydroxylase inhibitor or a HIF-alpha stabilizer, or a pharmaceutically acceptable salt thereof.

In another aspect, the invention features a method of treating or preventing a lung disease that is acute lung injury (ALI) in a patient in need thereof, comprising administering to the patient a compound that is a HIF prolyl hydroxylase inhibitor or a HIF-alpha stabilizer, or a pharmaceutically acceptable salt thereof.

In embodiments, a patient has a viral infection, sepsis, pneumonia, aspiration, trauma, pancreatitis, blood transfusion, and/or smoke or toxic gas inhalation.

In embodiments, an acute lung injury (ALI) is induced by or associated with a viral infection, sepsis, pneumonia, aspiration, trauma, pancreatitis, blood transfusion, and/or smoke or toxic gas inhalation.

In embodiments, a patient is mechanically ventilated.

In another aspect, the invention features a method of treating or preventing a lung disease that is acute lung injury (ALI) in a patient in need thereof, comprising administering to the patient a compound that is a HIF prolyl hydroxylase inhibitor or a HIF-alpha stabilizer, or a pharmaceutically acceptable salt thereof, and wherein said ALI is induced by or associated with a ventilator.

In embodiments, a patient has a viral infection, sepsis, pneumonia, aspiration, trauma, pancreatitis, blood transfusion, and/or smoke or toxic gas inhalation.

In another aspect, the invention features a method of treating or preventing a lung disease that is acute lung injury (ALI) in a patient having a respiratory viral infection, comprising administering to the patient a compound that is a HIF prolyl hydroxylase inhibitor or a HIF-alpha stabilizer, or a pharmaceutically acceptable salt thereof.

In another aspect, the invention features a method of treating or preventing a lung disease that is acute respiratory distress syndrome (ARDS) in a patient having a respiratory viral infection, comprising administering to the patient a compound that is a HIF prolyl hydroxylase inhibitor or a HIF-alpha stabilizer, or a pharmaceutically acceptable salt thereof.

In embodiments, a respiratory viral infection is infected by a coronavirus, an influenza A, an influenza B, a Rhinovirus, a respiratory syncytial virus (RSV), an adenovirus, a human parainfluenza virus (HPIV) or an enterovirus.

In embodiments, a respiratory viral infection is infected by a coronavirus.

In embodiments, a coronavirus is the SARS-CoV, MERS-CoV, or SARS-CoV-2.

In embodiments, a respiratory viral infection is COVID-19.

In embodiments, an acute lung injury develops acute respiratory distress syndrome (ARDS).

In embodiments, a patient with ALI or ARDS develops pulmonary hypertension.

In embodiments, a patient with ALI or ARDS develops multi-organ failure.

In embodiments, multi-organ failure comprise heart failure, liver failure, lung failure kidney failure, and gastrointestinal (GI) system failure.

In embodiments, the ALI or ARDS is characterized by accumulation of inflammatory cells into the lungs, cytokine release, inflammatory activation of recruited or resident cells, disruption of the alveolar-capillary barrier function, pulmonary edema, attenuated gas exchange, or lung inflammation, or any combination thereof.

In embodiments, the ALI or ARDS is characterized by accumulation of inflammatory cells into the lungs, cytokine release, inflammatory activation of recruited or resident cells, disruption of the alveolar-capillary barrier function, pulmonary edema, attenuated gas exchange, or any combination thereof.

In embodiments, the ALI or ARDS is induced by or associated with the viral infection.

In another aspect, the invention features a method of treating or preventing a lung disease that is acute lung injury (ALI) in a patient having a pulmonary viral infection, comprising administering to the patient a compound that is a HIF prolyl hydroxylase inhibitor or a HIF-alpha stabilizer, or a pharmaceutically acceptable salt thereof.

In another aspect, the invention features a method of treating or preventing a lung disease that is acute respiratory distress syndrome (ARDS) in a patient having a pulmonary viral infection, comprising administering to the patient a compound that is a HIF prolyl hydroxylase inhibitor or a HIF-alpha stabilizer, or a pharmaceutically acceptable salt thereof.

In embodiments, a respiratory viral infection is infected by a coronavirus, an influenza A, an influenza B, a Rhinovirus, a respiratory syncytial virus (RSV), an adenovirus, a human parainfluenza virus (HPIV) or an enterovirus.

In embodiments, a respiratory viral infection is infected by a coronavirus.

In embodiments, a coronavirus is the SARS-CoV, MERS-CoV, or SARS-CoV-2.

In embodiments, a respiratory viral infection is COVID-19.

In embodiments, a patient with acute lung injury develops acute respiratory distress syndrome (ARDS).

In embodiments, a patient with ALI or ARDS develops pulmonary hypertension.

In embodiments, a patient with ALI or ARDS develops multi-organ failure.

In embodiments, multi-organ failure comprise heart failure, liver failure, lung failure kidney failure, and gastrointestinal (GI) system failure.

In embodiments, the ALI or ARDS is characterized by accumulation of inflammatory cells into the lungs, cytokine release, inflammatory activation of recruited or resident cells, disruption of the alveolar-capillary barrier function, pulmonary edema, attenuated gas exchange, or lung inflammation, or any combination thereof.

In embodiments, the ALI or ARDS is characterized by accumulation of inflammatory cells into the lungs, cytokine release, inflammatory activation of recruited or resident cells, disruption of the alveolar-capillary barrier function, pulmonary edema, attenuated gas exchange, or any combination thereof.

In embodiments, the ALI or ARDS is induced by or associated with the viral infection.

In another aspect, the invention features a method of treating or preventing a lung disease that is acute lung injury (ALI) in a patient infected with a coronavirus, comprising administering to the patient a compound that is a HIF prolyl hydroxylase inhibitor or a HIF-alpha stabilizer, or a pharmaceutically acceptable salt thereof.

In another aspect, the invention features a method of treating or preventing a lung disease that is acute respiratory distress syndrome (ARDS) in a patient infected with a coronavirus, comprising administering to the patient a compound that is a HIF prolyl hydroxylase inhibitor or a HIF-alpha stabilizer, or a pharmaceutically acceptable salt thereof.

In embodiments, a coronavirus is the SARS-CoV, MERS-CoV, or SARS-CoV-2.

In embodiments, a patient is infected with SARS-CoV-2.

In embodiments, a patient with ALI or ARDS develops pulmonary hypertension.

In embodiments, a patient with ALI or ARDS develops multi-organ failure.

In embodiments, multi-organ failure comprises heart failure, liver failure, lung failure kidney failure, and gastrointestinal (GI) system failure.

In embodiments, the ALI or ARDS is characterized by accumulation of inflammatory cells into the lungs, cytokine release, inflammatory activation of recruited or resident cells, disruption of the alveolar-capillary barrier function, pulmonary edema, attenuated gas exchange, or lung inflammation, or any combination thereof.

In embodiments, the ALI or ARDS is characterized by accumulation of inflammatory cells into the lungs, cytokine release, inflammatory activation of recruited or resident cells, disruption of the alveolar-capillary barrier function, pulmonary edema, attenuated gas exchange, or any combination thereof.

In embodiments, the ALI or ARDS is induced by or associated with the viral infection.

In embodiments, a patient is an adult.

In embodiments, a patient exhibits one or more symptoms of hypoxia.

In embodiments, a patient has a lower oxygen saturation of hemoglobin than the standard normal oxygen saturation as clinically defined.

In embodiments, a patient has an oxygen saturation of hemoglobin that is about 94% or less.

In another aspect, the invention features a method of reducing mortality and morbidity related to acute lung injury (ALI) or acute respiratory distress syndrome (ARDS) in a patient having a respiratory viral infection, comprising administering to a patient in need thereof a compound that is a HIF prolyl hydroxylase inhibitor or a HIF-alpha stabilizer, or a pharmaceutically acceptable salt thereof.

In embodiments, a patient has a lower respiratory infection.

In embodiments, a patient has an upper respiratory infection.

In another aspect, the invention features a method of reducing mortality and morbidity related to acute lung injury (ALI) or acute respiratory distress syndrome (ARDS) in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In embodiments, a viral infection is induced by or associated with a virus that could lead to viral pneumonia.

In embodiments, a viral infection is induced by or associated with a coronavirus, an influenza A, an influenza B, a Rhinovirus, a respiratory syncytial virus (RSV), an adenovirus, a human parainfluenza virus (HPIV) or an enterovirus.

In another aspect, the invention features a method of reducing mortality and morbidity related to acute lung injury (ALI) or acute respiratory distress syndrome (ARDS) in a patient infected with a coronavirus, comprising administering to a patient in need thereof a compound that is a HIF prolyl hydroxylase inhibitor or a HIF-alpha stabilizer, or a pharmaceutically acceptable salt thereof.

In embodiments, an acute lung injury (ALI) or acute respiratory distress syndrome (ARDS) is induced by or associated with the virus.

In embodiments, a patient is infected by a coronavirus that is SARS-CoV, MERS-CoV, or SARS-CoV-2.

In embodiments, a patient has COVID-19.

In embodiments, a patient is receiving mechanical ventilation.

In embodiments, a patient has ventilator induced ALI.

In another aspect, the invention features a method of reducing incidence, severity, or risk of acute lung injury (ALI) or acute respiratory distress syndrome (ARDS) in a patient having a respiratory viral infection, comprising administering to a patient in need thereof a compound that is a HIF prolyl hydroxylase inhibitor or a HIF-alpha stabilizer, or a pharmaceutically acceptable salt thereof.

In embodiments, a patient has a lower respiratory infection.

In embodiments, a patient has an upper respiratory infection.

In another aspect, the invention features a method of reducing incidence, severity, or risk of acute lung injury (ALI) or acute respiratory distress syndrome (ARDS) in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In embodiments, a viral infection is induced by or associated with a virus that could lead to viral pneumonia.

In embodiments, a viral infection is induced by or associated with a coronavirus, an influenza A, an influenza B, a Rhinovirus, a respiratory syncytial virus (RSV), an adenovirus, a human parainfluenza virus (HPIV) or an enterovirus.

In another aspect, the invention features a method of reducing incidence, severity, or risk of acute lung injury (ALI) or acute respiratory distress syndrome (ARDS) in a patient infected with a coronavirus, comprising administering to a patient in need thereof a compound that is a HIF prolyl hydroxylase inhibitor or a HIF-alpha stabilizer, or a pharmaceutically acceptable salt thereof.

In embodiments, an acute lung injury (ALI) or acute respiratory distress syndrome (ARDS) is induced by or associated with the virus.

In embodiments, a patient is infected by a coronavirus that is SARS-CoV, MERS-CoV, or SARS-CoV-2.

In embodiments, a patient has COVID-19.

In embodiments, a patient is receiving mechanical ventilation.

In embodiments, a patient has ventilator induced ALI.

In embodiments, a patient is an adult.

In embodiments, a patient exhibits one or more symptoms of hypoxia.

In embodiments, a patient has a lower oxygen saturation of hemoglobin than the standard normal oxygen saturation as clinically defined.

In embodiments, a patient has an oxygen saturation of hemoglobin that is about 94% or less.

In another aspect, the invention features a method of treating or preventing lung inflammation or pneumonia in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to lung inflammation or pneumonia in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of lung inflammation or pneumonia in a patient having a respiratory viral infection, comprising administering to a patient in need thereof a compound that is a HIF prolyl hydroxylase inhibitor or a HIF-alpha stabilizer, or a pharmaceutically acceptable salt thereof.

In embodiments, a patient has a lower respiratory infection.

In embodiments, a patient has an upper respiratory infection.

In another aspect, the invention features a method of treating or preventing lung inflammation or pneumonia in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to lung inflammation or pneumonia in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of lung inflammation or pneumonia in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In embodiments, a viral infection is induced by or associated with a virus that could lead to viral pneumonia.

In embodiments, a viral infection is induced by or associated with a coronavirus, an influenza A, an influenza B, a Rhinovirus, a respiratory syncytial virus (RSV), an adenovirus, a human parainfluenza virus (HPIV) or an enterovirus.

In another aspect, the invention features a method of treating or preventing lung inflammation or pneumonia in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to lung inflammation or pneumonia in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of lung inflammation or pneumonia in a patient infected with a coronavirus, comprising administering to a patient in need thereof a compound that is a HIF prolyl hydroxylase inhibitor or a HIF-alpha stabilizer, or a pharmaceutically acceptable salt thereof.

In embodiments, a patient is infected by a coronavirus that is SARS-CoV, MERS-CoV, or SARS-CoV-2.

In embodiments, a patient has COVID-19.

In embodiments, a lung inflammation or pneumonia is induced by or associated with the viral infection.

In embodiments, a lung inflammation or pneumonia is induced by or associated with COVID-19.

In another aspect, the invention features a method of treating or preventing COVID-19 related pneumonia, comprising administering to a patient in need thereof a compound that is a HIF prolyl hydroxylase inhibitor or a HIF-alpha stabilizer, or a pharmaceutically acceptable salt thereof, and wherein the patient has acute lung injury (ALI), acute respiratory distress syndrome (ARDS), and/or organ failure.

In embodiments, any of the acute lung injury (ALI), acute respiratory distress syndrome (ARDS), and/or organ failure is associated with COVID-19.

In another aspect, the invention features a method of treating or preventing COVID-19 related acute lung injury (ALI) in a patient having pneumonia, comprising administering to a patient in need thereof a compound that is a HIF prolyl hydroxylase inhibitor or a HIF-alpha stabilizer, or a pharmaceutically acceptable salt thereof.

In another aspect, the invention features a method of treating or preventing COVID-19 related acute respiratory distress syndrome (ARDS)) in a patient having pneumonia, comprising administering to a patient in need thereof a compound that is a HIF prolyl hydroxylase inhibitor or a HIF-alpha stabilizer, or a pharmaceutically acceptable salt thereof.

In another aspect, the invention features a method of treating or preventing COVID-19 related organ failure, comprising administering to a patient in need thereof a compound that is a HIF prolyl hydroxylase inhibitor or a HIF-alpha stabilizer, or a pharmaceutically acceptable salt thereof.

In embodiments, a patient is receiving mechanical ventilation.

In another aspect, the invention features a method of treating or preventing cardiac dysfunction in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to an adverse cardiac event in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of an adverse cardiac event in a patient having a respiratory viral infection, comprising administering to a patient in need thereof a compound that is a HIF prolyl hydroxylase inhibitor or a HIF-alpha stabilizer, or a pharmaceutically acceptable salt thereof.

In embodiments, a patient has a lower respiratory infection.

In embodiments, a patient has an upper respiratory infection.

In another aspect, the invention features a method of treating or preventing cardiac dysfunction in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to an adverse cardiac event in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of an adverse cardiac event in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In embodiments, a viral infection is induced by or associated with a virus that could lead to viral pneumonia.

In embodiments, a viral infection is induced by or associated with a coronavirus, an influenza A, an influenza B, a Rhinovirus, a respiratory syncytial virus (RSV), an adenovirus, a human parainfluenza virus (HPIV) or an enterovirus.

In another aspect, the invention features a method of treating or preventing cardiac dysfunction in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to an adverse cardiac event in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of an adverse cardiac event in a patient infected with a coronavirus, comprising administering to a patient in need thereof a compound that is a HIF prolyl hydroxylase inhibitor or a HIF-alpha stabilizer, or a pharmaceutically acceptable salt thereof.

In embodiments, a patient is infected by a coronavirus that is SARS-CoV, MERS-CoV, or SARS-CoV-2.

In embodiments, a patient has COVID-19.

In embodiments, a cardiac dysfunction is induced by or associated with the viral infection.

In embodiments, a cardiac dysfunction is induced by or associated with COVID-19.

In embodiments, an adverse cardiac event is induced by or associated with the viral infection.

In embodiments, an adverse cardiac event is induced by or associated with COVID-19.

In embodiments, a patient is receiving mechanical ventilation.

In another aspect, the invention features a method of treating or preventing hypotension in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to hypotension in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of hypotension in a patient having a respiratory viral infection, comprising administering to a patient in need thereof a compound that is a HIF prolyl hydroxylase inhibitor or a HIF-alpha stabilizer, or a pharmaceutically acceptable salt thereof.

In embodiments, a patient has a lower respiratory infection.

In embodiments, a patient has an upper respiratory infection.

In another aspect, the invention features a method of treating or preventing hypotension in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to hypotension in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of hypotension in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In embodiments, a viral infection is induced by or associated with a virus that could lead to viral pneumonia.

In embodiments, a viral infection is induced by or associated with a coronavirus, an influenza A, an influenza B, a Rhinovirus, a respiratory syncytial virus (RSV), an adenovirus, a human parainfluenza virus (HPIV) or an enterovirus.

In another aspect, the invention features a method of treating or preventing hypotension in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to hypotension in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of hypotension in a patient infected with a coronavirus, comprising administering to a patient in need thereof a compound that is a HIF prolyl hydroxylase inhibitor or a HIF-alpha stabilizer, or a pharmaceutically acceptable salt thereof.

In embodiments, a patient is infected by a coronavirus that is SARS-CoV, MERS-CoV, or SARS-CoV-2.

In embodiments, a patient has COVID-19.

In embodiments, hypotension is induced by or associated with the viral infection.

In embodiments, hypotension is induced by or associated with COVID-19.

In embodiments, a patient is receiving mechanical ventilation.

In another aspect, the invention features a method of reducing incidence, severity, or risk of disseminated intravascular coagulation in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of treating or preventing disseminated intravascular coagulation in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to disseminated intravascular coagulation in a patient having a respiratory viral infection, comprising administering to a patient in need thereof a compound that is a HIF prolyl hydroxylase inhibitor or a HIF-alpha stabilizer, or a pharmaceutically acceptable salt thereof.

In embodiments, a patient has a lower respiratory infection.

In embodiments, a patient has an upper respiratory infection.

In another aspect, the invention features a method of reducing mortality and morbidity related to disseminated intravascular coagulation in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of treating or preventing disseminated intravascular coagulation in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of disseminated intravascular coagulation in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In embodiments, a viral infection is induced by or associated with a virus that could lead to viral pneumonia.

In embodiments, a viral infection is induced by or associated with a coronavirus, an influenza A, an influenza B, a Rhinovirus, a respiratory syncytial virus (RSV), an adenovirus, a human parainfluenza virus (HPIV) or an enterovirus.

In another aspect, the invention features a method of treating or preventing disseminated intravascular coagulation in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to disseminated intravascular coagulation in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of disseminated intravascular coagulation in a patient infected with a coronavirus, comprising administering to a patient in need thereof a compound that is a HIF prolyl hydroxylase inhibitor or a HIF-alpha stabilizer, or a pharmaceutically acceptable salt thereof.

In embodiments, a patient is infected by a coronavirus that is SARS-CoV, MERS-CoV, or SARS-CoV-2.

In embodiments, a patient has COVID-19.

In embodiments, a disseminated intravascular coagulation is induced by or associated with the viral infection.

In embodiments, a disseminated intravascular coagulation is induced by or associated with COVID-19.

In embodiments, a patient is receiving mechanical ventilation.

In another aspect, the invention features a method of treating or preventing kidney diseases in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to kidney diseases in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of kidney diseases in a patient having a respiratory viral infection, comprising administering to a patient in need thereof a compound that is a HIF prolyl hydroxylase inhibitor or a HIF-alpha stabilizer, or a pharmaceutically acceptable salt thereof.

In embodiments, a patient has a lower respiratory infection.

In embodiments, a patient has an upper respiratory infection.

In another aspect, the invention features a method of treating or preventing kidney diseases in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to kidney diseases in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of kidney diseases in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In embodiments, a viral infection is induced by or associated with a virus that could lead to viral pneumonia.

In embodiments, a viral infection is induced by or associated with a coronavirus, an influenza A, an influenza B, a Rhinovirus, a respiratory syncytial virus (RSV), an adenovirus, a human parainfluenza virus (HPIV) or an enterovirus.

In another aspect, the invention features a method of treating or preventing kidney diseases in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to kidney diseases in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of kidney diseases in a patient infected with a coronavirus, comprising administering to a patient in need thereof a compound that is a HIF prolyl hydroxylase inhibitor or a HIF-alpha stabilizer, or a pharmaceutically acceptable salt thereof.

In embodiments, a patient is infected by a coronavirus that is SARS-CoV, MERS-CoV, or SARS-CoV-2.

In embodiments, a patient has COVID-19.

In embodiments, a kidney disease is induced by or associated with the viral infection.

In embodiments, a kidney disease is induced by or associated with COVID-19.

In embodiments, a patient is receiving mechanical ventilation.

In another aspect, the invention features a method of treating or preventing liver failure in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to liver failure in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of liver failure in a patient having a respiratory viral infection, comprising administering to a patient in need thereof a compound that is a HIF prolyl hydroxylase inhibitor or a HIF-alpha stabilizer, or a pharmaceutically acceptable salt thereof.

In embodiments, a patient has a lower respiratory infection.

In embodiments, a patient has an upper respiratory infection.

In another aspect, the invention features a method of treating or preventing liver failure in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to liver failure in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of liver failure in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In embodiments, a viral infection is induced by or associated with a virus that could lead to viral pneumonia.

In embodiments, a viral infection is induced by or associated with a coronavirus, an influenza A, an influenza B, a Rhinovirus, a respiratory syncytial virus (RSV), an adenovirus, a human parainfluenza virus (HPIV) or an enterovirus.

In another aspect, the invention features a method of treating or preventing liver failure in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to liver failure in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of liver failure in a patient infected with a coronavirus, comprising administering to a patient in need thereof a compound that is a HIF prolyl hydroxylase inhibitor or a HIF-alpha stabilizer, or a pharmaceutically acceptable salt thereof.

In embodiments, a patient is infected by a coronavirus that is SARS-CoV, MERS-CoV, or SARS-CoV-2.

In embodiments, a patient has COVID-19.

In embodiments, liver failure is induced by or associated with the viral infection.

In embodiments, liver failure is induced by or associated with COVID-19.

In embodiments, a patient is receiving mechanical ventilation.

In another aspect, the invention features a method of treating or preventing pancreas injury in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to pancreas injury in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of pancreas injury in a patient having a respiratory viral infection, comprising administering to a patient in need thereof a compound that is a HIF prolyl hydroxylase inhibitor or a HIF-alpha stabilizer, or a pharmaceutically acceptable salt thereof.

In embodiments, a patient has a lower respiratory infection.

In embodiments, a patient has an upper respiratory infection.

In another aspect, the invention features a method of treating or preventing pancreas injury in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to pancreas injury in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of pancreas injury in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In embodiments, a viral infection is induced by or associated with a virus that could lead to viral pneumonia.

In embodiments, a viral infection is induced by or associated with a coronavirus, an influenza A, an influenza B, a Rhinovirus, a respiratory syncytial virus (RSV), an adenovirus, a human parainfluenza virus (HPIV) or an enterovirus.

In another aspect, the invention features a method of treating or preventing pancreas injury in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to pancreas injury in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of pancreas injury in a patient infected with a coronavirus, comprising administering to a patient in need thereof a compound that is a HIF prolyl hydroxylase inhibitor or a HIF-alpha stabilizer, or a pharmaceutically acceptable salt thereof.

In embodiments, a patient is infected by a coronavirus that is SARS-CoV, MERS-CoV, or SARS-CoV-2.

In embodiments, a patient has COVID-19.

In embodiments, a pancreas injury is induced by or associated with the viral infection.

In embodiments, a pancreas injury is induced by or associated with COVID-19.

In embodiments, a patient is receiving mechanical ventilation.

In another aspect, the invention features a method of treating or preventing multi-organ failure in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to multi-organ failure in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of multi-organ failure in a patient having a respiratory viral infection, comprising administering to a patient in need thereof a compound that is a HIF prolyl hydroxylase inhibitor or a HIF-alpha stabilizer, or a pharmaceutically acceptable salt thereof.

In embodiments, a patient has a lower respiratory infection.

In embodiments, a patient has an upper respiratory infection.

In another aspect, the invention features a method of treating or preventing multi-organ failure in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to multi-organ failure in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of multi-organ failure in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In embodiments, a viral infection is induced by or associated with a virus that could lead to viral pneumonia.

In embodiments, a viral infection is induced by or associated with a coronavirus, an influenza A, an influenza B, a Rhinovirus, a respiratory syncytial virus (RSV), an adenovirus, a human parainfluenza virus (HPIV) or an enterovirus.

In another aspect, the invention features a method of treating or preventing multi-organ failure in a patient having a coronavirus infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to multi-organ failure in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of multi-organ failure in a patient infected with a coronavirus, comprising administering to a patient in need thereof a compound that is a HIF prolyl hydroxylase inhibitor or a HIF-alpha stabilizer, or a pharmaceutically acceptable salt thereof.

In embodiments, a patient is infected by a coronavirus that is SARS-CoV, MERS-CoV, or SARS-CoV-2.

In embodiments, a patient has COVID-19.

In embodiments, multi-organ failure is induced by or associated with the viral infection.

In embodiments, multi-organ failure is induced by or associated with COVID-19.

In embodiments, a patient is receiving mechanical ventilation.

In another aspect, the invention features a method of treating or preventing septic shock in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to septic shock in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of septic shock in a patient having a respiratory viral infection, comprising administering to a patient in need thereof a compound that is a HIF prolyl hydroxylase inhibitor or a HIF-alpha stabilizer, or a pharmaceutically acceptable salt thereof.

In embodiments, a patient has a lower respiratory infection.

In embodiments, a patient has an upper respiratory infection.

In another aspect, the invention features a method of treating or preventing septic shock in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to septic shock in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of septic shock in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In embodiments, a viral infection is induced by or associated with a virus that could lead to viral pneumonia.

In embodiments, a viral infection is induced by or associated with a coronavirus, an influenza A, an influenza B, a Rhinovirus, a respiratory syncytial virus (RSV), an adenovirus, a human parainfluenza virus (HPIV) or an enterovirus.

In another aspect, the invention features a method of treating or preventing septic shock in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to septic shock in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of septic shock in a patient infected with a coronavirus, comprising administering to a patient in need thereof a compound that is a HIF prolyl hydroxylase inhibitor or a HIF-alpha stabilizer, or a pharmaceutically acceptable salt thereof.

In embodiments, a patient is infected by a coronavirus that is SARS-CoV, MERS-CoV, or SARS-CoV-2.

In embodiments, a patient has COVID-19.

In embodiments, septic shock is induced by or associated with the viral infection.

In embodiments, septic shock is induced by or associated with COVID-19.

In embodiments, a patient is receiving mechanical ventilation.

In another aspect, the invention features a method of treating or preventing sepsis in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to sepsis in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of sepsis in a patient having a respiratory viral infection, comprising administering to a patient in need thereof a compound that is a HIF prolyl hydroxylase inhibitor or a HIF-alpha stabilizer, or a pharmaceutically acceptable salt thereof.

In embodiments, a patient has a lower respiratory infection.

In embodiments, a patient has an upper respiratory infection.

In another aspect, the invention features a method of treating or preventing sepsis in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to sepsis in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of sepsis in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In embodiments, a viral infection is induced by or associated with a virus that could lead to viral pneumonia.

In embodiments, a viral infection is induced by or associated with a coronavirus, an influenza A, an influenza B, a Rhinovirus, a respiratory syncytial virus (RSV), an adenovirus, a human parainfluenza virus (HPIV) or an enterovirus.

In another aspect, the invention features a method of treating or preventing sepsis in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to sepsis in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of sepsis in a patient infected with a coronavirus, comprising administering to a patient in need thereof a compound that is a HIF prolyl hydroxylase inhibitor or a HIF-alpha stabilizer, or a pharmaceutically acceptable salt thereof.

In embodiments, a patient is infected by a coronavirus that is SARS-CoV, MERS-CoV, or SARS-CoV-2.

In embodiments, a patient has COVID-19.

In embodiments, sepsis is induced by or associated with the viral infection.

In embodiments, sepsis is induced by or associated with COVID-19.

In embodiments, a patient is receiving mechanical ventilation.

In another aspect, the invention features a method of treating or preventing cytokine release syndrome in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to cytokine release syndrome in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of cytokine release syndrome in a patient having a respiratory viral infection, comprising administering to a patient in need thereof a compound that is a HIF prolyl hydroxylase inhibitor or a HIF-alpha stabilizer, or a pharmaceutically acceptable salt thereof.

In embodiments, a patient has a lower respiratory infection.

In embodiments, a patient has an upper respiratory infection.

In another aspect, the invention features a method of treating or preventing cytokine release syndrome in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to cytokine release syndrome in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of cytokine release syndrome in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In embodiments, a viral infection is induced by or associated with a virus that could lead to viral pneumonia.

In embodiments, a viral infection is induced by or associated with a coronavirus, an influenza A, an influenza B, a Rhinovirus, a respiratory syncytial virus (RSV), an adenovirus, a human parainfluenza virus (HPIV) or an enterovirus.

In another aspect, the invention features a method of treating or preventing cytokine release syndrome in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to cytokine release syndrome in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of cytokine release syndrome in a patient infected with a coronavirus, comprising administering to a patient in need thereof a compound that is a HIF prolyl hydroxylase inhibitor or a HIF-alpha stabilizer, or a pharmaceutically acceptable salt thereof.

In embodiments, a patient is infected by a coronavirus that is SARS-CoV, MERS-CoV, or SARS-CoV-2.

In embodiments, a patient has COVID-19.

In embodiments, a cytokine release syndrome is induced by or associated with the viral infection.

In embodiments, a cytokine release syndrome is induced by or associated with COVID-19.

In embodiments, a patient is receiving mechanical ventilation.

In another aspect, the invention features a method of treating or preventing neurological disorder in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to neurological disorder in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of neurological disorder in a patient having a respiratory viral infection, comprising administering to a patient in need thereof a compound that is a HIF prolyl hydroxylase inhibitor or a HIF-alpha stabilizer, or a pharmaceutically acceptable salt thereof.

In embodiments, a patient has a lower respiratory infection.

In embodiments, a patient has an upper respiratory infection.

In another aspect, the invention features a method of treating or preventing neurological disorder in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to neurological disorder in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of neurological disorder in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In embodiments, a viral infection is induced by or associated with a virus that could lead to viral pneumonia.

In embodiments, a viral infection is induced by or associated with a coronavirus, an influenza A, an influenza B, a Rhinovirus, a respiratory syncytial virus (RSV), an adenovirus, a human parainfluenza virus (HPIV) or an enterovirus.

In another aspect, the invention features a method of treating or preventing neurological disorder in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to neurological disorder in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of neurological disorder in a patient infected with a coronavirus, comprising administering to a patient in need thereof a compound that is a HIF prolyl hydroxylase inhibitor or a HIF-alpha stabilizer, or a pharmaceutically acceptable salt thereof.

In embodiments, a patient is infected by a coronavirus that is SARS-CoV, MERS-CoV, or SARS-CoV-2.

In embodiments, a patient has COVID-19.

In embodiments, a neurological disorder is induced by or associated with the viral infection.

In embodiments, a neurological disorder is induced by or associated with COVID-19.

In embodiments, a patient is receiving mechanical ventilation.

In another aspect, the invention features a method of treating or preventing pulmonary barotrauma in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to pulmonary barotrauma in a patient having a respiratory viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk pulmonary barotrauma in a patient having a respiratory viral infection, comprising administering to a patient in need thereof a compound that is a HIF prolyl hydroxylase inhibitor or a HIF-alpha stabilizer, or a pharmaceutically acceptable salt thereof.

In embodiments, a patient has a lower respiratory infection.

In embodiments, a patient has an upper respiratory infection.

In another aspect, the invention features a method of treating or preventing pulmonary barotrauma in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to pulmonary barotrauma in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of pulmonary barotrauma in a patient having a pulmonary viral infection, comprising administering to a patient in need thereof a compound that is a HIF prolyl hydroxylase inhibitor or a HIF-alpha stabilizer, or a pharmaceutically acceptable salt thereof.

In embodiments, a viral infection is induced by or associated with a virus that could lead to viral pneumonia.

In embodiments, a viral infection is induced by or associated with a coronavirus, an influenza A, an influenza B, a Rhinovirus, a respiratory syncytial virus (RSV), an adenovirus, a human parainfluenza virus (HPIV) or an enterovirus.

In another aspect, the invention features a method of treating or preventing pulmonary barotrauma in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing mortality and morbidity related to pulmonary barotrauma in a patient infected with a coronavirus, comprising administering to a patient in need thereof a compound that is a HIF prolyl hydroxylase inhibitor or a HIF-alpha stabilizer, or a pharmaceutically acceptable salt thereof.

In another aspect, the invention features a method of reducing incidence, severity, or risk of pulmonary barotrauma in a patient infected with a coronavirus, comprising administering to a patient in need thereof a compound that is a HIF prolyl hydroxylase inhibitor or a HIF-alpha stabilizer, or a pharmaceutically acceptable salt thereof.

In embodiments, a patient is infected by a coronavirus that is SARS-CoV, MERS-CoV, or SARS-CoV-2.

In embodiments, a patient has COVID-19.

In embodiments, pulmonary barotrauma is induced by or associated with the viral infection.

In embodiments, pulmonary barotrauma is induced by or associated with COVID-19.

In embodiments, a patient is receiving mechanical ventilation.

In another aspect, the invention features a method of treating or preventing organ dysfunction induced by or associated with acute lung injury (ALI), acute respiratory distress syndrome (ARDS), pneumonia, lung inflammation, or any combination thereof, comprising administering to a patient in need thereof a compound that is a HIF prolyl hydroxylase inhibitor or a HIF-alpha stabilizer, or a pharmaceutically acceptable salt thereof.

In embodiments, a patient is infected with coronavirus.

In embodiments, a patient is infected by a coronavirus that is SARS-CoV, MERS-CoV, or SARS-CoV-2.

In embodiments, a patient has COVID-19.

In embodiments, a patient has a respiratory viral infection.

In embodiments, a patient has a lower respiratory infection.

In embodiments, a patient has an upper respiratory infection.

In embodiments, a patient has a pulmonary viral infection.

In another aspect, the invention features a method for improving lung volumes in a patient in need thereof, comprising administering to a patient in need thereof a compound that is a HIF prolyl hydroxylase inhibitor or a HIF-alpha stabilizer, or a pharmaceutically acceptable salt thereof.

In another aspect, the invention features a method for improving pulmonary compliance in a patient in need thereof, comprising administering to a patient in need thereof a compound that is a HIF prolyl hydroxylase inhibitor or a HIF-alpha stabilizer, or a pharmaceutically acceptable salt thereof.

In another aspect, the invention features a method for promoting fibroproliferative repair in a patient in need thereof, comprising administering to a patient in need thereof a compound that is a HIF prolyl hydroxylase inhibitor or a HIF-alpha stabilizer, or a pharmaceutically acceptable salt thereof.

In another aspect, the invention features a method for regulating innate and adaptive immunity, comprising administering to a patient in need thereof a compound that is a HIF prolyl hydroxylase inhibitor or a HIF-alpha stabilizer, or a pharmaceutically acceptable salt thereof.

In another aspect, the invention features a method for promoting regulatory T-cells, lymphocytes and B cells, comprising administering to a patient in need thereof a compound that is a HIF prolyl hydroxylase inhibitor or a HIF-alpha stabilizer, or a pharmaceutically acceptable salt thereof.

In another aspect, the invention features a method for treating/preventing bronchial inflammation, comprising administering to a patient in need thereof a compound that is a HIF prolyl hydroxylase inhibitor or a HIF-alpha stabilizer, or a pharmaceutically acceptable salt thereof.

In another aspect, the invention features a method for reducing cytokine production, comprising administering to a patient in need thereof a compound that is a HIF prolyl hydroxylase inhibitor or a HIF-alpha stabilizer, or a pharmaceutically acceptable salt thereof.

In another aspect, the invention features a method for improving dyspnea, comprising administering to a patient in need thereof a compound that is a HIF prolyl hydroxylase inhibitor or a HIF-alpha stabilizer, or a pharmaceutically acceptable salt thereof.

In another aspect, the invention features a method for improving arterial $PaO_2$, comprising administering to a patient in need thereof a compound that is a HIF prolyl hydroxylase inhibitor or a HIF-alpha stabilizer, or a pharmaceutically acceptable salt thereof.

In embodiments, a patient has a viral infection.

In embodiments, a viral infection is induced by or associated with a coronavirus, an influenza A, an influenza B, a Rhinovirus, a respiratory syncytial virus (RSV), an adenovirus, a human parainfluenza virus (HPIV) or an enterovirus.

In embodiments, a viral infection is induced by or associated with coronavirus.

In embodiments, a coronavirus is the SARS-CoV, MERS-CoV, or SARS-CoV-2.

In embodiments, a patient has COVID-19.

In another aspect, the invention features a method for treating or preventing acute respiratory distress syndrome (ARDS) in a hospitalized patient with COVID-19, the method comprising administering to said patient a compound that is a HIF prolyl hydroxylase inhibitor or a HIF-alpha stabilizer, or a pharmaceutically acceptable salt thereof.

In embodiments, a patient is an adult.

In embodiments, a patient exhibits one or more symptoms of hypoxia.

In embodiments, a patient has a lower oxygen saturation of hemoglobin than the normal oxygen saturation level as clinically defined.

In embodiments, a patient has an oxygen saturation of hemoglobin that is about 94% or less.

In embodiments, a patient has a pre-existing respiratory or pulmonary disease.

In embodiments, a pre-existing respiratory or pulmonary disease is acute lung injury, bronchitis, pneumonia, pulmonary fibrosis, asthma, and acute respiratory distress syndrome, or pulmonary hypertension.

In embodiments, a patient does not have a pre-existing respiratory or pulmonary disease.

In embodiments, a patient is an adult aged 45 years and above, aged 65 years and above, aged 80 years and above, over 80 years of age, aged 45-60 years, aged 60-80 years, or has underlying medical conditions.

In embodiments, underlying medical conditions comprise liver disease, heart conditions, kidney disease, obesity, diabetes, or being immunocompromised.

In embodiments, a patient has a body mass index (BMI) that is 25 or above or is 30 or above.

In embodiments, a patient has one or more clinically-recognized symptoms associated with the respiratory viral infection or the coronavirus infection, wherein the respiratory viral infection or the coronavirus infection is COVID-19.

In embodiments, the one or more symptoms associated with COVID-19 are fever, dry cough, fatigue, coughing up sputum from the lungs, bone or joint pain, sore throat, headache, chills, nausea or vomiting, stuffy nose, pressure or pain in the chest, shortness of breath, sudden confusion, digestive issues, conjunctivitis, bluish face or lips, or loss of smell or taste.

In embodiments, a patient has decreased oxygen saturation relative to normal levels as clinically defined.

In embodiments, the decreased oxygen saturation is an oxygen saturation of about 94% or less.

In embodiments, a patient has an elevated level of an inflammation marker.

In embodiments, an elevated level of an inflammation marker is detected in the serum of the patient.

In embodiments, an elevated level of an inflammation marker is detected in the lung of the patient.

In embodiments, an inflammation marker is a presence of ground-glass opacity.

In embodiments, a patient has a positive diagnostic test for SARS-CoV-2.

In embodiments, a compound stabilizes HIFα.

In embodiments, a compound inhibits hydroxylation of HIFα.

In embodiments, a HIF prolyl hydroxylase inhibitor or the HIF-alpha stabilizer has a structure of Formula (I), Formula (II), or Formula (III).

Formula (I)

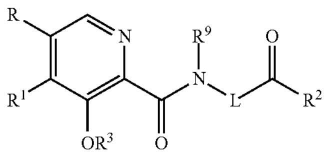

Formula (II)

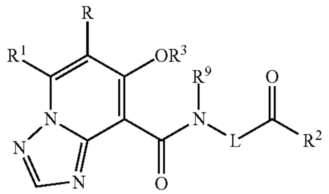

Formula (III)

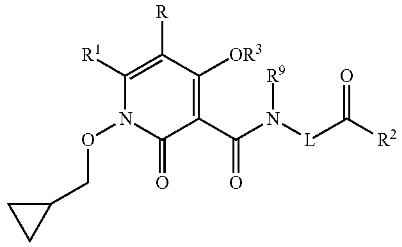

or a pharmaceutically acceptable salt thereof, wherein

R and $R^1$ are each independently:

(i) hydrogen (ii) substituted or unsubstituted phenyl;

(iii) substituted or unsubstituted heteroaryl; or (iv) substituted or unsubstituted alkyl;

said substitution selected from:

(i) $C_1$-$C_4$ alkyl;

(ii) $C_3$-$C_4$ cycloalkyl;

(iii) $C_1$-$C_4$ alkoxy;

(iv) $C_3$-$C_4$ cycloalkoxy;

(v) $C_1$-$C_4$ haloalkyl;

(vi) $C_3$-$C_4$ halocycloalkyl;

(vii) halogen;

(viii) cyano;

(ix) $NHC(O)R^4$;

(x) $C(O)NR^{5a}R^{5b}$;

(xi) phenyl; and (xii) heteroaryl; or (xiii) two substituents are taken together to form a fused ring having from 5 to 7 atoms;

$R^4$ is a $C_1$-$C_4$ alkyl or $C_3$-$C_4$ cycloalkyl;

$R^{5a}$ a and $R^{5b}$ are each independently selected from:

(i) hydrogen;

(ii) $C_1$-$C_4$ alkyl;

(iii) $C_3$-$C_4$ cycloalkyl; or (iv) $R^{6a}$ and $R^{5b}$ are taken together to form a ring having from 3 to 7 atoms;

$R^2$ is selected from:

(i) $OR^6$ (ii) $NR^{7a}R^{7b}$; and $R^6$ is selected from hydrogen and $C_1$-$C_4$ alkyl or $C_3$-$C_4$ cycloalkyl;

$R^{7a}$ and $R^{7b}$ are each independently selected from:

(i) hydrogen;

(ii) $C_1$-$C_4$ alkyl or $C_3$-$C_4$ cycloalkyl; or (iii) $R^{7a}$ and $R^{7b}$ are taken together to form a ring having from 3 to 7 atoms;

$R^3$ is selected from hydrogen, methyl, and ethyl;

L is a linking unit having a structure —$[C(R^{8a}R^{8b})]_n$—

$R^{8a}$ and $R^{8b}$ are each independently selected from hydrogen, methyl and ethyl;

n is an integer from 1 to 3; and $R^9$ is selected from hydrogen and methyl.

In embodiments, a HIF prolyl hydroxylase inhibitor or the HIF-alpha stabilizer has a structure of Formula (IV)

Formula (IV)

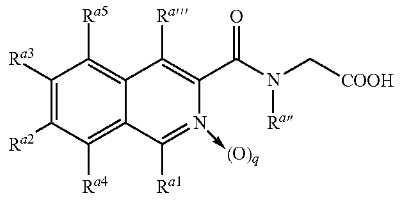

or a pharmaceutically acceptable salt thereof, wherein q is zero or one;

$R^{a1}$ is selected from the group consisting of hydrogen, alkyl, Substituted alkyl, alkoxy, substituted alkoxy, amino, substituted amino, aminoacyl, aryl, substituted aryl, halo, heteroaryl, substituted heteroaryl, heterocyclic, substituted heterocyclic, and —$XR^{a6}$ where X is oxygen, —$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted hetero cyclic, and $R^{a7}$ is hydrogen, alkyl or aryl or, when X is —$NR^{a7}$—, then $R^{a7}$ and $R^{a6}$, together with the nitrogen atom to which they are bound, can be joined to form a heterocyclic or substituted heterocyclic group;

$R^{a2}$ and $R^{a1}$ are independently selected from the group consisting of hydrogen, alkyl, substituted alkyl, aryl, substituted aryl, heteroaryl, substituted heteroaryl, halo, hydroxy, cyano. —$S(O)_n$—$N(R^{a6})$—$R^{a6}$ where n is 0, 1, or 2, —$NR^{a6}C(O)NR^{a6}R^{a6}$, —$XR^{a6}$ where X is oxygen, —$S(O)_n$—, or —$NR^{a7}$— where n is zero, one or two, each $R^{a6}$ is independently selected from the group consisting of hydrogen, alkyl, Substituted alkyl, aryl, substituted aryl, cycloalkyl, substituted cycloalkyl, heteroaryl, substituted heteroaryl, heterocyclic and substituted heterocyclic provided that when X is —SO— or —$SO_2$—, then $R^{a6}$ is not hydrogen, and $R^{a7}$ is selected from the group consisting of hydrogen, alkyl, aryl, or $R^{a2}$, $R^{a3}$ together with the carbon atom pendent thereto, form an aryl substituted aryl, heteroaryl, or substituted heteroaryl;

$R^{a4}$ and $R^{a5}$ are independently selected from the group consisting of hydrogen, halo, alkyl, substituted alkyl, alkoxy, Substituted alkoxy, aryl, substituted aryl, heteroaryl, substituted heteroaryl and —$XR^{a6}$ where X is oxygen, —$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl or, when X is —$NR^{a7}$—, then $R^{a7}$ and $R^{a6}$, together with the nitrogen atom to which they are bound, can be joined to form a heterocyclic or Substituted heterocyclic group;

$R^{a''}$ is selected from the group consisting of hydrogen, alkyl and substituted alkyl;

$R^{a'''}$ is selected from the group consisting of hydroxy, alkoxy, substituted alkoxy, acyloxy, cycloalkoxy, substituted cycloalkoxy, aryloxy, substituted aryloxy, heteroaryloxy, substituted heteroaryloxy, aryl, —S(O)—$R^{a10}$ wherein $R^{a10}$ is selected from the group consisting of alkyl, substituted alkyl, cycloalkyl, substituted cycloalkyl, aryl, substituted aryl, heteroaryl and substituted heteroaryl and n is zero, one or two;

or a pharmaceutically acceptable salt, ester, or prodrug thereof;

with the proviso that when $R^{a''}$ is hydrogen and q is zero, then at least one of the following occurs:

1) $R^{a1}$ is fluoro, bromo, iodo, alkyl, substituted alkyl, alkoxy, aminoacyl, Substituted alkoxy, aryl, substituted aryl, heteroaryl, substituted heteroaryl, heterocyclic, substituted heterocyclic, and —$XR^{a6}$ where X is oxygen, —$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl; or 2) $R^{a2}$ is substituted alkyl, aryl, substituted aryl, heteroaryl, substituted heteroaryl, fluoro, bromo, iodo, cyano, —$XR^{a6}$ where X is oxygen, —$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl provided that:

a) when $R^{a2}$ is substituted alkyl such a substituent does not include trifluoromethyl;

b) —$XR^{a6}$ is not alkoxy; and c) when —$XR^{a6}$ is substituted alkoxy such a substituent does not include benzyl or benzyl substituted by a substituent selected from the group consisting of ($C_1$-$C_5$) alkyl and ($C_1$-$C_5$) alkoxy or does not include a fluoroalkoxy substituent of the formula:

$$—O—[CH_2]_x—C_fH_{(2f+1-g)}F_g$$

where x is zero or one; f is an integer of from 1 to 5; and g is an integer of from 1 to (2f+1); or 3) $R^{a3}$ is substituted alkyl, aryl, substituted aryl, heteroaryl, substituted heteroaryl, bromo, iodo, —$XR^{a6}$ where X is oxygen-$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl provided that:

a) when $R^{a3}$ is substituted alkyl such a substituent does not include trifluoromethyl;

b) —$XR^{a6}$ is not alkoxy; and c) when $XR^{a6}$ is substituted alkoxy such a substituent does not include benzyl or benzyl substituted by a substituent selected from the group consisting of ($C_1$-$C_5$) alkyl and (C—C) alkoxy or does not include a fluoroalkoxy substituent of the formula:

$$—O—[CH_2]_x—C_fH_{(2f+1-g)}F_g$$

where x is zero or one; f is an integer of from 1 to 5; and g is an integer of from 1 to (2f+1); or 4) $R^{a4}$ is iodo, substituted alkyl, aryl, substituted aryl, heteroaryl, substituted heteroaryl, —$XR^{a6}$ where X is oxygen-$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl provided that:

a) when $R^{a4}$ is substituted alkyl such a substituent does not include trifluoromethyl;

b) —$XR^{a6}$ is not alkoxy; and c) when $XR^{a6}$ is substituted alkoxy such a substituent does not include benzyl or benzyl substituted by a substituent selected from the group consisting of ($C_1$-$C_5$) alkyl and (C—C) alkoxy or does not include a fluoroalkoxy substituent of the formula:

$$—O—[CH_2]_x—C_fH_{(2f+1-g)}F_g$$

where x is zero or one; f is an integer of from 1 to 5; and g is an integer of from 1 to (2f+1); or 5) $R^{a5}$ is iodo, substituted alkyl, aryl, substituted aryl, heteroaryl, substituted heteroaryl, —$XR^{a6}$ where X is oxygen, —$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl provided that:

a) when $R^{a5}$ is substituted alkyl such a substituent does not include trifluoromethyl;

b) —$XR^{a6}$ is not alkoxy; and c) when $XR^{a6}$ is substituted alkoxy such a substituent does not include benzyl or benzyl substituted by a substituent selected from the group consisting of ($C_1$-$C_5$) alkyl and (C—C) alkoxy or does not include a fluoroalkoxy substituent of the formula:

$$—O—[CH_2]_x—C_fH_{(2f+1-g)}F_g$$

where x is zero or one; f is an integer of from 1 to 5; and g is an integer of from 1 to (2f+1);

and with the further following proviso:

that when $R^{a1}$, $R^{a3}$, $R^{a4}$, and $R^{a5}$ are hydrogen, then $R^{a2}$ is not bromo.

In embodiments, a HIF prolyl hydroxylase inhibitor or the HIF-alpha stabilizer has a structure of Formula (V)

Formula (V)

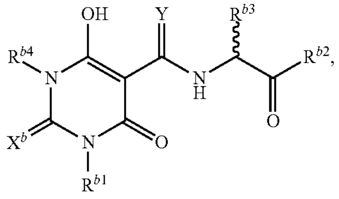

or a pharmaceutically acceptable salt thereof, wherein $R^{b1}$ and $R^{b4}$ are each independently selected from the group consisting of hydrogen, —$NR^{b5}R^{b6}$, $C_1$-$C_{10}$ alkyl, $C_2$-$C_{10}$ alkenyl, $C_2$-$C_{10}$ alkynyl, $C_3$-$C_8$ cycloalkyl, $C_3$-$C_8$ cycloalkyl-$C_1$-$C_{10}$ alkyl, $C_5$-$C_8$ cycloalkenyl, $C_5$-$C_8$ cycloalkenyl-$C_1$-$C_{10}$ alkyl, $C_3$-$C_8$ heterocycloalkyl, $C_3$-$C_8$ heterocycloalkyl-$C_1$-$C_{10}$ alkyl, aryl, aryl-$C_1$-$C_{10}$ alkyl, heteroaryl and heteroaryl-$C_1$-$C_{10}$ alkyl;

$R^{b2}$ is —$NR^{b7}R^{b8}$ or —$OR^{b9}$;

$R^{b3}$ is H or $C_1$-$C_4$ alkyl;

where $R^{b5}$ and $R^{b6}$ are each independently selected from the group consisting of hydrogen, $C_1$-$C_{10}$ alkyl, $C_3$-$C_8$ cycloalkyl, $C_3$-$C_8$ cycloalkyl-$C_1$-$C_{10}$ alkyl, $C_3$-$C_8$ heterocycloalkyl, $C_3$-$C_8$ heterocycloalkyl-$C_1$-$C_{10}$ alkyl, aryl, aryl-$C_1$-$C_{10}$ alkyl, heteroaryl and heteroaryl-$C_1$-$C_{10}$ alkyl, —$C(O)C_1$-$C_4$ alkyl, —$C(O)C_3$-$C_6$ cycloalkyl, —$C(O)C_3$-$C_6$ heterocycloalkyl, —C(O)aryl, —C(O)heteroaryl and $S(O)_2$ $C_1$-$C_4$ alkyl, or, when $R^{b5}$ and $R^{b6}$ are attached to the same nitrogen, $R^{b5}$ and $R^{b6}$ taken together with the nitrogen to which they are attached form a 5- or 6- or 7-membered saturated ring optionally containing one other heteroatom selected from oxygen, nitrogen and sulphur, $R^{b7}$ and $R^{b8}$ are each independently selected from the group consisting of hydrogen, $C_1$-$C_{10}$ alkyl, $C_2$-$C_{10}$ alkenyl, $C_3$-$C_8$ cycloalkyl, $C_3$-$C_8$ heterocycloalkyl, aryl, and heteroaryl, and $R^{b9}$ is H or a cation, or $C_1$-$C_{10}$ alkyl which is unsubstituted or substituted with one or more substituents independently selected from the group consisting of $C_3$-$C_6$ cycloalkyl, heterocycloalkyl, aryl and heteroaryl;

$X^b$ is O or S; and

Y is O or S;

where any carbon or heteroatom of $R^{b1}$, $R^{b2}$, $R^{b3}$, $R^{b4}$, $R^{b5}$, $R^{b6}$, $R^{b7}$, $R^{b8}$, $R^{b9}$ is unsubstituted or is substituted with one or more substituents independently selected from $C_1$-$C_6$ alkyl, $C_1$-$C_6$ haloalkyl, halogen, —$OR^{b10}$, —$NR^{b5}R^{b6}$, oxo, cyano, nitro, —$C(O)R^{b10}$, —$C(O)OR^{b10}$, —$SR^{b10}$, —$S(O)R^{b10}$, —$S(O)_2R^{b10}$, —$CONR^{b5}R^{b6}$, —$N(R^{b5})C(O)R^{b10}$, —$N(R^{b5})C(O)OR^{b10}$, —$OC(O)NR^{b5}R^{b6}$, —$N(R^{b5})C(O)NR^{b5}R^{b6}$, —$SO_2NR^{b5}R^{b6}$, —$N(R^{b5})SO_2R^{b10}$, $C_2$-$C_{10}$ alkenyl, $C_2$-$C_{10}$ alkynyl, $C_3$-$C_6$ cycloalkyl, $C_3$-$C_6$ heterocycloalkyl, aryl, $C_1$-$C_6$ alkyl-aryl, heteroaryl and $C_1$-$C_6$ alkyl-heteroaryl, wherein $R^{b5}$ and $R^{b6}$ are the same as defined above and $R^{b10}$ is selected from hydrogen, $C_1$-$C_{10}$ alkyl, $C_2$-$C_{10}$ alkenyl, $C_2$-$C_{10}$ alkynyl. —$C(O)C_1$-$C_4$ alkyl, —C(O)aryl, —C(O)heteroaryl, —$C(O)C_3$-$C_6$ cycloalkyl, —$C(O)C_3$-$C_6$ heterocycloalkyl, —$S(O)_2C_1$-$C_4$ alkyl, $C_3$-$C_8$ cycloalkyl, $C_3$-$C_8$ heterocycloalkyl, $C_6$-$C_{14}$ aryl, aryl-$C_1$-$C_{10}$ alkyl, heteroaryl and heteroaryl-$C_1$-$C_{10}$ alkyl;

In embodiments, a HIF prolyl hydroxylase inhibitor or the HIF-alpha stabilizer has a structure of Formula (VI)

Formula (VI)

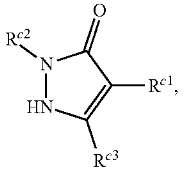

or a pharmaceutically acceptable salt thereof, wherein $R^{c1}$ represents a heteroaryl group of the formula

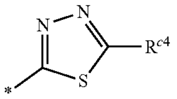 or 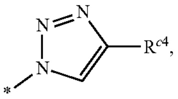

wherein

* denotes the linkage point with the dihydropyrazolone ring and $R^{c4}$ denotes hydrogen, fluorine, chlorine, bromine, cyano, $C_1$-$C_4$ alkyl, trifluoromethyl, hydroxymethyl, $C_1$-$C_4$ alkoxy, trifluoromethoxy, hydroxycarbonyl or $C_1$-$C_4$ alkoxycarbonyl;

$R^{c2}$ represents a heteroaryl group of the formula

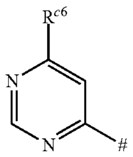 or 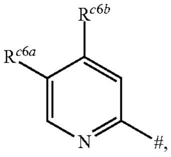

wherein denotes the linkage point with the dihydropyrazolone ring and $R^{c6}$, $R^{c6a}$ and $R^{c6b}$ are identical or different and independently of one another denote hydrogen or a substituent chosen from the group consisting of fluorine, chlorine, bromine, cyano, $C_1$-$C_6$ alkyl, trifluoromethyl, hydroxyl, $C_1$-$C_6$ alkoxy, trifluoromethoxy, amino, mono-$C_1$-$C_4$ alkylamino, di-$C_1$-$C_4$ alkylamino, hydroxycarbonyl, $C_1$-$C_4$ alkoxycarbonyl, 4- to 6-membered heterocycloalkyl, phenyl and 5- or 6-membered heteroaryl, wherein $C_1$-$C_6$ alkyl in its turn can be substituted by hydroxyl, $C_1$-$C_4$ alkoxy or amino and 4- to 6-membered heterocycloalkyl, phenyl and 5- or 6-membered heteroaryl in their turn can in each case be substituted once or twice in an identical or different manner by fluorine, chlorine, bromine, cyano, $C_1$-$C_4$ alkyl, trifluoromethyl, hydroxyl, $C_1$-$C_4$ alkoxy, trifluoromethoxy, oxo, amino, mono-$C_1$-$C_4$ alkylamino, di-$C_1$-$C_4$ alkylamino, hydroxycarbonyl or $C_1$-$C_4$ alkoxycarbonyl, and $R^{c3}$ represents hydrogen, or a salt thereof.

In embodiments, a HIF prolyl hydroxylase inhibitor or a HIF-alpha stabilizer, or a pharmaceutically acceptable salt thereof, is administered orally, intravenously, intramuscularly, by inhalation or transdermally.

In embodiments, a HIF prolyl hydroxylase inhibitor or a HIF-alpha stabilizer, or a pharmaceutically acceptable salt thereof, is administered orally.

In embodiments, a HIF prolyl hydroxylase inhibitor or a HIF-alpha stabilizer, or a pharmaceutically acceptable salt thereof, is administered to a subject patient at a dose of about 100-1500 mg or of about 150 mg to 1800 mg per day.

In embodiments, a HIF prolyl hydroxylase inhibitor or the HIF-alpha stabilizer is vadadustat (AKB-6548), roxadustat (FG-4592), daprodustat (GSK-12788363), molidustat (BAY 85-3934), enarodustat (JTZ-951) or desidustat (ZYAN1).

In embodiments, a HIF prolyl hydroxylase inhibitor or the HIF-alpha stabilizer is vadadustat (AKB-6548).

In embodiments, vadadustat (AKB-6548) is administered at a dose of 150 mg to 1000 mg per day.

In embodiments, vadadustat (AKB-6548) is administered at a dose of 150 mg to 1800 mg per day.

In embodiments, vadadustat (AKB-6548) is administered at a dose of 900 mg to 1800 mg per day.

In embodiments, vadadustat (AKB-6548) is administered at a dose of 900, 1050, 1200, 1350, 1500, 1650, or 1800 mg per day.

In embodiments, vadadustat (AKB-6548) is administered at an initial dose of 900 mg per day.

In embodiments, vadadustat (AKB-6548) is administered at a dose of 900 mg per day throughout the treatment period.

In embodiments, a HIF prolyl hydroxylase inhibitor or the HIF-alpha stabilizer is administered to the patient for up to about one month.

In embodiments, a HIF prolyl hydroxylase inhibitor or the HIF-alpha stabilizer is administered to the patient for up to about four weeks (about 28 days), three weeks (about 21 days), two weeks (about 14 days), or one week (about 7 days).

In embodiments, a HIF prolyl hydroxylase inhibitor or the HIF-alpha stabilizer is administered in combination with another treatment.

In embodiments, treatment comprises an antiviral agent or oxygen therapy.

In embodiments, oxygen therapy comprises mechanical ventilation.

In embodiments, the severity of disease is maintained or reduced following commencement of administering the HIF prolyl hydroxylase inhibitor or the HIF-alpha stabilizer to the patient.

In embodiments, the severity of disease is assessed according to the following ordinal scale where increasing numbers denote increased severity:

| Score | Descriptor | Patient State | |
|---|---|---|---|
| 0 | No clinical or virological evidence of infection | Uninfected | Uninfected/ Ambulatory |
| 1 | Not hospitalized, no limitation of patient's activities | Infected (Ambulatory) | |
| 2 | Not hospitalized, limitation of patient's activities and/or requiring home oxygen | | |
| 3 | Patient is hospitalized but does not receive oxygen therapy-no longer requires ongoing medical care | Infected-Hospitalized (Mild Disease) | Hospitalized but not intubated |
| 4 | Patient is hospitalized but does not require oxygen therapy-requiring ongoing care (COVID-19 related or otherwise) | | |

-continued

| Score | Descriptor | Patient State | |
|---|---|---|---|
| 5 | Patient is hospitalized and requiring supplemental oxygen | | |
| 6 | Patient is hospitalized and receives oxygen therapy that is non-invasive ventilation or high flow oxygen devices | Infected-Hospitalized (Severe Disease) | Hospitalized and intubated |
| 7 | Patient is hospitalized and receives invasive mechanical ventilation and additional organ support such as pressors, renal replacement therapy (RRT), and/or extracorporeal membrane oxygenation (ECMO) | | |

In embodiments, the severity of disease is maintained and the patient's condition stabilizes following commencement of administering the HIF prolyl hydroxylase inhibitor or the HIF-alpha stabilizer to the patient.

In embodiments, a patient's score does not change and the patient's condition stabilizes following commencement of administering the HIF prolyl hydroxylase inhibitor or the HIF-alpha stabilizer to the patient.

In embodiments, the severity of disease decreases following commencement of administering the HIF prolyl hydroxylase inhibitor or the HIF-alpha stabilizer to the patient.

In embodiments, a patient's score decreases by at least one point following commencement of administering the HIF prolyl hydroxylase inhibitor or the HIF-alpha stabilizer to the patient.

In embodiments, a patient's severity of disease is assessed as uninfected/ambulatory.

In embodiments, a patient's severity of disease is assessed as hospitalized but not intubated.

In embodiments, a patient's severity of disease is assessed as hospitalized and intubated.

In embodiments, a patient's category decreases by at least one category following commencement of administering the HIF prolyl hydroxylase inhibitor or the HIF-alpha stabilizer to the patient.

In embodiments, a patient is hypoxic.

In embodiments, a patient has an oxygen saturation value that is about 94% or less.

In embodiments, a patient's oxygen saturation value improves to a value of about 95% or greater following commencement of administering the HIF prolyl hydroxylase inhibitor or the HIF-alpha stabilizer to the patient.

In embodiments, a patient has hypotension.

In embodiments, a patient receives vasopressor therapy.

In embodiments, a vasopressor therapy is reduced or discontinued following commencement of administering the HIF prolyl hydroxylase inhibitor or the HIF-alpha stabilizer to the patient.

In embodiments, a patient is hospitalized.

In embodiments, a patient does not receive oxygen therapy.

In embodiments, a patient has a score of 1, 2, and/or 3 according to the ordinal scale described herein.

In embodiments, a patient receives oxygen therapy.

In embodiments, a patient has a score of 4, 5, 6, or 7 according to the ordinal scale described herein.

In embodiments, a patient receives oxygen therapy by mask or nasal prongs.

In embodiments, a patient receives oxygen therapy by intubation and mechanical ventilation.

In embodiments, a patient has multi-organ injuries and receives additional organ support therapy.

In embodiments, a patient has any of a cardiovascular injury, a neurological injury, a kidney disease, a liver injury, or a pancreas injury.

In embodiments, a patient has a heart injury and/or a lung injury.

In embodiments, a patient receives organ support therapy that is vapopressor therapy, renal replacement therapy (RRT), and/or extracorporeal membrane oxygenation (ECMO).

In embodiments, an organ support therapy received by the patient is discontinued following commencement of administering the HIF prolyl hydroxylase inhibitor or the HIF-alpha stabilizer to the patient.

In embodiments, an oxygen therapy received by the patient is discontinued following commencement of administering the HIF prolyl hydroxylase inhibitor or the HIF-alpha stabilizer to the patient.

In embodiments, a patient has increased ventilator-free survival following discontinuation of mechanical ventilation.

In embodiments, a patient receives vadadustat, or a pharmaceutically acceptable salt thereof.

DETAILED DESCRIPTION OF THE INVENTION

Definitions

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference for all purposes.

Animal: As used herein, the term "animal" refers to any member of the animal kingdom. In some embodiments, "animal" refers to humans, at any stage of development. In some embodiments, "animal" refers to non-human animals, at any stage of development. In embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the term "biologically active" refers to a characteristic of any agent that has activity in a biological system, and particularly in an organism. For instance, an agent that, when administered to an organism, has a biological effect on that organism, is considered to be biologically active.

Dose(s): As used herein, the term "dose(s)" means a quantity of the compound or a pharmaceutically acceptable salt, solvate, or hydrate thereof to be administered at one time. A dose may comprise a single unit dosage form, or alternatively may comprise more than a single unit dosage form (e.g., a single dose may comprise two tablets), or even less than a single unit dosage form (e.g., a single dose may comprise half of a tablet).

Daily dose: As used herein, the term "daily dose" means a quantity of the compound, or a pharmaceutically acceptable salt, solvate, or hydrate thereof that is administered in a 24-hour period. Accordingly, a daily dose may be administered all at once (i.e., once daily dosing) or alternatively the daily dosing may be divided such that administration of the compound is twice daily, three times daily, or even four times daily.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control sample or subject (or multiple control samples or subjects) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Administration: As used herein, the term "administration" typically refers to the administration of a composition to a subject or system. Those of ordinary skill in the art will be aware of a variety of routes that may, in appropriate circumstances, be utilized for administration to a subject, for example a human subject. For example, in embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In embodiments, administration may involve dosing that is intermittent (e.g., a plurality of doses separated in time) and/or periodic (e.g., individual doses separated by a common period of time) dosing. In embodiments, administration may involve continuous dosing (e.g., perfusion) for at least a selected period of time.

Hospitalization: The term "hospitalization", as used herein, is defined as an overnight admission with observation of a minimum of 24 hours.

Pharmaceutically acceptable: The term "pharmaceutically acceptable", as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

Subject and Patient: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. As used herein, the term "patient" refers to a human. In embodiments, a patient may be suffering from, and/or susceptible to a disease, disorder, and/or condition. A patient can be afflicted with or is susceptible to a disease or disorder but may or may not display symptoms of the disease or disorder. A subject can be a patient.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one-unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Preventing: The term "prevent," "preventing," or "prevention," as used herein refers to an effect that mitigates an undesired effect, e.g., an undesirable drug-drug interaction or the formation of a drug-iron chelate. Prevention does not require the 100% elimination of the possibility of an event. Rather, it denotes that the likelihood of the occurrence of the event has been reduced by the compound or method.

As used herein, the term "HIF prolyl hydroxylase" is art-recognized and may be abbreviated as "PHD". HIF prolyl hydroxylase is also known as "prolyl hydroxylase domain-containing protein" which may be abbreviated as "PHD." In this regard, there are three different PHD isoforms, PHD1, PHD2, and PHD3, also referred to as EGLN2, EGLN1, and EGLN3, or HPH3, HPH2, and HPH1, respectively.

Alkyl: As used herein, the term "alkyl" means acyclic linear and branched hydrocarbon groups, e.g. "$C_1$-$C_{20}$ alkyl" refers to alkyl groups having 1-20 carbons. An alkyl group may be linear or branched. Examples of alkyl groups include, but are not limited to, methyl, ethyl, n-propyl, isopropyl, butyl, isobutyl, sec-butyl, tert-butyl, pentyl, isopentyl tert-pentyl, hexyl, isohexyl, and the like. Other alkyl groups will be readily apparent to those of skill in the art given the benefit of the present disclosure. An alkyl group may be unsubstituted or substituted with one or more substituent groups as described herein. For example, an alkyl group may be substituted with one or more (e.g., 1, 2, 3, 4, 5, or 6 independently selected substituents) of halogen, haloalkyl (e.g., —$CH_2F$ and —$CH_2Cl$, as well as perhaloalkyl groups such as $CF_3$ and $CCl_3$), —$CO_2R'$, —CN, —OH, —OR', —$NH_2$, —NHR', —$N(R')_2$, —SR' or —$SR_2R'$, wherein each instance of R' independently is $C_1$-$C_3$ alkyl. In embodiments, the alkyl is unsubstituted. In embodiments, the alkyl is substituted (e.g., with 1, 2, 3, 4, 5, or 6 substituent groups as described herein).

Alkoxy: The term "alkoxy," as used herein, a monovalent substituent which consists of a linear or branched, substituted or unsubstituted, acyclic or cyclic alkyl group linked through an ether oxygen and having its free valence bond from the ether oxygen such as, for example methoxy, ethoxy, 1- and 2-propoxy, 1-butoxy, 1,2-dimethylethoxy, 1- and 2-pentoxy-, 3-hexoxy- and the like.

Alkylene: The term "alkylene," as used herein, represents a saturated divalent straight or branched chain hydrocarbon group, e.g., a "$C_1$-$C_{10}$ alkylene" group having 1-10 carbons. Alkylene groups are exemplified by methylene, ethylene, isopropylene and the like. An alkylene may be unsubstituted or substituted with substituent groups as described herein. In embodiments, an alkylene group is unsubstituted Aryl: The terms "aryl" and "ar-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. For example, the aryl group is a $C_{6-10}$ aryl group (i.e., phenyl and naphthyl). Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

Benzyloxy: As used herein, the term "benzyloxy" refers to a monovalent substituent which consists of a substituted or unsubstituted benzyl group linked through an ether oxygen and having its free valence bond from the ether oxygen.

Cycloalkyl: As used herein, the term "cycloalkyl" means a nonaromatic, saturated, cyclic group, e.g. "$C_3$-$C_{10}$ cycloalkyl." In embodiments, a heterocyclyl is monocyclic. In embodiments, a heterocyclyl is polycyclic (e.g., bicyclic or tricyclic). In polycyclic cycloalkyl groups, individual rings can be fused, bridged, or spirocyclic. Examples of a cycloalkyl group include cyclopropyl, cyclobutyl, cyclopentyl, cyclohexyl, norbornanyl, bicyclo[3.2.1]octanyl, octahydropentalenyl, and spiro[4.5]decanyl, and the like. The term "cycloalkyl" may be used interchangeably with the term "carbocycle". A cycloalkyl group may be unsubstituted or substituted with one or more substituent groups as described herein. For example, a cycloalkyl group may be substituted with one or more (e.g., 1, 2, 3, 4, 5, or 6 independently selected substituents) of halogen, —$CO_2R'$, —CN, —OH, —OR', —$NH_2$, —NHR', —$N(R')_2$, —SR' or —$SO_2R'$, wherein each instance of R' independently is $C_1$-$C_3$ alkyl. In embodiments, the cycloalkyl is unsubstituted. In embodiments, the cycloalkyl is substituted (e.g., with 1, 2, 3, 4, 5, or 6 substituent groups as described herein).

Halo or Halogen: As used herein, the term "halo" or "halogen" means fluorine, chlorine, bromine, or iodine.

Heterocyclyl: As used herein, the term "heterocyclyl" means a nonaromatic, cyclic structure having at least one of any type of heteroatom as ring atoms, having any degree of unsaturation, and excludes aromatic heterocyclic rings that are defined as "heteroaryl" herein. For example, a "3- to 10-membered heterocyclyl" refers to heterocyclics having 3-10 ring atoms that are carbon or heteroatoms as described herein. The one or more heteroatoms may be selected from nitrogen, sulfur, and oxygen. The term "heterocycle", "heterocyclyl", "heterocyclic", "heterocycloalkyl," and "heterocyclic ring" can be used interchangeably. A heterocyclyl group can be attached as a substituent via a carbon atom or a heteroatom (e.g. a nitrogen atom). In embodiments, a heterocyclyl is monocyclic. In embodiments, a heterocyclyl is polycyclic (e.g., bicyclic or tricyclic). Examples include 2-tetrahydrofuranyl, 3-tetrahydrofuranyl, dihydrofuranyl, tetrahydropyranyl, pyranyl, thiopyranyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 1,3-oxazolidin-3-yl, isothiazolidinyl, 1,3-thiazolidin-3-yl, 1,2-pyrazolidin-2-yl, 1,3-pyrazolidin-1-yl, 1,2-tetrahydrothiazin-2-yl, 1,3-tetrahydrothiazin-3-yl, tetrahydrothiadiazinyl, 1,2-tetrahydrodiazin-2-yl, 1,3-tetrahydrodiazin-1-yl, tetrahydroazepinyl, piperizin-2-onyl, piperizin-3-onyl, 2-pyrrolinyl, 3-pyrrolinyl, imidazolidinyl, 2-imidazolidinyl, 1,4-dioxanyl, and 4-thiazolidinyl, and the like. A heterocyclyl group may be unsubstituted or substituted with one or more substituent groups as described herein. For example, a heterocyclyl group may be substituted with one or more (e.g., 1, 2, 3, 4, 5, or 6 independently selected substituents) of halogen, —$CO_2R'$, —CN, —OH, —OR', —$NH_2$, —NHR', —$N(R')_2$, —SR' or —$SO_2R'$, wherein each instance of R' independently is $C_1$-$C_3$ alkyl. In embodiments, the heterocyclyl is unsubstituted. In embodiments, the heterocyclyl is substituted (e.g., with 1, 2, 3, 4, 5, or 6 substituent groups as described herein).

Heteroaryl: As used herein, the term "heteroaryl" means an aromatic moiety having at least one of any type of heteroatom as ring atoms. For example, a "5- to 14-membered heteroaryl" refers to heteroaryls having 5-14 ring atoms that are carbon or heteroatoms as described herein. The one or more heteroatoms may be selected from nitrogen, sulfur, and oxygen. A heteroaryl group can be attached as a substituent via a carbon atom or a heteroatom (e.g. a nitrogen atom). In embodiments, a heteroaryl is monocyclic. In embodiments, a heteroaryl is polycyclic (e.g., bicyclic or tricyclic). In embodiments, polycyclic heteroaryls comprise a cyclic group that is non-aromatic (e.g., a heteroaryl fused to a cycloalkyl or a heterocyclyl group as described herein). The term "heteroaryl" may be used interchangeably with the term "heteroaryl ring" or the term "heteroaromatic". Examples include 5-membered monocyclic rings such as pyrrolyl, imidazolyl, pyrazolyl, triazolyl, furyl, oxazolyl, isoxazolyl, oxadiazolyl, thiadiazolyl, thiazolyl, isothiazolyl, and the like; and 6-membered monocyclic rings such as pyridyl, pyrazinyl, pyrimidinyl, pyridazinyl, triazinyl and the like. For further examples, see, e.g., Katritzky, Handbook of Heterocyclic Chemistry. Further specific examples of heteroaryl rings include 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl and carbazolyl. The term "heteroaryl" also refers to rings that are optionally substituted. A heteroaryl group may be optionally substituted with one or more functional groups discussed below. Still other examples include indolyl, azaindolyl, benzimidazolyl, indazolyl, imidazopyridinyl, imidazopyrimidinyl, pyrrolopyrimidinyl, pyrrolopyridinyl, pyrazolopyridinyl, pyrazolopyrimidinyl, quinolyl, isoquinolyl, benzoxazolyl, benzathiazolyl, benzothiophenyl, benzofuranyl, and isobenzofuranyl, and the like. A heteroaryl group may be unsubstituted or substituted with one or more substituent groups as described herein. For example, a heteroaryl group may be substituted with one or more (e.g., 1, 2, 3, 4, 5, or 6 independently selected substituents) of halogen, —$CO_2R'$, —CN, —OH, —OR', —$NH_2$, —NHR', —$N(R')_2$, —SR' or —$SO_2R'$, wherein each instance of R' independently is $C_1$-$C_3$ alkyl. In embodiments, the heteroaryl is unsubstituted. In embodiments, the heteroaryl is substituted (e.g., with 1, 2, 3, 4, 5, or 6 substituent groups as described herein).

Hypoxia-Inducible Factor (HIF) and HIF Prolyl 4-Hydroxylases (HIF PH)

Described herein are therapeutic methods comprising administering to a patient in need thereof a compound that is a HIF prolyl hydroxylase inhibitor or a HIF-alpha stabilizer, or a pharmaceutically acceptable salt thereof.

Hypoxia-inducible factor (HIF) is a heterodimeric transcription factor consisting of an oxygen-sensitive HIF-α subunit and a constitutively expressed HIF-β subunit. Under normoxic conditions, the HIF-α subunit is produced and continuously degraded with a $t^{1/2}$ of approximately 5 minutes. In response to hypoxic conditions, levels of HIFα are elevated in most cells because of a decrease in HIFα prolyl hydroxylation.

Prolyl hydroxylation of HIFα is accomplished by a family of proteins variously termed the prolyl hydroxylase domain-containing proteins (PHD1, 2, and 3), also known as HIF prolyl hydroxylases (HIF-PH-3, 2, and 1) or EGLN-2, 1, and 3, which use physiological levels of oxygen to hydroxylate specific proline residues of HIF-α, signaling proteasomal degradation of HIF-α (Ke et al. (2006) Mol. Pharmacol. 70 (5):1469-80). Under hypoxic conditions the activity of HIF-PHs is decreased, degradation of HIF-α is inhibited and cellular levels of HIF-α are increased. Stabilization of HIF-α allows it to translocate to the nucleus and dimerize with the HIF-β subunit where it binds to cis-acting hypoxia-response elements and activates the transcription of target genes involved in erythropoiesis and iron homeostasis. The HIF-PHs thus function as critical sensors of cellular oxygen levels, and regulate oxygen homeostasis in response to hypoxia through inhibition of hydroxylation thus leading to stabilization of HIF-α, which in turn signals gene transcription and translation of proteins necessary for the cellular and organ responses to poor oxygenation (Myllylharju et al. (2013) Acta Physiol 208 (2):148-65).

HIF Prolyl 4-Hydroxylases (HIF-PH), are 2-oxoglutarate-dependent dioxygenases that require oxygen for hydroxylation of proline residues in the oxygen-dependent degradation domain of HIF α, and also require $Fe^{2+}$ and ascorbate as essential cofactors. Each of the 3 known HIF-PHs regulate HIF 1α and HIF 2α in a non-redundant manner that is dependent upon the degree of hypoxia and the relative abundance of the specific HIF-PH in different tissues. PHD2 is the abundant isoform present in most cells during normoxia (Appelhoff 2004). During hypoxia, messenger ribonucleic acid (mRNA) and protein for PHD2 and 3 were shown to increase with marked upregulation of PHD3 (Appelhoff 2004). Although all 3 HIF-PHs contribute to the regulation of HIF 1α and HIF 2α, PHD2 was shown to preferentially interact with HIF-1α, while PHD3 and PHD1 preferentially inhibit HIF 2α (Appelhoff et al. (2004) J. Biol. Chem. 279 (37):38458-65).

Compounds of the Invention

Provided herein are exemplary compounds for use in methods for treating and/or preventing a disease or condition, methods for reducing mortality and morbidity related to a disease or condition, and methods for reducing incidence, severity, or risk of a disease or condition, wherein the disease or condition in is as described anywhere herein. Compounds that can be used with the compositions and formulations provided herein are HIF prolyl hydroxylase inhibitors or HIF-alpha stabilizers.

Non-limiting examples of HIF prolyl hydroxylase inhibitors or HIF-alpha stabilizers include vadadustat (AKB-6548), roxadustat (FG-4592), daprodustat (GSK-12788363), molidustat (BAY 85-3934), enarodustat (JTZ-951), or desidustat (ZYAN1), and compounds described in U.S. Pat. Nos. 8,759,345, 8,937,078, 8,796,263, 9,273,034, 8,530,404, 7,696,223, 7,629,357, 8,927,591, 8,269,008, 8,952,160, 8,952,160, 8,927,591, 8,921,389, 8,916,585, 8,703,795, 8,921,389, 7,662,854, and 9,040,522; in International Publication No. WO2020/072645; in U.S. Provisional Patent Application Nos. 62/947,170, 62/947,179, 62/992,585, 62/992,606, and 62/992,616; and in "Recent Advances in Developing Inhibitors for Hypoxia-Inducible Factor Prolyl Hydroxylases and Their Therapeutic Implications" (Kim et al. Molecules 2015, 20, 20551-20568; see, e.g., any of the compounds described therein, including any of the compounds described in any of Tables 2, 3, or 4), each of which is hereby incorporated by reference in its entirety. In embodiments, a suitable compound is described in any of International Publication No. WO2020/072645; and in U.S. Provisional Patent Application Nos. 62/947,170, 62/947,179, 62/992,585, 62/992,606, and 62/992,616.

Certain exemplary compounds are described herein.

Formula (I): Vadadustat and Other Compounds

Exemplary compounds that can be used in any of the methods described herein include those described in U.S. Pat. Nos. 7,811,595, 8,343,952, 8,323,671, 8,598,210, 8,722,895, 8,940,773, and 9,598,370; and in U.S. Publication No. US 20190192494A1, each of which is incorporated by reference in its entirety. In embodiments, a compound, or pharmaceutically acceptable salt thereof, is described in any of claims 1-32 of U.S. Pat. No. 7,811,595.

In embodiments, suitable compounds include a compound having a structure according to Formula (I), Formula (I)

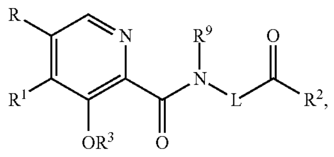

or a pharmaceutically acceptable salt thereof, wherein,

R and $R^1$ are each independently:
- (i) hydrogen
- (ii) substituted or unsubstituted phenyl;
- (iii) substituted or unsubstituted heteroaryl; or
- (iv) substituted or unsubstituted alkyl;

said substitution selected from:
- (i) $C_1$-$C_4$ alkyl;
- (ii) $C_3$-$C_4$ cycloalkyl;
- (iii) $C_1$-$C_4$ alkoxy;
- (iv) $C_3$-$C_4$ cycloalkoxy;
- (v) $C_1$-$C_4$ haloalkyl;
- (vi) $C_3$-$C_4$ halocycloalkyl;
- (vii) halogen;
- (viii) cyano;
- (ix) $NHC(O)R^4$;
- (x) $C(O)NR^{5a}R^{5b}$;
- (xi) phenyl; and
- (xii) heteroaryl; or
- (xiii) two substituents are taken together to form a fused ring having from 5 to 7 atoms;

$R^4$ is a $C_1$-$C_4$ alkyl or $C_3$-$C_4$ cycloalkyl;

$R^{5a}$ and $R^{5b}$ are each independently selected from:
- (i) hydrogen;
- (ii) $C_1$-$C_4$ alkyl;
- (iii) $C_3$-$C_4$ cycloalkyl; or
- (iv) $R^{5a}$ and $R^{5b}$ are taken together to form a ring having from 3 to 7 atoms;

$R^2$ is selected from:
- (i) $OR^6$
- (ii) $NR^{7a}R^{7b}$; and $R^6$ is selected from hydrogen and $C_1$-$C_4$ alkyl or $C_3$-$C_4$ cycloalkyl;

$R^{7a}$ and $R^{7b}$ are each independently selected from:
- (i) hydrogen;
- (ii) $C_1$-$C_4$ alkyl or $C_3$-$C_4$ cycloalkyl; or
- (iii) $R^{7a}$ and $R^{7b}$ are taken together to form a ring having from 3 to 7 atoms;

$R^3$ is selected from hydrogen, methyl, and ethyl;

L is a linking unit having a structure $—[C(R^{8a}R^{8b})]_n—$ $R^{8a}$ and $R^{8b}$ are each independently selected from hydrogen, methyl and ethyl;

n is an integer from 1 to 3; and $R^9$ is selected from hydrogen and methyl.

In embodiments, R is hydrogen.

In embodiments, R is unsubstituted phenyl. In embodiments, R is substituted phenyl. In embodiments, R is phenyl substituted with $C_1$-$C_4$ alkyl. In embodiments, R is phenyl substituted with $C_3$-$C_4$ cycloalkyl. In embodiments, R is phenyl substituted with $C_1$-$C_4$ alkoxy. In embodiments, R is phenyl substituted with $C_3$-$C_4$ cycloalkoxy. In embodiments, R is phenyl substituted with $C_1$-$C_4$ haloalkyl. In embodiments, R is phenyl substituted with $C_3$-$C_4$ halocycloalkyl. In embodiments, R is phenyl substituted with halogen. In embodiments, R is phenyl substituted with cyano. In embodiments, R is phenyl substituted with $NHC(O)R^4$, wherein $R^4$ is a $C_1$-$C_4$ alkyl or $C_3$-$C_4$ cycloalkyl. In embodiments, R is phenyl substituted with $C(O)NR^{5a}R^{5b}$, wherein $R^{5a}$ and $R^{5b}$ are each independently selected from hydrogen, $C_1$-$C_4$ alkyl, $C_3$-$C_4$ cycloalkyl; or $R^{5a}$ and $R^{5b}$ are taken together to form a ring having from 3 to 7 atoms. In embodiments, R is phenyl substituted with phenyl. In embodiments, R is phenyl substituted with heteroaryl. In embodiments, R is phenyl substituted with two substituents independently selected from the group consisting of $C_1$-$C_4$ alkyl, $C_3$-$C_4$ cycloalkyl, $C_1$-$C_4$ alkoxy, $C_3$-$C_4$ cycloalkoxy, $C_1$-$C_4$ haloalkyl, $C_3$-$C_4$ halocycloalkyl, $NHC(O)R^4$, $C(O)NR^{5a}R^{5b}$, phenyl and heteroaryl, wherein the two substituents are taken together to form a fused ring having from 5 to 7 atoms, and wherein $R^4$ is a $C_1$-$C_4$ alkyl or $C_3$-$C_4$ cycloalkyl, $R^{5a}$ and $R^{5b}$ are each independently selected from hydrogen, $C_1$-$C_4$ alkyl, $C_3$-$C_4$ cycloalkyl, or $R^{5a}$ and $R^{5b}$ are taken together to form a ring having from 3 to 7 atoms.

In embodiments, R is unsubstituted heteroaryl. In embodiments, R is substituted heteroaryl. In embodiments, R is heteroaryl substituted with $C_1$-$C_4$ alkyl. In embodiments, R is heteroaryl substituted with $C_3$-$C_4$ cycloalkyl. In embodiments, R is heteroaryl substituted with $C_1$-$C_4$ alkoxy. In embodiments, R is heteroaryl substituted with $C_3$-$C_4$ cycloalkoxy. In embodiments, R is heteroaryl substituted with $C_1$-$C_4$ haloalkyl. In embodiments, R is heteroaryl substituted with $C_3$-$C_4$ halocycloalkyl. In embodiments, R is heteroaryl substituted with halogen. In embodiments, R is heteroaryl substituted with cyano. In embodiments, R is heteroaryl substituted with $NHC(O)R^4$, wherein $R^4$ is a $C_1$-$C_4$ alkyl or $C_3$-$C_4$ cycloalkyl. In embodiments, R is heteroaryl substituted with $C(O)NR^{5a}R^{5b}$, wherein $R^{5a}$ and $R^{5b}$ are each independently selected from hydrogen, $C_1$-$C_4$ alkyl, $C_3$-$C_4$ cycloalkyl; or $R^{5a}$ and $R^{5b}$ are taken together to form a ring having from 3 to 7 atoms. In embodiments, R is heteroaryl substituted with phenyl. In embodiments, R is heteroaryl substituted with heteroaryl. In embodiments, R is heteroaryl substituted with two substituents independently selected from the group consisting of $C_1$-$C_4$ alkyl, $C_3$-$C_4$ cycloalkyl, $C_1$-$C_4$ alkoxy, $C_3$-$C_4$ cycloalkoxy, $C_1$-$C_4$ haloalkyl, $C_3$-$C_4$ halocycloalkyl, $NHC(O)R^4$, $C(O)NR^{5a}R^{5b}$, phenyl and heteroaryl, wherein the two substituents are taken together to form a fused ring having from 5 to 7 atoms, and wherein $R^4$ is a $C_1$-$C_4$ alkyl or $C_3$-$C_4$ cycloalkyl, $R^{5a}$ and $R^{5b}$ are each independently selected from hydrogen, $C_1$-$C_4$ alkyl, $C_3$-$C_4$ cycloalkyl, or $R^{5a}$ and $R^{5b}$ are taken together to form a ring having from 3 to 7 atoms.

In embodiments, R is unsubstituted alkyl. In embodiments, R is substituted alkyl. In embodiments, R is alkyl substituted with $C_1$-$C_4$ alkyl. In embodiments, R is alkyl substituted with $C_3$-$C_4$ cycloalkyl. In embodiments, R is alkyl substituted with $C_1$-$C_4$ alkoxy. In embodiments, R is alkyl substituted with $C_3$-$C_4$ cycloalkoxy. In embodiments, R is alkyl substituted with $C_1$-$C_4$ haloalkyl. In embodiments, R is alkyl substituted with $C_3$-$C_4$ halocycloalkyl. In embodiments, R is alkyl substituted with halogen. In embodiments, R is alkyl substituted with cyano. In embodiments, R is alkyl substituted with $NHC(O)R^4$, wherein $R^4$ is a $C_1$-$C_4$ alkyl or $C_3$-$C_4$ cycloalkyl. In embodiments, R is alkyl substituted with $C(O)NR^{5a}R^{5b}$, wherein $R^{5a}$ and $R^{5b}$ are each independently selected from hydrogen, $C_1$-$C_4$ alkyl, $C_3$-$C_4$ cycloalkyl; or $R^{5a}$ and $R^{5b}$ are taken together to form a ring having from 3 to 7 atoms. In embodiments, R is alkyl substituted with phenyl. In embodiments, R is alkyl substituted with heteroaryl. In embodiments, R is alkyl substituted with two substituents independently selected from the group consisting of $C_1$-$C_4$ alkyl, $C_3$-$C_4$ cycloalkyl, $C_1$-$C_4$ alkoxy, $C_3$-$C_4$ cycloalkoxy, $C_1$-$C_4$ haloalkyl, $C_3$-$C_4$ halocycloalkyl, $NHC(O)R^4$, $C(O)NR^{5a}R^{5b}$, phenyl and heteroaryl, wherein the two substituents are taken together to form a fused ring having from 5 to 7 atoms, and wherein $R^4$ is a $C_1$-$C_4$ alkyl or $C_3$-$C_4$ cycloalkyl, $R^{5a}$ and $R^{5b}$ are each independently selected from hydrogen, $C_1$-$C_4$ alkyl, $C_3$-$C_4$ cycloalkyl, or $R^{5a}$ and $R^{5b}$ are taken together to form a ring having from 3 to 7 atoms.

In embodiments, R is substituted or unsubstituted phenyl. In embodiments, R is chosen from 2-fluorophenyl, 3-fluorophenyl, 4-fluorophenyl, 2-chlorophenyl, 3-chlorophenyl, and 4-chlorophenyl. In embodiments, R is chosen from 2-methoxyphenyl, 3-methoxyphenyl, 4-methoxyphenyl, 2-ethoxyphenyl, 3-ethoxyphenyl, 4-ethoxyphenyl, 2-iso-propoxyphenyl, 3-iso-propoxyphenyl, 4-iso-propoxyphenyl, 2-cyanophenyl, 3-cyanophenyl, and 4-cyanophenyl.

In embodiments, R is a unit having the formula:

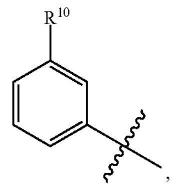

where exemplary groups for $R^{10}$ are as described herein.

In embodiments, $R^{10}$ has the formula —$C(O)NR^{5a}R^{5b}$; $R^{5a}$ and $R^{5b}$ are each hydrogen or $R^{5a}$ and $R^{5b}$ are taken together to from a ring having 5 or 6 atoms. In embodiments, $R^{5a}$ and $R^{5b}$ are taken together to form a pyrrolidin-1-yl ring.

In embodiments, $R^{10}$ has the formula —$NHC(O)R^4$; $R^4$ is a unit chosen from methyl, ethyl, n-propyl, iso-propyl, and cyclopropyl.

In embodiments, $R^{10}$ is a heteroaryl unit chosen from 1,2,3,4-tetrazol-5-yl, [1,2,4]triazol-5-yl, imidazol-2-yl, furan-2-yl, furan-3-yl, thiophene-2-yl, and thiophene-3-yl.

In embodiments, R is substituted or unsubstituted heteroaryl. In embodiments, R is a unit chosen from pyridin-2-yl, pyridin-3-yl, pyridin-4-yl, pyrimidin-2-yl, pyrimidin-4-yl, pyrimidin-5-yl, isoquinolin-1-yl, isoquinolin-3-yl, and isoquinolin-4-yl.

In embodiments, R is a unit chosen from thiazol-2-yl, thiazol-4-yl, 1,2,3,4-tetrazol-5-yl, [1,2,4]triazol-5-yl, imidazol-2-yl, furan-2-yl, furan-3-yl, thiophene-2-yl, and thiophene-3-yl.

In embodiments, $R^1$ is hydrogen.

In embodiments, $R^1$ is unsubstituted phenyl. In embodiments, $R^1$ is substituted phenyl. In embodiments, $R^1$ is phenyl substituted with $C_1$-$C_4$ alkyl. In embodiments, $R^1$ is phenyl substituted with $C_3$-$C_4$ cycloalkyl. In embodiments, $R^1$ is phenyl substituted with $C_1$-$C_4$ alkoxy. In embodiments, $R^1$ is phenyl substituted with $C_3$-$C_4$ cycloalkoxy. In embodiments, $R^1$ is phenyl substituted with $C_1$-$C_4$ haloalkyl. In embodiments, $R^1$ is phenyl substituted with $C_3$-$C_4$ halocycloalkyl. In embodiments, $R^1$ is phenyl substituted with halogen. In embodiments, $R^1$ is phenyl substituted with cyano. In embodiments, $R^1$ is phenyl substituted with $NHC(O)R^4$, wherein $R^4$ is a $C_1$-$C_4$ alkyl or $C_3$-$C_4$ cycloalkyl. In embodiments, $R^1$ is phenyl substituted with $C(O)NR^{5a}R^{5b}$, wherein $R^{5a}$ and $R^{5b}$ are each independently selected from hydrogen, $C_1$-$C_4$ alkyl, $C_3$-$C_4$ cycloalkyl; or $R^{5a}$ and $R^{5b}$ are taken together to form a ring having from 3 to 7 atoms. In embodiments, $R^1$ is phenyl substituted with phenyl. In embodiments, $R^1$ is phenyl substituted with heteroaryl. In embodiments, $R^1$ is phenyl substituted with two substituents independently selected from the group consisting of $C_1$-$C_4$ alkyl, $C_3$-$C_4$ cycloalkyl, $C_1$-$C_4$ alkoxy, $C_3$-$C_4$ cycloalkoxy, $C_1$-$C_4$ haloalkyl, $C_3$-$C_4$ halocycloalkyl, $NHC(O)R^4$, $C(O)NR^{5a}R^{5b}$, phenyl and heteroaryl, wherein the two substituents are taken together to form a fused ring having from 5 to 7 atoms, and wherein $R^4$ is a $C_1$-$C_4$ alkyl or $C_3$-$C_4$ cycloalkyl, $R^{5a}$ and $R^{5b}$ are each independently selected from hydrogen, $C_1$-$C_4$ alkyl, $C_3$-$C_4$ cycloalkyl, or $R^{5a}$ and $R^{5b}$ are taken together to form a ring having from 3 to 7 atoms.

In embodiments, $R^1$ is unsubstituted heteroaryl. In embodiments, $R^1$ is substituted heteroaryl. In embodiments, $R^1$ is heteroaryl substituted with $C_1$-$C_4$ alkyl. In embodiments, $R^1$ is heteroaryl substituted with $C_3$-$C_4$ cycloalkyl. In embodiments, $R^1$ is heteroaryl substituted with $C_1$-$C_4$ alkoxy. In embodiments, $R^1$ is heteroaryl substituted with $C_3$-$C_4$ cycloalkoxy. In embodiments, $R^1$ is heteroaryl substituted with $C_1$-$C_4$ haloalkyl. In embodiments, $R^1$ is heteroaryl substituted with $C_3$-$C_4$ halocycloalkyl. In embodiments, $R^1$ is heteroaryl substituted with halogen. In embodiments, $R^1$ is heteroaryl substituted with cyano. In embodiments, $R^1$ is heteroaryl substituted with $NHC(O)R^4$, wherein $R^4$ is a $C_1$-$C_4$ alkyl or $C_3$-$C_4$ cycloalkyl. In embodiments, $R^1$ is heteroaryl substituted with $C(O)NR^{5a}R^{5b}$, wherein $R^{5a}$ and $R^{5b}$ are each independently selected from hydrogen, $C_1$-$C_4$ alkyl, $C_3$-$C_4$ cycloalkyl; or $R^{5a}$ and $R^{5b}$ are taken together to form a ring having from 3 to 7 atoms. In embodiments, $R^1$ is heteroaryl substituted with phenyl. In embodiments, $R^1$ is heteroaryl substituted with heteroaryl. In embodiments, $R^1$ is heteroaryl substituted with two substituents independently selected from the group consisting of $C_1$-$C_4$ alkyl, $C_3$-$C_4$ cycloalkyl, $C_1$-$C_4$ alkoxy, $C_3$-$C_4$ cycloalkoxy, $C_1$-$C_4$ haloalkyl, $C_3$-$C_4$ halocycloalkyl, $NHC(O)R^4$, $C(O)NR^{5a}R^{5b}$, phenyl and heteroaryl, wherein the two substituents are taken together to form a fused ring having from 5 to 7 atoms, and wherein $R^4$ is a $C_1$-$C_4$ alkyl or $C_3$-$C_4$ cycloalkyl, $R^{5a}$ and $R^{5b}$ are each independently selected from hydrogen, $C_1$-$C_4$ alkyl, $C_3$-$C_4$ cycloalkyl, or $R^{5a}$ and $R^{5b}$ are taken together to form a ring having from 3 to 7 atoms.

In embodiments, $R^1$ is unsubstituted alkyl. In embodiments, $R^1$ is substituted alkyl. In embodiments, $R^1$ is alkyl substituted with $C_1$-$C_4$ alkyl. In embodiments, $R^1$ is alkyl substituted with $C_3$-$C_4$ cycloalkyl. In embodiments, $R^1$ is alkyl substituted with $C_1$-$C_4$ alkoxy. In embodiments, $R^1$ is alkyl substituted with $C_3$-$C_4$ cycloalkoxy. In embodiments, $R^1$ is alkyl substituted with $C_1$-$C_4$ haloalkyl. In embodiments, $R^1$ is alkyl substituted with $C_3$-$C_4$ halocycloalkyl. In embodiments, $R^1$ is alkyl substituted with halogen. In embodiments, $R^1$ is alkyl substituted with cyano. In embodiments, $R^1$ is alkyl substituted with $NHC(O)R^4$, wherein $R^4$ is a $C_1$-$C_4$ alkyl or $C_3$-$C_4$ cycloalkyl. In embodiments, $R^1$ is alkyl substituted with $C(O)NR^{5a}R^{5b}$, wherein $R^{5a}$ and $R^{5b}$ are each independently selected from hydrogen, $C_1$-$C_4$ alkyl, $C_3$-$C_4$ cycloalkyl; or $R^{5a}$ and $R^{5b}$ are taken together to form a ring having from 3 to 7 atoms. In embodiments, $R^1$ is alkyl substituted with phenyl. In embodiments, $R^1$ is alkyl substituted with heteroaryl. In embodiments, $R^1$ is alkyl substituted with two substituents independently selected from the group consisting of $C_1$-$C_4$ alkyl, $C_3$-$C_4$ cycloalkyl, $C_1$-$C_4$ alkoxy, $C_3$-$C_4$ cycloalkoxy, $C_1$-$C_4$ haloalkyl, $C_3$-$C_4$ halocycloalkyl, $NHC(O)R^4$, $C(O)NR^{5a}R^{5b}$, phenyl and heteroaryl, wherein the two substituents are taken together to form a fused ring having from 5 to 7 atoms, and wherein $R^4$ is a $C_1$-$C_4$ alkyl or $C_3$-$C_4$ cycloalkyl, $R^{5a}$ and $R^{5b}$ are each independently selected from hydrogen, $C_1$-$C_4$ alkyl, $C_3$-$C_4$ cycloalkyl, or $R^{5a}$ and $R^{5b}$ are taken together to form a ring having from 3 to 7 atoms.

In embodiments, $R^1$ is chosen from 2-methoxyphenyl, 3-methoxyphenyl, 4-methoxyphenyl, 2-ethoxyphenyl, 3-ethoxyphenyl, 4-ethoxyphenyl, 2-iso-propoxyphenyl, 3-iso-propoxyphenyl, 4-iso-propoxyphenyl, 2-cyanophenyl, 3-cyanophenyl, and 4-cyanophenyl.

In embodiments, $R^2$ is $OR^6$, wherein $R^6$ is hydrogen, $C_1$-$C_4$ alkyl or $C_3$-$C_4$ cycloalkyl. In embodiments, $R^2$ is $NR^{7a}R^{7b}$, wherein $R^{7a}$ and $R^{7b}$ are each independently selected from the group consisting of hydrogen, $C_1$-$C_4$ alkyl, $C_3$-$C_4$ cycloalkyl, or $R^{7a}$ and $R^{7b}$ are taken together to form a ring having from 3 to 7 atoms.

In embodiments, $R^6$ is hydrogen. In embodiments, $R^6$ is methyl.

In embodiments, $R^2$ is $—NR^{7a}R^{7b}$; $R^{7a}$ and $R^{7b}$ are each independently hydrogen, methyl, or ethyl. In embodiments, $R^2$ is chosen from $—NH_2$, $—NHCH_3$, and $—N(CH_3)_2$.

In embodiments, $R^3$ is hydrogen. In embodiments, $R^3$ is methyl. In embodiments, $R^3$ is ethyl.

In embodiments, L is a linking unit having a structure $—[C(R^{8a}R^{8b})]_n—$, wherein $R^{8a}$ and $R^{8b}$ are each independently selected from the group consisting of hydrogen, methyl and ethyl.

In embodiments, L is chosen from $—CH_2—$, $—CH_2CH_2—$, and $—C(CH_3)_2—$. In embodiments, L is $—CH_2—$. In embodiments, L is $—CH_2CH_2—$. In embodiments, L is $—C(CH_3)_2—$.

In embodiments, n is an integer from 1 to 3. In embodiments, n is 1. In embodiments, n is 2. In embodiments, n is 3.

In embodiments, $R^9$ is hydrogen. In embodiments, $R^9$ is methyl.

In embodiments, a compound according to Formula (I) has the following structure:

Formula (Ia)

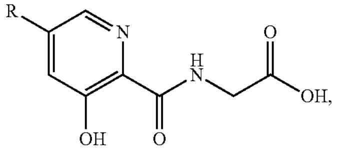

or a pharmaceutically acceptable salt thereof, wherein R is as defined anywhere herein.

In embodiments, a compound according to Formula (I) has the following structure:

Formula (Ib)

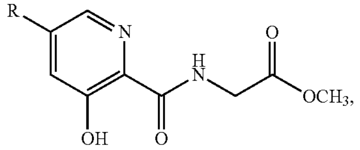

or a pharmaceutically acceptable salt thereof, wherein R is as defined anywhere herein.

In embodiments, a compound according to Formula (I) has the following structure:

Formula (Ic)

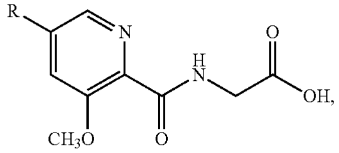

or a pharmaceutically acceptable salt thereof, wherein R is as defined anywhere herein.

In embodiments, R is a heteroaryl unit chosen from thiazol-2-yl, thiazol-4-yl, 1,2,3,4-tetrazol-5-yl, [1,2,4]triazol-5-yl, imidazol-2-yl, furan-2-yl, furan-3-yl, thiophene-2-yl, thiophene-3-yl, pyridin-2-yl, pyridin-3-yl, pyridin-4-yl, pyrimidin-2-yl, pyrimidin-4-yl, pyrimidin-5-yl, isoquinolin-1-yl, isoquinolin-3-yl, and isoquinolin-4-yl.

In embodiments, a compound according to Formula (I) has the following structure:

Formula (Id)

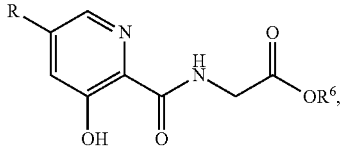

or a pharmaceutically acceptable salt thereof, wherein

R is selected from 2-chlorophenyl, 3-chlorophenyl, 4-chlorophenyl, 2-cyanophenyl, 3-cyanophenyl, and 4-cyanophenyl; and $R^6$ is selected from hydrogen, methyl, and ethyl.

In embodiments, a compound is selected from the group consisting of:

{[5-(3-Chloro-phenyl)-3-hydroxy-pyridine-2-carbonyl]-amino}-acetic acid methyl ester;

{[5-(4-Chloro-phenyl)-3-hydroxy-pyridine-2-carbonyl]-amino}-acetic acid methyl ester;

{[5-(2-Chloro-phenyl)-3-hydroxy-pyridine-2-carbonyl]-amino}-acetic acid methyl ester;

{[5-(4-Fluoro-phenyl)-3-hydroxy-pyridine-2-carbonyl]-amino}-acetic acid methyl ester;

[(3-Hydroxy-5-(4-methylphenyl)-pyridine-2-carbonyl)-amino]-acetic acid methyl ester;

{[3-Hydroxy-5-(4-isopropyl-phenyl)-pyridine-2-carbonyl]-amino}-acetic acid methyl ester;

{[5-(4-Ethyl-phenyl)-3-hydroxy-pyridine-2-carbonyl]-amino}-acetic acid methyl ester;

{[3-Hydroxy-5-(3-trifluoromethyl-phenyl)-pyridine-2-carbonyl]-amino}-acetic acid methyl ester;

{[5-(4-Cyano-phenyl)-3-hydroxy-pyridine-2-carbonyl]-amino}-acetic acid methyl ester;

{[5-(3-Cyano-phenyl)-3-hydroxy-pyridine-2-carbonyl]-amino}-acetic acid methyl ester;

{[5-(3-Carbamoyl-phenyl)-3-hydroxy-pyridine-2-carbonyl]-amino}-acetic acid methyl ester;

({3-Hydroxy-5-[3-(pyrrolidine-1-carbonyl)-phenyl]-pyridine-2-carbonyl}-amino)-acetic acid methyl ester;

({5-[3-(Cyclopropanecarbonyl-amino)-phenyl]-3-hydroxy-pyridine-2-carbonyl}-amino)-acetic acid methyl ester;

({3-Hydroxy-5-[3-(2H-tetrazol-5-yl)-phenyl]-pyridine-2-carbonyl}-amino)-acetic acid methyl ester;

[(5-Hydroxy-[3,3']bipyridinyl-6-carbonyl)-amino]-acetic acid methyl ester

[(5'-Hydroxy-[2,3']bipyridinyl-6'-carbonyl)-amino]-acetic acid methyl ester;

[(3-Hydroxy-5-pyrimidin-5-yl-pyridine-2-carbonyl)-amino]-acetic acid methyl ester;

[(3-Hydroxy-5-isoquinolin-4-yl-pyridine-2-carbonyl)-amino]-acetic acid methyl ester;

[(3-Hydroxy-5-thiazol-2-yl-pyridine-2-carbonyl)-amino]-acetic acid methyl ester;

{[5-(3-Chlorophenyl)-3-hydroxypyridine-2-carbonyl] amino}-acetic acid;

{[5-(4-Chlorophenyl)-3-hydroxypyridine-2-carbonyl] amino}-acetic acid;

{[5-(2-Chlorophenyl)-3-hydroxypyridine-2-carbonyl] amino}-acetic acid;

{[5-(4-Fluorophenyl)-3-hydroxypyridine-2-carbonyl] amino}-acetic acid;

[(3-Hydroxy-5-(4-methylphenyl)pyridine-2-carbonyl) amino]-acetic acid;

{[5-(4-Ethylphenyl)-3-hydroxypyridine-2-carbonyl] amino}-acetic acid;

{[3-Hydroxy-5-(4-isopropylphenyl)pyridine-2-carbonyl] amino}-acetic acid;

{[3-Hydroxy-5-(3-trifluoromethylphenyl)pyridine-2-carbonyl]amino}-acetic acid;

{[5-(4-Cyanophenyl)-3-hydroxypyridine-2-carbonyl] amino}-acetic acid;

{[5-(3-Cyanophenyl)-3-hydroxypyridine-2-carbonyl] amino}-acetic acid;

{[5-(5-Chloro-2-methylphenyl)-3-hydroxypyridine-2-carbonyl]amino}-acetic acid;

{[3-Hydroxy-5-(4-isopropoxyphenyl)pyridine-2-carbonyl] amino}-acetic acid;

({5-[3-(Cyclopropanecarbonylamino)phenyl]-3-hydroxy-pyridine-2-carbonyl}-amino)-acetic acid;

({3-Hydroxy-5-[3-(pyrrolidine-1-carbonyl)phenyl]-pyridine-2-carbonyl}amino)-acetic acid;

({3-Hydroxy-5-[3-(2H-tetrazol-5-yl)phenyl]-pyridine-2-carbonyl}-amino)-acetic acid;

[(5'-Hydroxy-[2,3']bipyridinyl-6'-carbonyl)-amino]-acetic acid;

[(5-Hydroxy-[3,3']bipyridinyl-6-carbonyl)-amino]-acetic acid;

[(3-Hydroxy-5-pyrimidin-5-yl-pyridine-2-carbonyl)-amino]-acetic acid;

[(3-Hydroxy-5-isoquinolin-4-yl-pyridine-2-carbonyl)-amino]-acetic acid;

[(3-Hydroxy-5-thiazol-2-yl-pyridine-2-carbonyl)-amino]-acetic acid;

{[5-(2,3-Dihydro-benzo[1,4]dioxin-6-yl)-3-hydroxy-pyridine-2-carbonyl]-amino}-acetic acid;

5-(Chlorophenyl)-N-(2-amino-2-oxo-1,1-dimethylethyl)-3-hydroxylpyridin-2-yl amide;

5-(Chlorophenyl)-N-(2-amino-2-oxoethyl)-3-hydroxylpyridin-2-yl amide;

5-(Chlorophenyl)-N-(2-amino-2-oxo-1-methylethyl)-3-hydroxylpyridin-2-yl amide;

5-(4-Methylphenyl)-N-(2-methylamino-2-oxoethyl)-3-hydroxylpyridin-2-yl amide;

5-(3-Chlorophenyl)-N-(2-methylamino-2-oxoethyl)-3-hydroxylpyridin-2-yl amide;

2-{[5-(3-Chloro-phenyl)-3-hydroxy-pyridine-2-carbonyl]-amino}-2-methyl-propionic acid methyl ester;

2-{[5-(3-Chlorophenyl)-3-hydroxy-pyridine-2-carbonyl]-amino}-2-methyl-propionic acid 3-[(3-Hydroxy-5-(4-methylphenyl)-pyridine-2-carbonyl)-amino]-propionic acid ethyl ester;

3-[(3-Hydroxy-5-(3-chlorophenyl)-pyridine-2-carbonyl)-amino]-propionic acid ethyl ester;

3-{[5-(3-Chlorophenyl)-3-hydroxy-pyridine-2-carbonyl]-amino}-propionic acid;

3-[(3-Hydroxy-5-(4-methylphenyl)-pyridine-2-carbonyl)-amino]-propionic acid;

5-(Chlorophenyl)-N-(3-amino-3-oxo-1,1-dimethylpropyl)-3-hydroxylpyridin-2-yl amide; and 5-(3-Chlorophenyl)-N-(2-dimethylamino-2-oxoethyl)-3-hydroxylpyridin-2-yl amide; or a pharmaceutically acceptable salt thereof.

In embodiments, compounds are salts comprising anions chosen from chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, and citrate.

In embodiments, compounds are salts comprising cations chosen from sodium, lithium, potassium, calcium, magnesium, and bismuth.

In embodiments, a compound is {[5-(3-chlorophenyl)-3-hydroxypyridine-2-carbonyl]amino}acetic acid (Compound 1), or a pharmaceutically acceptable salt thereof. Compound 1, also referred to as vadadustat or AKB-6548, has the following structure:

Compound 1

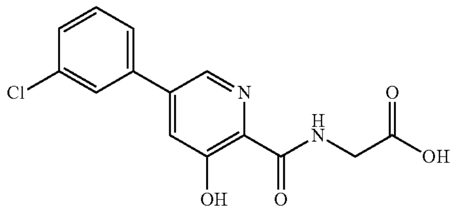 [SMILES: O=C(O)CNC(=O)c1ncc(-c2cccc(Cl)c2)cc1O]

(vadadustat, or AKB-6548)

In embodiments, a compound is {[5-(3-fluorophenyl)-3-hydroxypyridine-2-carbonyl]amino}acetic acid (Compound Ia), or a pharmaceutically acceptable salt thereof. Compound 1a, also referred to as AKB-6899, has the following structure:

Compound 1a

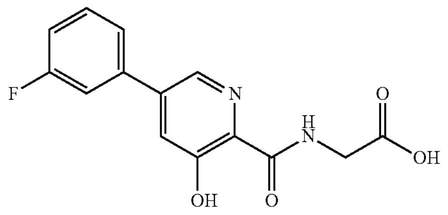

(AKB-6899)

Formula (II): Enarodustat and Other Compounds

Exemplary compounds that can be used in any of the methods described herein include those described in U.S. Pat. No. 8,283,465, U.S. Publication No. US20160145254A1, and U.S. Publication No. US20200017492A1, each of which is incorporated by reference in its entirety. In embodiments, a compound, or pharmaceutically acceptable salt thereof, is described in any of claims 1-30 of U.S. Pat. No. 8,283,465.

In embodiments, suitable compounds include a compound having a structure according to Formula (II), Formula (II)

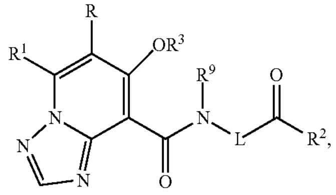

or a pharmaceutically acceptable salt thereof, wherein

R and $R^1$ are each independently:

(i) hydrogen (ii) substituted or unsubstituted phenyl;

(iii) substituted or unsubstituted heteroaryl; or (iv) substituted or unsubstituted alkyl;

said substitution selected from:

(i) $C_1$-$C_4$ alkyl;

(ii) $C_3$-$C_4$ cycloalkyl;

(iii) $C_1$-$C_4$ alkoxy;

(iv) $C_3$-$C_4$ cycloalkoxy;

(v) $C_1$-$C_4$ haloalkyl;

(vi) $C_3$-$C_4$ halocycloalkyl;

(vii) halogen;

(viii) cyano;

(ix) $NHC(O)R^4$;

(x) $C(O)NR^{5a}R^{5b}$;

phenyl; and (xii) heteroaryl; or (xiii) two substituents are taken together to form a fused ring having from 5 to 7 atoms;

$R^4$ is a $C_1$-$C_4$ alkyl or $C_3$-$C_4$ cycloalkyl;

$R^{5a}$ and $R^{5b}$ are each independently selected from:

(i) hydrogen;

(ii) $C_1$-$C_4$ alkyl;

(iii) $C_3$-$C_4$ cycloalkyl; or (iv) $R^{5a}$ and $R^{5b}$ are taken together to form a ring having from 3 to 7 atoms;

$R^2$ is selected from:

(i) $OR^6$ (ii) $NR^{7a}R^{7b}$; and $R^6$ is selected from hydrogen and $C_1$-$C_4$ alkyl or $C_3$-$C_4$ cycloalkyl;

$R^{7a}$ and $R^{7b}$ are each independently selected from:

(i) hydrogen;

(ii) $C_1$-$C_4$ alkyl or $C_3$-$C_4$ cycloalkyl; or (iii) $R^{7a}$ and $R^{7b}$ are taken together to form a ring having from 3 to 7 atoms;

$R^3$ is selected from hydrogen, methyl, and ethyl;

L is a linking unit having a structure $-[C(R^{8a}R^{8b})]_n-$ $R^{8a}$ and $R^{8b}$ are each independently selected from hydrogen, methyl and ethyl;

n is an integer from 1 to 3; and $R^9$ is selected from hydrogen and methyl.

In embodiments, R is hydrogen.

In embodiments, R is unsubstituted phenyl. In embodiments, R is substituted phenyl. In embodiments, R is phenyl substituted with $C_1$-$C_4$ alkyl. In embodiments, R is phenyl substituted with $C_3$-$C_4$ cycloalkyl. In embodiments, R is phenyl substituted with $C_1$-$C_4$ alkoxy. In embodiments, R is phenyl substituted with $C_3$-$C_4$ cycloalkoxy. In embodiments, R is phenyl substituted with $C_1$-$C_4$ haloalkyl. In embodiments, R is phenyl substituted with $C_3$-$C_4$ halocycloalkyl. In embodiments, R is phenyl substituted with halogen. In embodiments, R is phenyl substituted with cyano. In embodiments, R is phenyl substituted with $NHC(O)R^4$, wherein $R^4$ is a $C_1$-$C_4$ alkyl or $C_3$-$C_4$ cycloalkyl. In embodiments, R is phenyl substituted with $C(O)NR^{5a}R^{5b}$, wherein $R^{5a}$ and $R^{5b}$ are each independently selected from hydrogen, $C_1$-$C_4$ alkyl, $C_3$-$C_4$ cycloalkyl; or $R^{5a}$ and $R^{5b}$ are taken together to form a ring having from 3 to 7 atoms. In embodiments, R is phenyl substituted with phenyl. In embodiments, R is phenyl substituted with heteroaryl. In embodiments, R is phenyl substituted with two substituents independently selected from the group consisting of $C_1$-$C_4$ alkyl, $C_3$-$C_4$ cycloalkyl, $C_1$-$C_4$ alkoxy, $C_3$-$C_4$ cycloalkoxy, $C_1$-$C_4$ haloalkyl, $C_3$-$C_4$ halocycloalkyl, $NHC(O)R^4$, $C(O)NR^{5a}R^{5b}$, phenyl and heteroaryl, wherein the two substituents are taken together to form a fused ring having from 5 to 7 atoms, and wherein $R^4$ is a $C_1$-$C_4$ alkyl or $C_3$-$C_4$ cycloalkyl, $R^{5a}$ and $R^{5b}$ are each independently selected from hydrogen, $C_1$-$C_4$ alkyl, $C_3$-$C_4$ cycloalkyl, or $R^{5a}$ and $R^{5b}$ are taken together to form a ring having from 3 to 7 atoms.

In embodiments, R is unsubstituted heteroaryl. In embodiments, R is substituted heteroaryl. In embodiments, R is heteroaryl substituted with $C_1$-$C_4$ alkyl. In embodiments, R is heteroaryl substituted with $C_3$-$C_4$ cycloalkyl. In embodiments, R is heteroaryl substituted with $C_1$-$C_4$ alkoxy. In embodiments, R is heteroaryl substituted with $C_3$-$C_4$ cycloalkoxy. In embodiments, R is heteroaryl substituted with $C_1$-$C_4$ haloalkyl. In embodiments, R is heteroaryl substituted with $C_3$-$C_4$ halocycloalkyl. In embodiments, R is heteroaryl substituted with halogen. In embodiments, R is heteroaryl substituted with cyano. In embodiments, R is heteroaryl substituted with $NHC(O)R^4$, wherein $R^4$ is a $C_1$-$C_4$ alkyl or $C_3$-$C_4$ cycloalkyl. In embodiments, R is heteroaryl substituted with $C(O)NR^{5a}R^{5b}$, wherein $R^{5a}$ and $R^{5b}$ are each independently selected from hydrogen, $C_1$-$C_4$ alkyl, $C_3$-$C_4$ cycloalkyl; or $R^{5a}$ and $R^{5b}$ are taken together to form a ring having from 3 to 7 atoms. In embodiments, R is heteroaryl substituted with phenyl. In embodiments, R is heteroaryl substituted with heteroaryl. In embodiments, R is heteroaryl substituted with two substituents independently selected from the group consisting of $C_1$-$C_4$ alkyl, $C_3$-$C_4$ cycloalkyl, $C_1$-$C_4$ alkoxy, $C_3$-$C_4$ cycloalkoxy, $C_1$-$C_4$ haloalkyl, $C_3$-$C_4$ halocycloalkyl, $NHC(O)R^4$, $C(O)NR^{5a}R^{5b}$, phenyl and heteroaryl, wherein the two substituents are taken together to form a fused ring having from 5 to 7 atoms, and wherein $R^4$ is a $C_1$-$C_4$ alkyl or $C_3$-$C_4$ cycloalkyl, $R^{5a}$ and $R^{5b}$ are each independently selected from hydrogen, $C_1$-$C_4$ alkyl, $C_3$-$C_4$ cycloalkyl, or $R^{5a}$ and $R^{5b}$ are taken together to form a ring having from 3 to 7 atoms.

In embodiments, R is unsubstituted alkyl. In embodiments, R is substituted alkyl. In embodiments, R is alkyl substituted with $C_1$-$C_4$ alkyl. In embodiments, R is alkyl substituted with $C_3$-$C_4$ cycloalkyl. In embodiments, R is alkyl substituted with $C_1$-$C_4$ alkoxy. In embodiments, R is alkyl substituted with $C_3$-$C_4$ cycloalkoxy. In embodiments, R is alkyl substituted with $C_1$-$C_4$ haloalkyl. In embodiments, R is alkyl substituted with $C_3$-$C_4$ halocycloalkyl. In embodiments, R is alkyl substituted with halogen. In embodiments, R is alkyl substituted with cyano. In embodiments, R is alkyl substituted with NHC(O)$R^4$, wherein $R^4$ is a $C_1$-$C_4$ alkyl or $C_3$-$C_4$ cycloalkyl. In embodiments, R is alkyl substituted with C(O)N$R^{5a}R^{5b}$, wherein $R^{5a}$ and $R^{5b}$ are each independently selected from hydrogen, $C_1$-$C_4$ alkyl, $C_3$-$C_4$ cycloalkyl; or $R^{5a}$ and $R^{5b}$ are taken together to form a ring having from 3 to 7 atoms. In embodiments, R is alkyl substituted with phenyl. In embodiments, R is alkyl substituted with heteroaryl. In embodiments, R is alkyl substituted with two substituents independently selected from the group consisting of $C_1$-$C_4$ alkyl, $C_3$-$C_4$ cycloalkyl, $C_1$-$C_4$ alkoxy, $C_3$-$C_4$ cycloalkoxy, $C_1$-$C_4$ haloalkyl, $C_3$-$C_4$ halocycloalkyl, NHC(O)$R^4$, C(O)N$R^{5a}R^{5b}$, phenyl and heteroaryl, wherein the two substituents are taken together to form a fused ring having from 5 to 7 atoms, and wherein $R^4$ is a $C_1$-$C_4$ alkyl or $C_3$-$C_4$ cycloalkyl, $R^{5a}$ and $R^{5b}$ are each independently selected from hydrogen, $C_1$-$C_4$ alkyl, $C_3$-$C_4$ cycloalkyl, or $R^{5a}$ and $R^{5b}$ are taken together to form a ring having from 3 to 7 atoms.

In embodiments, R is substituted or unsubstituted alkyl. In embodiments, R is a $C_1$-$C_6$ alkyl. In embodiments, R is a $C_3$-$C_8$ cycloalkyl. In embodiments, R is a $C_6$-$C_{14}$ aryl. In embodiments, R is a $C_6$-$C_{14}$ aryl. In embodiments, R is a $C_6$-$C_{14}$ aryl-$C_1$-$C_6$ alkyl group.

In embodiments, $R^1$ is hydrogen.

In embodiments, $R^1$ is unsubstituted phenyl. In embodiments, $R^1$ is substituted phenyl. In embodiments, $R^1$ is phenyl substituted with $C_1$-$C_4$ alkyl. In embodiments, $R^1$ is phenyl substituted with $C_3$-$C_4$ cycloalkyl. In embodiments, $R^1$ is phenyl substituted with $C_1$-$C_4$ alkoxy. In embodiments, $R^1$ is phenyl substituted with $C_3$-$C_4$ cycloalkoxy. In embodiments, $R^1$ is phenyl substituted with $C_1$-$C_4$ haloalkyl. In embodiments, $R^1$ is phenyl substituted with $C_3$-$C_4$ halocycloalkyl. In embodiments, $R^1$ is phenyl substituted with halogen. In embodiments, $R^1$ is phenyl substituted with cyano. In embodiments, $R^1$ is phenyl substituted with NHC(O)$R^4$, wherein $R^4$ is a $C_1$-$C_4$ alkyl or $C_3$-$C_4$ cycloalkyl. In embodiments, $R^1$ is phenyl substituted with C(O)N$R^{5a}R^{5b}$, wherein $R^{5a}$ and $R^{5b}$ are each independently selected from hydrogen, $C_1$-$C_4$ alkyl, $C_3$-$C_4$ cycloalkyl; or $R^{5a}$ and $R^{5b}$ are taken together to form a ring having from 3 to 7 atoms. In embodiments, $R^1$ is phenyl substituted with phenyl. In embodiments, $R^1$ is phenyl substituted with heteroaryl. In embodiments, $R^1$ is phenyl substituted with two substituents independently selected from the group consisting of $C_1$-$C_4$ alkyl, $C_3$-$C_4$ cycloalkyl, $C_1$-$C_4$ alkoxy, $C_3$-$C_4$ cycloalkoxy, $C_1$-$C_4$ haloalkyl, $C_3$-$C_4$ halocycloalkyl, NHC(O)$R^4$, C(O)N$R^{5a}R^{5b}$, phenyl and heteroaryl, wherein the two substituents are taken together to form a fused ring having from 5 to 7 atoms, and wherein $R^4$ is a $C_1$-$C_4$ alkyl or $C_3$-$C_4$ cycloalkyl, $R^{5a}$ and $R^{5b}$ are each independently selected from hydrogen, $C_1$-$C_4$ alkyl, $C_3$-$C_4$ cycloalkyl, or $R^{5a}$ and $R^{5b}$ are taken together to form a ring having from 3 to 7 atoms.

In embodiments, $R^1$ is unsubstituted heteroaryl. In embodiments, $R^1$ is substituted heteroaryl. In embodiments, $R^1$ is heteroaryl substituted with $C_1$-$C_4$ alkyl. In embodiments, $R^1$ is heteroaryl substituted with $C_3$-$C_4$ cycloalkyl. In embodiments, $R^1$ is heteroaryl substituted with $C_1$-$C_4$ alkoxy. In embodiments, $R^1$ is heteroaryl substituted with $C_3$-$C_4$ cycloalkoxy. In embodiments, $R^1$ is heteroaryl substituted with $C_1$-$C_4$ haloalkyl. In embodiments, $R^1$ is heteroaryl substituted with $C_3$-$C_4$ halocycloalkyl. In embodiments, $R^1$ is heteroaryl substituted with halogen. In embodiments, $R^1$ is heteroaryl substituted with cyano. In embodiments, $R^1$ is heteroaryl substituted with NHC(O)$R^4$, wherein $R^4$ is a $C_1$-$C_4$ alkyl or $C_3$-$C_4$ cycloalkyl. In embodiments, $R^1$ is heteroaryl substituted with C(O)N$R^{5a}R^{5b}$, wherein $R^{5a}$ and $R^{5b}$ are each independently selected from hydrogen, $C_1$-$C_4$ alkyl, $C_3$-$C_4$ cycloalkyl; or $R^{5a}$ and $R^{5b}$ are taken together to form a ring having from 3 to 7 atoms. In embodiments, $R^1$ is heteroaryl substituted with phenyl. In embodiments, $R^1$ is heteroaryl substituted with heteroaryl. In embodiments, $R^1$ is heteroaryl substituted with two substituents independently selected from the group consisting of $C_1$-$C_4$ alkyl, $C_3$-$C_4$ cycloalkyl, $C_1$-$C_4$ alkoxy, $C_3$-$C_4$ cycloalkoxy, $C_1$-$C_4$ haloalkyl, $C_3$-$C_4$ halocycloalkyl, NHC(O)$R^4$, C(O)N$R^{5a}R^{5b}$, phenyl and heteroaryl, wherein the two substituents are taken together to form a fused ring having from 5 to 7 atoms, and wherein $R^4$ is a $C_1$-$C_4$ alkyl or $C_3$-$C_4$ cycloalkyl, $R^{5a}$ and $R^{5b}$ are each independently selected from hydrogen, $C_1$-$C_4$ alkyl, $C_3$-$C_4$ cycloalkyl, or $R^{5a}$ and $R^{5b}$ are taken together to form a ring having from 3 to 7 atoms.

In embodiments, $R^1$ is unsubstituted alkyl. In embodiments, $R^1$ is substituted alkyl. In embodiments, $R^1$ is alkyl substituted with $C_1$-$C_4$ alkyl. In embodiments, $R^1$ is alkyl substituted with $C_3$-$C_4$ cycloalkyl. In embodiments, $R^1$ is alkyl substituted with $C_1$-$C_4$ alkoxy. In embodiments, $R^1$ is alkyl substituted with $C_3$-$C_4$ cycloalkoxy. In embodiments, $R^1$ is alkyl substituted with $C_1$-$C_4$ haloalkyl. In embodiments, $R^1$ is alkyl substituted with $C_3$-$C_4$ halocycloalkyl. In embodiments, $R^1$ is alkyl substituted with halogen. In embodiments, $R^1$ is alkyl substituted with cyano. In embodiments, $R^1$ is alkyl substituted with NHC(O)$R^4$, wherein $R^4$ is a $C_1$-$C_4$ alkyl or $C_3$-$C_4$ cycloalkyl. In embodiments, $R^1$ is alkyl substituted with C(O)N$R^{5a}R^{5b}$, wherein $R^{5a}$ and $R^{5b}$ are each independently selected from hydrogen, $C_1$-$C_4$ alkyl, $C_3$-$C_4$ cycloalkyl; or $R^{5a}$ and $R^{5b}$ are taken together to form a ring having from 3 to 7 atoms. In embodiments, $R^1$ is alkyl substituted with phenyl. In embodiments, $R^1$ is alkyl substituted with heteroaryl. In embodiments, $R^1$ is alkyl substituted with two substituents independently selected from the group consisting of $C_1$-$C_4$ alkyl, $C_3$-$C_4$ cycloalkyl, $C_1$-$C_4$ alkoxy, $C_3$-$C_4$ cycloalkoxy, $C_1$-$C_4$ haloalkyl, $C_3$-$C_4$ halocycloalkyl, NHC(O)$R^4$, C(O)N$R^{5a}R^{5b}$, phenyl and heteroaryl, wherein the two substituents are taken together to form a fused ring having from 5 to 7 atoms, and wherein $R^4$ is a $C_1$-$C_4$ alkyl or $C_3$-$C_4$ cycloalkyl, $R^{5a}$ and $R^{5b}$ are each independently selected from hydrogen, $C_1$-$C_4$ alkyl, $C_3$-$C_4$ cycloalkyl, or $R^{5a}$ and $R^{5b}$ are taken together to form a ring having from 3 to 7 atoms.

In embodiments, $R^1$ is $C_1$-$C_{10}$ alkyl. In embodiments, $R^1$ is $C_3$-$C_8$ unsubstituted cycloalkyl. In embodiments, $R^1$ is substituted $C_3$-$C_8$ cycloalkyl. In embodiments, $R^1$ is $C_3$-$C_8$ cycloalkyl substituted with 1 to 5 substituents independently selected from the group consisting of halogen, $C_1$-$C_6$ alkyl, $C_3$-$C_8$ cycloalkyl, cyano, and $C_1$-$C_6$ haloalkyl. In embodiments, $R^1$ is unsubstituted $C_3$-$C_8$ cycloalkenyl. In embodiments, $R^1$ is substituted $C_3$-$C_8$ cycloalkenyl. In embodiments, $R^1$ is $C_3$-$C_8$ cycloalkenyl substituted with 1 to 5 substituents independently selected from the group consisting of halogen, $C_1$-$C_6$ alkyl, $C_3$-$C_8$ cycloalkyl, cyano, and $C_1$-$C_6$ haloalkyl.

In embodiments, $R^1$ is unsubstituted $C_6$-$C_{14}$ aryl. In embodiments, $R^1$ is substituted $C_6$-$C_{14}$ aryl. In embodiments, $R^1$ is $C_6$-$C_{14}$ aryl substituted with 1 to 5 substituents independently selected from the group consisting of halogen, $C_1$-$C_6$ alkyl, $C_3$-$C_8$ cycloalkyl, cyano, and $C_1$-$C_6$ haloalkyl. In embodiments, $R^1$ is unsubstituted heteroaryl, wherein the heteroaryl has, besides carbon atom, 1 to 6 hetero atoms selected from nitrogen atom, oxygen atom and sulfur atom. In embodiments, $R^1$ is substituted $C_6$-$C_{14}$ heteroaryl, wherein the heteroaryl has, besides carbon atom, 1 to 6 hetero atoms selected from nitrogen atom, oxygen atom and sulfur atom. In embodiments, $R^1$ is heteroaryl substituted with 1 to 5 substituents independently selected from the group consisting of halogen, $C_1$-$C_6$ alkyl, $C_3$-$C_8$ cycloalkyl, cyano, and $C_1$-$C_6$ haloalkyl, and wherein the heteroaryl has, besides carbon atom, 1 to 6 hetero atoms selected from nitrogen atom, oxygen atom and sulfur atom.

In embodiments, $R^1$ is a $C_6$-$C_{14}$ aryl-$C_1$-$C_6$ alkyl group, wherein $C_6$-$C_{14}$ aryl is optionally substituted by the same or different 1 to 5 substituents selected from the group consisting of halogen, $C_1$-$C_6$ alkyl, $C_3$-$C_8$ cycloalkyl, cyano, and $C_1$-$C_6$ haloalkyl. In embodiments, $R^1$ is a $C_3$-$C_8$ cycloalkyl-$C_1$-$C_6$ alkyl group, wherein $C_3$-$C_8$ cycloalkyl is optionally substituted with 1 to 5 substituents independently selected from the group consisting of halogen, $C_1$-$C_6$ alkyl, $C_3$-$C_8$ cycloalkyl, cyano, and $C_1$-$C_6$ haloalkyl. In embodiments, $R^1$ is a phenyl-$C_1$-$C_6$ alkyl group.

In embodiments, $R^2$ is $OR^6$, wherein $R^6$ is hydrogen, $C_1$-$C_4$ alkyl or $C_3$-$C_4$ cycloalkyl. In embodiments, $R^2$ is $NR^{7a}R^{7b}$, wherein $R^{7a}$ and $R^{7b}$ are each independently selected from the group consisting of hydrogen, $C_1$-$C_4$ alkyl, $C_3$-$C_4$ cycloalkyl, or $R^{7a}$ and $R^{7b}$ are taken together to form a ring having from 3 to 7 atoms.

In embodiments, $R^3$ is hydrogen. In embodiments, $R^3$ is methyl. In embodiments, $R^3$ is ethyl.

In embodiments, L is a linking unit having a structure $—[C(R^{8a}R^{8b})]_n—$, wherein $R^{8a}$ and $R^{8b}$ are each independently selected from the group consisting of hydrogen, methyl and ethyl.

In embodiments, n is an integer from 1 to 3. In embodiments, n is 1. In embodiments, n is 2. In embodiments, n is 3.

In embodiments, $R^9$ is hydrogen. In embodiments, $R^9$ is methyl.

In embodiments, a compound is [(7-hydroxy-5-phenethyl [1,2,4] triazolo [1,5-a] pyridine-8-carbonyl)aminoacetic acid (Compound 2), or a pharmaceutically acceptable salt thereof. Compound 2, also referred to as enarodustat, or JTZ-951, has the following structure:

Compound 2

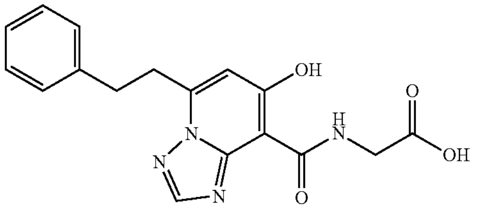

(enarodustat, or JTZ-951)

Formula (III): Desidustat and Related Compounds

Exemplary compounds that can be used in any of the methods described herein include those described in U.S. Pat. No. 9,394,300, and U.S. Publication No. US 20190359574A1, each of which is incorporated by reference in its entirety. In embodiments, a compound, or pharmaceutically acceptable salt thereof, is described in any of claims 1-10 of U.S. Pat. No. 9,394,300.

In embodiments, suitable compounds include a compound having a structure according to Formula (III), Formula (III)

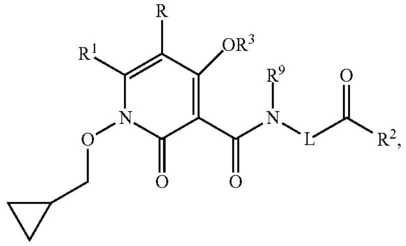

or a pharmaceutically acceptable salt thereof, wherein,

R and $R^1$ are each independently:
- (i) hydrogen
- (ii) substituted or unsubstituted phenyl;
- (iii) substituted or unsubstituted heteroaryl; or
- (iv) substituted or unsubstituted alkyl;

said substitution selected from:
- (i) $C_1$-$C_4$ alkyl;
- (ii) $C_3$-$C_4$ cycloalkyl;
- (iii) $C_1$-$C_4$ alkoxy;
- (iv) $C_3$-$C_4$ cycloalkoxy;
- (v) $C_1$-$C_4$ haloalkyl;
- (vi) $C_3$-$C_4$ halocycloalkyl;
- (vii) halogen;
- (viii) cyano;
- (ix) $NHC(O)R^4$;
- (x) $C(O)NR^{5a}R^{5b}$;
- (xi) phenyl; and
- (xii) heteroaryl; or
- (xiii) two substituents are taken together to form a fused ring having from 5 to 7 atoms;

$R^4$ is a $C_1$-$C_4$ alkyl or $C_3$-$C_4$ cycloalkyl;

$R^{5a}$ and $R^{5b}$ are each independently selected from:
- (i) hydrogen;
- (ii) $C_1$-$C_4$ alkyl;
- (iii) $C_3$-$C_4$ cycloalkyl; or
- (iv) $R^{5a}$ and $R^{5b}$ are taken together to form a ring having from 3 to 7 atoms;

$R^2$ is selected from:
- (i) $OR^6$
- (ii) $NR^{7a}R^{7b}$; and $R^6$ is selected from hydrogen and $C_1$-$C_4$ alkyl or $C_3$-$C_4$ cycloalkyl;

$R^{7a}$ and $R^{7b}$ are each independently selected from:
- (i) hydrogen;
- (ii) $C_1$-$C_4$ alkyl or $C_3$-$C_4$ cycloalkyl; or
- (iii) $R^{7a}$ and $R^{7b}$ are taken together to form a ring having from 3 to 7 atoms;

$R^3$ is selected from hydrogen, methyl, and ethyl;

L is a linking unit having a structure $—[C(R^{8a}R^{8b})]_n—$ $R^{8a}$ and $R^{8b}$ are each independently selected from hydrogen, methyl and ethyl;

n is an integer from 1 to 3; and $R^9$ is selected from hydrogen and methyl.

In embodiments, R is hydrogen.

In embodiments, R is unsubstituted phenyl. In embodiments, R is substituted phenyl. In embodiments, R is phenyl substituted with $C_1$-$C_4$ alkyl. In embodiments, R is phenyl substituted with $C_3$-$C_4$ cycloalkyl. In embodiments, R is phenyl substituted with $C_1$-$C_4$ alkoxy. In embodiments, R is phenyl substituted with $C_3$-$C_4$ cycloalkoxy. In embodiments, R is phenyl substituted with $C_1$-$C_4$ haloalkyl. In embodiments, R is phenyl substituted with $C_3$-$C_4$ halocycloalkyl. In embodiments, R is phenyl substituted with halogen. In embodiments, R is phenyl substituted with cyano. In embodiments, R is phenyl substituted with $NHC(O)R^4$, wherein $R^4$ is a $C_1$-$C_4$ alkyl or $C_3$-$C_4$ cycloalkyl. In embodiments, R is phenyl substituted with $C(O)NR^{5a}R^{5b}$, wherein $R^{5a}$ and $R^{5b}$ are each independently selected from hydrogen, $C_1$-$C_4$ alkyl, $C_3$-$C_4$ cycloalkyl; or $R^{5a}$ and $R^{5b}$ are taken together to form a ring having from 3 to 7 atoms. In embodiments, R is phenyl substituted with phenyl. In embodiments, R is phenyl substituted with heteroaryl. In embodiments, R is phenyl substituted with two substituents independently selected from the group consisting of $C_1$-$C_4$ alkyl, $C_3$-$C_4$ cycloalkyl, $C_1$-$C_4$ alkoxy, $C_3$-$C_4$ cycloalkoxy, $C_1$-$C_4$ haloalkyl, $C_3$-$C_4$ halocycloalkyl, $NHC(O)R^4$, $C(O)NR^{5a}R^{5b}$, phenyl and heteroaryl, wherein the two substituents are taken together to form a fused ring having from 5 to 7 atoms, and wherein $R^4$ is a $C_1$-$C_4$ alkyl or $C_3$-$C_4$ cycloalkyl, $R^{5a}$ and $R^{5b}$ are each independently selected from hydrogen, $C_1$-$C_4$ alkyl, $C_3$-$C_4$ cycloalkyl, or $R^{5a}$ and $R^{5b}$ are taken together to form a ring having from 3 to 7 atoms.

In embodiments, R is unsubstituted heteroaryl. In embodiments, R is substituted heteroaryl. In embodiments, R is heteroaryl substituted with $C_1$-$C_4$ alkyl. In embodiments, R is heteroaryl substituted with $C_3$-$C_4$ cycloalkyl. In embodiments, R is heteroaryl substituted with $C_1$-$C_4$ alkoxy. In embodiments, R is heteroaryl substituted with $C_3$-$C_4$ cycloalkoxy. In embodiments, R is heteroaryl substituted with $C_1$-$C_4$ haloalkyl. In embodiments, R is heteroaryl substituted with $C_3$-$C_4$ halocycloalkyl. In embodiments, R is heteroaryl substituted with halogen. In embodiments, R is heteroaryl substituted with cyano. In embodiments, R is heteroaryl substituted with $NHC(O)R^4$, wherein $R^4$ is a $C_1$-$C_4$ alkyl or $C_3$-$C_4$ cycloalkyl. In embodiments, R is heteroaryl substituted with $C(O)NR^{5a}R^{5b}$, wherein $R^{5a}$ and $R^{5b}$ are each independently selected from hydrogen, $C_1$-$C_4$ alkyl, $C_3$-$C_4$ cycloalkyl; or $R^{5a}$ and $R^{5b}$ are taken together to form a ring having from 3 to 7 atoms. In embodiments, R is heteroaryl substituted with phenyl. In embodiments, R is heteroaryl substituted with heteroaryl. In embodiments, R is heteroaryl substituted with two substituents independently selected from the group consisting of $C_1$-$C_4$ alkyl, $C_3$-$C_4$ cycloalkyl, $C_1$-$C_4$ alkoxy, $C_3$-$C_4$ cycloalkoxy, $C_1$-$C_4$ haloalkyl, $C_3$-$C_4$ halocycloalkyl, $NHC(O)R^4$, $C(O)NR^{5a}R^{5b}$, phenyl and heteroaryl, wherein the two substituents are taken together to form a fused ring having from 5 to 7 atoms, and wherein $R^4$ is a $C_1$-$C_4$ alkyl or $C_3$-$C_4$ cycloalkyl, $R^{5a}$ and $R^{5b}$ are each independently selected from hydrogen, $C_1$-$C_4$ alkyl, $C_3$-$C_4$ cycloalkyl, or $R^{5a}$ and $R^{5b}$ are taken together to form a ring having from 3 to 7 atoms.

In embodiments, R is unsubstituted alkyl. In embodiments, R is substituted alkyl. In embodiments, R is alkyl substituted with $C_1$-$C_4$ alkyl. In embodiments, R is alkyl substituted with $C_3$-$C_4$ cycloalkyl. In embodiments, R is alkyl substituted with $C_1$-$C_4$ alkoxy. In embodiments, R is alkyl substituted with $C_3$-$C_4$ cycloalkoxy. In embodiments, R is alkyl substituted with $C_1$-$C_4$ haloalkyl. In embodiments, R is alkyl substituted with $C_3$-$C_4$ halocycloalkyl. In embodiments, R is alkyl substituted with halogen. In embodiments, R is alkyl substituted with cyano. In embodiments, R is alkyl substituted with $NHC(O)R^4$, wherein $R^4$ is a $C_1$-$C_4$ alkyl or $C_3$-$C_4$ cycloalkyl. In embodiments, R is alkyl substituted with $C(O)NR^{5a}R^{5b}$, wherein $R^{5a}$ and $R^{5b}$ are each independently selected from hydrogen, $C_1$-$C_4$ alkyl, $C_3$-$C_4$ cycloalkyl; or $R^{5a}$ and $R^{5b}$ are taken together to form a ring having from 3 to 7 atoms. In embodiments, R is alkyl substituted with phenyl. In embodiments, R is alkyl substituted with heteroaryl. In embodiments, R is alkyl substituted with two substituents independently selected from the group consisting of $C_1$-$C_4$ alkyl, $C_3$-$C_4$ cycloalkyl, $C_1$-$C_4$ alkoxy, $C_3$-$C_4$ cycloalkoxy, $C_1$-$C_4$ haloalkyl, $C_3$-$C_4$ halocycloalkyl, $NHC(O)R^4$, $C(O)NR^{5a}R^{5b}$, phenyl and heteroaryl, wherein the two substituents are taken together to form a fused ring having from 5 to 7 atoms, and wherein $R^4$ is a $C_1$-$C_4$ alkyl or $C_3$-$C_4$ cycloalkyl, $R^{5a}$ and $R^{5b}$ are each independently selected from hydrogen, $C_1$-$C_4$ alkyl, $C_3$-$C_4$ cycloalkyl, or $R^{5a}$ and $R^{5b}$ are taken together to form a ring having from 3 to 7 atoms.

In embodiments, $R^1$ is hydrogen.

In embodiments, $R^1$ is unsubstituted phenyl. In embodiments, $R^1$ is substituted phenyl. In embodiments, $R^1$ is phenyl substituted with $C_1$-$C_4$ alkyl. In embodiments, $R^1$ is phenyl substituted with $C_3$-$C_4$ cycloalkyl. In embodiments, $R^1$ is phenyl substituted with $C_1$-$C_4$ alkoxy. In embodiments, $R^1$ is phenyl substituted with $C_3$-$C_4$ cycloalkoxy. In embodiments, $R^1$ is phenyl substituted with $C_1$-$C_4$ haloalkyl. In embodiments, $R^1$ is phenyl substituted with $C_3$-$C_4$ halocycloalkyl. In embodiments, $R^1$ is phenyl substituted with halogen. In embodiments, $R^1$ is phenyl substituted with cyano. In embodiments, $R^1$ is phenyl substituted with $NHC(O)R^4$, wherein $R^4$ is a $C_1$-$C_4$ alkyl or $C_3$-$C_4$ cycloalkyl. In embodiments, $R^1$ is phenyl substituted with $C(O)NR^{5a}R^{5b}$, wherein $R^{5a}$ and $R^{5b}$ are each independently selected from hydrogen, $C_1$-$C_4$ alkyl, $C_3$-$C_4$ cycloalkyl; or $R^{5a}$ and $R^{5b}$ are taken together to form a ring having from 3 to 7 atoms. In embodiments, $R^1$ is phenyl substituted with phenyl. In embodiments, $R^1$ is phenyl substituted with heteroaryl. In embodiments, $R^1$ is phenyl substituted with two substituents independently selected from the group consisting of $C_1$-$C_4$ alkyl, $C_3$-$C_4$ cycloalkyl, $C_1$-$C_4$ alkoxy, $C_3$-$C_4$ cycloalkoxy, $C_1$-$C_4$ haloalkyl, $C_3$-$C_4$ halocycloalkyl, $NHC(O)R^4$, $C(O)NR^{5a}R^{5b}$, phenyl and heteroaryl, wherein the two substituents are taken together to form a fused ring having from 5 to 7 atoms, and wherein $R^4$ is a $C_1$-$C_4$ alkyl or $C_3$-$C_4$ cycloalkyl, $R^{5a}$ and $R^{5b}$ are each independently selected from hydrogen, $C_1$-$C_4$ alkyl, $C_3$-$C_4$ cycloalkyl, or $R^{5a}$ and $R^{5b}$ are taken together to form a ring having from 3 to 7 atoms.

In embodiments, $R^1$ is unsubstituted heteroaryl. In embodiments, $R^1$ is substituted heteroaryl. In embodiments, $R^1$ is heteroaryl substituted with $C_1$-$C_4$ alkyl. In embodiments, $R^1$ is heteroaryl substituted with $C_3$-$C_4$ cycloalkyl. In embodiments, $R^1$ is heteroaryl substituted with $C_1$-$C_4$ alkoxy. In embodiments, $R^1$ is heteroaryl substituted with $C_3$-$C_4$ cycloalkoxy. In embodiments, $R^1$ is heteroaryl substituted with $C_1$-$C_4$ haloalkyl. In embodiments, $R^1$ is heteroaryl substituted with $C_3$-$C_4$ halocycloalkyl. In embodiments, $R^1$ is heteroaryl substituted with halogen. In embodiments, $R^1$ is heteroaryl substituted with cyano. In embodiments, $R^1$ is heteroaryl substituted with $NHC(O)R^4$, wherein $R^4$ is a $C_1$-$C_4$ alkyl or $C_3$-$C_4$ cycloalkyl. In embodiments, $R^1$ is heteroaryl substituted with $C(O)NR^{5a}R^{5b}$, wherein $R^{5a}$ and $R^{5b}$ are each independently selected from hydrogen, $C_1$-$C_4$ alkyl, $C_3$-$C_4$ cycloalkyl; or $R^{5a}$ and $R^{5b}$ are taken together to form a ring having from 3 to 7 atoms. In embodiments, $R^1$ is heteroaryl substituted with phenyl. In embodiments, $R^1$ is heteroaryl substituted with heteroaryl. In embodiments, $R^1$ is heteroaryl substituted with two substituents independently selected from the group consisting of $C_1$-$C_4$ alkyl, $C_3$-$C_4$ cycloalkyl, $C_1$-$C_4$ alkoxy, $C_3$-$C_4$ cycloalkoxy, $C_1$-$C_4$ haloalkyl, $C_3$-$C_4$ halocycloalkyl, NHC(O)$R^4$, C(O)$NR^{5a}R^{5b}$, phenyl and heteroaryl, wherein the two substituents are taken together to form a fused ring having from 5 to 7 atoms, and wherein $R^4$ is a $C_1$-$C_4$ alkyl or $C_3$-$C_4$ cycloalkyl, $R^{5a}$ and $R^{5b}$ are each independently selected from hydrogen, $C_1$-$C_4$ alkyl, $C_3$-$C_4$ cycloalkyl, or $R^{5a}$ and $R^{5b}$ are taken together to form a ring having from 3 to 7 atoms.

In embodiments, $R^1$ is unsubstituted alkyl. In embodiments, $R^1$ is substituted alkyl. In embodiments, $R^1$ is alkyl substituted with $C_1$-$C_4$ alkyl. In embodiments, $R^1$ is alkyl substituted with $C_3$-$C_4$ cycloalkyl. In embodiments, $R^1$ is alkyl substituted with $C_1$-$C_4$ alkoxy. In embodiments, $R^1$ is alkyl substituted with $C_3$-$C_4$ cycloalkoxy. In embodiments, $R^1$ is alkyl substituted with $C_1$-$C_4$ haloalkyl. In embodiments, $R^1$ is alkyl substituted with $C_3$-$C_4$ halocycloalkyl. In embodiments, $R^1$ is alkyl substituted with halogen. In embodiments, $R^1$ is alkyl substituted with cyano. In embodiments, $R^1$ is alkyl substituted with NHC(O)$R^4$, wherein $R^4$ is a $C_1$-$C_4$ alkyl or $C_3$-$C_4$ cycloalkyl. In embodiments, $R^1$ is alkyl substituted with C(O)$NR^{5a}R^{5b}$, wherein $R^{5a}$ and $R^{5b}$ are each independently selected from hydrogen, $C_1$-$C_4$ alkyl, $C_3$-$C_4$ cycloalkyl; or $R^{5a}$ and $R^{5b}$ are taken together to form a ring having from 3 to 7 atoms. In embodiments, $R^1$ is alkyl substituted with phenyl. In embodiments, $R^1$ is alkyl substituted with heteroaryl. In embodiments, $R^1$ is alkyl substituted with two substituents independently selected from the group consisting of $C_1$-$C_4$ alkyl, $C_3$-$C_4$ cycloalkyl, $C_1$-$C_4$ alkoxy, $C_3$-$C_4$ cycloalkoxy, $C_1$-$C_4$ haloalkyl, $C_3$-$C_4$ halocycloalkyl, NHC(O)$R^4$, C(O)$NR^{5a}R^{5b}$, phenyl and heteroaryl, wherein the two substituents are taken together to form a fused ring having from 5 to 7 atoms, and wherein $R^4$ is a $C_1$-$C_4$ alkyl or $C_3$-$C_4$ cycloalkyl, $R^{5a}$ and $R^{5b}$ are each independently selected from hydrogen, $C_1$-$C_4$ alkyl, $C_3$-$C_4$ cycloalkyl, or $R^{5a}$ and $R^{5b}$ are taken together to form a ring having from 3 to 7 atoms.

In embodiments, R and $R^1$ are taken together to form a fused ring having from 5 to 7 atoms. In embodiments, R and $R^1$ are taken together to form a fused ring that is an aryl. In embodiments, R and $R^1$ are taken together to form a fused ring that is a phenyl.

In embodiments, $R^2$ is $OR^6$, wherein $R^6$ is hydrogen, $C_1$-$C_4$ alkyl or $C_3$-$C_4$ cycloalkyl. In embodiments, $R^2$ is $NR^{7a}R^{7b}$, wherein $R^{7a}$ and $R^{7b}$ are each independently selected from the group consisting of hydrogen, $C_1$-$C_4$ alkyl, $C_3$-$C_4$ cycloalkyl, or $R^{7a}$ and $R^{7b}$ are taken together to form a ring having from 3 to 7 atoms.

In embodiments, $R^3$ is hydrogen. In embodiments, $R^3$ is methyl. In embodiments, $R^3$ is ethyl.

In embodiments, L is a linking unit having a structure $—[C(R^{8a}R^{8b})]_n—$, wherein $R^{8a}$ and $R^{8b}$ are each independently selected from the group consisting of hydrogen, methyl and ethyl.

In embodiments, n is an integer from 1 to 3. In embodiments, n is 1. In embodiments, n is 2. In embodiments, n is 3.

In embodiments, $R^9$ is hydrogen. In embodiments, $R^9$ is methyl.

In embodiments, a compound is 2-(1-(cyclopropylmethoxy)-4-hydroxy-2-oxo-1,2-dihydroquinoline-3-carboxamido) acetic acid (Compound 3), or a pharmaceutically acceptable salt thereof. Compound 3, also referred to as desidustat, or ZYAN1, has the following structure:

Compound 3

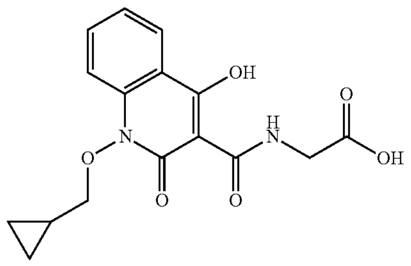

(desidustat, or ZYAN1)

Formula (IV): Roxadustat and Related Compounds

Still other compounds that can be useful in the methods described herein include those described in U.S. Pat. No. 7,323,475, which is incorporated by reference in its entirety. In embodiments, a compound, or a pharmaceutically acceptable salt thereof, is described in any of claims 1-46 of U.S. Pat. No. 7,323,475.

In embodiments, suitable compounds include a compound having a structure according to Formula (IV), Formula (IV)

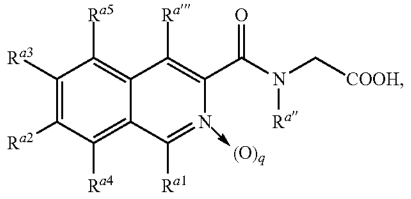

or a pharmaceutically acceptable salt thereof, wherein q is zero or one;

$R^{a1}$ is selected from the group consisting of hydrogen, alkyl, Substituted alkyl, alkoxy, substituted alkoxy, amino, substituted amino, aminoacyl, aryl, substituted aryl, halo, heteroaryl, substituted heteroaryl, heterocyclic, substituted heterocyclic, and $—XR^{a6}$ where X is oxygen, $—S(O)_n—$, or $—NR^{a7}—$ where n is zero, one or two, $R^{a6}$ is selected from the group consisting of alkyl, substituted alkyl, aryl, substituted aryl, heteroaryl, substituted heteroaryl, heterocyclic and substituted hetero cyclic, and $R^{a7}$ is hydrogen, alkyl or aryl or, when X is $—NR^{a7}—$, then $R^{a7}$ and $R^{a6}$, together with the nitrogen atom to which they are bound, can be joined to form a heterocyclic or substituted heterocyclic group;

$R^{a2}$ and $R^{a3}$ are independently selected from the group consisting of hydrogen, alkyl, substituted alkyl, aryl, substituted aryl, heteroaryl, substituted heteroaryl, halo, hydroxy, cyano. $—S(O)_n—N(R^{a6})—R^{a6}$ where n is 0, 1, or 2, $—NR^{a6}C(O)NR^{a6}R^{a6}$, $—XR^{a6}$ where X is oxygen, $—S(O)_n—$, or $—NR^{a7}—$ where n is zero, one or two, each $R^{a6}$ is independently selected from the group consisting of hydrogen, alkyl, Substituted alkyl, aryl, substituted aryl, cycloalkyl, substituted cycloalkyl, heteroaryl, substituted heteroaryl, heterocyclic and substituted heterocyclic provided that when X is —SO— or $—SO_2—$, then $R^{a6}$ is not hydrogen, and $R^{a7}$ is selected from the group consisting of hydrogen, alkyl, aryl, or $R^{a2}$, $R^{a3}$ together with the carbon atom pendent thereto, form an aryl substituted aryl, heteroaryl, or substituted heteroaryl;

$R^{a4}$ and $R^{a5}$ are independently selected from the group consisting of hydrogen, halo, alkyl, substituted alkyl, alkoxy, Substituted alkoxy, aryl, substituted aryl, heteroaryl, substituted heteroaryl and —$XR^{a6}$ where X is oxygen, —$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl or, when X is —$NR^{a7}$—, then $R^{a7}$ and $R^{a6}$, together with the nitrogen atom to which they are bound, can be joined to form a heterocyclic or Substituted heterocyclic group;

$R^{a''}$ is selected from the group consisting of hydrogen, alkyl and substituted alkyl;

$R^{a'''}$ is selected from the group consisting of hydroxy, alkoxy, substituted alkoxy, acyloxy, cycloalkoxy, substituted cycloalkoxy, aryloxy, substituted aryloxy, heteroaryloxy, substituted heteroaryloxy, aryl, —S(O)—$R^{a10}$ wherein $R^{a10}$ is selected from the group consisting of alkyl, substituted alkyl, cycloalkyl, substituted cycloalkyl, aryl, substituted aryl, heteroaryl and substituted heteroaryl and n is zero, one or two;

or a pharmaceutically acceptable salt, ester, or prodrug thereof;

with the proviso that when $R^{a''}$ is hydrogen and q is zero, then at least one of the following occurs:

1) $R^{a1}$ is fluoro, bromo, iodo, alkyl, substituted alkyl, alkoxy, aminoacyl, Substituted alkoxy, aryl, substituted aryl, heteroaryl, substituted heteroaryl, heterocyclic, substituted heterocyclic, and —$XR^{a6}$ where X is oxygen, —$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl; or 2) $R^{a2}$ is substituted alkyl, aryl, substituted aryl, heteroaryl, substituted heteroaryl, fluoro, bromo, iodo, cyano, —$XR^{a6}$ where X is oxygen, —$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl provided that:
   a) when $R^{a2}$ is substituted alkyl such a substituent does not include trifluoromethyl;
   b) —$XR^{a6}$ is not alkoxy; and
   c) when —$XR^{a6}$ is substituted alkoxy such a substituent does not include benzyl or benzyl substituted by a substituent selected from the group consisting of ($C_1$-$C_5$) alkyl and ($C_1$-$C_5$) alkoxy or does not include a fluoroalkoxy substituent of the formula:

$$—O—[CH_2]_x—C_fH_{(2f+1-g)}F_g$$

where x is zero or one; f is an integer of from 1 to 5; and g is an integer of from 1 to (2f+1); or 3) $R^{a3}$ is substituted alkyl, aryl, substituted aryl, heteroaryl, substituted heteroaryl, bromo, iodo, —$XR^{a6}$ where X is oxygen-$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl provided that:
   a) when $R^{a3}$ is substituted alkyl such a substituent does not include trifluoromethyl;
   b) —$XR^{a6}$ is not alkoxy; and
   c) when $XR^{a6}$ is substituted alkoxy such a substituent does not include benzyl or benzyl substituted by a substituent selected from the group consisting of ($C_1$-$C_5$) alkyl and (C—C) alkoxy or does not include a fluoroalkoxy substituent of the formula:

$$—O—[CH_2]_x—C_fH_{(2f+1-g)}F_g$$

where x is zero or one; f is an integer of from 1 to 5; and g is an integer of from 1 to (2f+1); or 4) $R^{a4}$ is iodo, substituted alkyl, aryl, substituted aryl, heteroaryl, substituted heteroaryl, —$XR^{a6}$ where X is oxygen-$S(O)_n$, —, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl provided that:
   a) when $R^{a4}$ is substituted alkyl such a substituent does not include trifluoromethyl;
   b) —$XR^{a6}$ is not alkoxy; and
   c) when $XR^{a6}$ is substituted alkoxy such a substituent does not include benzyl or benzyl substituted by a substituent selected from the group consisting of ($C_1$-$C_5$) alkyl and (C—C) alkoxy or does not include a fluoroalkoxy substituent of the formula:

$$—O—[CH_2]_x—C_fH_{(2f+1-g)}F_g$$

where x is zero or one; f is an integer of from 1 to 5; and g is an integer of from 1 to (2f+1); or 5) $R^{a5}$ is iodo, substituted alkyl, aryl, substituted aryl, heteroaryl, substituted heteroaryl, —$XR^{a6}$ where X is oxygen, —$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl provided that:
   a) when $R^{a5}$ is substituted alkyl such a substituent does not include trifluoromethyl;
   b) —$XR^{a6}$ is not alkoxy; and
   c) when $XR^{a6}$ is substituted alkoxy such a substituent does not include benzyl or benzyl substituted by a substituent selected from the group consisting of ($C_1$-$C_5$) alkyl and (C—C) alkoxy or does not include a fluoroalkoxy substituent of the formula:

$$—O—[CH_2]_x—C_fH_{(2f+1-g)}F_g$$

where x is zero or one; f is an integer of from 1 to 5; and g is an integer of from 1 to (2f+1);

and with the further following proviso:

that when $R^{a1}$, $R^{a3}$, $R^{a4}$, and $R^{a5}$ are hydrogen, then $R^{a2}$ is not bromo.

In embodiments, a compound according to Formula (IV) has the following structure:

Formula (IVa)

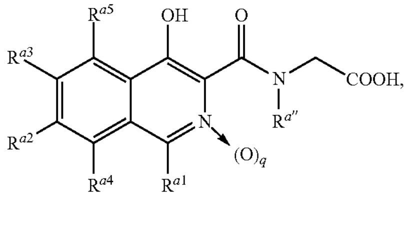

or a pharmaceutically acceptable salt thereof, wherein
q is zero or one;
$R^{a''}$ is selected from hydrogen and alkyl:

$R^{a1}$ is selected from the group consisting of hydrogen, alkyl, Substituted alkyl, alkoxy, substituted alkoxy, aryl, substituted aryl, halo, heteroaryl, substituted heteroaryl, heterocyclic, substituted heterocyclic, and —$XR^{a6}$ where X is oxygen, —$S(O)_n$—, or —$NR^{a7}$— where n is zero, one or two, $R^{a6}$ is selected from the group consisting of alkyl, Substituted alkyl, aryl, sub stituted aryl, heteroaryl, substituted heteroaryl, heterocyclic and substituted heterocyclic, and $R^{a7}$ is hydrogen, alkyl or aryl;

$R^{a2}$ and $R^{a3}$ are independently selected from the group consisting of hydrogen, alkyl, substituted alkyl, aryl, substituted aryl, heteroaryl, substituted heteroaryl, halo, hydroxy, cyano, —$XR^{a6}$ where X is oxygen, —$S(O)_n$—, or —$NR^{a7}$— where n is zero, one or two, $R^{a6}$ is selected from the group consisting of alkyl, Substituted alkyl, aryl, substituted aryl, heteroaryl, substituted heteroaryl, heterocyclic and substituted heterocyclic, and $R^{a7}$ is hydrogen, alkyl or aryl;

$R^{a4}$ and $R^{a5}$ are independently selected from the group consisting of hydrogen, halo, alkyl, substituted alkyl, alkoxy, substituted alkoxy, aryl, substituted aryl, heteroaryl, substituted heteroaryl, and —$XR^{a6}$ where X is oxygen, —$S(O)_n$—, or —$NR^{a7}$— where n is zero, one or two, $R^{a6}$ is selected from the group consisting of alkyl, Substituted alkyl, aryl, substituted aryl, heteroaryl, substituted heteroaryl, heterocyclic and substituted heterocyclic, and $R^{a7}$ is hydrogen, alkyl or aryl;

or a pharmaceutically acceptable salt or prodrug thereof.

In embodiments, a compound according to Formula (IV) has the following structure:

Formula (IVb)

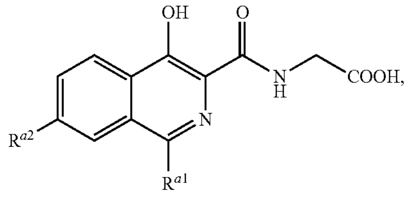

or a pharmaceutically acceptable salt thereof, wherein $R^{a1}$ is selected from the group consisting of hydrogen, halo, alkyl, substituted alkyl, alkoxy, substituted alkoxy, amino, substituted amino, aminoacyl, aryl, substituted aryl, heteroaryl, substituted heteroaryl, heterocyclic, substituted heterocyclic, and —$XR^{a6}$ where X is oxygen, —$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl or, when X is —$NR^{a7}$—, then $R^{a7}$ and $R^{a6}$, together with the nitrogen atom to which they are bound, can be joined to form a heterocyclic or substituted heterocyclic group; and $R^{a2}$ is selected from the group consisting of hydrogen, alkyl, substituted alkyl, aryl, substituted aryl, heteroaryl, substituted heteroaryl, halo, hydroxy, cyano, —$S(O)_n$—$N(R^{a6})$—$R^{a6}$ where n is 0, 1 or 2, —$NR^{a6}C(O)NR^{a6}R^{a6}$, $XR^{a6}$ where X is oxygen, —$S(O)_n$—, or —$NR^{a7}$— where n is zero, one or two, each $R^{a6}$ is independently selected from the group consisting of hydrogen, alkyl, substituted alkyl, aryl, substituted aryl, heteroaryl, substituted heteroaryl, heterocyclic and substituted heterocyclic, provided that when X is —SO— or —$SO^2$—, then $R^{a6}$ is not hydrogen, and $R^{a7}$ is selected from the group consisting of hydrogen, alkyl, aryl, or $R^{a2}$, $R^{a3}$ together with the carbon atom pendent thereto, form an aryl, substituted aryl, heteroaryl, or substituted heteroaryl;

or a pharmaceutically acceptable salt, ester, or prodrug thereof;

with the proviso that at least one of the following occurs:

1) $R^{a1}$ is fluoro, bromo, iodo, alkyl, substituted alkyl, alkoxy, aminoacyl, substituted alkoxy, aryl, substituted aryl, heteroaryl, substituted heteroaryl, heterocyclic, substituted heterocyclic, and —$XR^{a6}$ where X is oxygen, —$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl; or
2) $R^{a2}$ is substituted alkyl, aryl, substituted aryl, heteroaryl, substituted heteroaryl, fluoro, bromo, iodo, cyano, —$XR^{a6}$ where X is oxygen, —$S(O)_n$—, or $NR^{a7}$ where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl provided that:
   a) when $R^{a2}$ is substituted alkyl such a substituent does not include trifluoromethyl;
   b) —$XR^{a6}$ is not alkoxy; and
   c) when —$XR^{a6}$ is substituted alkoxy such a substituent does not include benzyl or benzyl substituted by a substituent selected from the group consisting of $(C_1\text{-}C_5)$ alkyl and $(C_1\text{-}C_5)$ alkoxy or does not include a fluoroalkoxy substituent of the formula:

$$—O—[CH_2]_x—C_fH_{(2f+1-g)}F_g$$

where x is zero or one; f is an integer of from 1 to 5; and g is an integer of from 1 to (2f+1).

In embodiments, a compound is (1-methyl-4-hydroxy-7-phenoxy-isoquinoline carbonyl)-amino-acetic acid (Compound 4), or a pharmaceutically acceptable salt thereof. Compound 4, also referred to as roxadustat, or FG-4592, has the following structure:

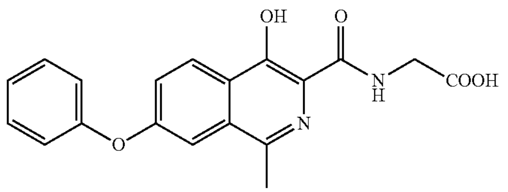

(roxadustat, or FG-4592)

Formula (V): Daprodustat and Related Compounds

Still other compounds that can be useful in the methods described herein include those described in U.S. Pat. No. 8,324,208, which is incorporated by reference in its entirety. In embodiments, a compound, or a pharmaceutically acceptable salt thereof, is described in any of claims 1-16 of U.S. Pat. No. 8,324,208.

In embodiments, suitable compounds include a compound having a structure according to Formula (V), Formula (V)

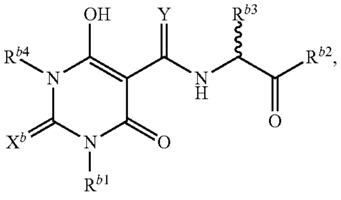

or a pharmaceutically acceptable salt thereof, wherein $R^{b1}$ and $R^{b4}$ are each independently selected from the group consisting of hydrogen, —$NR^{b5}R^{b6}$, $C_1$-$C_{10}$ alkyl, $C_2$-$C_{10}$ alkenyl, $C_2$-$C_{10}$ alkynyl, $C_3$-$C_8$ cycloalkyl, $C_3$-$C_8$ cycloalkyl-$C_1$-$C_{10}$ alkyl, $C_5$-$C_8$ cycloalkenyl, $C_5$-$C_8$ cycloalkenyl-$C_1$-$C_{10}$ alkyl, $C_3$-$C_8$ heterocycloalkyl, $C_3$-$C_8$ heterocycloalkyl-$C_1$-$C_{10}$ alkyl, aryl, aryl-$C_1$-$C_{10}$ alkyl, heteroaryl and heteroaryl-$C_1$-$C_{10}$ alkyl;

$R^{b2}$ is —$NR^{b7}R^{b8}$ or —$OR^{b9}$;

$R^{b3}$ is H or $C_1$-$C_4$ alkyl;

where $R^{b5}$ and $R^{b6}$ are each independently selected from the group consisting of hydrogen, $C_1$-$C_{10}$ alkyl, $C_3$-$C_8$ cycloalkyl, $C_3$-$C_8$ cycloalkyl-$C_1$-$C_{10}$ alkyl, $C_3$-$C_8$ heterocycloalkyl, $C_3$-$C_8$ heterocycloalkyl-$C_1$-$C_{10}$ alkyl, aryl, aryl-$C_1$-$C_{10}$ alkyl, heteroaryl and heteroaryl-$C_1$-$C_{10}$ alkyl, —$C(O)C_1$-$C_4$ alkyl, —$C(O)C_3$-$C_6$ cycloalkyl, —$C(O)C_3$-$C_6$ heterocycloalkyl, —C(O)aryl, —C(O)heteroaryl and —$S(O)_2$ $C_1$-$C_4$ alkyl, or, when $R^{b5}$ and $R^{b6}$ are attached to the same nitrogen, $R^{b5}$ and $R^{b6}$ taken together with the nitrogen to which they are attached forma 5- or 6- or 7-membered saturated ring optionally containing one other heteroatom selected from oxygen, nitrogen and sulphur, $R^{b7}$ and $R^{b8}$ are each independently selected from the group consisting of hydrogen, $C_1$-$C_{10}$ alkyl, $C_2$-$C_{10}$ alkenyl, $C_3$-$C_8$ cycloalkyl, $C_3$-$C_8$ heterocycloalkyl, aryl, and heteroaryl, and $R^{b9}$ is H or a cation, or $C_1$-$C_{10}$ alkyl which is unsubstituted or substituted with one or more substituents independently selected from the group consisting of $C_3$-$C_6$ cycloalkyl, heterocycloalkyl, aryl and heteroaryl;

$X^b$ is O or S; and

Y is O or S;

where any carbon or heteroatom of $R^{b1}$, $R^{b2}$, $R^{b3}$, $R^{b4}$, $R^{b5}$, $R^{b6}$, $R^{b7}$, $R^{b8}$, $R^{b9}$ is unsubstituted or is substituted with one or more substituents independently selected from $C_1$-$C_6$ alkyl, $C_1$-$C_6$ haloalkyl, halogen, —$OR^{b10}$, —$NR^{b5}R^{b6}$, oxo, cyano, nitro, —$C(O)R^{b10}$, —C(O) $OR^{b10}$, —$SR^{b10}$, —$S(O)R^{b10}$, —$S(O)_2R^{b10}$, —$CONR^{b5}R^{b6}$, —$N(R^{b5})C(O)R^{b10}$, —$N(R^{b5})C(O)$ $OR^{b10}$, —$OC(O)NR^{b5}R^{b6}$', —$N(R^{b5})C(O)NR^{b5}R^{b6}$, —$SO_2NR^{b5}R^{b6}$, —$N(R^{b5})SO_2R^{b10}$, $C_2$-$C_{10}$ alkenyl, $C_2$-$C_{10}$ alkynyl, $C_3$-$C_6$ cycloalkyl, $C_3$-$C_6$ heterocycloalkyl, aryl, $C_1$-$C_6$ alkyl-aryl, heteroaryl and $C_1$-$C_6$ alkyl-heteroaryl, wherein $R^{b5}$ and $R^{b6}$ are the same as defined above and $R^{b10}$ is selected from hydrogen, $C_1$-$C_{10}$ alkyl, $C_2$-$C_{10}$ alkenyl, $C_2$-$C_{10}$ alkynyl. —$C(O)C_1$-$C_4$ alkyl, —C(O)aryl, —C(O)heteroaryl, —$C(O)C_3$-$C_6$ cycloalkyl, —$C(O)C_3$-$C_6$ heterocycloalkyl, —$S(O)_2C_1$-$C_4$ alkyl, $C_3$-$C_8$ cycloalkyl, $C_3$-$C_8$ heterocycloalkyl, $C_6$-$C_{14}$ aryl, aryl-$C_1$-$C_{10}$ alkyl, heteroaryl and heteroaryl-$C_1$-$C_{10}$ alkyl;

In embodiments, $X^b$ is 0. In embodiments, Y is O.

In embodiments, $R^{b1}$ and $R^{b4}$ are each independently selected from the group consisting of hydrogen, —$NR^{b5}R^{b6}$ $C_1$-$C_{10}$ alkyl, $C_2$-$C_{10}$ alkenyl, $C_2$-$C_{10}$ alkynyl, $C_3$-$C_8$ cycloalkyl, $C_3$-$C_8$ cycloalkyl-$C_1$-$C_{10}$ alkyl, $C_5$-$C_8$ cycloalkenyl, $C_5$-$C_8$ cycloalkenyl-$C_1$-$C_{10}$ alkyl, $C_3$-$C_8$ heterocycloalkyl, $C_3$-$C_8$ heterocycloalkyl-$C_1$-$C_{10}$ alkyl, aryl, aryl-$C_1$-$C_{10}$ alkyl, heteroaryl and heteroaryl-$C_1$-$C_{10}$ alkyl. In embodiments, $R^{b1}$ is $C_3$-$C_8$ cycloalkyl. In embodiments, $R^{b4}$ is $C_3$-$C_8$ cycloalkyl.

In embodiments, $R^{b2}$ is —$OR^{b9}$, wherein $R^{b9}$ is H or a cation. In embodiments, $R^{b2}$ is OH.

In embodiments, $R^{b3}$ is H.

In embodiments, a compound is N-(1,3-Dicyclohexyl-6-hydroxy-2,4-dioxo-1,2,3,4-tetrahydro-5-pyrimidinyl)carbonylglycine (Compound 5), or a pharmaceutically acceptable salt thereof. Compound 5, also referred to as daprodustat, or GSK-12788363, has the following structure:

Compound 5

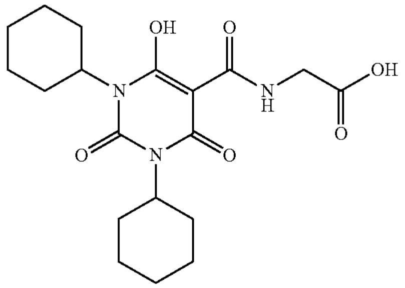

(daprodustat, or GSK-12788363)

Formula (VI): Molidustat and Related Compounds

Still other compounds that can be useful in the methods described herein include those described in U.S. Pat. No. 8,389,520, which is incorporated by reference in its entirety. In embodiments, a compound, or a pharmaceutically acceptable salt thereof, is described in any of claims 1-10 of U.S. Pat. No. 8,389,520.

In embodiments, suitable compounds include a compound having a structure according to Formula (VI), Formula (VI)

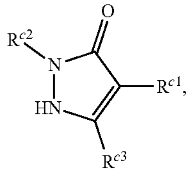

or a pharmaceutically acceptable salt thereof, wherein $R^{c1}$ represents a heteroaryl group of the formula

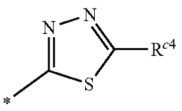

or

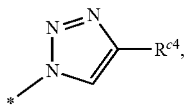

wherein

* denotes the linkage point with the dihydropyrazolone ring and $R^{c4}$ denotes hydrogen, fluorine, chlorine, bromine, cyano, $C_1$-$C_4$ alkyl, trifluoromethyl, hydroxymethyl, $C_1$-$C_4$ alkoxy, trifluoromethoxy, hydroxycarbonyl or $C_1$-$C_4$ alkoxycarbonyl;

$R^{c2}$ represents a heteroaryl group of the formula

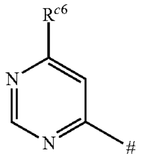
or
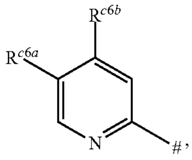
, wherein denotes the linkage point with the dihydropyrazolone ring and $R^{c6}$, $R^{c6a}$ and $R^{c6b}$ are identical or different and independently of one another denote hydrogen or a substituent chosen from the group consisting of fluorine, chlorine, bromine, cyano, $C_1$-$C_6$ alkyl, trifluoromethyl, hydroxyl, $C_1$-$C_6$ alkoxy, trifluoromethoxy, amino, mono-$C_1$-$C_4$ alkylamino, di-$C_1$-$C_4$ alkylamino, hydroxycarbonyl, $C_1$-$C_4$ alkoxycarbonyl, 4- to 6-membered heterocycloalkyl, phenyl and 5- or 6-membered heteroaryl, wherein $C_1$-$C_6$ alkyl in its turn can be substituted by hydroxyl, $C_1$-$C_4$ alkoxy or amino and 4- to 6-membered heterocycloalkyl, phenyl and 5- or 6-membered heteroaryl in their turn can in each case be substituted once or twice in an identical or different manner by fluorine, chlorine, bromine, cyano, $C_1$-$C_4$ alkyl, trifluoromethyl, hydroxyl, $C_1$-$C_4$ alkoxy, trifluoromethoxy, oxo, amino, mono-$C_1$-$C_4$ alkylamino, di-$C_1$-$C_4$ alkylamino, hydroxycarbonyl or $C_1$-$C_4$ alkoxycarbonyl, and $R^{c3}$ represents hydrogen, or a salt thereof.

In embodiments, $R^{c1}$ is a heteroaryl group of the formula

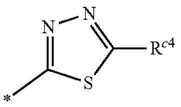
or
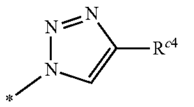

wherein * denotes the linkage point with the dihydropyrazolone ring, and wherein $R^{c4}$ is hydrogen, fluorine, chlorine, bromine, cyano, $C_1$-$C_4$ alkyl, trifluoromethyl, hydroxymethyl, $C_1$-$C_4$ alkoxy, trifluoromethoxy, hydroxycarbonyl or $C_1$-$C_4$ alkoxycarbonyl.

In embodiments, $R^{c2}$ is a heteroaryl group of the formula

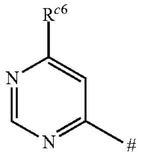
or
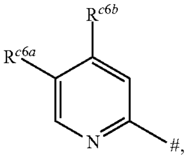
, wherein # denotes the linkage point with the dihydropyrazolone ring and wherein $R^{c6}$, $R^{c6a}$ and $R^{c6b}$ are identical or different and independently of one another denote hydrogen or a substituent chosen from the group consisting of fluorine, chlorine, bromine, cyano, $C_1$-$C_6$ alkyl, trifluoromethyl, hydroxyl, $C_1$-$C_6$ alkoxy, trifluoromethoxy, amino, mono-$C_1$-$C_4$ alkylamino, di-$C_1$-$C_4$ alkylamino, hydroxycarbonyl, $C_1$-$C_4$ alkoxycarbonyl, 4- to 6-membered heterocycloalkyl, phenyl and 5- or 6-membered heteroaryl. In embodiments, a $C_1$-$C_6$ alkyl is unsubstituted $C_1$-$C_6$ alkyl. In embodiments, a $C_1$-$C_6$ alkyl is substituted $C_1$-$C_6$ alkyl. In embodiments, a $C_1$-$C_6$ alkyl is substituted with hydroxyl, $C_1$-$C_4$ alkoxy or amino. In embodiments, a 4- to 6-membered heterocycloalkyl is unsubstituted. In embodiments, a 4- to 6-membered heterocycloalkyl is substituted. In embodiments, a 4- to 6-membered heterocycloalkyl is substituted with once or twice in an identical or different manner by fluorine, chlorine, bromine, cyano, $C_1$-$C_4$ alkyl, trifluoromethyl, hydroxyl, $C_1$-$C_4$ alkoxy, trifluoromethoxy, oxo, amino, mono-$C_1$-$C_4$ alkylamino, di-$C_1$-$C_4$ alkylamino, hydroxycarbonyl or $C_1$-$C_4$ alkoxycarbonyl. In embodiments, a phenyl is unsubstituted. In embodiments, a phenyl is substituted. In embodiments, a phenyl is substituted with once or twice in an identical or different manner by fluorine, chlorine, bromine, cyano, $C_1$-$C_4$ alkyl, trifluoromethyl, hydroxyl, $C_1$-$C_4$alkoxy, trifluoromethoxy, oxo, amino, mono-$C_1$-$C_4$ alkylamino, di-$C_1$-$C_4$ alkylamino, hydroxycarbonyl or $C_1$-$C_4$ alkoxycarbonyl. In embodiments, a 5- or 6-membered heteroaryl is unsubstituted. In embodiments, a 5- or 6-membered heteroaryl is substituted. In embodiments, a 5- or 6-membered heteroaryl is substituted with once or twice in an identical or different manner by fluorine, chlorine, bromine, cyano, $C_1$-$C_4$ alkyl, trifluoromethyl, hydroxyl, $C_1$-$C_4$alkoxy, trifluoromethoxy, oxo, amino, mono-$C_1$-$C_4$ alkylamino, di-$C_1$-$C_4$ alkylamino, hydroxycarbonyl or $C_1$-$C_4$ alkoxycarbonyl.

In embodiments, $R^{c3}$ is hydrogen.

In embodiments, a compound 2-(6-Morpholin-4-ylpyrimidin-4-yl)-4-(1H-1,2,3-triazol-1-yl)-1,2-dihydro-3H-pyrazol-3-one (Compound 6), or a pharmaceutically acceptable salt thereof. Compound 6, also referred to as molidustat, or BAY 85-3934, has the following structure:

Compound 6

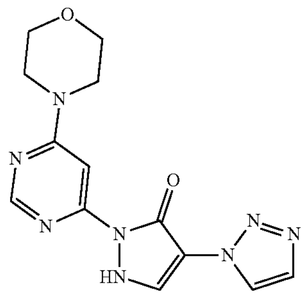

(molidustat, or BAY 85-3934)

Methods of Treatment

HIF Stabilization and Hypoxia Signaling in Human Diseases

Described herein are new therapeutic methods comprising administering compounds that can stabilize HIF and inhibit HIF prolyl hydroxylase (HIF-PH). In particular, methods described herein can be useful for treating a disease or condition in patients in need thereof, such as a patient having a viral infection (e.g., a respiratory or pulmonary viral infection such as COVID-19 or another coronavirus infection). For example, methods described herein can be useful for treating or preventing acute respiratory distress syndrome (ARDS) in a patient in need thereof (e.g., a patient with COVID-19 such as a hospitalized patient with COVID-19), where the method comprises administering a compound that can stabilize HIF and inhibit HIF prolyl hydroxylase (HIF-PH) (e.g., vadadustat).

Methods described herein can also be useful for treating/preventing organ injury (e.g. organ injury that occurs concurrently, or as induced by or associated with an infection). In embodiments, an organ injury is an acute organ injury. For example, methods described herein can be useful for treating or preventing acute lung injury (ALI), acute respiratory distress syndrome (ARDS), cardiovascular injury, injury to the liver, injury to the pancreas, neurological injury, kidney diseases, and/or multi-organ failure.

Suitable HIF prolyl hydroxylase inhibitors or HIF-alpha stabilizers include (but are not limited to) those described herein, including compounds according to any one of Formulas (I)-(VI), such as vadadustat (AKB-6548), roxadustat (FG-4592), daprodustat (GSK-12788363), molidustat (BAY 85-3934), enarodustat (JTZ-951), or desidustat (ZYAN1), or any pharmaceutically acceptable salt thereof. In embodiments, a compound is vadadustat.

Exemplary methods are described herein.

Viral Infections

Methods described herein can be useful for treating patients having a viral infection, including pulmonary viral infections and/or respiratory viral infections. For example, methods described herein can be beneficial for patients having a coronavirus infection (e.g., COVID-19). Methods described herein also can be beneficial in treating or preventing organ injury in patients having a viral infection (e.g., a pulmonary or respiratory viral infection). For example, methods described herein can be useful for treating and/or preventing injury to the lung (e.g., acute lung injury (ALI) and/or acute respiratory distress syndrome (ARDS)), liver, and/or heart (e.g., cardiovascular injury), and kidney diseases. Further, methods described herein are useful for treating or preventing injury to multiple organs (e.g., multi-organ failure and/or septic shock).

Suitable HIF prolyl hydroxylase inhibitors or HIF-alpha stabilizers include (but are not limited to) those described herein, including compounds according to any one Formulas (I)-(VI), such as vadadustat (AKB-6548), roxadustat (FG-4592), daprodustat (GSK-12788363), molidustat (BAY 85-3934), enarodustat (JTZ-951), or desidustat (ZYAN1), or any pharmaceutically acceptable salt thereof. In embodiments, a compound is vadadustat.

Exemplary viral infections are described herein.

Viruses

Coronaviruses

In embodiments, methods described herein can treat: a coronavirus infection (e.g., a pulmonary coronavirus infection and/or a respiratory coronavirus infection), one or more conditions (e.g., organ injury) induced by or associated with a coronavirus infection (e.g., a pulmonary coronavirus infection and/or a respiratory coronavirus infection), and/or one of more conditions in a patient having a coronavirus infection (e.g., a pulmonary coronavirus infection and/or a respiratory coronavirus infection).

Coronaviruses (CoVs) are a family of single-stranded RNA viruses. CoVs have been demonstrated to cross species barriers and can cause illness in human ranging in degrees of severity. Coronavirus infection, as used herein, means an infection, including a patient being infected, with any coronavirus virus including HCoV-NL63, HCoV-OC43, HCoV-229E, HCoV-HKU1, SARS-CoV (Severe Acute Respiratory Syndrome-Coronavirus), CoV MERS (Middle East Respiratory Syndrome virus, previously called “EMC”), and SARS-CoV-2 (Severe Acute Respiratory Syndrome Coronavirus 2, the virus that causes COVID-19 disease).

Coronaviruses cause approximately 10-15% of all upper and lower respiratory tract infections. They account for significant hospitalizations of children under 18 years of age, the elderly and immunocompromised individuals. According to a number of international studies 5-10% of the acute respiratory diseases are caused by HCoV-NL63. These numbers are probably an underestimation since during diagnostic screening for respiratory viruses tests for HCoV's are frequently not included. Another aspect HCoV-NL63 infection is the co-infection with other human coronaviruses, influenza A, respiratory syncytial virus (RSV), parainfluenza virus human metapneumovirus. In children they are associated with acute respiratory tract illness, pneumonia and Croup leading in many cases to hospitalization.

In particular, methods described herein can be beneficial to a patient infected by a coronavirus that is SARS-CoV, MERS-CoV, or SARS-CoV-2 (e.g., having a respiratory viral infection and/or a pulmonary viral infection). In embodiments, a patient is infected by SARS-CoV-2: patients with COVID-19 therefore can benefit from methods described herein for treating conditions induced by or associated with the viral infection or conditions present in the patient.

Influenza Viruses

In embodiments, methods described herein can treat: an influenza virus infection (e.g., a pulmonary influenza virus infection and/or a respiratory influenza virus infection), one or more conditions (e.g., organ injury) induced by or associated with an influenza virus infection (e.g., a pulmonary influenza virus infection and/or a respiratory influenza virus infection), and/or one of more conditions in a patient having an influenza virus infection (e.g., a pulmonary influenza virus infection and/or a respiratory influenza virus infection).

Influenza viruses are divided into three types, type A, B and C, based upon differences in internal antigenic proteins. The Influenza A virus may be further classified into various subtypes according to the different HA and NA viral proteins displayed on the surface of the virus. Each subtype of virus can mutate into a variety of strains with differing pathogenic profiles. Currently, there are 16 known HA antigen subtypes (H1 to H16) and 9 known NA antigen subtypes (N1 to N9). Influenza A viruses can infect humans, birds, pigs, horses, and other animals. A subset of Influenza A virus subtypes, including but not limited to, H1N1, H2N2, H3N2, H5N1, H7N7, H1N2, H9N2, H7N2, H7N3, and H10N7 subtypes, have been confirmed to infect humans. All combinations of the 16 HA and 9 NA subtypes have been identified in avian species. In addition, Influenza B virus and Influenza C virus can also infect humans.

Due to viral recombination, prior immunity to one strain does not necessarily confer protection to the next. Upon infection, a new virus replicates unchecked, while the host mounts a highly inflammatory primary immune response. An influenza infection produces an acute set of symptoms including headache, cough, sore throat, rhinitis, fever and general malaise. In severe cases or situations involving pre-existing pulmonary or cardiovascular disease, hospitalization is required. Pneumonia due to direct viral infection or due to secondary bacterial or viral invasion is the most frequent complication.

The outcome of influenza infection is dependent on both the virus and the host. The genetic makeup of the HA and NA genes confers virulence. For example, introduction of HA and NA genes from pandemic H5N1 strains to a relatively mild virus transforms the virus into a highly virulent strain in mice. During replication, Influenza virus utilizes host protein production machinery and as a result, causes death of the infected cell (cytopathology). Such respiratory epithelial cell destruction produces an array of signals initiating an inflammatory reaction (cytokine cascade) that promotes the recruitment of inflammatory cells (e.g., neutrophils and CD4+/CD8+ T cells) to the delicate surface of the lung, leading to consolidation of air spaces and a decline in arterial oxygen saturation. In eliminating the virus, the host response causes further respiratory cell death, and the responding inflammatory cells (e.g., T cells) produce an additional battery of inflammatory mediators (e.g., TNFα and IFNγ), which in excess lead to a cytokine storm, causing capillary leak and resulting in pulmonary edema and leukocyte transudation into the airspaces, thereby initiating the acute respiratory distress syndrome (ARDS). More chronic symptoms of disease, such as cachexia, fever and appetite suppression, are directly linked to the concentration of systemic mediators/cytokines that accumulate. Therefore, the whole cascade is initiated by virus-induced cytopathology, but mortality is ultimately determined by the magnitude of the inflammation that results from the immune response. Both the viral-induced cytopathology and the host inflammatory response can predispose the infected subject to secondary bacterial infection, further increasing morbidity and mortality.

Respiratory Syncytial Virus (RSV)

In embodiments, methods described herein can treat: a respiratory syncytial virus infection (e.g., a pulmonary RSV infection and/or a respiratory RSV infection), one or more conditions (e.g., organ injury) induced by or associated with a RSV infection (e.g., a pulmonary RSV infection and/or a respiratory RSV infection), and/or one of more conditions in a patient having a RSV infection (e.g., a pulmonary RSV infection and/or a respiratory RSV infection).

Respiratory syncytial virus, or RSV, is a member of Paramyxoviridae family of nonsegmented, negative-sense, single-stranded RNA genome viruses. It is a common respiratory virus that usually causes mild, cold-like symptoms. But it can cause serious lung infections. In fact, it is a leading cause of lower respiratory tract infections in infants, young children, and the elderly or immunocompromised.

Adenovirus

In embodiments, methods described herein can treat: an adenovirus infection (e.g., a pulmonary adenovirus infection and/or a respiratory adenovirus infection), one or more conditions (e.g., organ injury) induced by or associated with an adenovirus infection (e.g., a pulmonary adenovirus infection and/or a respiratory adenovirus infection), and/or one of more conditions in a patient having an adenovirus infection (e.g., a pulmonary adenovirus infection and/or a respiratory adenovirus infection).

Adenovirus is a one of the common viruses that cause a range of illness, including cold-like symptoms, fever, sore throat, bronchitis, pneumonia, diarrhea, and pink eye (conjunctivitis). Adenovirus, a member of the Adenoviridae family, is a nonenveloped (without an outer lipid bilayer) virus with an icosahedral nucleocapsid containing a double stranded DNA genome. The classification of Adenoviridae can be complex. In humans, there are 57 accepted human adenovirus types (HAdV-1 to 57) in seven species (Human adenovirus A to G), and different types/serotypes are associated with different conditions.

Human Parainfluenza Virus (HPIV)

In embodiments, methods described herein can treat: a human parainfluenza virus infection (e.g., a pulmonary human parainfluenza virus infection and/or a respiratory human parainfluenza virus infection), one or more conditions (e.g., organ injury) induced by or associated with a human parainfluenza virus infection (e.g., a pulmonary human parainfluenza virus infection and/or a respiratory human parainfluenza virus infection), and/or one of more conditions in a patient having a human parainfluenza virus infection (e.g., a pulmonary human parainfluenza virus infection and/or a respiratory human parainfluenza virus infection).

Human parainfluenza virus (HPIV). There are four viruses in this group (HPIV-1 to 4), each one of which causes different symptoms and illnesses. All forms of HPIV can cause an infection in either the upper or lower respiratory area of a person's body. HPIV-1 is the leading cause of croup in children, which is a respiratory illness that manifests as swelling near the vocal cords and in other parts of the upper respiratory system. HPIV-1 is responsible for outbreaks of croup in the autumn.

Parainfluenza Viruses (PIV)

In embodiments, methods described herein can treat: a parainfluenza virus infection (e.g., a pulmonary parainfluenza virus infection and/or a respiratory parainfluenza virus infection), one or more conditions (e.g., organ injury) induced by or associated with a parainfluenza virus infection (e.g., a pulmonary parainfluenza virus infection and/or a respiratory parainfluenza virus infection), and/or one of more conditions in a patient having a parainfluenza virus infection (e.g., a pulmonary parainfluenza virus infection and/or a respiratory parainfluenza virus infection).

Parainfluenza viruses (PIV) are paramyxoviruses of the order Mononegavirales, the family Paramyxoviridae, and the subfamily Paramyxovirinae. Human PIVs (HPIVs) are currently divided into 5 serotypes—HPIV-1, HPIV-2, HPIV-3, HPIV-4a, and HPIV-4b—in 2 different genera: Respirovirus (HPIV-1 and HPIV-3) and Rubulavirus (HPIV-2 and HPIV-4). Each one causes different symptoms and illnesses. HPIVs primarily affect young children, in whom the pathogenic spectrum includes upper and lower respiratory tract infections. They are responsible for 30%-40% of all acute respiratory tract infections in infants and children. These conditions include common cold with fever, laryngotracheobronchitis (croup), bronchiolitis, and pneumonia. HPIVs are also a cause of community-acquired respiratory tract infections of variable severity in adults.

Enterovirus

In embodiments, methods described herein can treat: an enterovirus infection (e.g., a pulmonary enterovirus infection and/or a respiratory enterovirus infection), one or more conditions (e.g., organ injury) induced by or associated with an enterovirus infection (e.g., a pulmonary enterovirus infection and/or a respiratory enterovirus infection), and/or one of more conditions in a patient having an enterovirus infection (e.g., a pulmonary enterovirus infection and/or a respiratory enterovirus infection).

Enterovirus is a member of the picornavirus family, a large and diverse group of small RNA viruses characterized by a single positive-strand genomic RNA. The enterovirus genus includes fifteen species (enterovirus A to L and rhinovirus A to C). Enteroviruses affect millions of people worldwide each year and are often found in the respiratory secretions (e.g., saliva, sputum, or nasal mucus) and stool of an infected person. Historically, poliomyelitis was the most significant disease caused by an enterovirus, namely poliovirus. There are 81 non-polio and 3 polio enteroviruses that can cause disease in humans. Of the 81 non-polio types, there are 22 Coxsackie A viruses, 6 Coxsackie B viruses, 28 echoviruses, and 25 other enteroviruses.

Rhinoviruses

In embodiments, methods described herein can treat: a rhinovirus infection (e.g., a pulmonary rhinovirus infection and/or a respiratory rhinovirus infection), one or more conditions (e.g., organ injury) induced by or associated with a rhinovirus infection (e.g., a pulmonary rhinovirus infection and/or a respiratory rhinovirus infection), and/or one of more conditions in a patient having a rhinovirus infection (e.g., a pulmonary rhinovirus infection and/or a respiratory rhinovirus infection).

Rhinoviruses is one of the most common causative agent in humans for the common cold. Rhinoviruses belong to the Enterovirus genus in the family Picornaviridae. There are three species of rhinovirus (A, B, and C) which include approximately 160 recognized types of human rhinovirus that differ according to the virus's surface proteins. The species of rhinovirus have been associated with the severity of the infection caused by the virus. For example, rhinovirus C appear to cause more severe infections that rhinoviruses A and B. The mode of transmission for rhinoviruses are predominately via aerosols of respiratory droplets and from virus-contaminated surfaces.

Respiratory Viral Infection and Pulmonary Viral Infection

Methods described herein can be useful for treating viral infections such as respiratory viral infections and/or pulmonary viral infections (e.g., COVID-19 related pneumonia). For example, methods described herein can be useful in treating conditions induced by or associated with a respiratory viral infection and/or a pulmonary viral infection. Further, methods described herein can be useful in treating a condition in a patient having a respiratory viral infection and/or a pulmonary viral infection.

Suitable HIF prolyl hydroxylase inhibitors or HIF-alpha stabilizers include (but are not limited to) those described herein, including compounds according to any one Formulas (I)-(VI), such as vadadustat (AKB-6548), roxadustat (FG-4592), daprodustat (GSK-12788363), molidustat (BAY 85-3934), enarodustat (JTZ-951), or desidustat (ZYAN1), or any pharmaceutically acceptable salt thereof. In embodiments, a compound is vadadustat.

Respiratory viral infection commonly affect the upper (sinuses, nasal passages, pharynx, and larynx) or lower (trachea, the bronchi and bronchioles, and the alveoli, which make up the lungs) respiratory tract. It may cause coughing, sneezing, runny noses, sore throats or fever. Respiratory means something that affects the lungs and airways (breathing passages). Viral means something that is caused by a virus. Viruses that cause VRIs include respiratory syncytial viruses (RSV), influenza viruses, parainfluenza viruses, adenoviruses and rhinoviruses. Rhinoviruses are the viruses that cause the common cold. Although respiratory infections can be classified by the causative virus, they are generally classified clinically according to syndrome, such as the common cold, bronchiolitis, croup, pneumonia. While specific pathogens commonly cause characteristic clinical manifestations (e.g., rhinovirus typically causes the common cold, respiratory syncytial virus (RSV) typically causes bronchiolitis), each can cause many of the viral respiratory syndromes. Severity of viral respiratory illness varies widely. Morbidity may result directly from viral infection or may be indirect, due to exacerbation underlying medical conditions.

In embodiments, the invention relates to a method for treating a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a respiratory viral infection is induced by or associated with a virus that could lead to viral pneumonia. In embodiments, a respiratory viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a respiratory viral infection is induced by or associated with a coronavirus. In embodiments, a coronavirus is the SARS-CoV, MERS-CoV, or SARS-CoV-2. In embodiments, a coronavirus is SARS-CoV-2.

In embodiments, a respiratory viral infection is lower respiratory infection. In embodiments, a respiratory viral infection is upper respiratory infection. In embodiments, a respiratory viral infection is pulmonary viral infection.

In embodiments, a respiratory viral infection is COVID-19.

In embodiments, a respiratory viral infection induces a lung disease. In embodiments, a lung disease is acute lung injury (ALI). In embodiments, a lung disease is bronchitis. In embodiments, a lung disease is pneumonia. In embodiments, a lung disease is pulmonary fibrosis. In embodiments, a lung disease is asthma. In embodiments, a lung disease is acute respiratory distress syndrome (ARDS).

In embodiments, the invention relates to a method for treating a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a pulmonary viral infection is induced by or associated with a virus that could lead to viral pneumonia. In embodiments, a pulmonary viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a pulmonary viral infection is induced by or associated with a coronavirus. In embodiments, a coronavirus is the SARS-CoV, MERS-CoV, or SARS-CoV-2. In embodiments, a coronavirus is SARS-CoV-2.

In embodiments, a pulmonary viral infection is COVID-19.

In embodiments, a pulmonary viral infection induces a lung disease. In embodiments, a lung disease is acute lung injury (ALI). In embodiments, a lung disease is bronchitis. In embodiments, a lung disease is pneumonia. In embodiments, a lung disease is pulmonary fibrosis. In embodiments, a lung disease is asthma. In embodiments, a lung disease is acute respiratory distress syndrome (ARDS).

In embodiments, a patient with lung disease develops pulmonary hypertension. In embodiments, a patient with lung disease develops multiorgan failure. In embodiments, the multiorgan failure comprises heart failure, liver failure, lung failure kidney failure, and gastrointestinal (GI) system failure. In embodiments, a patient with lung disease develops heart failure. In embodiments, a patient with lung disease develops liver failure. In embodiments, a patient with lung disease develops lung failure. In embodiments, a patient with lung disease develops kidney failure. In embodiments, a patient with lung disease develops gastrointestinal (GI) system failure.

In embodiments, a respiratory and/or pulmonary infection induces heart diseases (e.g. cardiac dysfunction and/or adverse cardiac events, or hypotension), liver diseases (e.g. liver failure), kidney diseases, and/or other diseases or conditions (e.g. septic shock, sepsis, cytokine release syndrome, disseminated intravascular coagulation, pancreas injury, neurological disorder, and pulmonary barotrauma).

Exemplary methods of administration (including exemplary dosage amounts) are provided herein.

COVID-19 and Coronavirus Infection

Methods described herein can be useful for treating viral infections such as coronavirus infections. For example, methods described herein can be useful in treating or preventing conditions induced by or associated with a coronavirus infection, such as COVID-19. Further, methods described herein can be useful in treating or preventing a condition in a patient having a coronavirus infection (e.g. a patient infected by SARS-CoV-2).

Suitable HIF prolyl hydroxylase inhibitors or HIF-alpha stabilizers include (but are not limited to) those described herein, including compounds according to any one Formulas (I)-(VI), such as vadadustat (AKB-6548), roxadustat (FG-4592), daprodustat (GSK-12788363), molidustat (BAY 85-3934), enarodustat (JTZ-951), or desidustat (ZYAN1), or any pharmaceutically acceptable salt thereof. In embodiments, a compound is vadadustat.

Coronaviruses such as the human CoV isolates 229E and OC43 cause mild and self-limiting infections of the respiratory tract such as the common cold. Novel isolates HCoV-NL63 and HCoV-HKU1 have also been associated with common cold.

Some novel emerging coronaviruses have resulted in serious global outbreaks such as SARS in 2003, MERS in 2012 and COVID-19 in 2019.

In embodiments, the invention relates to a method for treating a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a coronavirus is the SARS-CoV, MERS-CoV, or SARS-CoV-2. In embodiments, a coronavirus is SARS-CoV-2.

In embodiments, a coronavirus infection induces a lung disease. In embodiments, a lung disease is acute lung injury (ALI). In embodiments, a lung disease is bronchitis. In embodiments, a lung disease is pneumonia. In embodiments, a lung disease is pulmonary fibrosis. In embodiments, a lung disease is asthma. In embodiments, a lung disease is acute respiratory distress syndrome (ARDS).

In embodiments, a coronavirus infection induces heart diseases (e.g. cardiac dysfunction and/or adverse cardiac events, or hypotension), liver diseases (e.g. liver failure), kidney diseases, and/or other diseases or conditions (e.g. septic shock, sepsis, cytokine release syndrome, disseminated intravascular coagulation, pancreas injury, neurological disorder, and pulmonary barotrauma).

In embodiments, a coronavirus infection is COVID-19.

In embodiments, the invention relates to a method for treating or preventing COVID-19, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to COVID-19, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of COVID-19, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a patient with COVID-19 develops multiorgan failure. In embodiments, multiorgan failure comprises heart failure, liver failure, lung failure kidney failure, and gastrointestinal (GI) system failure.

In embodiments, COVID-19 induces lung diseases (e.g. acute lung injury, acute respiratory distress syndrome, lung inflammation, and pneumonia). In embodiments, the invention relates to a method for treating or preventing of lung diseases (e.g. acute lung injury, acute respiratory distress syndrome, lung inflammation, and pneumonia) induced by and/or related to COVID-19, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, COVID-19 induces heart diseases (e.g. cardiac dysfunction and/or adverse cardiac events, or hypotension). In embodiments, the invention relates to a method for treating or preventing of heart diseases (e.g. cardiac dysfunction and/or adverse cardiac events, or hypotension) induced by and/or related to COVID-19, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, COVID-19 induces liver diseases (e.g. liver failure). In embodiments, the invention relates to a method for treating or preventing of liver diseases (e.g. liver failure) induced by and/or related to COVID-19, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, COVID-19 induces kidney diseases. In embodiments, the invention relates to a method for treating or preventing of kidney diseases induced by and/or related to COVID-19, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, COVID-19 induces other diseases or conditions (e.g. septic shock, sepsis, cytokine release syndrome, disseminated intravascular coagulation, pancreas injury, neurological disorder, and pulmonary barotrauma). In embodiments, the invention relates to a method for treating or preventing of other diseases or conditions (e.g. septic shock, sepsis, cytokine release syndrome, disseminated intravascular coagulation, pancreas injury, neurological disorder, multiorgan disorder/dysfunction and pulmonary barotrauma) induced by and/or related to COVID-19, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating or preventing COVID-19 related acute lung injury (ALI) in a patient in need thereof, comprising administering to the patient a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating or preventing COVID-19 related acute respiratory distress syndrome (ARDS) in a patient in need thereof, comprising administering to the patient a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating or preventing acute respiratory distress syndrome (ARDS) in a hospitalized patient with COVID-19, comprising administering to the patient a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating or preventing COVID-19 related pneumonia in a patient in need thereof, comprising administering to the patient a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating or preventing COVID-19 related organ failure in a patient in need thereof, comprising administering to the patient a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a patient has been diagnosed with COVID-19. In embodiments, a patient is suspected to have COVID-19. In embodiments, a patient is hospitalized.

Exemplary methods of administration (including exemplary dosage amounts) are provided herein.

HIF Stabilization and Lung Injury (Including Lung Diseases)

Methods described herein can be useful for treating or prevention lung diseases such as acute lung injury (ALI), acute respiratory distress syndrome (ARDS), lung inflammation and/or pneumonia in a patient in need thereof. For example, methods described herein can be useful in treating or preventing lung diseases in a patient having a respiratory viral infection, a pulmonary viral infection, and/or a coronavirus infection (e.g., COVID-19 related pneumonia). In embodiments, the lung disease is induced by or associated with a viral infection. Further, methods described herein can also be useful in treating or preventing lung diseases in a patient without viral infection.

Suitable HIF prolyl hydroxylase inhibitors or HIF-alpha stabilizers include (but are not limited to) those described herein, including compounds according to any one Formulas (I)-(VI), such as vadadustat (AKB-6548), roxadustat (FG-4592), daprodustat (GSK-12788363), molidustat (BAY 85-3934), enarodustat (JTZ-951), or desidustat (ZYAN1), or any pharmaceutically acceptable salt thereof. In embodiments, a compound is vadadustat.

Hypoxia itself may contribute to lung injury and thereby perpetuate the injury by impairing endothelial cells, attracting white blood cells, and promoting inflammation. Stabilizing HIF has been shown to be protective during ALI. HIF has been suggested to promote repair and spreading of alveolar type 2 (ATII) cells after ALI. Alveolar type I (ATI) cells are extremely thin squamous cells that line the alveoli and are involved in gas exchange. The ATII cells synthesize, store, and release surfactant to lower surface tension to increase lung compliance and are also involved in repair following alveolar injury—the ATII cells can proliferate and differentiate into ATI cells. A third cell type, the alveolar macrophage, are phagocytic cells that ingest foreign particles. As with cardiac disease, long term upregulation of HIF may have deleterious effects on chronic lung conditions such as pulmonary hypertension, pulmonary fibrosis, and chronic obstructive pulmonary disease, although this seems less relevant to the acute application envisioned here.

Acute Lung Injury (ALI) and Acute Respiratory Distress Syndrome (ARDS)

In embodiments, described herein are methods for treating or prevention lung diseases such as acute lung injury (ALI) and/or acute respiratory distress syndrome (ARDS). For example, methods described herein can be useful in treating or preventing lung diseases in a patient having a viral infection (e.g. respiratory viral infection, pulmonary viral infection, and/or coronavirus infection), sepsis, pneumonia, aspiration, trauma, pancreatitis, blood transfusion, and/or smoke or toxic gas inhalation. In embodiments, methods described herein can be useful for treating or preventing acute respiratory distress syndrome (ARDS) in a patient in need thereof (e.g., a patient with COVID-19 such as a hospitalized patient with COVID-19), where the method comprises administering a compound that can stabilize HIF and inhibit HIF prolyl hydroxylase (HIF-PH) (e.g., vadadustat).

Acute lung injury (ALI) and acute respiratory distress syndrome (ARDS) represent a spectrum of acute respiratory failure with diffuse, bilateral lung injury and severe hypoxemia caused by non-cardiogenic pulmonary edema. Failure may be initiated by pulmonary or extrapulmonary insults (e.g. pneumonia, sepsis, trauma, aspiration) that increase alveolar epithelial endothelial permeability, flood alveoli, and reduce lung compliance.

The severity of hypoxaemia distinguishes ALI from ARDS: when hypoxaemia is severe (partial arterial pressure of oxygen (PaO2)/fractional concentration of oxygen in inspired air (FIO2)<200 mmHg or 26.7 kPa), the disorder is termed ARDS, whereas less severe abnormalities of gas exchange (PaO2/FIO2<300 mmHg or 40 kPa) are termed ALI.

In embodiments, acute lung injury (ALI) or acute respiratory distress syndrome (ARDS) is characterized by accumulation of inflammatory cells into the lungs, cytokine release, inflammatory activation of recruited or resident cells, disruption of the alveolar-capillary barrier function, pulmonary edema, attenuated gas exchange, or lung inflammation, or any combination thereof.

In embodiments, the invention relates to a method for treating or preventing a lung disease that is acute lung injury (ALI) in a patient in need thereof, comprising administering to the patient a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, an acute lung injury (ALI) is induced by or associated with a viral infection, sepsis, pneumonia, aspiration, trauma, pancreatitis, blood transfusion, and/or smoke or toxic gas inhalation. In embodiments, an acute lung injury (ALI) is induced by or associated with a viral infection (e.g. respiratory viral infection, pulmonary viral infection, and/or coronavirus infection). In embodiments, an acute lung injury (ALI) is induced by or associated with a ventilator. In embodiment, an acute lung injury (ALI) is induced by or associated with COVID-19.

In embodiments, a patient has a viral infection, sepsis, pneumonia, aspiration, trauma, pancreatitis, blood transfusion, and/or smoke or toxic gas inhalation. In embodiments, a patient is mechanically ventilated. In embodiments, a patient has a viral infection.

In embodiments, the invention relates to a method for treating or preventing a lung disease that is acute lung injury (ALI) in a patient in need thereof, wherein said ALI is induced by or associated with a ventilator, comprising administering to the patient a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating or preventing a lung disease that is acute lung injury (ALI) in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating or preventing a lung disease that is acute respiratory distress syndrome (ARDS) in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to a lung disease that is acute lung injury (ALI) in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to a lung disease that is acute respiratory distress syndrome (ARDS) in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of a lung disease that is acute lung injury (ALI) in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of a lung disease that is acute respiratory distress syndrome (ARDS) in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a respiratory viral infection is induced by or associated with a virus that could lead to viral pneumonia. In embodiments, a respiratory viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a respiratory viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a respiratory viral infection is COVID-19.

In embodiments, the invention relates to a method for treating or preventing a lung disease that is acute lung injury (ALI) in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating or preventing a lung disease that is acute respiratory distress syndrome (ARDS) in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to a lung disease that is acute lung injury (ALI) in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to a lung disease that is acute respiratory distress syndrome (ARDS) in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of a lung disease that is acute lung injury (ALI) in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of a lung disease that is acute respiratory distress syndrome (ARDS) in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a pulmonary viral infection is induced by or associated with a virus that could lead to viral pneumonia. In embodiments, a pulmonary viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a pulmonary viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a pulmonary viral infection is COVID-19.

In embodiments, the invention relates to a method for treating or preventing a lung disease that is acute lung injury (ALI) in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating or preventing a lung disease that is acute respiratory distress syndrome (ARDS) in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to a lung disease that is acute lung injury (ALI) in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to a lung disease that is acute respiratory distress syndrome (ARDS) in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of a lung disease that is acute lung injury (ALI) in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of a lung disease that is acute respiratory distress syndrome (ARDS) in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a coronavirus infection is induced by or associated with a virus that could lead to viral pneumonia. In embodiments, a coronavirus infection is induced by or associated with SARS-CoV, MERS-CoV, or SARS-CoV-2. In embodiments, a coronavirus infection is induced by or associated with SARS-CoV-2.

In embodiments, a coronavirus infection is COVID-19.

In embodiments, an acute lung injury (ALI) and/or acute respiratory distress syndrome (ARDS) is induced by or associated with a viral infection (e.g. respiratory viral infection, pulmonary viral infection, and/or coronavirus infection). In embodiment, an acute lung injury (ALI) and/or acute respiratory distress syndrome (ARDS) is induced by or associated with COVID-19. In embodiment, an acute lung injury (ALI) and/or acute respiratory distress syndrome (ARDS) is induced by or associated with COVID-19.

In embodiments, a patient with acute lung injury (ALI) develops acute respiratory distress syndrome (ARDS). In embodiments, a patient with ALI or ARDS develops pulmonary hypertension. In embodiments, a patient with ALI or ARDS develops multiorgan failure. In embodiments, multiorgan failure comprises heart failure, liver failure, lung failure kidney failure, and gastrointestinal (GI) system failure. In embodiments, a patient with lung disease develops heart failure. In embodiments, a patient with lung disease develops liver failure. In embodiments, a patient with lung disease develops lung failure. In embodiments, a patient with lung disease develops kidney failure. In embodiments, a patient with lung disease develops gastrointestinal (GI) system failure.

In embodiments, an acute lung injury (ALI) or acute respiratory distress syndrome (ARDS) induces organ dysfunction, and the invention relates to a method for treating or preventing of organ dysfunction induced by or associated with acute lung injury (ALI) or acute respiratory distress syndrome (ARDS), comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a viral infection is a coronavirus infection. In embodiments, the coronavirus is SARS-CoV, MERS-CoV, or SARS-CoV-2. In embodiments, the coronavirus is SARS-CoV-2. In embodiments, a patient has COVID-19. In embodiments, a patient has been diagnosed with COVID-19. In embodiments, a patient is suspected to have COVID-19. In embodiments, a patient is hospitalized.

In embodiments, the invention relates to a method for treating or preventing acute respiratory distress syndrome (ARDS) in a hospitalized patient with COVID-19, comprising administering to the patient a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

Lung Inflammation and Pneumonia

Pneumonia is an inflammatory condition of the lung affecting primarily the small air sacs known as alveoli. It is usually caused by a virus, bacteria, fungi or other germs. It happens when an infection causes alveoli to fill with fluid or pus. That can make it hard for you to breathe in enough oxygen to reach your bloodstream. Symptoms typically include some combination of productive or dry cough, chest pain, fever and difficulty breathing, and the severity of the condition is variable.

In embodiments, the invention relates to a method for treating or preventing a lung disease that is lung inflammation in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating or preventing a lung disease that is pneumonia in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to a lung disease that is lung inflammation in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to a lung disease that is pneumonia in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of a lung disease that is lung inflammation in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of a lung disease that is pneumonia in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a respiratory viral infection is induced by or associated with a virus that could lead to viral pneumonia. In embodiments, a respiratory viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a respiratory viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a respiratory viral infection is COVID-19.

In embodiments, the invention relates to a method for treating or preventing a lung disease that is lung inflammation in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating or preventing a lung disease that is pneumonia in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to a lung disease that is lung inflammation in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to a lung disease that is pneumonia in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of a lung disease that is lung inflammation in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of a lung disease that is pneumonia in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a pulmonary viral infection is induced by or associated with a virus that could lead to viral pneumonia. In embodiments, a pulmonary viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a pulmonary viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a pulmonary viral infection is COVID-19.

In embodiments, the invention relates to a method for treating or preventing a lung disease that is lung inflammation in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating or preventing a lung disease that is pneumonia in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to a lung disease that is lung inflammation in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to a lung disease that is pneumonia in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of a lung disease that is lung inflammation in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of a lung disease that is pneumonia in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a coronavirus infection is induced by or associated with a virus that could lead to viral pneumonia. In embodiments, a coronavirus infection is induced by or associated with SARS-CoV, MERS-CoV, or SARS-CoV-2. In embodiments, a coronavirus infection is induced by SARS-CoV-2.

In embodiments, a coronavirus infection is COVID-19.

In embodiments, a lung inflammation and/or pneumonia is induced by or associated with a viral infection (e.g. respiratory viral infection, pulmonary viral infection, and/or coronavirus infection). In embodiment, a lung inflammation and/or pneumonia is induced by or associated with COVID-19.

In embodiments, a patient with lung inflammation or pneumonia develops pulmonary hypertension. In embodiments, a patient with lung inflammation or pneumonia develops multiorgan failure. In embodiments, the multiorgan failure comprises heart failure, liver failure, lung failure kidney failure, and gastrointestinal (GI) system failure. In embodiments, a patient with lung inflammation or pneumonia develops heart failure. In embodiments, a patient with lung inflammation or pneumonia develops liver failure. In embodiments, a patient with lung inflammation or pneumonia develops lung failure. In embodiments, a patient with lung inflammation or pneumonia develops kidney failure. In embodiments, a patient with lung inflammation or pneumonia develops gastrointestinal (GI) system failure.

In embodiments, lung inflammation or pneumonia induces organ dysfunction, and the invention relates to a method for treating or preventing of organ dysfunction induced by or associated with lung inflammation or pneumonia, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a viral infection is a coronavirus infection. In embodiments, the coronavirus is SARS-CoV, MERS-CoV, or SARS-CoV-2. In embodiments, the coronavirus is SARS-CoV-2. In embodiments, a patient has COVID-19. In embodiments, a patient has been diagnosed with COVID-19. In embodiments, a patient is suspected to have COVID-19. In embodiments, a patient is hospitalized.

HIF Stabilization and Cardiovascular Injury and Diseases (Including Heart Diseases)

Methods described herein can be useful for treating or prevention cardiovascular conditions and diseases, including heart diseases such as cardiac dysfunction and/or hypotension. For example, methods described herein can be useful in treating or preventing cardiovascular conditions or diseases (such as heart diseases) in a patient having a respiratory viral infection, a pulmonary viral infection, and/or a coronavirus infection (e.g., COVID-19 related pneumonia). In embodiments, the cardiovascular disease or condition (e.g., heart disease) is induced by or associated with a viral infection (e.g., COVID-19 related pneumonia). In embodiments, the cardiovascular disease or condition (e.g., heart disease) occurs independently of a viral infection.

Suitable HIF prolyl hydroxylase inhibitors or HIF-alpha stabilizers include (but are not limited to) those described herein, including compounds according to any one Formulas (I)-(VI), such as vadadustat (AKB-6548), roxadustat (FG-4592), daprodustat (GSK-12788363), molidustat (BAY 85-3934), enarodustat (JTZ-951), or desidustat (ZYAN1), or any pharmaceutically acceptable salt thereof. In embodiments, a compound is vadadustat.

HIF stabilization increased nitric oxide (NO) synthase and heme oxygenase 1 (HO1) both of which decrease inflammatory responses. HIF is a central component of ischemic preconditioning (IPC) in the heart. IPC involves administering short, repetitive bouts of ischemia and reperfusion to increase the hearts ability to tolerate a subsequent bout of prolonged ischemia. HIF also contributed to ischemic postconditioning, repeated bouts of ischemia following a bout of prolonged ischemia, which is known to decrease myocardial infarct size. Long term upregulation of HIF may have deleterious effects on the heart in conditions such as congestive heart failure, although this seems less relevant to the acute application envisioned here.

Cardiac Dysfunction

In embodiments, the invention relates to a method for treating or preventing cardiac dysfunction and/or adverse cardiac events in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to cardiac dysfunction and/or adverse cardiac events in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of cardiac dysfunction and/or adverse cardiac events in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a respiratory viral infection is induced by or associated with a virus that could lead to viral pneumonia. In embodiments, a respiratory viral infection is induced by a coronavirus, an influenza A, an influenza B, a Rhinovirus, a respiratory syncytial virus (RSV), an adenovirus, a human parainfluenza virus (HPIV) or an enterovirus. In embodiments, a respiratory viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a respiratory viral infection is COVID-19.

In embodiments, the invention relates to a method for treating or preventing cardiac dysfunction and/or adverse cardiac events in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to cardiac dysfunction and/or adverse cardiac events in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of cardiac dysfunction and/or adverse cardiac events in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a pulmonary viral infection is induced by or associated with a virus that could lead to viral pneumonia. In embodiments, a pulmonary viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a pulmonary viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a pulmonary viral infection is COVID-19.

In embodiments, the invention relates to a method for treating or preventing cardiac dysfunction and/or adverse cardiac events in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to cardiac dysfunction and/or adverse cardiac events in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of cardiac dysfunction and/or adverse cardiac events in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a coronavirus infection is induced by or associated with a virus that could lead to viral pneumonia. In embodiments, a coronavirus infection is induced by or associated with SARS-CoV, MERS-CoV, or SARS-CoV-2. In embodiments, a coronavirus infection is induced by or associated with SARS-CoV-2.

In embodiments, a coronavirus infection is COVID-19.

In embodiments, a cardiac dysfunction and/or adverse cardiac events is induced by or associated with a viral infection (e.g. respiratory viral infection, pulmonary viral infection, and/or coronavirus infection). In embodiment, a cardiac dysfunction and/or adverse cardiac events is induced by or associated with COVID-19.

In embodiments, a patient with cardiac dysfunction and/or adverse cardiac events develops multiorgan failure. In embodiments, the multiorgan failure comprises heart failure, liver failure, lung failure kidney failure, and gastrointestinal (GI) system failure. In embodiments, a patient with cardiac dysfunction and/or adverse cardiac events develops heart failure. In embodiments, a patient with cardiac dysfunction and/or adverse cardiac events develops liver failure. In embodiments, a patient with cardiac dysfunction and/or adverse cardiac events develops lung failure. In embodiments, a patient with cardiac dysfunction and/or adverse cardiac events develops kidney failure. In embodiments, a patient with cardiac dysfunction and/or adverse cardiac events develops gastrointestinal (GI) system failure.

In embodiments, a cardiac dysfunction and/or adverse cardiac events induces organ dysfunction, and the invention relates to a method for treating or preventing of organ dysfunction induced by or associated with cardiac dysfunction and/or adverse cardiac events, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such a vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a viral infection is a coronavirus infection. In embodiments, the coronavirus is SARS-CoV, MERS-CoV, or SARS-CoV-2. In embodiments, the coronavirus is SARS-CoV-2. In embodiments, a patient has COVID-19. In embodiments, a patient has been diagnosed with COVID-19. In embodiments, a patient is suspected to have COVID-19. In embodiments, a patient is hospitalized.

Hypotension

Hypotension is low blood pressure. In healthy people, low blood pressure without any symptoms is not usually a concern and does not need to be treated. But low blood pressure can be a sign of an underlying problem, where it may cause inadequate blood flow to the heart, brain, and other vital organs.

In embodiments, the invention relates to a method for treating or preventing hypotension in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to hypotension in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of hypotension in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), (JTZ-951), or desidustat (ZYAN1), or a pharmaceutically acceptable salt thereof. In embodiments, a compound is vadadustat.

In embodiments, a respiratory viral infection is induced by or associated with a virus that could lead to viral pneumonia. In embodiments, a respiratory viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a respiratory viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a respiratory viral infection is COVID-19.

In embodiments, the invention relates to a method for treating or preventing hypotension in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to hypotension in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of hypotension in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include embodiments, a compound is vadadustat.

In embodiments, a pulmonary viral infection is induced by or associated with a virus that could lead to viral pneumonia. In embodiments, a pulmonary viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a pulmonary viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a pulmonary viral infection is COVID-19.

In embodiments, the invention relates to a method for treating or preventing hypotension in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to hypotension in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of hypotension in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (GF-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a coronavirus infection is induced by or associated with a virus that could lead to viral pneumonia. In embodiments, a coronavirus infection is induced by or associated with SARS-CoV, MERS-CoV, or SARS-CoV-2. In embodiments, a coronavirus infection is induced by or associated with SARS-CoV-2.

In embodiments, a coronavirus infection is COVID-19.

In embodiments, a hypotension is induced by or associated with a viral infection (e.g. respiratory viral infection, pulmonary viral infection, and/or coronavirus infection). In embodiment, a hypotension is induced by or associated with COVID-19.

In embodiments, a patient with hypotension develops multiorgan failure. In embodiments, the multiorgan failure comprises heart failure, liver failure, lung failure, kidney failure, and gastrointestinal (GI) system failure. In embodiments, a patient with hypotension develops heart failure. In embodiments, a patient with hypotension develops liver failure. In embodiments, a patient with hypotension develops lung failure. In embodiments, a patient with hypotension develops kidney failure. In embodiments, a patient with hypotension develops gastrointestinal (GI) system failure.

In embodiments, a hypotension induces organ dysfunction, and the invention relates to a method for treating or preventing of organ dysfunction induced by or associated with hypotension, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a viral infection is a coronavirus infection. In embodiments, the coronavirus is SARS-CoV, MERS-CoV, or SARS-CoV-2. In embodiments, the coronavirus is SARS-CoV-2. In embodiments, a patient has COVID-19. In embodiments, a patient has been diagnosed with COVID-19. In embodiments, a patient is suspected to have COVID-19. In embodiments, a patient is hospitalized.

HIF Stabilization and Liver Injury (including Liver Diseases)

Methods described herein can be useful for treating or preventing liver injury in a patient, including liver diseases such as liver failure. For example, methods described herein can be useful in treating or preventing liver injury in a patient having a respiratory viral infection, a pulmonary viral infection, and/or a coronavirus infection (e.g., COVID-19 related pneumonia). In embodiments, the liver injury is induced by or associated with a viral infection (e.g., COVID-19 related pneumonia). In embodiments, the liver injury occurs independently of a viral infection.

In embodiments, liver injury is characterized by abnormal levels of any abnormality in aspartate transaminase (AST), alanine transaminase (ALT), gamma-glutamyltransferase (GGT), and/or alkaline phosphatase (ALP).

Suitable HIF prolyl hydroxylase inhibitors or HIF-alpha stabilizers include (but are not limited to) those described herein, including compounds according to any one Formulas (I)-(VI), such as vadadustat (AKB-6548), roxadustat (FG-4592), daprodustat (GSK-12788363), molidustat (BAY 85-3934), enarodustat (JTZ-951), or desidustat (ZYAN1), or any pharmaceutically acceptable salt thereof. In embodiments, a compound is vadadustat.

HIF has been shown to be beneficial in ischemia reperfusion (IR) injury of the liver. Pharmacological induction of HIF ameliorates the IR liver injuries by upregulating HIF1A-dependent antioxidant genes and reducing mitochondrial damage. A transgenic mouse model lacking PHD1 (therefore activating HIF) displays tolerance to acute hypoxia and protection against IR liver injury. PHD deletion also promoted liver regeneration in a hepatectomy model. As with the heart and lung, HIF upregulation has negative long term consequence in conditions such as liver fibrosis.

Liver Failure

Liver failure is the loss of liver function characterized by increased serum alanine and aspartate aminotransferase levels, prothrombin time, and serum bilirubin. Common causes for this condition are acetaminophen (APAP) overdose, excessive alcohol consumption, acute viral hepatitis, and IRI. Treatment is focused on reversing APAP overdose by N-acetylcysteine or providing supportive management until the liver function returns back to normal.

In embodiments, the invention relates to a method for treating or preventing liver failure in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG- 4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to liver failure in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of liver failure in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a respiratory viral infection is induced by or associated with a virus that could lead to viral pneumonia. In embodiments, a respiratory viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a respiratory viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a respiratory viral infection is COVID-19.

In embodiments, the invention relates to a method for treating or preventing liver failure in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to liver failure in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of liver failure in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a pulmonary viral infection is induced by or associated with a virus that could lead to viral pneumonia. In embodiments, a pulmonary viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a pulmonary viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a pulmonary viral infection is COVID-19.

In embodiments, the invention relates to a method for treating or preventing liver failure in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to liver failure in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of liver failure in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a coronavirus infection is induced by or associated with a virus that could lead to viral pneumonia. In embodiments, a coronavirus infection is induced by or associated with SARS-CoV, MERS-CoV, or SARS-CoV-2. In embodiments, a coronavirus infection is induced by or associated with SARS-CoV-2.

In embodiments, a coronavirus infection is COVID-19.

In embodiments, a liver failure is induced by or associated with a viral infection (e.g. respiratory viral infection, pulmonary viral infection, and/or coronavirus infection). In embodiment, a liver failure is induced by or associated with COVID-19.

In embodiments, a patient with liver failure develops multiorgan failure. In embodiments, the multiorgan failure comprises heart failure, liver failure, lung failure kidney failure, and gastrointestinal (GI) system failure. In embodiments, a patient with liver failure develops heart failure. In embodiments, a patient with liver failure develops lung failure. In embodiments, a patient with liver failure develops kidney failure. In embodiments, a patient with liver failure develops gastrointestinal (GI) system failure.

In embodiments, a liver failure induces organ dysfunction, and the invention relates to a method for treating or preventing of organ dysfunction induced by or associated with liver failure, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a viral infection is a coronavirus infection. In embodiments, the coronavirus is SARS-CoV, MERS-CoV, or SARS-CoV-2. In embodiments, the coronavirus is SARS-CoV-2. In embodiments, a patient has COVID-19. In embodiments, a patient has been diagnosed with COVID-19. In embodiments, a patient is suspected to have COVID-19. In embodiments, a patient is hospitalized.

HIF Stabilization and Kidney Diseases

Methods described herein can be useful for treating or preventing kidney diseases. For example, methods described herein can be useful in treating or preventing kidney diseases in a patient having a respiratory viral infection, a pulmonary viral infection, and/or a coronavirus infection (e.g., COVID-19 related pneumonia). In embodiments, the kidney disease is induced by or associated with a viral infection (e.g., COVID-19 related pneumonia). In embodiments, the kidney disease occurs independently of a viral infection.

Suitable HIF prolyl hydroxylase inhibitors or HIF-alpha stabilizers include (but are not limited to) those described herein, including compounds according to any one Formulas (I)-(VI), such as vadadustat (AKB-6548), roxadustat (FG-4592), daprodustat (GSK-12788363), molidustat (BAY 85-3934), enarodustat (JTZ-951), or desidustat (ZYAN1), or any pharmaceutically acceptable salt thereof. In embodiments, a compound is vadadustat.

In embodiments, the invention relates to a method for treating or preventing kidney diseases in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat embodiments, a compound is vadadustat.

In embodiments, the invention relates to a method for reducing mortality and morbidity related to kidney diseases in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of kidney diseases in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a respiratory viral infection is induced by or associated with a virus that could lead to viral pneumonia. In embodiments, a respiratory viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a respiratory viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a respiratory viral infection is COVID-19.

In embodiments, the invention relates to a method for treating or preventing kidney diseases in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat embodiments, a compound is vadadustat.

In embodiments, the invention relates to a method for reducing mortality and morbidity related to kidney diseases in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of kidney diseases in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a pulmonary viral infection is induced by or associated with a virus that could lead to viral pneumonia. In embodiments, a pulmonary viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a pulmonary viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a pulmonary viral infection is COVID-19.

In embodiments, the invention relates to a method for treating or preventing kidney diseases in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to kidney diseases in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of kidney diseases in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a coronavirus infection is induced by or associated with a virus that could lead to viral pneumonia. In embodiments, a coronavirus infection is induced by or associated with SARS-CoV, MERS-CoV, or SARS-CoV-2. In embodiments, a coronavirus infection is induced by or associated with SARS-CoV-2.

In embodiments, a coronavirus infection is COVID-19.

In embodiments, a kidney disease is induced by a viral infection (e.g. respiratory viral infection, pulmonary viral infection, and/or coronavirus infection). In embodiment, a kidney disease is induced by COVID-19.

In embodiments, a patient with kidney disease develops multiorgan failure. In embodiments, the multiorgan failure comprises heart failure, liver failure, lung failure kidney failure, and gastrointestinal (GI) system failure. In embodiments, a patient with kidney disease develops heart failure. In embodiments, a patient with kidney disease develops liver failure. In embodiments, a patient with kidney disease develops lung failure. In embodiments, a patient with kidney disease develops kidney failure. In embodiments, a patient with kidney disease develops gastrointestinal (GI) system failure.

In embodiments, a kidney disease induces organ dysfunction, and the invention relates to a method for treating or preventing of organ dysfunction induced by or associated with kidney diseases, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a viral infection is a coronavirus infection. In embodiments, the coronavirus is SARS-CoV, MERS-CoV, or SARS-CoV-2. In embodiments, the coronavirus is SARS-CoV-2. In embodiments, a patient has COVID-19. In embodiments, a patient has been diagnosed with COVID-19. In embodiments, a patient is suspected to have COVID-19. In embodiments, a patient is hospitalized.

HIF Stabilization for Treating Other Diseases

Methods described herein can be useful for treating or prevention other diseases, including those associated with viral infection. For example, methods described herein can be useful in treating or preventing diseases (e.g. septic shock, sepsis, cytokine release syndrome, disseminated intravascular coagulation, pancreas injury, neurological disorder, multiorgan disorder/dysfunction and pulmonary barotrauma) in a patient having a respiratory viral infection, a pulmonary viral infection, and/or a coronavirus infection (e.g., COVID-19 related pneumonia). In embodiments, the diseases described herein is induced by or associated with a viral infection (e.g., COVID-19 related pneumonia). In embodiments, diseases described herein occur independently of a viral infection.

Suitable HIF prolyl hydroxylase inhibitors or HIF-alpha stabilizers include (but are not limited to) those described herein, including compounds according to any one Formulas (I)-(VI), such as vadadustat (AKB-6548), roxadustat (FG-4592), daprodustat (GSK-12788363), molidustat (BAY 85-3934), enarodustat (JTZ-951), or desidustat (ZYAN1), or any pharmaceutically acceptable salt thereof. In embodiments, a compound is vadadustat.

Septic Shock

Septic shock, namely, infection throughout the body, is a potentially fatal medical condition that occurs when sepsis, which is organ injury or damage in response to infection, leads to dangerously low blood pressure and abnormalities in cellular metabolism.

In embodiments, the invention relates to a method for treating or preventing septic shock in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to septic shock in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of septic shock in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a respiratory viral infection is induced by or associated with a virus that could lead to viral pneumonia. In embodiments, a respiratory viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a respiratory viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a respiratory viral infection is COVID-19.

In embodiments, the invention relates to a method for treating or preventing septic shock in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to septic shock in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of septic shock in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a pulmonary viral infection is induced by or associated with a virus that could lead to viral pneumonia. In embodiments, a pulmonary viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a pulmonary viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a pulmonary viral infection is COVID-19.

In embodiments, the invention relates to a method for treating or preventing septic shock in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to septic shock in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of septic shock in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a coronavirus infection is induced by or associated with a virus that could lead to viral pneumonia. In embodiments, a coronavirus infection is induced by or associated with SARS-CoV, MERS-CoV, or SARS-CoV-2. In embodiments, a coronavirus infection is induced by or associated with SARS-CoV-2.

In embodiments, a coronavirus infection is COVID-19.

In embodiments, a septic shock is induced by or associated with a viral infection (e.g. respiratory viral infection, pulmonary viral infection, and/or coronavirus infection). In embodiment, a septic shock is induced by or associated with COVID-19.

In embodiments, a patient with septic shock develops multiorgan failure. In embodiments, the multiorgan failure comprises heart failure, liver failure, lung failure kidney failure, and gastrointestinal (GI) system failure. In embodiments, a patient with septic shock develops heart failure. In embodiments, a patient with septic shock develops liver failure. In embodiments, a patient with septic shock develops lung failure. In embodiments, a patient with septic shock develops kidney failure. In embodiments, a patient with septic shock develops gastrointestinal (GI) system failure.

In embodiments, a septic shock induces organ dysfunction, and the invention relates to a method for treating or preventing of organ dysfunction induced by or associated with septic shock, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a viral infection is a coronavirus infection. In embodiments, the coronavirus is SARS-CoV, MERS-CoV, or SARS-CoV-2. In embodiments, the coronavirus is SARS-CoV-2. In embodiments, a patient has COVID-19. In embodiments, a patient has been diagnosed with COVID-19. In embodiments, a patient is suspected to have COVID-19. In embodiments, a patient is hospitalized.

Sepsis

Sepsis is a potentially life-threatening condition caused by the body's response to an infection. The body normally releases chemicals into the bloodstream to fight an infection. Sepsis occurs when the body's response to these chemicals is out of balance, triggering changes that can damage multiple organ systems.

In embodiments, the invention relates to a method for treating or preventing sepsis in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to sepsis in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of sepsis in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a respiratory viral infection is induced by or associated with a virus that could lead to viral pneumonia. In embodiments, a respiratory viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a respiratory viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a respiratory viral infection is COVID-19.

In embodiments, the invention relates to a method for treating or preventing sepsis in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to sepsis in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of sepsis in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a pulmonary viral infection is induced by or associated with a virus that could lead to viral pneumonia. In embodiments, a pulmonary viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a pulmonary viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a pulmonary viral infection is COVID-19.

In embodiments, the invention relates to a method for treating or preventing sepsis in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to sepsis in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such a vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of sepsis in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a coronavirus infection is induced by or associated with a virus that could lead to viral pneumonia. In embodiments, a coronavirus infection is induced by or associated with SARS-CoV, MERS-CoV, or SARS-CoV-2. In embodiments, a coronavirus infection is induced by or associated with SARS-CoV-2.

In embodiments, a coronavirus infection is COVID-19.

In embodiments, a sepsis is induced by or associated with a viral infection (e.g. respiratory viral infection, pulmonary viral infection, and/or coronavirus infection). In embodiment, a sepsis is induced by or associated with COVID-19.

In embodiments, a patient with sepsis develops multiorgan failure. In embodiments, the multiorgan failure comprises heart failure, liver failure, lung failure kidney failure, and gastrointestinal (GI) system failure. In embodiments, a patient with sepsis develops heart failure. In embodiments, a patient with sepsis develops liver failure. In embodiments, a patient with sepsis develops lung failure. In embodiments, a patient with sepsis develops kidney failure. In embodiments, a patient with sepsis develops gastrointestinal (GI) system failure.

In embodiments, a sepsis induces organ dysfunction, and the invention relates to a method for treating or preventing of organ dysfunction induced by or associated with sepsis, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a viral infection is a coronavirus infection. In embodiments, the coronavirus is SARS-CoV, MERS-CoV, or SARS-CoV-2. In embodiments, the coronavirus is SARS-CoV-2. In embodiments, a patient has COVID-19. In embodiments, a patient has been diagnosed with COVID-19. In embodiments, a patient is suspected to have COVID-19. In embodiments, a patient is hospitalized.

Cytokine Release Syndrome (Cytokine Storm)

Cytokine release syndrome (CRS) is an acute systemic inflammatory syndrome characterized by fever and multiple organ dysfunction that is associated with chimeric antigen receptor (CAR)-T cell therapy, therapeutic antibodies, and haploidentical allogeneic transplantation.

In embodiments, the invention relates to a method for treating or preventing cytokine release syndrome in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to cytokine release syndrome in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of cytokine release syndrome in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a respiratory viral infection is induced by or associated with a virus that could lead to viral pneumonia. In embodiments, a respiratory viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a respiratory viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a respiratory viral infection is COVID-19.

In embodiments, the invention relates to a method for treating or preventing cytokine release syndrome in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to cytokine release syndrome in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of cytokine release syndrome in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a pulmonary viral infection is induced by or associated with a virus that could lead to viral pneumonia. In embodiments, a pulmonary viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a pulmonary viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a pulmonary viral infection is COVID-19.

In embodiments, the invention relates to a method for treating or preventing cytokine release syndrome in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to cytokine release syndrome in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of cytokine release syndrome in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a coronavirus infection is induced by or associated with a virus that could lead to viral pneumonia. In embodiments, a coronavirus infection is induced by or associated with SARS-CoV, MERS-CoV, or SARS-CoV-2. In embodiments, a coronavirus infection is induced by or associated with SARS-CoV-2.

In embodiments, a coronavirus infection is COVID-19.

In embodiments, a cytokine release syndrome is induced by or associated with a viral infection (e.g. respiratory viral infection, pulmonary viral infection, and/or coronavirus infection). In embodiment, a cytokine release syndrome is induced by or associated with COVID-19.

In embodiments, a patient with cytokine release syndrome develops multiorgan failure. In embodiments, the multiorgan failure comprises heart failure, liver failure, lung failure kidney failure, and gastrointestinal (GI) system failure. In embodiments, a patient with cytokine release syndrome develops heart failure. In embodiments, a patient with cytokine release syndrome develops liver failure. In embodiments, a patient with cytokine release syndrome develops lung failure. In embodiments, a patient with cytokine release syndrome develops kidney failure. In embodiments, a patient with cytokine release syndrome develops gastrointestinal (GI) system failure.

In embodiments, a cytokine release syndrome induces organ dysfunction, and the invention relates to a method for treating or preventing of organ dysfunction induced by or associated with cytokine release syndrome, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a viral infection is a coronavirus infection. In embodiments, the coronavirus is SARS-CoV, MERS-CoV, or SARS-CoV-2. In embodiments, the coronavirus is SARS-CoV-2. In embodiments, a patient has COVID-19. In embodiments, a patient has been diagnosed with COVID-19. In embodiments, a patient is suspected to have COVID-19. In embodiments, a patient is hospitalized.

Disseminated Intravascular Coagulation

Disseminated intravascular coagulation is a condition in which small blood clots develop throughout the bloodstream, blocking small blood vessels. The increased clotting depletes the platelets and clotting factors needed to control bleeding, causing excessive bleeding.

In embodiments, the invention relates to a method for treating or preventing disseminated intravascular coagulation in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to disseminated intravascular coagulation in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of disseminated intravascular coagulation in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a respiratory viral infection is induced by or associated with a virus that could lead to viral pneumonia. In embodiments, a respiratory viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a respiratory viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a respiratory viral infection is COVID-19.

In embodiments, the invention relates to a method for treating or preventing disseminated intravascular coagulation in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to disseminated intravascular coagulation in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of disseminated intravascular coagulation in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a pulmonary viral infection is induced by or associated with a virus that could lead to viral pneumonia. In embodiments, a pulmonary viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a pulmonary viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a pulmonary viral infection is COVID-19.

In embodiments, the invention relates to a method for treating or preventing disseminated intravascular coagulation in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to disseminated intravascular coagulation in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of disseminated intravascular coagulation in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a coronavirus infection is induced by or associated with a virus that could lead to viral pneumonia. In embodiments, a coronavirus infection is induced by or associated with SARS-CoV, MERS-CoV, or SARS-CoV-2. In embodiments, a coronavirus infection is induced by or associated with SARS-CoV-2.

In embodiments, a coronavirus infection is COVID-19.

In embodiments, a disseminated intravascular coagulation is induced by or associated with a viral infection (e.g. respiratory viral infection, pulmonary viral infection, and/or coronavirus infection). In embodiment, a disseminated intravascular coagulation is induced by or associated with COVID-19.

In embodiments, a patient with disseminated intravascular coagulation develops multiorgan failure. In embodiments, the multiorgan failure comprises heart failure, liver failure, lung failure kidney failure, and gastrointestinal (GI) system failure. In embodiments, a patient with disseminated intravascular coagulation develops heart failure. In embodiments, a patient with disseminated intravascular coagulation develops liver failure. In embodiments, a patient with disseminated intravascular coagulation develops lung failure. In embodiments, a patient with disseminated intravascular coagulation develops kidney failure. In embodiments, a patient with disseminated intravascular coagulation develops gastrointestinal (GI) system failure.

In embodiments, a disseminated intravascular coagulation induces organ dysfunction, and the invention relates to a method for treating or preventing of organ dysfunction induced by or associated with disseminated intravascular coagulation, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a viral infection is a coronavirus infection. In embodiments, the coronavirus is SARS-CoV, MERS-CoV, or SARS-CoV-2. In embodiments, the coronavirus is SARS-CoV-2. In embodiments, a patient has COVID-19. In embodiments, a patient has been diagnosed with COVID-19. In embodiments, a patient is suspected to have COVID-19. In embodiments, a patient is hospitalized.

Pancreas Injury

A pancreas injury is some form of trauma sustained by the pancreas. The injury can be sustained through either blunt forces, such as a motor vehicle accident, or penetrative forces, such as that of a gunshot wound. The pancreas is one of the least commonly injured organs in abdominal trauma.

In embodiments, the invention relates to a method for treating or preventing pancreas injury in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to pancreas injury in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of pancreas injury in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a respiratory viral infection is induced by or associated with a virus that could lead to viral pneumonia. In embodiments, a respiratory viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a respiratory viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a respiratory viral infection is COVID-19.

In embodiments, the invention relates to a method for treating or preventing pancreas injury in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to pancreas injury in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of pancreas injury in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a pulmonary viral infection is induced by or associated with a virus that could lead to viral pneumonia. In embodiments, a pulmonary viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a pulmonary viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a pulmonary viral infection is COVID-19.

In embodiments, the invention relates to a method for treating or preventing pancreas injury in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to pancreas injury in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of pancreas injury in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a coronavirus infection is induced by or associated with a virus that could lead to viral pneumonia. In embodiments, a coronavirus infection is induced by or associated with SARS-CoV, MERS-CoV, or SARS-CoV-2. In embodiments, a coronavirus infection is induced by or associated with SARS-CoV-2.

In embodiments, a coronavirus infection is COVID-19.

In embodiments, a pancreas injury is induced by or associated with a viral infection (e.g. respiratory viral infection, pulmonary viral infection, and/or coronavirus infection). In embodiment, a pancreas injury is induced by or associated with COVID-19.

In embodiments, a patient with pancreas injury develops multiorgan failure. In embodiments, the multiorgan failure comprises heart failure, liver failure, lung failure kidney failure, and gastrointestinal (GI) system failure. In embodiments, a patient with pancreas injury develops heart failure. In embodiments, a patient with pancreas injury develops liver failure. In embodiments, a patient with pancreas injury develops lung failure. In embodiments, a patient with pancreas injury develops kidney failure. In embodiments, a patient with pancreas injury develops gastrointestinal (GI) system failure.

In embodiments, a pancreas injury induces organ dysfunction, and the invention relates to a method for treating or preventing of organ dysfunction induced by or associated with pancreas injury, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a viral infection is a coronavirus infection. In embodiments, the coronavirus is SARS-CoV, MERS-CoV, or SARS-CoV-2. In embodiments, the coronavirus is SARS-CoV-2. In embodiments, a patient has COVID-19. In embodiments, a patient has been diagnosed with COVID-19. In embodiments, a patient is suspected to have COVID-19. In embodiments, a patient is hospitalized.

Neurological Disorder

A neurological disorder is any disorder of the nervous system. Structural, biochemical or electrical abnormalities in the brain, spinal cord or other nerves can result in a range of symptoms.

In embodiments, the invention relates to a method for treating or preventing neurological disorder in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat embodiments, a compound is vadadustat.

In embodiments, the invention relates to a method for reducing mortality and morbidity related to neurological disorder in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of neurological disorder in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a respiratory viral infection is induced by or associated with a virus that could lead to viral pneumonia. In embodiments, a respiratory viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a respiratory viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a respiratory viral infection is COVID-19.

In embodiments, the invention relates to a method for treating or preventing neurological disorder in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat embodiments, a compound is vadadustat.

In embodiments, the invention relates to a method for reducing mortality and morbidity related to neurological disorder in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of neurological disorder in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a pulmonary viral infection is induced by or associated with a virus that could lead to viral pneumonia. In embodiments, a pulmonary viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a pulmonary viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a pulmonary viral infection is COVID-19.

In embodiments, the invention relates to a method for treating or preventing neurological disorder in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to neurological disorder in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of neurological disorder in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a coronavirus infection is induced by or associated with a virus that could lead to viral pneumonia. In embodiments, a coronavirus infection is induced by or associated with SARS-CoV, MERS-CoV, or SARS-CoV-2. In embodiments, a coronavirus infection is induced by or associated with SARS-CoV-2.

In embodiments, a coronavirus infection is COVID-19.

In embodiments, a neurological disorder is induced by or associated with a viral infection (e.g. respiratory viral infection, pulmonary viral infection, and/or coronavirus infection). In embodiment, a neurological disorder is induced by or associated with COVID-19.

In embodiments, a patient with neurological disorder develops multiorgan failure. In embodiments, the multiorgan failure comprises heart failure, liver failure, lung failure kidney failure, and gastrointestinal (GI) system failure. In embodiments, a patient with neurological disorder develops heart failure. In embodiments, a patient with neurological disorder develops liver failure. In embodiments, a patient with neurological disorder develops lung failure. In embodiments, a patient with neurological disorder develops kidney failure. In embodiments, a patient with neurological disorder develops gastrointestinal (GI) system failure.

In embodiments, a neurological disorder induces organ dysfunction, and the invention relates to a method for treating or preventing of organ dysfunction induced by or associated with neurological disorder, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a viral infection is a coronavirus infection. In embodiments, the coronavirus is SARS-CoV, MERS-CoV, or SARS-CoV-2. In embodiments, the coronavirus is SARS-CoV-2. In embodiments, a patient has COVID-19. In embodiments, a patient has been diagnosed with COVID-19. In embodiments, a patient is suspected to have COVID-19. In embodiments, a patient is hospitalized.

Pulmonary Barotrauma

Pulmonary barotrauma is physical damage to body tissues caused by a difference in pressure between a gas space inside, or in contact with, the body, and the surrounding gas or fluid. Pulmonary barotrauma is damage to the lung from rapid or excessive pressure changes, as may occur when a patient is on a ventilator and is subjected to high airway pressure.

In embodiments, the invention relates to a method for treating or preventing pulmonary barotrauma in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to pulmonary barotrauma in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of pulmonary barotrauma in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a respiratory viral infection is induced by or associated with a virus that could lead to viral pneumonia. In embodiments, a respiratory viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a respiratory viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a respiratory viral infection is COVID-19.

In embodiments, the invention relates to a method for treating or preventing pulmonary barotrauma in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to pulmonary barotrauma in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of pulmonary barotrauma in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a pulmonary viral infection is induced by or associated with a virus that could lead to viral pneumonia. In embodiments, a pulmonary viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a pulmonary viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a pulmonary viral infection is COVID-19.

In embodiments, the invention relates to a method for treating or preventing pulmonary barotrauma in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to pulmonary barotrauma in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of pulmonary barotrauma in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a coronavirus infection is induced by or associated with a virus that could lead to viral pneumonia. In embodiments, a coronavirus infection is induced by or associated with SARS-CoV, MERS-CoV, or SARS-CoV-2. In embodiments, a coronavirus infection is induced by or associated with SARS-CoV-2.

In embodiments, a coronavirus infection is COVID-19.

In embodiments, a pulmonary barotrauma is induced by or associated with a viral infection (e.g. respiratory viral infection, pulmonary viral infection, and/or coronavirus infection). In embodiment, a pulmonary barotrauma is induced by or associated with COVID-19.

In embodiments, a viral infection is a coronavirus infection. In embodiments, the coronavirus is SARS-CoV, MERS-CoV, or SARS-CoV-2. In embodiments, the coronavirus is SARS-CoV-2. In embodiments, a patient has COVID-19. In embodiments, a patient has been diagnosed with COVID-19. In embodiments, a patient is suspected to have COVID-19. In embodiments, a patient is hospitalized.

Multi-Organ Failure

Multiple organ failure (MOF) is a syndrome that represents a complicated and dynamic pathophysiologic pathway leading to organ functional derangement and eventual death. Severe hemorrhagic shock begins an inflammatory cascade that cannot be reversed in some patients despite adequate resuscitation.

In embodiments, the invention relates to a method for treating or preventing multiple organ failure in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to multiple organ failure in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of multiple organ failure in a patient having a respiratory viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a respiratory viral infection is induced by or associated with a virus that could lead to viral pneumonia. In embodiments, a respiratory viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a respiratory viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a respiratory viral infection is COVID-19.

In embodiments, the invention relates to a method for treating or preventing multiple organ failure in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to multiple organ failure in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of multiple organ failure in a patient having a pulmonary viral infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a pulmonary viral infection is induced by or associated with a virus that could lead to viral pneumonia. In embodiments, a pulmonary viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a pulmonary viral infection is induced by or associated with a coronavirus. In embodiments, a coronavirus is SARS-CoV, MERS-CoV, or SARS-CoV-2. In embodiments, a coronavirus is SARS-CoV-2.

In embodiments, a pulmonary viral infection is COVID-19.

In embodiments, the invention relates to a method for treating or preventing multiple organ failure in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing mortality and morbidity related to multiple organ failure in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing incidence, severity, or risk of multiple organ failure in a patient having a coronavirus infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a coronavirus infection is induced by or associated with a virus that could lead to viral pneumonia. In embodiments, a coronavirus infection is induced by or associated with SARS-CoV, MERS-CoV, or SARS-CoV-2. In embodiments, a coronavirus infection is induced by or associated with SARS-CoV-2.

In embodiments, a coronavirus infection is COVID-19.

In embodiments, a multiple organ failure is induced by or associated with a viral infection (e.g. respiratory viral infection, pulmonary viral infection, and/or coronavirus infection). In embodiment, a multiple organ failure is induced by or associated with COVID-19.

In embodiments, a viral infection is a coronavirus infection. In embodiments, the coronavirus is SARS-CoV, MERS-CoV, or SARS-CoV-2. In embodiments, the coronavirus is SARS-CoV-2. In embodiments, a patient has COVID-19. In embodiments, a patient has been diagnosed with COVID-19. In embodiments, a patient is suspected to have COVID-19. In embodiments, a patient is hospitalized.

Induced Organ Dysfunction

Methods described herein can be useful for treating or prevention organ dysfunction induced by or associated with a condition or disease as described anywhere herein (e.g. COVID-19, acute lung injury, acute respiratory distress syndrome, lung inflammation, or pneumonia).

Suitable HIF prolyl hydroxylase inhibitors or HIF-alpha stabilizers include (but are not limited to) those described herein, including compounds according to any one Formulas (I)-(VI), such as vadadustat (AKB-6548), roxadustat (FG-4592), daprodustat (GSK-12788363), molidustat (BAY 85-3934), enarodustat (JTZ-951), or desidustat (ZYAN1), or any pharmaceutically acceptable salt thereof. In embodiments, a compound is vadadustat.

In embodiments, the invention relates to a method for treating and/or preventing organ dysfunction induced by or associated with a disease or condition as described herein, such as COVID-19, lung diseases (e.g. acute lung injury, acute respiratory distress syndrome, lung inflammation, and/or pneumonia), heart diseases (e.g. cardiac dysfunction and/or hypotension), kidney diseases, and other diseases (e.g. septic shock, and/or cytokine release syndrome), or any combination thereof. In embodiments, the invention relates to a method for treating and/or preventing organ dysfunction induced by or associated with a disease or condition as described herein, or any combination thereof, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating and/or preventing organ dysfunction induced by or associated with COVID-19, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating and/or preventing organ dysfunction induced by or associated with acute lung injury (ALI), comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating and/or preventing organ dysfunction induced by or associated with acute respiratory distress syndrome (ARDS), comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating and/or preventing organ dysfunction induced by or associated with lung inflammation, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating and/or preventing organ dysfunction induced by or associated with pneumonia, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating and/or preventing organ dysfunction induced by or associated with cardiac dysfunction and/or adverse cardiac events, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating and/or preventing organ dysfunction induced by or associated with hypotension, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating and/or preventing organ dysfunction induced by or associated with liver failure, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating and/or preventing organ dysfunction induced by or associated with kidney diseases, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating and/or preventing organ dysfunction induced by or associated with septic shock, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating and/or preventing organ dysfunction induced by or associated with sepsis, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating and/or preventing organ dysfunction induced by or associated with cytokine release syndrome (cytokine storm), comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating and/or preventing organ dysfunction induced by or associated with disseminated intravascular coagulation, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating and/or preventing organ dysfunction induced by or associated with pancreas injury, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat embodiments, a compound is vadadustat.

In embodiments, the invention relates to a method for treating and/or preventing organ dysfunction induced by or associated with neurological disorder, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating and/or preventing organ dysfunction induced by or associated with COVID-19, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a patient has a disease or condition as described as anywhere herein. In embodiments, a patient has COVID-19. In embodiments, a patient has been diagnosed with COVID-19. In embodiments, a patient is suspected to have COVID-19. In embodiments, a patient is hospitalized.

Additional Therapeutic Uses

Methods described herein can be useful for in a patient I need thereof (e.g. a patient having a respiratory viral infection, a pulmonary viral infection, and/or a coronavirus infection).

In embodiments, the invention relates to a method for improving lung volumes in a patient in need thereof, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for improving pulmonary compliance in a patient in need thereof, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for promoting fibroproliferative repair in a patient in need thereof, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for regulating innate and adaptive immunity in a patient in need thereof, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for promoting regulatory T-cells, lymphocytes and B cells in a patient in need thereof, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for treating/preventing bronchial inflammation in a patient in need thereof, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for reducing cytokine production in a patient in need thereof, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for improving dyspnea in a patient in need thereof, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the invention relates to a method for improving arterial $PaO_2$ in a patient in need thereof, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a patient has a viral infection. In embodiments, a viral infection is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a viral infection is induced by or associated with a coronavirus. In embodiments, a coronavirus is SARS-CoV, MERS-CoV, or SARS-CoV-2. In embodiments, a coronavirus is SARS-CoV-2. In embodiments, a patient has COVID-19. In embodiments, a patient has been diagnosed with COVID-19. In embodiments, a patient is suspected to have COVID-19. In embodiments, a patient is hospitalized.

Combination Therapy

In embodiments, a HIF prolyl hydroxylase inhibitor or a HIF-alpha stabilizer may be administered in combination with another medicament or another therapy.

In embodiments, the other medicament or therapy is an antiviral agent.

In embodiments, a HIF prolyl hydroxylase inhibitor or a HIF-alpha stabilizer, is administered in combination with an antiviral agent. Various antiviral agents are known in the art. In some embodiments, an antiviral agent is a neuraminidase inhibitor and/or an adamantine derivative. Non-limiting examples of suitable neuraminidase inhibitor include Tamiflu® and Relenza®. Non-limiting examples of adamantine derivatives include amantadine and rimantadine. In some embodiments, a HIF prolyl hydroxylase inhibitor or a HIF-alpha stabilizer, is administered in combination with one or more of the following antiviral drugs: Remdesivir, Chloroquine, Lopinavir and ritonavir, APN01, Favilavir, Baricitinib, Abacavir, Acyclovir, Adefovir, Amantadine, Ampligen, Amprenavir, Arbidol, Atazanavir, Atripla, Balavir, Baloxavir marboxil, Biktarvy, Cidofovir, Combivir, Darunavir, Delavirdine, Descovy, Didanosine, Docosanol, Dolutegravir, Ecoliever, Edoxudine, Efavirenz, Emtricitabine, Enfuvirtide, Entecavir, Famciclovir, Fomivirsen, Fosamprenavir, Foscarnet, Fosfonet, Ibacitabine, Idoxuridine, Imiquimod, Imunovir, Indinavir, Inosine, Integrase inhibitor, Interferon type I, Interferon type II, Interferon type III, Interferon, Lamivudine, Lopinavir, Loviride, Maraviroc, Methisazone, Moroxydine, Nelfinavir, Nevirapine, Nexavir, Nitazoxanide, Norvir, Nucleoside analogues, Oseltamivir, Peginterferon alfa-2a, Penciclovir, Peramivir, Pleconaril, Podophyllotixin, Protease inhibitor, Pyramidine, Raltegravir, Reverse transcriptase inhibitor, Ribavirin, Rimantadine, Ritonavir, Saquinavir, Sofosbuvir, Stavudine, Telaprevir, Tenofovir alafenamide, Tenofovir disoproxil, Tenofovir, Tipranavir, Trifluridine, Trizivir, Tromantadine, Truvada, Valaciclovir, Valganciclovir, Vicriviroc, Vidarabine, Viramidine, Zalcitabine, Zanamivir, Zidovudine.

In some embodiments, administration of the HIF prolyl hydroxylase inhibitor or HIF-alpha stabilizer occurs simultaneously with the antiviral drug.

In some embodiments, administration of the HIF prolyl hydroxylase inhibitor or HIF-alpha stabilizer occurs after administration of the antiviral drug. For example, administration of the HIF prolyl hydroxylase inhibitor or HIF-alpha stabilizer occurs about 6 hours, 12 hours, 24 hours, 2 days, 3 days, 4 days, or 5 days after administration of the antiviral drug. In some embodiments, administration of the HIF prolyl hydroxylase inhibitor or HIF-alpha stabilizer occurs more than 5 days after administration of the antiviral drug.

In some embodiments, administration of the HIF prolyl hydroxylase inhibitor or HIF-alpha stabilizer occurs before administration of the antiviral drug. For example, administration of the antiviral drug occurs about 6 hours, 12 hours, 24 hours, 2 days, 3 days, 4 days, or 5 days after administration of the HIF prolyl hydroxylase inhibitor or HIF-alpha stabilizer. In some embodiments, administration of the antiviral drug occurs more than 5 days after administration of the HIF prolyl hydroxylase inhibitor or HIF-alpha stabilizer.

In embodiments, the other medicament or therapy is oxygen therapy. In embodiments, an oxygen therapy comprises mechanical ventilation. In embodiments, a patient is receiving mechanical ventilation.

In some embodiments, administration of the HIF prolyl hydroxylase inhibitor or HIF-alpha stabilizer occurs during the use of oxygen therapy.

In some embodiments, administration of the HIF prolyl hydroxylase inhibitor or HIF-alpha stabilizer occurs after the use of oxygen therapy. For example, administration of the HIF prolyl hydroxylase inhibitor or HIF-alpha stabilizer occurs about 1 day, 2 days, 3 days, 4 days, or 5 days after the use of oxygen therapy. In some embodiments, administration of the HIF prolyl hydroxylase inhibitor or HIF-alpha stabilizer occurs more than 5 days after the use of oxygen therapy.

In some embodiments, administration of the HIF prolyl hydroxylase inhibitor or HIF-alpha stabilizer occurs before the use of oxygen therapy. For example, the use of oxygen therapy occurs about 1 day, 2 days, 3 days, 4 days, or 5 days after administration of the HIF prolyl hydroxylase inhibitor or HIF-alpha stabilizer. In some embodiments, the use of oxygen therapy occurs more than 5 days after administration of the HIF prolyl hydroxylase inhibitor or HIF-alpha stabilizer.

Patient Populations and Severity of the Disease

Patient Populations

In embodiments, the invention relates to methods for treating and/or preventing a disease or condition as described anywhere herein. In particular, methods described herein can be useful for treating acute respiratory and pulmonary inflammatory conditions such as in patients having a viral infection (e.g., patients having a pulmonary viral infection (e.g., a coronavirus infection such as COVID-19) or a respiratory viral infection (e.g., a coronavirus infection such as COVID-19) and/or preventing organ injury that occurs concurrently or as a result of an infection, comprising administering to a patient in need thereof a compound that is a HIF prolyl hydroxylase inhibitor or a HIF-alpha stabilizer. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. An embodiments, a compound is vadadustat.

In embodiments, a HIF prolyl hydroxylase inhibitor or a HIF-alpha stabilizer is administered to a patient in need thereof.

In embodiments, a patient has a viral infection. In embodiments, a viral infection is a respiratory viral infection (e.g. upper respiratory infection and/or lower respiratory infection). In embodiments, a viral infection is a pulmonary viral infection. In embodiments, a viral infection (e.g. respiratory viral infection and/or pulmonary viral infection) is induced by or associated with a virus that could lead to viral pneumonia. In embodiments, a viral infection (e.g. respiratory viral infection and/or pulmonary viral infection) is induced by or associated with a coronavirus, an influenza A, an influenza B, a Rhinovirus, a respiratory syncytial virus (RSV), an adenovirus, a human parainfluenza virus (HPIV) or an enterovirus. In embodiments, a viral infection (e.g. respiratory viral infection and/or pulmonary viral infection) is induced by or associated with a coronavirus. In embodiments, a coronavirus is the SARS-CoV, MERS-CoV, or SARS-CoV-2. In embodiments, a coronavirus is SARS-CoV-2. In embodiments, a patient has disease or condition induced by or associated with a viral infection. In embodiments, a patient has a disease or condition described anywhere herein.

In embodiments, a patient has one or more clinically-recognized symptoms associated with the respiratory viral infection. In embodiments, a patient has one or more clinically-recognized symptoms associated with the pulmonary viral infection. In embodiments, a patient has one or more clinically-recognized symptoms associated with the coronavirus infection. In embodiments, a patient has one or more clinically-recognized symptoms associated the diseases or conditions described herein, such as lung diseases (e.g. acute lung injury, acute respiratory distress syndrome, lung inflammation and/or pneumonia), heart diseases (e.g. cardiac dysfunction, and/or hypotension), liver diseases (e.g. liver failure), kidney diseases, and other diseases (e.g. septic shock, and/or cytokine release syndrome). In embodiments, a patient has one or more clinically-recognized symptoms associated with COVID-19. Examples of symptoms associated with COVID-19 include fever, dry cough, fatigue, coughing up sputum from the lungs, bone or joint pain, sore throat, headache, chills, nausea or vomiting, stuffy nose, pressure or pain in the chest, shortness of breath, sudden confusion, digestive issues, conjunctivitis, bluish face or lips, and loss of smell or taste.

In embodiments, a patient exhibits one or more symptoms of hypoxia. In embodiments, the one or more symptoms include changes in the color of the skin, confusion, cough, fast heart rate, rapid breathing, shortness of breath, sweating, and/or wheezing. In embodiments, a patient has decreased oxygen saturation of hemoglobin relative to normal levels. In embodiments, a patient an oxygen saturation of hemoglobin that is 94% or less.

In embodiments, a patient has an elevated level of an inflammation marker. In embodiments, the elevated level of an inflammation marker is detected in the serum of a patient. In embodiments, the elevated level of an inflammation marker is detected in the lung of a patient. In embodiments, a patient has elevated levels of interleukin-6 (IL-6). In embodiments, a patient has elevated levels of interleukin-8 (IL-8). In embodiments, a patient has elevated levels of tumor necrosis factor $\alpha$ (TNF-$\alpha$). In embodiments, a patient has elevated levels of C-reactive protein (CRP). In embodiments, a patient has elevated levels of gamma interferon (IFN-$\gamma$)-inducible protein 10 (IP-10). In embodiments, a patient has a presence of ground-glass opacity. In embodiments, a HIF prolyl hydroxylase inhibitor or a HIF-alpha stabilizer is administered to a patient in need thereof, wherein the patient has a positive diagnostic test for SARS-CoV-2.

In embodiments, a patient has one or more of the following: reduced peripheral lymphocytes, elevated levels of C-reactive protein (CRP), elevated levels of IL-6, or abnormal coagulation parameters.

In embodiments, a patient has a pre-existing respiratory or pulmonary disease before the development of a disease or condition as described herein. Examples of pre-existing respiratory or pulmonary diseases include acute lung injury, bronchitis, pneumonia, pulmonary fibrosis, asthma, and acute respiratory distress syndrome, or pulmonary hypertension. In embodiments, a patient does not has a pre-existing respiratory or pulmonary disease before the development of a disease or condition as described herein.

In embodiments, a patient is a child. In embodiments, a patient is an adult. In embodiments, a patient is an adult aged 45 years and above. In embodiments, a patient is an adult aged 65 years and above. In embodiments, a patient is an adult aged 80 years and above.

In embodiments, a patient is an adult aged 45-60 years. In embodiments, a patient is an adult aged 60-80 years. In embodiments, a patient is <about 65 years of age. In embodiments, a patient is ≥about 65 years of age and <about 80 years of age. In embodiments, a patient is ≥about 80 years of age.

In embodiments, a patient has serious underlying medical conditions. Examples of underlying medical conditions include liver disease, heart conditions, kidney disease, severe obesity, diabetes, and being immunocompromised. In embodiments, a patient has a body mass index (BMI) that is 25 or above or 30 or above.

In embodiment, a patient is/has 1, 2, 3, 4, 5, or all of the following: 1) men or women ≥18 years of age; 2) laboratory-confirmed diagnosis of COVID-19 by detection of SARS-CoV-2 RNA by RT-PCR from any specimen respiratory; 3) admitted to the hospital; 4) within 24 hours of hospital admission; 5) oxygen saturation of hemoglobin by pulse oximetry at room air≤94%; and 6) has not participated in any other clinical trial for the treatment for COVID-19. In embodiment, a patient is not/has not any or all of the following: 1) hypersensitivity to vadadustat or any of its excipients; 2) placed on mechanical ventilation prior to commencement of treatment; 3) hemoglobin more than 1 g/dL above the gender specific upper limit of normal (ULN) prior to commencement of treatment; 4) aspartate aminotransferase (AST), alanine aminotransferase (ALT), or total bilirubin >2.0×ULN prior to commencement of treatment; 5) women who are pregnant or breastfeeding, or positive pregnancy test prior to commencement of treatment; 6) on maintenance dialysis prior to commencement of treatment; and 7) have received a solid organ transplant prior to commencement of treatment.

Severity of the Disease

The primary endpoint should be responsive to the eligible patient population, intervention and course of illness of COVID-19. While all-cause mortality (ACM) is an important outcome, depending upon event rates observed in the Pilot Stage, the primary endpoint should be a composite measure of clinical improvement and/or survival, assessed at a pre-specified time (such as 28 days) post randomization. The National Institute of Allergy and Infectious Disease Ordinal Scale (NIAID-OS) can be used to measure illness severity over time. The primary outcome could be a measure of patients' clinical status at a particular time point after enrolment, depending upon frequency of outcome assessment (e.g., 14, 28, or 60 days). Agreement and consistency in recording of individual outcome events at particular time points will facilitate interpretation and combination of results across studies and trials. The definition of the endpoint should be fine-tuned for the Pivotal Phase, based on the Pilot Phase of the trial.

In embodiments, the severity of a diseases is maintained or reduced following commencement of administering a HIF prolyl hydroxylase inhibitor or a HIF-alpha stabilizer to the patient as described herein.

Suitable HIF prolyl hydroxylase inhibitors or HIF-alpha stabilizers include (but are not limited to) those described herein, including compounds according to any one Formulas (I)-(VI), such as vadadustat (AKB-6548), roxadustat (FG-4592), daprodustat (GSK-12788363), molidustat (BAY 85-3934), enarodustat (JTZ-951), or desidustat (ZYAN1), or any pharmaceutically acceptable salt thereof. In embodiments, a compound is vadadustat.

In embodiments, a disease is COVID-19.

In embodiments, the severity of diseases such as COVID-19 may be assessed according to the following ordinal scale where increasing numbers denote increased severity. Methods described herein can be useful for infected patients having any of the characteristics described for any of scores 1-7, regardless of whether the patient is formally scored.

| Score | Descriptor | Patient State | |
|---|---|---|---|
| 0 | No clinical or virological evidence of infection | Uninfected | Uninfected/ Ambulatory |
| 1 | Not hospitalized, no limitation of patient's activities | Infected (Ambulatory) | |
| 2 | Not hospitalized, limitation of patient's activities and/or requiring home oxygen | | |

-continued

| Score | Descriptor | Patient State | |
|---|---|---|---|
| 3 | Patient is hospitalized but does not receive oxygen therapy-no longer requires ongoing medical care | Infected-Hospitalized (Mild Disease) | Hospitalized but not intubated |
| 4 | Patient is hospitalized but does not require oxygen therapy-requiring ongoing care (COVID-19 related or otherwise) | | |
| 5 | Patient is hospitalized and requiring supplemental oxygen | Infected-Hospitalized | |
| 6 | Patient is hospitalized and receives oxygen therapy that is non-invasive ventilation or high flow oxygen devices | (Severe Disease) | Hospitalized and intubated |
| 7 | Patient is hospitalized and receives invasive mechanical ventilation and additional organ support such as pressors, renal replacement therapy (RRT), and/or extracorporeal membrane oxygenation (ECMO) | | |
| 8 | Death | Dead | Death |

In embodiments, the severity of disease as described herein is maintained and the patient's condition stabilizes following commencement of administering the HIF prolyl hydroxylase inhibitor or the HIF-alpha stabilizer to the patient. In embodiments, a patient's score does not change and the patient's condition stabilizes following commencement of administering the HIF prolyl hydroxylase inhibitor or the HIF-alpha stabilizer to the patient.

In embodiments, the severity of disease as described herein decreases following commencement of administering the HIF prolyl hydroxylase inhibitor or the HIF-alpha stabilizer to the patient. In embodiments, a patient's score decreases by at least one point following commencement of administering the HIF prolyl hydroxylase inhibitor or the HIF-alpha stabilizer to the patient. In embodiments, a patient's score decreases by one to three points following commencement of administering the HIF prolyl hydroxylase inhibitor or the HIF-alpha stabilizer to the patient. In embodiments, a patient's score decreases by four to six points following commencement of administering the HIF prolyl hydroxylase inhibitor or the HIF-alpha stabilizer to the patient. In embodiments, a patient's score decreases by six points or above following commencement of administering the HIF prolyl hydroxylase inhibitor or the HIF-alpha stabilizer to the patient.

In embodiments, a patient is assessed as uninfected/ambulatory. In embodiments, a patient is assessed as hospitalized but not intubated. In embodiments, a patient is assessed as hospitalized and intubated.

In embodiments, the severity of disease as described herein decreases following commencement of administering the HIF prolyl hydroxylase inhibitor or the HIF-alpha stabilizer to the patient. In embodiments, a patient's category decreases by at least one category following commencement of administering the HIF prolyl hydroxylase inhibitor or the HIF-alpha stabilizer to the patient. In embodiments, a patient's category decreases by two categories following commencement of administering the HIF prolyl hydroxylase inhibitor or the HIF-alpha stabilizer to the patient.

Exemplary decreased severity of a disease is described herein.

In embodiments, a patient is hypoxic. In embodiments, a patient exhibits one or more symptoms of hypoxia. In embodiments, the one or more symptoms include changes in the color of the skin, confusion, cough, fast heart rate, rapid breathing, shortness of breath, sweating, and/or wheezing. In embodiments, decreased severity of hypoxia includes the improvement in one or more symptoms described herein following commencement of administering the HIF prolyl hydroxylase inhibitor or the HIF-alpha stabilizer to the patient.

In embodiments, a patient has decreased oxygen saturation of hemoglobin relative to normal levels. In embodiments, a patient an oxygen saturation of hemoglobin that is 94% or less. In embodiments, decreased severity of a disease includes the improvement in oxygen saturation value. In embodiments, a patient's oxygen saturation value improves to a value of about 95% following commencement of administering the HIF prolyl hydroxylase inhibitor or the HIF-alpha stabilizer to the patient. In embodiments, a patient's oxygen saturation value improves to a value of about 95% or greater following commencement of administering the HIF prolyl hydroxylase inhibitor or the HIF-alpha stabilizer to the patient.

In embodiments, a patient has hypotension. In embodiments, a patient with hypotension receives vasopressor therapy. In embodiments, decreased severity of hypotension includes a reduced or discontinued vasopressor therapy following commencement of administering the HIF prolyl hydroxylase inhibitor or the HIF-alpha stabilizer to the patient.

In embodiments, a patient is hospitalized. In embodiments, a patient does not receive oxygen therapy. In embodiments, a patient has a score of 1, 2, and/or 3 according to the ordinal scale described herein. In embodiments, a decreased severity of the disease is a decrease of the patient's score (e.g. decreases by at least one point) following commencement of administering the HIF prolyl hydroxylase inhibitor or the HIF-alpha stabilizer to the patient.

In embodiments, a patient is hospitalized. In embodiments, a patient receives oxygen therapy. In embodiments, a patient has a score of 4, 5, 6, or 7 according to the ordinal scale described herein. In embodiments, a decreased severity of the disease is a decrease of the patient's score (e.g. decreases by at least one point, by one to three points, or by four points and above) following commencement of administering the HIF prolyl hydroxylase inhibitor or the HIF-alpha stabilizer to the patient.

In embodiments, a patient receives oxygen therapy. In embodiments, a patient receives oxygen therapy by mask or nasal prongs. In embodiments, a patient receives oxygen therapy by intubation and mechanical ventilation. In embodiments, a decreased severity of the disease is a discontinued oxygen therapy following commencement of administering the HIF prolyl hydroxylase inhibitor or the HIF-alpha stabilizer to the patient. In embodiments, a patient has increased ventilator-free survival following discontinuation of mechanical ventilation.

In embodiments, a patient has multi-organ injuries and/or diseases receives additional organ support therapy. In embodiments, a patient has any of a cardiovascular injury, a neurological injury, a liver injury, or a pancreas injury, and/or a kidney disease. In embodiments, a patient has a heart injury and/or a lung injury. In embodiments, a patient receives organ support therapy that is vapopressor therapy, renal replacement therapy (RRT), and/or extracorporeal membrane oxygenation (ECMO). In embodiments, a decreased severity of the disease is a discontinued organ support therapy following commencement of administering the HIF prolyl hydroxylase inhibitor or the HIF-alpha stabilizer to the patient. In embodiments, a patient has increased organ failure-free survival (e.g. kidney, cardiac) following commencement of administering the HIF prolyl hydroxylase inhibitor or the HIF-alpha stabilizer to the patient.

In embodiments, a patient receives vadadustat, or a pharmaceutically acceptable salt thereof.

Effects/Efficacy of Treatment and Endpoints

Efficacy of any method described herein can be assessed according to methods known in the art. Exemplary endpoints and effects of treatment are described herein.

For example, efficacy of a method described herein may be assessed by a change of one point or more (from baseline) on an ordinal scale for clinical improvement (e.g., the NIAID-OS). A change may be assessed any time during the period during which a HIF prolyl hydroxylase inhibitor or the HIF-alpha stabilizer (e.g., vadadustat). In embodiments, a change is assessed on, at, or by day 28 of treatment. In embodiments, a change is assessed on, at, or by day 21 of treatment. In embodiments, a change is assessed on, at, or by day 14 of treatment. In embodiments, a change is assessed on, at, or by day 7 of treatment. A change may be an improvement by one point or more. A change may be a worsening by one point or more. For example, a change may be worsening by one point or more (from baseline) on the NIAID ordinal scale for clinical improvement (e.g., on or at day 7 or day 14).

In embodiments, efficacy is assessed by the proportion of patients with each of the components of the NIAID ordinal scale for clinical improvement at day 7 and 14.

In embodiments, efficacy is assessed by the proportion of patient population assessed according to the NIAID ordinal scale, including according to any of the following four categories: 1) uninfected/ambulatory, 2) hospitalized but not intubated, 3) hospitalized and intubated, or 4) death.

In embodiments, efficacy is assessed by the time to each component of the NIAID ordinal scale.

In embodiments, efficacy is assessed by the time to improvement of at least 2 categories relative to baseline on an ordinal scale (e.g., the NIAID ordinal scale of clinical improvement).

In embodiments, efficacy is assessed by the time to any of the components of an ordinal scale such as the NIAID ordinal scale. In embodiments, efficacy is assessed by the time to any of the following four categories: 1) uninfected/ambulatory, 2) hospitalized but not intubated, 3) hospitalized and intubated, or 4) death.

In embodiments, efficacy is assessed by the proportion of patients with clinical diagnosis of ARDS.

In embodiments, efficacy is assessed by time to clinical diagnosis of ARDS.

In embodiments, efficacy is assessed by ventilator-free survival.

In embodiments, efficacy is assessed by organ failure-free survival (e.g., kidney, cardiac).

In embodiments, efficacy is assessed by a change in serum creatinine from baseline.

In embodiments, efficacy is assessed by overall total survival.

In embodiments, efficacy is assessed by the proportion of patients with clinical diagnosis of sepsis.

In embodiments, efficacy is assessed by the time to clinical failure. In embodiments, clinical failure is mechanical ventilation. In embodiments, clinical failure is mechanical ventilation. In embodiments, clinical failure is death or mechanical ventilation, whichever occurs first.

In embodiments, efficacy is assessed by the time to hospital discharge.

In embodiments, efficacy is assessed by the proportion of patients with acute kidney injury.

In embodiments, efficacy is assessed by the time to acute kidney injury.

In embodiments, efficacy is assessed by inducing known transcriptional targets of HIFs (e.g., erythropoietin, extracellular adenosine levels, circulating levels of CD73 (or ecto-5'-nucleotidase) VEGF (vascular endothelial growth factor), hypoxia-driven microRNAs that dampen lung inflammation).

In embodiments, efficacy is assessed using various laboratory measurements that include but not limited to serum creatinine, FGF-23 (or fibroblast growth factor 23), and markers of attenuated inflammation.

In embodiments, a method described herein (e.g., for the prevention and treatment of ARDS among COVID-19 patients) results in a change (e.g., a reduction by ≥1 point) on the NIAID ordinal scale for clinical improvement at day seven or day 14 of treatment.

NIAID Ordinal Scale (NIAID-OS)

| Score | Descriptor | Patient State | |
|---|---|---|---|
| 0 | No clinical or virological evidence of infection | Uninfected | Uninfected/ Ambulatory |
| 1 | Not hospitalized, no limitation of patient's activities | Infected (Ambulatory) | |
| 2 | Not hospitalized, limitation of patient's activities and/or requiring home oxygen | | |
| 3 | Patient is hospitalized but does not receive oxygen therapy-no longer requires ongoing medical care | Infected-Hospitalized (Mild Disease) | Hospitalized but not intubated |
| 4 | Patient is hospitalized but does not require oxygen therapy-requiring ongoing care (COVID-19 related or otherwise) | | |
| 5 | Patient is hospitalized and requiring supplemental oxygen | Infected-Hospitalized | |
| 6 | Patient is hospitalized and receives oxygen therapy that is non-invasive ventilation or high flow oxygen devices | (Severe Disease) | Hospitalized and intubated |
| 7 | Patient is hospitalized and receives invasive mechanical ventilation and additional organ support such as pressors, renal replacement therapy (RRT), and/or extracorporeal membrane oxygenation (ECMO) | | |
| 8 | Death | Dead | Death |

In embodiments, a method described herein (e.g., for the prevention and treatment of ARDS among COVID-19 patients such as hospitalized COVID-19 patients) results in a change (e.g., a decrease or a reduction) in the proportion of patients at day 14 who are dead (NIAID-OS 8); hospitalized, on invasive mechanical ventilation or ECMO (NIAID-OS 7); and/or hospitalized, on non-invasive ventilation or high flow oxygen devices (NIAID-OS 6).

In embodiments, a method described herein (e.g., for the prevention and treatment of ARDS among COVID-19 patients such as hospitalized COVID-19 patients) results in a change (e.g., an increase) in the proportion of patients with a score of 0 at 14 days on the MSOFA (Modified Sequential Organ Failure Assessment) scale:

| Organ System | 0 | 1 | 2 | 3 | 4 |
|---|---|---|---|---|---|
| Respiratory SpO2/FiO2 | >400 | ≤400 | ≤315 | ≤235 | ≤150 |
| Liver | No scleral icterus or jaundice | | | Scleral icterus or jaundice | |
| Cardiovascular, hypotension | No hypotension | MAP <70 mm Hg | Dopamine ≤5 or dobutamine any dose | Dopamine >5 Epinephrine ≤0.1 Norepinephrine ≤0.1 | Dopamine >15 Epinephrine >0.1 Norepinephrine >0.1 |
| CNS (central nervous system), Glasgow Coma Score | 15 | 13-14 | 10-12 | 6-9 | <6 |
| Renal, Creatinine mg/dL | <1.2 | 1.2-1.9 | 2.0-3.4 | 3.5-4.9 | >5.0 |

Note:
Discharged patient receives a score of 0 and dead patient receives a score of 20.

In embodiments, a method described herein (e.g., for the prevention and treatment of ARDS among COVID-19 patients such as hospitalized COVID-19 patients) results in a change (e.g., a decrease or a reduction) in the average MSOFA scores at day 7 and/or day 14.

In embodiments, a method described herein (e.g., for the prevention and treatment of ARDS among COVID-19 patients such as hospitalized COVID-19 patients) results in a change (e.g., a decrease or a reduction) in the proportion of patients who develop ARDS or experienced increased ARDS severity from baseline based on the Berlin scale.

In embodiments, a method described herein (e.g., for the prevention and treatment of ARDS among COVID-19 patients such as hospitalized COVID-19 patients) results in a change (e.g., an increase) in the ventilator-free survival at day 7 and day 14.

In embodiments, a method described herein (e.g., for the prevention and treatment of ARDS among COVID-19 patients such as hospitalized COVID-19 patients) results in a change (e.g., an increase) in the overall survival at day 7 and/or day 14.

In embodiments, a method described herein (e.g., for the prevention and treatment of ARDS among COVID-19 patients such as hospitalized COVID-19 patients) results in a change (e.g., a decrease or a reduction) in the proportion of patients with hypotension (MAP (Mean Arterial Pressure) <70 mm Hg or requirement for inotropes or vasopressors to maintain blood pressure) at day 7 and/or day 14.

In embodiments, a method described herein (e.g., for the prevention and treatment of ARDS among COVID-19 patients such as hospitalized COVID-19 patients) results in a change (e.g., a decrease or a reduction) in the proportion of patients with acute kidney injury at day 7 and day 14.

In embodiments, a method described herein (e.g., for the prevention and treatment of ARDS among COVID-19 patients such as hospitalized COVID-19 patients) results in a change (e.g., a decrease or a reduction) in the time to hospital discharge.

Efficacy of vadadustat may also be assessed using still other measures, including effects on: inducing known transcriptional targets of HIFs (e.g., erythropoietin, extracellular adenosine levels, circulating levels of CD73 (or ecto-5'-nucleotidase), VEGF (vascular endothelial growth factor), hypoxia-driven microRNAs that dampen lung inflammation). Various laboratory measurements include but not limited to serum creatinine, FGF-23 (or fibroblast growth factor 23), and markers of attenuated inflammation.

Pharmaceutical Compositions

Pharmaceutical compositions may be used in the preparation of individual, single unit dosage forms. Pharmaceutical compositions and dosage forms provided herein comprise a HIF prolyl hydroxylase inhibitor or a HIF-alpha stabilizer, such as a compound described herein (e.g., a compound having a structure according to any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof). Pharmaceutical compositions and dosage forms can further comprise one or more excipients. Like the amounts and types of excipients, the amounts and specific types of active ingredients in a dosage form may differ depending on factors including, but not limited to, the route by which it is to be administered to patients.

In embodiments, a HIF prolyl hydroxylase inhibitor or a HIF-alpha stabilizer may be administered by oral or parenteral route. As used herein, the term "parenteral" includes but not limited to subcutaneous, intradermal, intravascular injections, such as intravenous, intramuscular and any another similar injection or infusion technique; transdermal route; inhalation, and rectal route. In embodiments, a HIF prolyl hydroxylase inhibitor or a HIF-alpha stabilizer may be administered orally, such as in a tablet or capsule formulation. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

Oral Formulations

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art.

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, PA), and mixtures thereof.

A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM. Other suitable forms of microcrystalline cellulose include, but are not limited to, silicified microcrystalline cellulose, such as the materials sold as PROSOLV 50, PROSOLV 90, PROSOLV HD90, PROSOLV 90 LM, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

In embodiments, fillers may include, but are not limited to block copolymers of ethylene oxide and propylene oxide. Such block copolymers may be sold as POLOXAMER or PLURONIC, and include, but are not limited to POLOXAMER 188 NF, POLOXAMER 237 NF, POLOXAMER 338 NF, POLOXAMER 437 NF, and mixtures thereof.

In embodiments, fillers may include, but are not limited to isomalt, lactose, lactitol, mannitol, sorbitol xylitol, erythritol, and mixtures thereof.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 weight percent to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, povidone, crospovidone, polacrilin potassium, sodium starch glycolate, potato or tapioca starch, other starches, pre-gelatinized starch, other starches, clays, other algins, other celluloses, gums, and mixtures thereof.

Glidants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium stearyl fumarate, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional glidants include, for example, a syloid silica gel (AEROSIL200, manufactured by W.R. Grace Co. of Baltimore, MD), a coagulated aerosol of synthetic silica (marketed by Degussa Co. of Plano, TX), CAB-O-SIL (a pyrogenic colloidal silicon dioxide product sold by Cabot Co. of Boston, MA), and mixtures thereof. If used at all, glidants may be used in an amount of less than about 1 weight percent of the pharmaceutical compositions or dosage forms into which they are incorporated.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Doses and Dosing Regimens

In embodiments, a disease or condition as described herein, may be treated by administering to a patient in need thereof from about 100 mg to about 1800 mg, about 100 mg to about 1500 mg, about 150 mg to about 1200 mg, about 150 mg to about 1450 mg, about 200 mg to about 1400 mg, about 250 mg to about 1350 mg, about 300 mg to about 1300 mg, about 350 mg to about 1250 mg, about 400 mg to about 1200 mg, about 450 mg to about 1150 mg, about 500 mg to about 1100 mg, about 550 mg to about 1050 mg, about 600 mg to about 1000 mg, about 650 mg to about 950 mg, about 700 mg to about 900 mg, about 850 mg to about 950 mg, about 800 mg to about 1000 mg, about 750 mg to about 1050 mg, about 700 mg to about 1100 mg, about 650 mg to about 1150 mg, about 600 mg to about 1200 mg, about 150 mg to about 1800 mg, about 300 mg to about 1800 mg, about 450 mg to about 1800 mg, about 600 mg to about 1800 mg, about 750 mg to about 1800 mg, or about 900 mg to about 1800 mg of a HIF prolyl hydroxylase inhibitor or a HIF-alpha stabilizer. In embodiments, the dose of a HIF prolyl hydroxylase inhibitor or a HIF-alpha stabilizer is between 150 mg to 750 mg. In embodiments, the dose of a HIF prolyl hydroxylase inhibitor or a HIF-alpha stabilizer is between 900 mg to 1800 mg. In embodiments, the dose of a HIF prolyl hydroxylase inhibitor or a HIF-alpha stabilizer is between 150 mg to 1800 mg. In embodiments, the dose of a HIF prolyl hydroxylase inhibitor or a HIF-alpha stabilizer is between 150 mg to 1000 mg. In embodiments, the dose of a HIF prolyl hydroxylase inhibitor or a HIF-alpha stabilizer is about 100 mg, about 120 mg, about 140 mg, about 160 mg, about 180 mg, about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, about 500 mg, about 520 mg, about 540 mg, about 560 mg, about 580 mg, about 600 mg, about 620 mg, about 640 mg, about 660 mg, about 680 mg, about 700 mg, about 720 mg, about 740 mg, about 760 mg, about 780 mg, about 800 mg, about 820 mg, about 840 mg, about 860 mg, about 880 mg, about 900 mg, about 920 mg, about 940 mg, about 960 mg, about 980 mg, about 1000 mg, about 1020 mg, about 1040 mg, about 1060 mg, about 1080 mg, about 1100 mg, about 1120 mg, about 1140 mg, about 1160 mg, about 1180 mg, about 1200 mg, about 1220 mg, about 1240 mg, about 1260 mg, about 1280 mg, about 1300 mg, about 1320 mg, about 1340 mg, about 1360 mg, about 1380 mg, about 1400 mg, about 1420 mg, about 1440 mg, about 1460 mg, about 1480 mg, about 1500 mg, about 1650 mg, or about 1800 mg.

In embodiments, such doses may be administered orally, three times a week, once daily, twice daily, or three times daily. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the dose of a HIF prolyl hydroxylase inhibitor or a HIF-alpha stabilizer is about 150 mg to about 1500 mg, about 150 mg to about 1200 mg, about 150 mg to about 1800 mg, or about 900 mg to about 1800 mg. In embodiments, the dose of a HIF prolyl hydroxylase inhibitor or a HIF-alpha stabilizer is about 150 mg, about 300 mg, about 450 mg, about 600 mg, about 750 mg, about 900 mg, about 1050 mg, about 1200 mg, about 1350 mg, about 1500 mg, about 1650 mg, or about 1800 mg. In embodiments, the initial dose of a HIF prolyl hydroxylase inhibitor or a HIF-alpha stabilizer is about 900 mg. In embodiments, such doses may be administered orally, three times a week, once daily, twice daily, or three times daily. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, the dose of vadadustat is between about 100 mg to about 1800 mg, about 100 mg to about 1500 mg, about 150 mg to about 1450 mg, about 200 mg to about 1400 mg, about 250 mg to about 1350 mg, about 300 mg to about 1300 mg, about 350 mg to about 1250 mg, about 400 mg to about 1200 mg, about 450 mg to about 1150 mg, about 500 mg to about 1100 mg, about 550 mg to about 1050 mg, about 600 mg to about 1000 mg, about 650 mg to about 950 mg, about 700 mg to about 900 mg, about 850 mg to about 950 mg, about 800 mg to about 1000 mg, about 750 mg to about 1050 mg, about 700 mg to about 1100 mg, about 650 mg to about 1150 mg, about 600 mg to about 1200 mg, about 150 mg to about 1800 mg, about 300 mg to about 1800 mg, about 450 mg to about 1800 mg, about 600 mg to about 1800 mg, about 750 mg to about 1800 mg, or about 900 mg to about 1800 mg. In embodiments, the dose of vadadustat is between 150 mg to 750 mg. In embodiments, the dose of vadadustat is between 150 mg to 1000 mg. In embodiments, the dose of vadadustat is between 150 mg to 1800 mg. In embodiments, the dose of vadadustat is between 900 mg to 1800 mg. In embodiments, the dose of vadadustat is about 100 mg, about 120 mg, about 140 mg, about 160 mg, about 180 mg, about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, about 500 mg, about 520 mg, about 540 mg, about 560 mg, about 580 mg, about 600 mg, about 620 mg, about 640 mg, about 660 mg, about 680 mg, about 700 mg, about 720 mg, about 740 mg, about 760 mg, about 780 mg, about 800 mg, about 820 mg, about 840 mg, about 860 mg, about 880 mg, about 900 mg, about 920 mg, about 940 mg, about 960 mg, about 980 mg, about 1000 mg, about 1020 mg, about 1040 mg, about 1060 mg, about 1080 mg, about 1100 mg, about 1120 mg, about 1140 mg, about 1160 mg, about 1180 mg, about 1200 mg, about 1220 mg, about 1240 mg, about 1260 mg, about 1280 mg, about 1300 mg, about 1320 mg, about 1340 mg, about 1360 mg, about 1380 mg, about 1400 mg, about 1420 mg, about 1440 mg, about 1460 mg, about 1480 mg, about 1500 mg, about 1650 mg, or about 1800 mg. In embodiments, such doses may be administered orally, three times a week, once daily, twice daily, or three times daily.

In embodiments, the dose of vadadustat is about 150 mg, about 300 mg, about 450 mg, about 600 mg, about 750 mg, about 900 mg, about 1050 mg, about 1200 mg, about 1350 mg, about 1500 mg, about 1650 mg, or about 1800 mg. In embodiments, the initial dose of vadadustat is about 900 mg. In embodiments, such doses may be administered orally, three times a week, once daily, twice daily, or three times daily.

In embodiments, a dose of vadadustat is about 900 mg. For example, a method for treating or preventing acute respiratory distress syndrome (ARDS) can comprise administering to a patient in need thereof (e.g., a patient with COVID-19) about 900 mg vadadustat. In embodiments, a patient is hospitalized. In embodiments, an initial dose of vadadustat administered to a patient is about 900 mg. In embodiments, a dose is administered daily. In embodiments, a dose is administered once daily. In embodiments, a dose of vadadustat is adjusted by about 150 mg (e.g., lowered by about 150 mg or increased by about 150 mg).

In embodiments, a dose of vadadustat is about 900-1800 mg. For example, a method for treating or preventing acute respiratory distress syndrome (ARDS) can comprise administering to a patient in need thereof (e.g., a patient with COVID-19) about 900-1800 mg vadadustat. In embodiments, a patient is hospitalized. In embodiments, a dose is administered daily. In embodiments, a dose is administered once daily. In embodiments, a dose of vadadustat is adjusted by about 150 mg (e.g., lowered by about 150 mg or increased by about 150 mg), optionally where the maximum dose is about 1800 mg. In embodiments, a dose (e.g., a daily dose) of vadadustat is about 900, 1050, 1200, 1350, 1500, 1650, or 1800 mg.

In embodiments, a HIF prolyl hydroxylase inhibitor or HIF-alpha stabilizer is administered to a patient for up to about one month. In embodiments, a HIF prolyl hydroxylase inhibitor or the HIF-alpha stabilizer is administered to a patient for up to about four weeks (about 28 days), three weeks (about 21 days), two weeks (about 14 days), or one week (about 7 days). In embodiments, a HIF prolyl hydroxylase inhibitor or the HIF-alpha stabilizer is administered to a patient for up to about two weeks (about 14 days). Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

In embodiments, a HIF prolyl hydroxylase inhibitor or HIF-alpha stabilizer is administered orally. In embodiments, a HIF prolyl hydroxylase inhibitor or HIF-alpha stabilizer is administered to an intubated patient through a nasogastric tube. Examples of HIF prolyl hydroxylase inhibitors or HIF-alpha stabilizers include compounds of any one of Formulas (I)-(VI), or a compound such as vadadustat (AKB-6548), roxadustat (FG-4592), daprodustat (GSK-12788363), molidustat (BAY 85-3934), enarodustat (JTZ-951), or desidustat (ZYAN1), or a pharmaceutically acceptable salt thereof. In embodiments, a compound is vadadustat.

As an exemplary embodiment, a patient can receive a prolyl hydroxylase inhibitor or HIF-alpha stabilizer (e.g., oral administration of vadadustat) once daily (e.g., for 14 days). In embodiments, a patient (e.g., a patient having COVID-19) can receive said daily dose in order to treat or prevent Acute Respiratory Distress Syndrome (ARDS). In embodiments, a patient is hospitalized. In embodiments, a patient can receive a dose of about 150 mg-1800 mg vadadustat (e.g., about 900-1800 mg vadadustat). In embodiments, a patient receives an initial daily dose is about 900 mg vadadustat and/or receives a dose of about 900 mg vadadustat throughout the period of treatment. Vadadustat can be administered in unit dosage forms (e.g., a tablet) comprising about 75, 150, 300, 450, or 600 mg of the drug.

EXAMPLES

Example 1

Methods of Treating Patients Having COVID-19

Methods described herein can be useful for treating patients infected by the novel severe acute respiratory syndrome coronavirus 2 (SARS-CoV-2) and having COVID-19. The present example illustrates a method of treating or preventing COVID-19 related pneumonia and related conditions including acute lung injury (ALI), acute respiratory distress syndrome (ARDS), and associated organ failure (e.g., as described herein).

Patients who can receive therapy comprising administration of a compound or pharmaceutically acceptable salt thereof that is a HIF prolyl hydroxylase inhibitor or a HIF-alpha stabilizer (e.g., vadadustat) include adult patients with evidence of hypoxia such as an oxygen saturation level that is 94% or less. An adult patient can be about 45 years of age or about (e.g., about 45-60 years of age, about 60-80 years of age, or over about 80 years of age).

Patients can also be identified by the severity of their disease, including as described by the below ordinal scale. For example, a patient can be assessed according to the following ordinal scale or exhibit the severity of disease as described by any of scores 2-7 of this scale.

| Score | Descriptor | Patient State | |
|---|---|---|---|
| 0 | No clinical or virological evidence of infection | Uninfected | Uninfected/ Ambulatory |
| 1 | Not hospitalized, no limitation of patient's activities | Infected (Ambulatory) | |
| 2 | Not hospitalized, limitation of patient's activities and/or requiring home oxygen | | |
| 3 | Patient is hospitalized but does not receive oxygen therapy-no longer requires ongoing medical care | Infected-Hospitalized (Mild Disease) | Hospitalized but not intubated |
| 4 | Patient is hospitalized but does not require oxygen therapy-requiring ongoing care (COVID-19 related or otherwise) | | |
| 5 | Patient is hospitalized and requiring supplemental oxygen | Infected-Hospitalized (Severe Disease) | |
| 6 | Patient is hospitalized and receives oxygen therapy that is non-invasive ventilation or high flow oxygen devices | | Hospitalized and intubated |
| 7 | Patient is hospitalized and receives invasive mechanical ventilation and additional organ support such as pressors, renal replacement therapy (RRT), and/or extracorporeal membrane oxygenation (ECMO) | | |
| 8 | Death | Dead | Death |

Patients can receive daily doses of the compound (e.g., vadadustat) of about 100-1500 mg/day. The patient can receive therapy for time periods as described herein, including up to about one month (e.g., up to about 4 weeks (about 28 days), about 3 weeks (about 21 days), about 2 weeks (about 14 days), or about 1 week (about 7 days)). In embodiments, a patient receives a dose (e.g., a daily dose) of the compound (e.g., vadadustat) for up to about 2 weeks (about 14 days). In embodiments, a patient receives a dose of about 900 mg of vadadustat. In embodiments, a patient receives an initial dose of about 900 mg of vadadustat. In embodiments, a patient receives a dose of up to about 1800 mg of vadadustat (e.g., about 150, 300, 450, 600, 750, 900, 1050, 1200, 1350, 1500, 1650, or 1800 mg vadadustat or about 900 to about 1800 mg vadadustat).

Following commencement of treatment, the severity of disease may be maintained such that the patient's condition can stabilize. For example, a patient's score according to the ordinal scale can remain unchanged such that the patient's condition stabilizes following treatment with the HIF prolyl hydroxylase inhibitor or the HIF-alpha stabilizer (e.g., vadadustat) to the patient.

The severity of disease may decrease following commencement of administering the HIF prolyl hydroxylase inhibitor or the HIF-alpha stabilizer to the patient. For example, a patient's score as assessed by the ordinal scale can decrease by at least one point following commencement of administering the HIF prolyl hydroxylase inhibitor or the HIF-alpha stabilizer (e.g., vadadustat).

Further, the methods provided herein can treat or prevent other organ injury (including multi-organ injury) in a patient. Additional benefits of the treatment can include any of the following, or any combination thereof, following commencement of treatment:

a patient's oxygen saturation value can improve to a value of about 95% or greater;

an oxygen therapy received by the patient can be discontinued (e.g., mechanical ventilation is discontinued and the patient experiences increased ventilator-free survival or a patient no longer requires an oxygen therapy comprising a face mask, high flow oxygen, noninvasive mechanical ventilation, or intubation);

a vasopressor therapy is reduced or discontinued; and/or a patient whose hypotension exhibits clinical improvement.

Still further benefits of the treatment can include any of those described herein. For example, described herein is an exemplary method for treating or preventing acute respiratory distress syndrome (ARDS) in a patient having COVID-19.

Example 1a

Methods of Treating Patients Having COVID-19

This example describes use of 5-(3-chlorophenyl)-3-hydroxypyridine-2-carbonyl] amino} acetic acid (vadadustat) in a multicenter, randomized, double-blind, placebo-controlled Bayesian adaptive clinical for the prevention and treatment of acute respiratory distress syndrome (ARDS) in hospitalized patients with coronavirus disease 2019 (COVID-19).

Patients may be divided into the following age categories:

<65 years,

≥65 and <80 years, and

≥80 years.

Selection and Withdrawal of Subjects

Subjects may be selected for treatment based on the certain inclusion and exclusion criteria, including any or all of the exemplary criteria described herein.

Inclusion criteria may include any or all of the following:

1. Men and women ≥18 years of age.
2. Laboratory-confirmed diagnosis of COVID-19 by detection of SARS-CoV-2 RNA by RT-PCR (reverse transcription polymerase chain reaction) from any specimen respiratory.
3. Admitted to the hospital.
4. Within 24 hours of hospital admission.
5. Oxygen saturation of hemoglobin by pulse oximetry at room air ≤94%.
6. Participation in any other clinical trial for the treatment for COVID-19 is not allowed.
7. Understands the procedures and requirements of treatment and provides written informed consent and authorization for protected health information disclosure.

Exclusion may include any or all of the following:

1. Males with hemoglobin >17.5 g/dL or females >15.5 g/dL.
2. Hypersensitivity to vadadustat or any of its excipients.
3. Placed on mechanical ventilation before randomization.
4. Hemoglobin above the gender specific upper limit of normal (ULN) at randomization.
5. Aspartate aminotransferase (AST), alanine aminotransferase (ALT), or total bilirubin >2.0×ULN at randomization.
6. Patients who have erythrocytosis or polycethemia vera.
7. Patients receiving any of the following medications: sulfasalazine or other BCRP substrates, probenecid or other UGT and OAT1/3 inhibitors.
8. Women who are pregnant or breastfeeding, or positive pregnancy test before randomization.
9. Patients on maintenance dialysis.
10. Patients who have received a solid organ transplant.
11. Patients who are prisoners.

Vadadustat can be administered to a patient according to methods described herein. In some embodiments, vadadustat may be permanently discontinued if a patient meets any of the following prespecified criteria:

Patient completes 14 days of in-hospital treatment.

Patient is discharged before 14 days of treatment.

Patient dies.

If the patients develops ALT or AST >3×ULN or total bilirubin >3×ULN.

If the patient hemoglobin level are >17.5 g/dl for males or >15.5 g/dl for females.

Other reasons:

Unacceptable toxicity or drug intolerability.

Patient withdrawal of consent.

Patient becomes pregnant.

Study Design

Following screening, patients are randomized in a 1:1 ratio to either vadadustat 900 mg or placebo. Randomination is stratified by site, and MSOFA score at baseline (<4 and ≥4).

Treatment of Subjects

A subject may receive vadadustat (e.g., 900 mg vadadustat as 6 tablets once daily) for 14 days and without regard for meals at approximately the same time each day. Tablets can be crushed using a pill crusher and administered to an intubated patient through a nasogastric tube.

If a patient is receiving additional therapeutic agents concurrently with vadadustat therapy, doses of the additional therapeutic agents may be adjusted. For example, doses of the following concomitant medication may be adjusted during treatment as follows:

1. Simvastatin, maximum daily dose of 20 mg.
2. Rosuvastatin, maximum daily dose of 10 mg.
3. If the patient is currently taking erythropoiesis-stimulating agents or ESA (e.g., epoetin alfa, darbepoietin, or methoxy polyethylene glycol-epoetin beta), the medication should be discontinued.

All hospitalized patients with COVID-19 should receive prophylactic anticoagulation with LMWH (Low Molecular Weight Heparin) if no contraindications:

1. If CrCl (Creatinine clearance)>30 mL/min—use lovenox 40 mg sc qd.
2. If CrCl<30 mL/min—use UFH (unfractionated heparin).
3. In obese patients, increase lovenox dose to 40 mg bid.
4. If history of HIT (heparin-induced thrombocytopenia) or HITT (heparin-induced thrombocytopenia/thrombosis), use non heparin alternative.
5. If contraindications for AC (anticoagulation), do SCDs (sequential compression devices).

Patients can be identified by the severity of their disease, including as described herein, including according to the below scale based on the National Institute of Allergy and Infectious Disease Ordinal Scale (NIAID-OS).

| Score | Descriptor | Patient State | |
|---|---|---|---|
| 0 | No clinical or virological evidence of infection | Uninfected | Uninfected/Ambulatory |
| 1 | Not hospitalized, no limitation of patient's activities | Infected (Ambulatory) | |
| 2 | Not hospitalized, limitation of patient's activities and/or requiring home oxygen | | |
| 3 | Patient is hospitalized but does not receive oxygen therapy-no longer requires ongoing medical care | Infected-Hospitalized (Mild Disease) | Hospitalized but not intubated |
| 4 | Patient is hospitalized but does not require oxygen therapy-requiring ongoing care (COVID-19 related or otherwise) | | |
| 5 | Patient is hospitalized and requiring supplemental oxygen | Infected-Hospitalized | |
| 6 | Patient is hospitalized and receives oxygen therapy that is non-invasive ventilation or high flow oxygen devices | (Severe Disease) | Hospitalized and intubated |
| 7 | Patient is hospitalized and receives invasive mechanical ventilation and additional organ support such as pressors, renal replacement therapy (RRT), and/or extracorporeal membrane oxygenation (ECMO) | | |
| 8 | Death | Dead | Death |

For example, the efficacy of vadadustat (e.g., 900 mg per day) for the prevention and treatment of ARDS among COVID-19 patients may be measured by ≥1 point deterioration on the NIAID ordinal scale for clinical improvement at day seven or day 14 of treatment.

Efficacy of treatment can be assessed as described herein.

For example, efficacy may be assessed by a change of one point or more (from baseline) on the National Institute of Allergy and Infectious Disease Ordinal Scale (NIAID-OS) for clinical improvement. A change may be assessed on, at, or by day 7 of treatment or on, at, or by day 14 of treatment. A change may be an improvement by one point or more. A change may be a worsening by one point or more. For example, a change may be worsening by one point or more (from baseline) on the NIAID ordinal scale for clinical improvement (e.g., on or at day 7 or day 14).

Efficacy may also be assessed according to any of the following (including any combination thereof):

1. The proportion of patients at day 14 who are dead (8) or hospitalized, on invasive mechanical ventilation or ECMO (7) or hospitalized, on non-invasive ventilation or high flow oxygen devices (6) on the NIAID-OS.
2. Proportions of patients with a score of 0 at 14 days on the MSOFA (Modified Sequential Organ Failure Assessment) scale:

| Organ System | 0 | 1 | 2 | 3 | 4 |
|---|---|---|---|---|---|
| Respiratory SpO2/FiO2 | >400 | ≤400 | ≤315 | ≤235 | ≤150 |
| Liver | No scleral icterus or jaundice | | | Scleral icterus or jaundice | |
| Cardiovascular, hypotension | No hypotension | MAP <70 mm Hg | Dopamine ≤5 or dobutamine any dose | Dopamine >5 Epinephrine ≤0.1 Norepinephrine ≤0.1 | Dopamine >15 Epinephrine >0.1 Norepinephrine >0.1 |
| CNS (central nervous system), Glasgow Coma Score | 15 | 13-14 | 10-12 | 6-9 | <6 |
| Renal, Creatinine mg/dL | <1.2 | 1.2-1.9 | 2.0-3.4 | 3.5-4.9 | >5.0 |

Note:
Discharged patient receives a score of 0 and dead patient receives a score of 20.

3. Average MSOFA scores at day 7 and day 14.
4. Proportion of patients who develop ARDS or experienced increased ARDS severity from baseline based on the Berlin scale.
5. Ventilator-free survival at day 7 and day 14.
6. Overall survival at day 7 and day 14.
7. Proportion of patients with hypotension (MAP (Mean Arterial Pressure)<70 mm Hg or requirement for inotropes or vasopressors to maintain blood pressure) at day 7 and day 14.
8. Proportion of patients with acute kidney injury at day 7 and day 14.
9. Time to hospital discharge.

Results from the trial can indicate at least one of the following: a lower or a reduction in the proportion of patients at day 14 who are dead (8) or hospitalized, on invasive mechanical ventilation or ECMO (7) or hospitalized, on non-invasive ventilation or high flow oxygen devices (6) on the NIAID-OS for patients on vadadustat compared to placebo; an increase in the proportions of patients with a score of 0 at 14 days on the MSOFA for patients on vadadustat compared to placebo; a lower or a reduction in the average MSOFA scores at day 7 and day 14 for patients on vadadustat compared to placebo; a lower or a reduction in the proportion of patients who develop ARDS or experienced increased ARDS severity from baseline based on the Berlin scale for patients on vadadustat compared to placebo; a greater or an increase in the number of ventilator-free survival at day 7 and day 14 for patients on vadadustat compared to placebo; a greater or an increase in the number of overall survival at day 7 and day 14 for patients on vadadustat compared to placebo; a lower or a reduction in the proportion of patients with hypotension (MAP (Mean Arterial Pressure)<70 mm Hg or requirement for inotropes or vasopressors to maintain blood pressure) at day 7 and day 14 for patients on vadadustat compared to placebo; a lower or a reduction in the proportion of patients with acute kidney injury at day 7 and day 14 for patients on vadadustat versus placebo; and a shorter or a reduction in the time to hospital discharge for patients on vadadustat versus placebo.

Efficacy of vadadustat may also be assessed using still other measures, including effects on: inducing known transcriptional targets of HIFs (e.g., erythropoietin, extracellular adenosine levels, circulating levels of CD73 (or ecto-5'-nucleotidase), VEGF (vascular endothelial growth factor), hypoxia-driven microRNAs that dampen lung inflammation). Various laboratory measurements include but not limited to serum creatinine, FGF-23 (or fibroblast growth factor 23), and markers of attenuated inflammation.

Certain Exemplary Embodiments

Additional exemplary embodiments are described in the following numbered paragraphs 1-435.

1. A method of treating a respiratory viral infection, comprising administering to a patient in need thereof a compound that is a HIF prolyl hydroxylase inhibitor or a HIF-alpha stabilizer, or a pharmaceutically acceptable salt thereof.
2. The method of paragraph 1, wherein the respiratory viral infection is induced by or associated with a virus that could lead to viral pneumonia.
3. The method of paragraph 1 or 2, wherein the respiratory viral infection is induced by or associated with a coronavirus, an influenza A, an influenza B, a Rhinovirus, a respiratory syncytial virus (RSV), an adenovirus, a human parainfluenza virus (HPIV) or an enterovirus.
4. The method of any one of paragraphs 1-3, wherein the respiratory viral infection is induced by or associated with a coronavirus.
5. The method of paragraph 4, wherein the coronavirus is the SARS-CoV, MERS-CoV, or SARS-CoV-2.
6. The method of any one of paragraphs 1-5, wherein the respiratory viral infection is lower respiratory infection.
7. The method of any one of paragraphs 1-6, wherein the respiratory viral infection is pulmonary viral infection.
8. The method of any one of paragraphs 1-5, wherein the respiratory viral infection is upper respiratory infection.

9. The method of any one of paragraphs 1-8, wherein the respiratory viral infection is COVID-19.
10. The method of any one of paragraphs 1-9, wherein the respiratory viral infection induces a lung disease.
11. The method of paragraph 10, wherein the lung disease is selected from acute lung injury (ALI), bronchitis, pneumonia, pulmonary fibrosis, asthma, or acute respiratory distress syndrome (ARDS).
12. The method of paragraph 10 or 11, wherein the patient develops pulmonary hypertension.
13. The method of paragraph 10 or 11, wherein the patient develops multi-organ failure.
14. The method of paragraph 13, wherein the multi-organ failure comprise heart failure, liver failure, lung failure kidney failure, and gastrointestinal (GI) system failure.
15. A method of treating a pulmonary viral infection, comprising administering to a patient in need thereof a compound that is a HIF prolyl hydroxylase inhibitor or a HIF-alpha stabilizer, or a pharmaceutically acceptable salt thereof.
16. The method of paragraph 15, wherein the pulmonary viral infection is induced by or associated with a coronavirus, an influenza A, an influenza B, a Rhinovirus, a respiratory syncytial virus (RSV), an adenovirus, a human parainfluenza virus (HPIV) or an enterovirus.
17. The method of paragraph 15 or 16, wherein the pulmonary viral infection is induced by or associated with a coronavirus.
18. The method of paragraph 17, wherein the coronavirus is the SARS-CoV, MERS-CoV, or SARS-CoV-2.
19. The method of any one of paragraphs 15-18, wherein the pulmonary viral infection is COVID-19.
20. The method of any one of paragraphs 15-19, wherein the pulmonary viral infection induces a lung disease.
21. The method of paragraph 20, wherein the lung disease is selected from acute lung injury (ALI), bronchitis, pneumonia, pulmonary fibrosis, asthma, or acute respiratory distress syndrome (ARDS).
22. The method of paragraph 20 or 21, wherein the patient develops pulmonary hypertension.
23. The method of paragraph 20 or 21, wherein the patient develops multi-organ failure.
24. The method of paragraph 23, wherein the multi-organ failure comprises heart failure, liver failure, lung failure, kidney failure and gastrointestinal (GI) system failure.
25. A method of treating a coronavirus infection, comprising administering to a patient in need thereof a compound that is a HIF prolyl hydroxylase inhibitor or a HIF-alpha stabilizer, or a pharmaceutically acceptable salt thereof.
26. A method of treating or preventing a lung disease that is acute lung injury (ALI) in a patient in need thereof, comprising administering to the patient a compound that is a HIF prolyl hydroxylase inhibitor or a HIF-alpha stabilizer, or a pharmaceutically acceptable salt thereof.
27. The method of paragraph 26, wherein said patient has a viral infection, sepsis, pneumonia, aspiration, trauma, pancreatitis, blood transfusion, and/or smoke or toxic gas inhalation.
28. The method of paragraph 26 or 27, wherein said acute lung injury (ALI) is induced by or associated with a viral infection, sepsis, pneumonia, aspiration, trauma, pancreatitis, blood transfusion, and/or smoke or toxic gas inhalation.
29. The method of any one of paragraphs 26-28, wherein said patient is mechanically ventilated.
30. A method of treating or preventing a lung disease that is acute lung injury (ALI) in a patient in need thereof, comprising administering to the patient a compound that is a HIF prolyl hydroxylase inhibitor or a HIF-alpha stabilizer, or a pharmaceutically acceptable salt thereof, and
wherein said ALI is induced by or associated with a ventilator.
31. The method of paragraph 30, wherein said patient has a viral infection, sepsis, pneumonia, aspiration, trauma, pancreatitis, blood transfusion, and/or smoke or toxic gas inhalation.
32. A method of treating or preventing a lung disease that is acute lung injury (ALI) in a patient having a respiratory viral infection, comprising administering to the patient a compound that is a HIF prolyl hydroxylase inhibitor or a HIF-alpha stabilizer, or a pharmaceutically acceptable salt thereof.
33. A method of treating or preventing a lung disease that is acute respiratory distress syndrome (ARDS) in a patient having a respiratory viral infection, comprising administering to the patient a compound that is a HIF prolyl hydroxylase inhibitor or a HIF-alpha stabilizer, or a pharmaceutically acceptable salt thereof.
34. The method of paragraph 32 or 33, wherein the respiratory viral infection is infection by a coronavirus, an influenza A, an influenza B, a Rhinovirus, a respiratory syncytial virus (RSV), an adenovirus, a human parainfluenza virus (HPIV) or an enterovirus.
35. The method of any one of paragraphs 32-34, wherein the respiratory viral infection is infection by a coronavirus.
36. The method of paragraph 35, wherein the coronavirus is the SARS-CoV, MERS-CoV, or SARS-CoV-2.
37. The method of any one of paragraphs 32-36, wherein the respiratory viral infection is COVID-19.
38. The method of paragraph 32, wherein the patient with acute lung injury develops acute respiratory distress syndrome (ARDS).
39. The method of any one of paragraphs 32-38, wherein the patient with ALI or ARDS develops pulmonary hypertension.
40. The method of any one of paragraphs 32-38, wherein the patient with ALI or ARDS develops multi-organ failure.
41. The method of paragraph 40, wherein the multi-organ failure comprise heart failure, liver failure, lung failure kidney failure, and gastrointestinal (GI) system failure.
42. The method of any one of paragraphs 32-41, wherein ALI or ARDS is characterized by accumulation of inflammatory cells into the lungs, cytokine release, inflammatory activation of recruited or resident cells, disruption of the alveolar-capillary barrier function, pulmonary edema, attenuated gas exchange, or lung inflammation, or any combination thereof.
43. The method of any one of paragraphs 32-41, wherein ALI or ARDS is characterized by accumulation of inflammatory cells into the lungs, cytokine release, inflammatory activation of recruited or resident cells, disruption of the alveolar-capillary barrier function, pulmonary edema, attenuated gas exchange, or any combination thereof.
44. The method of any one of paragraphs 32-43, wherein ALI or ARDS is induced by or associated with the viral infection.
45. A method of treating or preventing a lung disease that is acute lung injury (ALI) in a patient having a pulmonary viral infection, comprising administering to the patient a compound that is a HIF prolyl hydroxylase inhibitor or a HIF-alpha stabilizer, or a pharmaceutically acceptable salt thereof.

46. A method of treating or preventing a lung disease that is acute respiratory distress syndrome (ARDS) in a patient having a pulmonary viral infection, comprising administering to the patient a compound that is a HIF prolyl hydroxylase inhibitor or a HIF-alpha stabilizer, or a pharmaceutically acceptable salt thereof.
47. The method of paragraph 45 or 46, wherein the pulmonary viral infection is infection by a coronavirus, an influenza A, an influenza B, a Rhinovirus, a respiratory syncytial virus (RSV), an adenovirus, a human parainfluenza virus (HPIV) or an enterovirus.
48. The method of any one of paragraphs 45-47, wherein the pulmonary viral infection is infection by a coronavirus.
49. The method of paragraph 48, wherein the coronavirus is the SARS-CoV, MERS-CoV, or SARS-CoV-2.
50. The method of any one of paragraphs 45-49, wherein the pulmonary viral infection is COVID-19.
51. The method of paragraph 45, wherein the patient with acute lung injury develops acute respiratory distress syndrome (ARDS).
52. The method of any one of paragraphs 45-51, wherein the patient with ALI or ARDS develops pulmonary hypertension.
53. The method of any one of paragraphs 45-51, wherein the patient with ALI or ARDS develops multi-organ failure.
54. The method of paragraph 53, wherein the multi-organ failure comprise heart failure, liver failure, lung failure kidney failure, and gastrointestinal (GI) system failure.
55. The method of any one of paragraphs 45-54, wherein ALI or ARDS is characterized by accumulation of inflammatory cells into the lungs, cytokine release, inflammatory activation of recruited or resident cells, disruption of the alveolar-capillary barrier function, pulmonary edema, attenuated gas exchange, or lung inflammation, or any combination thereof.
56. The method of any one of paragraphs 45-54, wherein ALI or ARDS is characterized by accumulation of inflammatory cells into the lungs, cytokine release, inflammatory activation of recruited or resident cells, disruption of the alveolar-capillary barrier function, pulmonary edema, attenuated gas exchange, or any combination thereof.
57. The method of any one of paragraphs 45-56, wherein ALI or ARDS is induced by or associated with the viral infection.
58. A method of treating or preventing a lung disease that is acute lung injury (ALI) in a patient infected with a coronavirus, comprising administering to the patient a compound that is a HIF prolyl hydroxylase inhibitor or a HIF-alpha stabilizer, or a pharmaceutically acceptable salt thereof.
59. A method of treating or preventing a lung disease that is acute respiratory distress syndrome (ARDS) in a patient infected with a coronavirus, comprising administering to the patient a compound that is a HIF prolyl hydroxylase inhibitor or a HIF-alpha stabilizer, or a pharmaceutically acceptable salt thereof.
60. The method of paragraph 58 or 59, wherein the coronavirus is the SARS-CoV, MERS-CoV, or SARS-CoV-2.
61. The method of any one of paragraphs 58-60, wherein the patient is infected with SARS-CoV-2.
62. The method of any one of paragraphs 58-61, wherein the patient with ALI or ARDS develops pulmonary hypertension.
63. The method of any one of paragraphs 58-61, wherein the patient with ALI or ARDS develops multi-organ failure.
64. The method of paragraph 63, wherein the multi-organ failure comprise heart failure, liver failure, lung failure kidney failure, and gastrointestinal (GI) system failure.
65. The method of any one of paragraphs 58-64, wherein ALI or ARDS is characterized by accumulation of inflammatory cells into the lungs, cytokine release, inflammatory activation of recruited or resident cells, disruption of the alveolar-capillary barrier function, pulmonary edema, attenuated gas exchange, or lung inflammation, or any combination thereof.
66. The method of any one of paragraphs 58-64, wherein ALI or ARDS is characterized by accumulation of inflammatory cells into the lungs, cytokine release, inflammatory activation of recruited or resident cells, disruption of the alveolar-capillary barrier function, pulmonary edema, attenuated gas exchange, or any combination thereof.
67. The method of any one of paragraphs 58-66, wherein ALI or ARDS is induced by or associated with the viral infection.
68. The method of any one of paragraphs 1-67, wherein said patient is an adult.
69. The method of any one of paragraphs 1-68, wherein said patient exhibits one or more symptoms of hypoxia.
70. The method of paragraph 69, wherein the one or more symptoms of hypoxia include changes in the color of the skin, confusion, cough, fast heart rate, rapid breathing, shortness of breath, sweating, and/or wheezing.
71. The method of paragraph 69, wherein the patient has a low oxygen saturation of hemoglobin.
72. The method of any one of paragraphs 1-71, wherein the patient has an oxygen saturation of hemoglobin that is about 94% or less.
73. A method of reducing mortality and morbidity related to acute lung injury (ALI) or acute respiratory distress syndrome (ARDS) in a patient having a respiratory viral infection, comprising administering to a patient in need thereof a compound that is a HIF prolyl hydroxylase inhibitor or a HIF-alpha stabilizer, or a pharmaceutically acceptable salt thereof.
74. The method of paragraph 73, wherein the patient has a lower respiratory infection.
75. The method of paragraph 73, wherein the patient has an upper respiratory infection.
76. A method of reducing mortality and morbidity related to acute lung injury (ALI) or acute respiratory distress syndrome (ARDS) in a patient having a pulmonary viral infection, comprising administering to a patient in need thereof a compound that is a HIF prolyl hydroxylase inhibitor or a HIF-alpha stabilizer, or a pharmaceutically acceptable salt thereof.
77. The method of any one of paragraphs 73-76, wherein the viral infection is induced by or associated with a virus that could lead to viral pneumonia.
78. The method of any one of paragraphs 73-77, wherein the viral infection is induced by or associated with a coronavirus, an influenza A, an influenza B, a Rhinovirus, a respiratory syncytial virus (RSV), an adenovirus, a human parainfluenza virus (HPIV) or an enterovirus.
79. A method of reducing mortality and morbidity related to acute lung injury (ALI) or acute respiratory distress syndrome (ARDS) in a patient infected with a coronavirus, comprising administering to a patient in need thereof a compound that is a HIF prolyl hydroxylase inhibitor or a HIF-alpha stabilizer, or a pharmaceutically acceptable salt thereof.

80. The method of any one of paragraphs 73-79, wherein the acute lung injury (ALI) or acute respiratory distress syndrome (ARDS) is induced by or associated with the virus.
81. The method of any one of paragraphs 73-80, wherein the patient is infected by a coronavirus that is SARS-CoV, MERS-CoV, or SARS-CoV-2.
82. The method of any one of paragraphs 73-81, wherein the patient has COVID-19.
83. The method of any one of paragraphs 73-82, wherein the patient is receiving mechanical ventilation.
84. The method of any one of paragraphs 73-83, wherein the patient has ventilator induced ALI.
85. A method of reducing incidence, severity, or risk of acute lung injury (ALI) or acute respiratory distress syndrome (ARDS) in a patient having a respiratory viral infection, comprising administering to a patient in need thereof a compound that is a HIF prolyl hydroxylase inhibitor or a HIF-alpha stabilizer, or a pharmaceutically acceptable salt thereof.
86. The method of paragraph 85, wherein the patient has a lower respiratory infection.
87. The method of paragraph 85, wherein the patient has an upper respiratory infection.
88. A method of reducing incidence, severity, or risk of acute lung injury (ALI) or acute respiratory distress syndrome (ARDS) in a patient having a pulmonary viral infection, comprising administering to a patient in need thereof a compound that is a HIF prolyl hydroxylase inhibitor or a HIF-alpha stabilizer, or a pharmaceutically acceptable salt thereof.
89. The method of any one of paragraphs 85-88, wherein the viral infection is induced by or associated with a virus that could lead to viral pneumonia.
90. The method of any one of paragraphs 85-89, wherein the viral infection is induced by or associated with a coronavirus, an influenza A, an influenza B, a Rhinovirus, a respiratory syncytial virus (RSV), an adenovirus, a human parainfluenza virus (HPIV) or an enterovirus.
91. A method of reducing incidence, severity, or risk of acute lung injury (ALI) or acute respiratory distress syndrome (ARDS) in a patient infected with a coronavirus, comprising administering to a patient in need thereof a compound that is a HIF prolyl hydroxylase inhibitor or a HIF-alpha stabilizer, or a pharmaceutically acceptable salt thereof.
92. The method of any one of paragraphs 85-91, wherein the acute lung injury (ALI) or acute respiratory distress syndrome (ARDS) is induced by or associated with the virus.
93. The method of any one of paragraphs 85-92, wherein the patient is infected by a coronavirus that is SARS-CoV, MERS-CoV, or SARS-CoV-2.
94. The method of any one of paragraphs 85-93, wherein the patient has COVID-19.
95. The method of any one of paragraphs 85-94, wherein the patient is receiving mechanical ventilation.
96. The method of any one of paragraphs 85-95, wherein the patient has ventilator induced ALI.
97. The method of any one of paragraphs 73-96, wherein said patient is an adult.
98. The method of any one of paragraphs 73-97, wherein said patient exhibits one or more symptoms of hypoxia.
99. The method of paragraph 98, wherein the patient has a lower oxygen saturation of hemoglobin compared to normal oxygen saturation.
100. The method of any one of paragraphs 73-99, wherein the patient has an oxygen saturation of hemoglobin that is about 94% or less.
101. A method of treating or preventing lung inflammation or pneumonia in a patient having a respiratory viral infection, comprising administering to a patient in need thereof a compound that is a HIF prolyl hydroxylase inhibitor or a HIF-alpha stabilizer, or a pharmaceutically acceptable salt thereof.
102. A method of reducing mortality and morbidity related to lung inflammation or pneumonia in a patient having a respiratory viral infection, comprising administering to a patient in need thereof a compound that is a HIF prolyl hydroxylase inhibitor or a HIF-alpha stabilizer, or a pharmaceutically acceptable salt thereof.
103. A method of reducing incidence, severity, or risk of lung inflammation or pneumonia in a patient having a respiratory viral infection, comprising administering to a patient in need thereof a compound that is a HIF prolyl hydroxylase inhibitor or a HIF-alpha stabilizer, or a pharmaceutically acceptable salt thereof.
104. The method of any one of paragraphs 101-103, wherein the patient has a lower respiratory infection.
105. The method of any one of paragraphs 101-103, wherein the patient has an upper respiratory infection.
106. A method of treating or preventing lung inflammation or pneumonia in a patient having a pulmonary viral infection, comprising administering to a patient in need thereof a compound that is a HIF prolyl hydroxylase inhibitor or a HIF-alpha stabilizer, or a pharmaceutically acceptable salt thereof.
107. A method of reducing mortality and morbidity related to lung inflammation or pneumonia in a patient having a pulmonary viral infection, comprising administering to a patient in need thereof a compound that is a HIF prolyl hydroxylase inhibitor or a HIF-alpha stabilizer, or a pharmaceutically acceptable salt thereof.
108. A method of reducing incidence, severity, or risk of lung inflammation or pneumonia in a patient having a pulmonary viral infection, comprising administering to a patient in need thereof a compound that is a HIF prolyl hydroxylase inhibitor or a HIF-alpha stabilizer, or a pharmaceutically acceptable salt thereof.
109. The method of any one of paragraphs 101-108, wherein the viral infection is induced by or associated with a virus that could lead to viral pneumonia.
110. The method of any one of paragraphs 101-109, wherein the viral infection is induced by or associated with a coronavirus, an influenza A, an influenza B, a Rhinovirus, a respiratory syncytial virus (RSV), an adenovirus, a human parainfluenza virus (HPIV) or an enterovirus.
111. A method of treating or preventing lung inflammation or pneumonia in a patient infected with a coronavirus, comprising administering to a patient in need thereof a compound that is a HIF prolyl hydroxylase inhibitor or a HIF-alpha stabilizer, or a pharmaceutically acceptable salt thereof.
112. A method of reducing mortality and morbidity related to lung inflammation or pneumonia in a patient infected with a coronavirus, comprising administering to a patient in need thereof a compound that is a HIF prolyl hydroxylase inhibitor or a HIF-alpha stabilizer, or a pharmaceutically acceptable salt thereof.
113. A method of reducing incidence, severity, or risk of lung inflammation or pneumonia in a patient infected with a coronavirus, comprising administering to a patient in need thereof a compound that is a HIF prolyl hydroxylase inhibitor or a HIF-alpha stabilizer, or a pharmaceutically acceptable salt thereof.

114. The method of any one of paragraphs 101-113, wherein the patient is infected by a coronavirus that is SARS-CoV, MERS-CoV, or SARS-CoV-2.

115. The method of any one of paragraphs 101-114, wherein the patient has COVID-19.

116. The method of any one of paragraphs 101-115, wherein the lung inflammation or pneumonia is induced by or associated with the viral infection.

117. The method of paragraph 116, wherein the lung inflammation or pneumonia is induced by or associated with COVID-19.

118. A method of treating or preventing COVID-19 related pneumonia, comprising administering to a patient in need thereof a compound that is a HIF prolyl hydroxylase inhibitor or a HIF-alpha stabilizer, or a pharmaceutically acceptable salt thereof, and wherein the patient has acute lung injury (ALI), acute respiratory distress syndrome (ARDS), and/or organ failure.

119. The method of paragraph 118, wherein any of the acute lung injury (ALI), acute respiratory distress syndrome (ARDS), and/or organ failure is COVID-19 related.

120. A method of treating or preventing COVID-19 related acute lung injury (ALI) in a patient having pneumonia, comprising administering to a patient in need thereof a compound that is a HIF prolyl hydroxylase inhibitor or a HIF-alpha stabilizer, or a pharmaceutically acceptable salt thereof.

121. A method of treating or preventing COVID-19 related acute respiratory distress syndrome (ARDS) in a patient having pneumonia, comprising administering to a patient in need thereof a compound that is a HIF prolyl hydroxylase inhibitor or a HIF-alpha stabilizer, or a pharmaceutically acceptable salt thereof.

122. A method of treating or preventing COVID-19 related organ failure, comprising administering to a patient in need thereof a compound that is a HIF prolyl hydroxylase inhibitor or a HIF-alpha stabilizer, or a pharmaceutically acceptable salt thereof.

123. The method of any one of paragraphs 101-122, wherein the patient is receiving mechanical ventilation.

124. A method of treating or preventing cardiac dysfunction in a patient having a respiratory viral infection, comprising administering to a patient in need thereof a compound that is a HIF prolyl hydroxylase inhibitor or a HIF-alpha stabilizer, or a pharmaceutically acceptable salt thereof.

125. A method of reducing mortality and morbidity related to an adverse cardiac event in a patient having a respiratory viral infection, comprising administering to a patient in need thereof a compound that is a HIF prolyl hydroxylase inhibitor or a HIF-alpha stabilizer, or a pharmaceutically acceptable salt thereof.

126. A method of reducing incidence, severity, or risk of an adverse cardiac event in a patient having a respiratory viral infection, comprising administering to a patient in need thereof a compound that is a HIF prolyl hydroxylase inhibitor or a HIF-alpha stabilizer, or a pharmaceutically acceptable salt thereof.

127. The method of any one of paragraphs 124-126, wherein the patient has a lower respiratory infection.

128. The method of any one of paragraphs 124-126, wherein the patient has an upper respiratory infection.

129. A method of treating or preventing cardiac dysfunction in a patient having a pulmonary viral infection, comprising administering to a patient in need thereof a compound that is a HIF prolyl hydroxylase inhibitor or a HIF-alpha stabilizer, or a pharmaceutically acceptable salt thereof.

130. A method of reducing mortality and morbidity related to an adverse cardiac event in a patient having a pulmonary viral infection, comprising administering to a patient in need thereof a compound that is a HIF prolyl hydroxylase inhibitor or a HIF-alpha stabilizer, or a pharmaceutically acceptable salt thereof.

131. A method of reducing incidence, severity, or risk of an adverse cardiac event in a patient having a pulmonary viral infection, comprising administering to a patient in need thereof a compound that is a HIF prolyl hydroxylase inhibitor or a HIF-alpha stabilizer, or a pharmaceutically acceptable salt thereof.

132. The method of any one of paragraphs 124-131, wherein the viral infection is induced by or associated with a virus that could lead to viral pneumonia.

133. The method of any one of paragraphs 124-132, wherein the viral infection is induced by or associated with a coronavirus, an influenza A, an influenza B, a Rhinovirus, a respiratory syncytial virus (RSV), an adenovirus, a human parainfluenza virus (HPIV) or an enterovirus.

134. A method of treating or preventing cardiac dysfunction in a patient infected with a coronavirus, comprising administering to a patient in need thereof a compound that is a HIF prolyl hydroxylase inhibitor or a HIF-alpha stabilizer, or a pharmaceutically acceptable salt thereof.

135. A method of reducing mortality and morbidity related to an adverse cardiac event in a patient infected with a coronavirus, comprising administering to a patient in need thereof a compound that is a HIF prolyl hydroxylase inhibitor or a HIF-alpha stabilizer, or a pharmaceutically acceptable salt thereof.

136. A method of reducing incidence, severity, or risk of an adverse cardiac event in a patient infected with a coronavirus, comprising administering to a patient in need thereof a compound that is a HIF prolyl hydroxylase inhibitor or a HIF-alpha stabilizer, or a pharmaceutically acceptable salt thereof.

137. The method of any one of paragraphs 124-136, wherein the patient is infected by a coronavirus that is SARS-CoV, MERS-CoV, or SARS-CoV-2.

138. The method of any one of paragraphs 124-137, wherein the patient has COVID-19.

139. The method of any one of paragraphs 124, 129, and 134, wherein the cardiac dysfunction is induced by or associated with the viral infection.

140. The method of paragraph 139, wherein the cardiac dysfunction is induced by or associated with COVID-19.

141. The method of any one of paragraphs 125-126, 130-131, and 135-136 wherein an adverse cardiac event is induced by or associated with the viral infection.

142. The method of paragraph 141, wherein an adverse cardiac event is induced by or associated with COVID-19.

143. The method of any one of paragraphs 124-142, wherein the patient is receiving mechanical ventilation.

144. A method of treating or preventing hypotension in a patient having a respiratory viral infection, comprising administering to a patient in need thereof a compound that is a HIF prolyl hydroxylase inhibitor or a HIF-alpha stabilizer, or a pharmaceutically acceptable salt thereof.

145. A method of reducing mortality and morbidity related to hypotension in a patient having a respiratory viral infection, comprising administering to a patient in need thereof a compound that is a HIF prolyl hydroxylase inhibitor or a HIF-alpha stabilizer, or a pharmaceutically acceptable salt thereof.

146. A method of reducing incidence, severity, or risk of hypotension in a patient having a respiratory viral infection, comprising administering to a patient in need thereof a compound that is a HIF prolyl hydroxylase inhibitor or a HIF-alpha stabilizer, or a pharmaceutically acceptable salt thereof.

147. The method of any one of paragraphs 144-146, wherein the patient has a lower respiratory infection.

148. The method of any one of paragraphs 144-146, wherein the patient has an upper respiratory infection.

149. A method of treating or preventing hypotension in a patient having a pulmonary viral infection, comprising administering to a patient in need thereof a compound that is a HIF prolyl hydroxylase inhibitor or a HIF-alpha stabilizer, or a pharmaceutically acceptable salt thereof.

150. A method of reducing mortality and morbidity related to hypotension in a patient having a pulmonary viral infection, comprising administering to a patient in need thereof a compound that is a HIF prolyl hydroxylase inhibitor or a HIF-alpha stabilizer, or a pharmaceutically acceptable salt thereof.

151. A method of reducing incidence, severity, or risk of hypotension in a patient having a pulmonary viral infection, comprising administering to a patient in need thereof a compound that is a HIF prolyl hydroxylase inhibitor or a HIF-alpha stabilizer, or a pharmaceutically acceptable salt thereof.

152. The method of any one of paragraphs 144-151, wherein the viral infection is induced by or associated with a virus that could lead to viral pneumonia.

153. The method of any one of paragraphs 144-152, wherein the viral infection is induced by or associated with a coronavirus, an influenza A, an influenza B, a Rhinovirus, a respiratory syncytial virus (RSV), an adenovirus, a human parainfluenza virus (HPIV) or an enterovirus.

154. A method of treating or preventing hypotension in a patient infected with a coronavirus, comprising administering to a patient in need thereof a compound that is a HIF prolyl hydroxylase inhibitor or a HIF-alpha stabilizer, or a pharmaceutically acceptable salt thereof.

155. A method of reducing mortality and morbidity related to hypotension in a patient infected with a coronavirus, comprising administering to a patient in need thereof a compound that is a HIF prolyl hydroxylase inhibitor or a HIF-alpha stabilizer, or a pharmaceutically acceptable salt thereof.

156. A method of reducing incidence, severity, or risk of hypotension in a patient infected with a coronavirus, comprising administering to a patient in need thereof a compound that is a HIF prolyl hydroxylase inhibitor or a HIF-alpha stabilizer, or a pharmaceutically acceptable salt thereof.

157. The method of any one of paragraphs 144-156, wherein the patient is infected by a coronavirus that is SARS-CoV, MERS-CoV, or SARS-CoV-2.

158. The method of any one of paragraphs 144-157, wherein the patient has COVID-19.

159. The method of any one of paragraphs 144-158, wherein the hypotension is induced by or associated with the viral infection.

160. The method of paragraph 159, wherein the hypotension is induced by or associated with COVID-19.

161. The method of any one of paragraphs 144-160, wherein the patient is receiving mechanical ventilation.

162. A method of reducing incidence, severity, or risk of disseminated intravascular coagulation in a patient having a respiratory viral infection, comprising administering to a patient in need thereof a compound that is a HIF prolyl hydroxylase inhibitor or a HIF-alpha stabilizer, or a pharmaceutically acceptable salt thereof.

163. A method of treating or preventing disseminated intravascular coagulation in a patient having a respiratory viral infection, comprising administering to a patient in need thereof a compound that is a HIF prolyl hydroxylase inhibitor or a HIF-alpha stabilizer, or a pharmaceutically acceptable salt thereof.

164. A method of reducing mortality and morbidity related to disseminated intravascular coagulation in a patient having a respiratory viral infection, comprising administering to a patient in need thereof a compound that is a HIF prolyl hydroxylase inhibitor or a HIF-alpha stabilizer, or a pharmaceutically acceptable salt thereof.

165. The method of any one of paragraphs 162-164, wherein the patient has a lower respiratory infection.

166. The method of any one of paragraphs 162-164, wherein the patient has an upper respiratory infection.

167. A method of reducing mortality and morbidity related to disseminated intravascular coagulation in a patient having a pulmonary viral infection, comprising administering to a patient in need thereof a compound that is a HIF prolyl hydroxylase inhibitor or a HIF-alpha stabilizer, or a pharmaceutically acceptable salt thereof.

168. A method of treating or preventing disseminated intravascular coagulation in a patient having a pulmonary viral infection, comprising administering to a patient in need thereof a compound that is a HIF prolyl hydroxylase inhibitor or a HIF-alpha stabilizer, or a pharmaceutically acceptable salt thereof.

169. A method of reducing incidence, severity, or risk of disseminated intravascular coagulation in a patient having a pulmonary viral infection, comprising administering to a patient in need thereof a compound that is a HIF prolyl hydroxylase inhibitor or a HIF-alpha stabilizer, or a pharmaceutically acceptable salt thereof.

170. The method of any one of paragraphs 162-169, wherein the viral infection is induced by or associated with a virus that could lead to viral pneumonia.

171. The method of any one of paragraphs 162-170, wherein the viral infection is induced by or associated with a coronavirus, an influenza A, an influenza B, a Rhinovirus, a respiratory syncytial virus (RSV), an adenovirus, a human parainfluenza virus (HPIV) or an enterovirus.

172. A method of treating or preventing disseminated intravascular coagulation in a patient infected with a coronavirus, comprising administering to a patient in need thereof a compound that is a HIF prolyl hydroxylase inhibitor or a HIF-alpha stabilizer, or a pharmaceutically acceptable salt thereof.

173. A method of reducing mortality and morbidity related to disseminated intravascular coagulation in a patient infected with a coronavirus, comprising administering to a patient in need thereof a compound that is a HIF prolyl hydroxylase inhibitor or a HIF-alpha stabilizer, or a pharmaceutically acceptable salt thereof.

174. A method of reducing incidence, severity, or risk of disseminated intravascular coagulation in a patient infected with a coronavirus, comprising administering to a patient in need thereof a compound that is a HIF prolyl hydroxylase inhibitor or a HIF-alpha stabilizer, or a pharmaceutically acceptable salt thereof.

175. The method of any one of paragraphs 162-174, wherein the patient is infected by a coronavirus that is SARS-CoV, MERS-CoV, or SARS-CoV-2.

176. The method of any one of paragraphs 162-175, wherein the patient has COVID-19.

177. The method of any one of paragraphs 162-176, wherein the disseminated intravascular coagulation is induced by or associated with the viral infection.

178. The method of paragraph 177, wherein the disseminated intravascular coagulation is induced by or associated with COVID-19.

179. The method of any one of paragraphs 162-178, wherein the patient is receiving mechanical ventilation.

180. A method of treating or preventing kidney diseases in a patient having a respiratory viral infection, comprising administering to a patient in need thereof a compound that is a HIF prolyl hydroxylase inhibitor or a HIF-alpha stabilizer, or a pharmaceutically acceptable salt thereof.

181. A method of reducing mortality and morbidity related to kidney diseases in a patient having a respiratory viral infection, comprising administering to a patient in need thereof a compound that is a HIF prolyl hydroxylase inhibitor or a HIF-alpha stabilizer, or a pharmaceutically acceptable salt thereof.

182. A method of reducing incidence, severity, or risk of kidney diseases in a patient having a respiratory viral infection, comprising administering to a patient in need thereof a compound that is a HIF prolyl hydroxylase inhibitor or a HIF-alpha stabilizer, or a pharmaceutically acceptable salt thereof.

183. The method of any one of paragraphs 180-182, wherein the patient has a lower respiratory infection.

184. The method of any one of paragraphs 180-103, wherein the patient has an upper respiratory infection.

185. A method of treating or preventing kidney diseases in a patient having a pulmonary viral infection, comprising administering to a patient in need thereof a compound that is a HIF prolyl hydroxylase inhibitor or a HIF-alpha stabilizer, or a pharmaceutically acceptable salt thereof.

186. A method of reducing mortality and morbidity related to kidney diseases in a patient having a pulmonary viral infection, comprising administering to a patient in need thereof a compound that is a HIF prolyl hydroxylase inhibitor or a HIF-alpha stabilizer, or a pharmaceutically acceptable salt thereof.

187. A method of reducing incidence, severity, or risk of kidney diseases in a patient having a pulmonary viral infection, comprising administering to a patient in need thereof a compound that is a HIF prolyl hydroxylase inhibitor or a HIF-alpha stabilizer, or a pharmaceutically acceptable salt thereof.

188. The method of any one of paragraphs 180-187, wherein the viral infection is induced by or associated with a virus that could lead to viral pneumonia.

189. The method of any one of paragraphs 180-188, wherein the viral infection is induced by or associated with a coronavirus, an influenza A, an influenza B, a Rhinovirus, a respiratory syncytial virus (RSV), an adenovirus, a human parainfluenza virus (HPIV) or an enterovirus.

190. A method of treating or preventing kidney diseases in a patient infected with a coronavirus, comprising administering to a patient in need thereof a compound that is a HIF prolyl hydroxylase inhibitor or a HIF-alpha stabilizer, or a pharmaceutically acceptable salt thereof.

191. A method of reducing mortality and morbidity related to kidney diseases in a patient infected with a coronavirus, comprising administering to a patient in need thereof a compound that is a HIF prolyl hydroxylase inhibitor or a HIF-alpha stabilizer, or a pharmaceutically acceptable salt thereof.

192. A method of reducing incidence, severity, or risk of kidney diseases in a patient infected with a coronavirus, comprising administering to a patient in need thereof a compound that is a HIF prolyl hydroxylase inhibitor or a HIF-alpha stabilizer, or a pharmaceutically acceptable salt thereof.

193. The method of any one of paragraphs 180-192, wherein the patient is infected by a coronavirus that is SARS-CoV, MERS-CoV, or SARS-CoV-2.

194. The method of any one of paragraphs 180-193, wherein the patient has COVID-19.

195. The method of any one of paragraphs 180-194, wherein the kidney diseases is induced by or associated with the viral infection.

196. The method of paragraph 195, wherein the kidney diseases is induced by or associated with COVID-19.

197. The method of any one of paragraphs 180-196, wherein the patient is receiving mechanical ventilation.

198. A method of treating or preventing liver failure in a patient having a respiratory viral infection, comprising administering to a patient in need thereof a compound that is a HIF prolyl hydroxylase inhibitor or a HIF-alpha stabilizer, or a pharmaceutically acceptable salt thereof.

199. A method of reducing mortality and morbidity related to liver failure in a patient having a respiratory viral infection, comprising administering to a patient in need thereof a compound that is a HIF prolyl hydroxylase inhibitor or a HIF-alpha stabilizer, or a pharmaceutically acceptable salt thereof.

200. A method of reducing incidence, severity, or risk of liver failure in a patient having a respiratory viral infection, comprising administering to a patient in need thereof a compound that is a HIF prolyl hydroxylase inhibitor or a HIF-alpha stabilizer, or a pharmaceutically acceptable salt thereof.

201. The method of any one of paragraphs 198-200, wherein the patient has a lower respiratory infection.

202. The method of any one of paragraphs 198-200, wherein the patient has an upper respiratory infection.

203. A method of treating or preventing liver failure in a patient having a pulmonary viral infection, comprising administering to a patient in need thereof a compound that is a HIF prolyl hydroxylase inhibitor or a HIF-alpha stabilizer, or a pharmaceutically acceptable salt thereof.

204. A method of reducing mortality and morbidity related to liver failure in a patient having a pulmonary viral infection, comprising administering to a patient in need thereof a compound that is a HIF prolyl hydroxylase inhibitor or a HIF-alpha stabilizer, or a pharmaceutically acceptable salt thereof.

205. A method of reducing incidence, severity, or risk of liver failure in a patient having a pulmonary viral infection, comprising administering to a patient in need thereof a compound that is a HIF prolyl hydroxylase inhibitor or a HIF-alpha stabilizer, or a pharmaceutically acceptable salt thereof.

206. The method of any one of paragraphs 198-205, wherein the viral infection is induced by or associated with a virus that could lead to viral pneumonia.

207. The method of any one of paragraphs 198-206, wherein the viral infection is induced by or associated with a coronavirus, an influenza A, an influenza B, a Rhinovirus, a respiratory syncytial virus (RSV), an adenovirus, a human parainfluenza virus (HPIV) or an enterovirus.

208. A method of treating or preventing liver failure in a patient infected with a coronavirus, comprising administering to a patient in need thereof a compound that is a HIF prolyl hydroxylase inhibitor or a HIF-alpha stabilizer, or a pharmaceutically acceptable salt thereof.

209. A method of reducing mortality and morbidity related to liver failure in a patient infected with a coronavirus, comprising administering to a patient in need thereof a compound that is a HIF prolyl hydroxylase inhibitor or a HIF-alpha stabilizer, or a pharmaceutically acceptable salt thereof.

210. A method of reducing incidence, severity, or risk of liver failure in a patient infected with a coronavirus, comprising administering to a patient in need thereof a compound that is a HIF prolyl hydroxylase inhibitor or a HIF-alpha stabilizer, or a pharmaceutically acceptable salt thereof.

211. The method of any one of paragraphs 198-210, wherein the patient is infected by a coronavirus that is SARS-CoV, MERS-CoV, or SARS-CoV-2.

212. The method of any one of paragraphs 198-211, wherein the patient has COVID-19.

213. The method of any one of paragraphs 198-212, wherein the liver failure is induced by or associated with the viral infection.

214. The method of paragraph 213, wherein the liver failure is induced by or associated with COVID-19.

215. The method of any one of paragraphs 198-214, wherein the patient is receiving mechanical ventilation.

216. A method of treating or preventing pancreas injury in a patient having a respiratory viral infection, comprising administering to a patient in need thereof a compound that is a HIF prolyl hydroxylase inhibitor or a HIF-alpha stabilizer, or a pharmaceutically acceptable salt thereof.

217. A method of reducing mortality and morbidity related to pancreas injury in a patient having a respiratory viral infection, comprising administering to a patient in need thereof a compound that is a HIF prolyl hydroxylase inhibitor or a HIF-alpha stabilizer, or a pharmaceutically acceptable salt thereof.

218. A method of reducing incidence, severity, or risk of pancreas injury in a patient having a respiratory viral infection, comprising administering to a patient in need thereof a compound that is a HIF prolyl hydroxylase inhibitor or a HIF-alpha stabilizer, or a pharmaceutically acceptable salt thereof.

219. The method of any one of paragraphs 216-218, wherein the patient has a lower respiratory infection.

220. The method of any one of paragraphs 216-218, wherein the patient has an upper respiratory infection.

221. A method of treating or preventing pancreas injury in a patient having a pulmonary viral infection, comprising administering to a patient in need thereof a compound that is a HIF prolyl hydroxylase inhibitor or a HIF-alpha stabilizer, or a pharmaceutically acceptable salt thereof.

222. A method of reducing mortality and morbidity related to pancreas injury in a patient having a pulmonary viral infection, comprising administering to a patient in need thereof a compound that is a HIF prolyl hydroxylase inhibitor or a HIF-alpha stabilizer, or a pharmaceutically acceptable salt thereof.

223. A method of reducing incidence, severity, or risk of pancreas injury in a patient having a pulmonary viral infection, comprising administering to a patient in need thereof a compound that is a HIF prolyl hydroxylase inhibitor or a HIF-alpha stabilizer, or a pharmaceutically acceptable salt thereof.

224. The method of any one of paragraphs 216-223, wherein the viral infection is induced by or associated with a virus that could lead to viral pneumonia.

225. The method of any one of paragraphs 216-224, wherein the viral infection is induced by or associated with a coronavirus, an influenza A, an influenza B, a Rhinovirus, a respiratory syncytial virus (RSV), an adenovirus, a human parainfluenza virus (HPIV) or an enterovirus.

226. A method of treating or preventing pancreas injury in a patient infected with a coronavirus, comprising administering to a patient in need thereof a compound that is a HIF prolyl hydroxylase inhibitor or a HIF-alpha stabilizer, or a pharmaceutically acceptable salt thereof.

227. A method of reducing mortality and morbidity related to pancreas injury in a patient infected with a coronavirus, comprising administering to a patient in need thereof a compound that is a HIF prolyl hydroxylase inhibitor or a HIF-alpha stabilizer, or a pharmaceutically acceptable salt thereof.

228. A method of reducing incidence, severity, or risk of pancreas injury in a patient infected with a coronavirus, comprising administering to a patient in need thereof a compound that is a HIF prolyl hydroxylase inhibitor or a HIF-alpha stabilizer, or a pharmaceutically acceptable salt thereof.

229. The method of any one of paragraphs 216-228, wherein the patient is infected by a coronavirus that is SARS-CoV, MERS-CoV, or SARS-CoV-2.

230. The method of any one of paragraphs 216-229, wherein the patient has COVID-19.

231. The method of any one of paragraphs 216-230, wherein pancreas injury is induced by or associated with the viral infection.

232. The method of paragraph 231, wherein the pancreas injury is induced by or associated with COVID-19.

233. The method of any one of paragraphs 216-232, wherein the patient is receiving mechanical ventilation.

234. A method of treating or preventing multi-organ failure in a patient having a respiratory viral infection, comprising administering to a patient in need thereof a compound that is a HIF prolyl hydroxylase inhibitor or a HIF-alpha stabilizer, or a pharmaceutically acceptable salt thereof.

235. A method of reducing mortality and morbidity related to multi-organ failure in a patient having a respiratory viral infection, comprising administering to a patient in need thereof a compound that is a HIF prolyl hydroxylase inhibitor or a HIF-alpha stabilizer, or a pharmaceutically acceptable salt thereof.

236. A method of reducing incidence, severity, or risk of multi-organ failure in a patient having a respiratory viral infection, comprising administering to a patient in need thereof a compound that is a HIF prolyl hydroxylase inhibitor or a HIF-alpha stabilizer, or a pharmaceutically acceptable salt thereof.

237. The method of any one of paragraphs 234-236, wherein the patient has a lower respiratory infection.

238. The method of any one of paragraphs 234-236, wherein the patient has an upper respiratory infection.

239. A method of treating or preventing multi-organ failure in a patient having a pulmonary viral infection, comprising administering to a patient in need thereof a compound that is a HIF prolyl hydroxylase inhibitor or a HIF-alpha stabilizer, or a pharmaceutically acceptable salt thereof.

240. A method of reducing mortality and morbidity related to multi-organ failure in a patient having a pulmonary viral infection, comprising administering to a patient in need thereof a compound that is a HIF prolyl hydroxylase inhibitor or a HIF-alpha stabilizer, or a pharmaceutically acceptable salt thereof.

241. A method of reducing incidence, severity, or risk of multi-organ failure in a patient having a pulmonary viral infection, comprising administering to a patient in need thereof a compound that is a HIF prolyl hydroxylase inhibitor or a HIF-alpha stabilizer, or a pharmaceutically acceptable salt thereof.

242. The method of any one of paragraphs 234-241, wherein the viral infection is induced by or associated with a virus that could lead to viral pneumonia.

243. The method of any one of paragraphs 234-242, wherein the viral infection is induced by or associated with a coronavirus, an influenza A, an influenza B, a Rhinovirus, a respiratory syncytial virus (RSV), an adenovirus, a human parainfluenza virus (HPIV) or an enterovirus.

244. A method of treating or preventing multi-organ failure in a patient having a coronavirus infection, comprising administering to a patient in need thereof a compound that is a HIF prolyl hydroxylase inhibitor or a HIF-alpha stabilizer, or a pharmaceutically acceptable salt thereof.

245. A method of reducing mortality and morbidity related to multi-organ failure in a patient infected with a coronavirus, comprising administering to a patient in need thereof a compound that is a HIF prolyl hydroxylase inhibitor or a HIF-alpha stabilizer, or a pharmaceutically acceptable salt thereof.

246. A method of reducing incidence, severity, or risk of multi-organ failure in a patient infected with a coronavirus, comprising administering to a patient in need thereof a compound that is a HIF prolyl hydroxylase inhibitor or a HIF-alpha stabilizer, or a pharmaceutically acceptable salt thereof.

247. The method of any one of paragraphs 234-246, wherein the patient is infected by a coronavirus that is SARS-CoV, MERS-CoV, or SARS-CoV-2.

248. The method of any one of paragraphs 234-247, wherein the patient has COVID-19.

249. The method of any one of paragraphs 234-248, wherein the multi-organ failure is induced by or associated with the viral infection.

250. The method of paragraph 249, wherein the multi-organ failure is induced by or associated with COVID-19.

251. The method of any one of paragraphs 234-249, wherein the patient is receiving mechanical ventilation.

252. A method of treating or preventing septic shock in a patient having a respiratory viral infection, comprising administering to a patient in need thereof a compound that is a HIF prolyl hydroxylase inhibitor or a HIF-alpha stabilizer, or a pharmaceutically acceptable salt thereof.

253. A method of reducing mortality and morbidity related to septic shock in a patient having a respiratory viral infection, comprising administering to a patient in need thereof a compound that is a HIF prolyl hydroxylase inhibitor or a HIF-alpha stabilizer, or a pharmaceutically acceptable salt thereof.

254. A method of reducing incidence, severity, or risk of septic shock in a patient having a respiratory viral infection, comprising administering to a patient in need thereof a compound that is a HIF prolyl hydroxylase inhibitor or a HIF-alpha stabilizer, or a pharmaceutically acceptable salt thereof.

255. The method of any one of paragraphs 252-254, wherein the patient has a lower respiratory infection.

256. The method of any one of paragraphs 252-254, wherein the patient has an upper respiratory infection.

257. A method of treating or preventing septic shock in a patient having a pulmonary viral infection, comprising administering to a patient in need thereof a compound that is a HIF prolyl hydroxylase inhibitor or a HIF-alpha stabilizer, or a pharmaceutically acceptable salt thereof.

258. A method of reducing mortality and morbidity related to septic shock in a patient having a pulmonary viral infection, comprising administering to a patient in need thereof a compound that is a HIF prolyl hydroxylase inhibitor or a HIF-alpha stabilizer, or a pharmaceutically acceptable salt thereof.

259. A method of reducing incidence, severity, or risk of septic shock in a patient having a pulmonary viral infection, comprising administering to a patient in need thereof a compound that is a HIF prolyl hydroxylase inhibitor or a HIF-alpha stabilizer, or a pharmaceutically acceptable salt thereof.

260. The method of any one of paragraphs 252-259, wherein the viral infection is induced by or associated with a virus that could lead to viral pneumonia.

261. The method of any one of paragraphs 252-260, wherein the viral infection is induced by or associated with a coronavirus, an influenza A, an influenza B, a Rhinovirus, a respiratory syncytial virus (RSV), an adenovirus, a human parainfluenza virus (HPIV) or an enterovirus.

262. A method of treating or preventing septic shock in a patient infected with a coronavirus, comprising administering to a patient in need thereof a compound that is a HIF prolyl hydroxylase inhibitor or a HIF-alpha stabilizer, or a pharmaceutically acceptable salt thereof.

263. A method of reducing mortality and morbidity related to septic shock in a patient infected with a coronavirus, comprising administering to a patient in need thereof a compound that is a HIF prolyl hydroxylase inhibitor or a HIF-alpha stabilizer, or a pharmaceutically acceptable salt thereof.

264. A method of reducing incidence, severity, or risk of septic shock in a patient infected with a coronavirus, comprising administering to a patient in need thereof a compound that is a HIF prolyl hydroxylase inhibitor or a HIF-alpha stabilizer, or a pharmaceutically acceptable salt thereof.

265. The method of any one of paragraphs 252-264, wherein the patient is infected by a coronavirus that is SARS-CoV, MERS-CoV, or SARS-CoV-2.

266. The method of any one of paragraphs 252-265, wherein the patient has COVID-19.

267. The method of any one of paragraphs 252-266, wherein the septic shock is induced by or associated with the viral infection.

268. The method of paragraph 267, wherein the septic shock is induced by or associated with COVID-19.

269. The method of any one of paragraphs 252-268, wherein the patient is receiving mechanical ventilation.

270. A method of treating or preventing sepsis in a patient having a respiratory viral infection, comprising administering to a patient in need thereof a compound that is a HIF prolyl hydroxylase inhibitor or a HIF-alpha stabilizer, or a pharmaceutically acceptable salt thereof.

271. A method of reducing mortality and morbidity related to sepsis in a patient having a respiratory viral infection, comprising administering to a patient in need thereof a compound that is a HIF prolyl hydroxylase inhibitor or a HIF-alpha stabilizer, or a pharmaceutically acceptable salt thereof.

272. A method of reducing incidence, severity, or risk of sepsis in a patient having a respiratory viral infection, comprising administering to a patient in need thereof a compound that is a HIF prolyl hydroxylase inhibitor or a HIF-alpha stabilizer, or a pharmaceutically acceptable salt thereof.

273. The method of any one of paragraphs 270-272, wherein the patient has a lower respiratory infection.

274. The method of any one of paragraphs 270-272, wherein the patient has an upper respiratory infection.

275. A method of treating or preventing sepsis in a patient having a pulmonary viral infection, comprising administering to a patient in need thereof a compound that is a HIF prolyl hydroxylase inhibitor or a HIF-alpha stabilizer, or a pharmaceutically acceptable salt thereof.

276. A method of reducing mortality and morbidity related to sepsis in a patient having a pulmonary viral infection, comprising administering to a patient in need thereof a compound that is a HIF prolyl hydroxylase inhibitor or a HIF-alpha stabilizer, or a pharmaceutically acceptable salt thereof.

277. A method of reducing incidence, severity, or risk of sepsis in a patient having a pulmonary viral infection, comprising administering to a patient in need thereof a compound that is a HIF prolyl hydroxylase inhibitor or a HIF-alpha stabilizer, or a pharmaceutically acceptable salt thereof.

278. The method of any one of paragraphs 270-277, wherein the viral infection is induced by or associated with a virus that could lead to viral pneumonia.

279. The method of any one of paragraphs 270-278, wherein the viral infection is induced by or associated with a coronavirus, an influenza A, an influenza B, a Rhinovirus, a respiratory syncytial virus (RSV), an adenovirus, a human parainfluenza virus (HPIV) or an enterovirus.

280. A method of treating or preventing sepsis in a patient infected with a coronavirus, comprising administering to a patient in need thereof a compound that is a HIF prolyl hydroxylase inhibitor or a HIF-alpha stabilizer, or a pharmaceutically acceptable salt thereof.

281. A method of reducing mortality and morbidity related to sepsis in a patient infected with a coronavirus, comprising administering to a patient in need thereof a compound that is a HIF prolyl hydroxylase inhibitor or a HIF-alpha stabilizer, or a pharmaceutically acceptable salt thereof.

282. A method of reducing incidence, severity, or risk of sepsis in a patient infected with a coronavirus, comprising administering to a patient in need thereof a compound that is a HIF prolyl hydroxylase inhibitor or a HIF-alpha stabilizer, or a pharmaceutically acceptable salt thereof.

283. The method of any one of paragraphs 270-282, wherein the patient is infected by a coronavirus that is SARS-CoV, MERS-CoV, or SARS-CoV-2.

284. The method of any one of paragraphs 270-283, wherein the patient has COVID-19.

285. The method of any one of paragraphs 270-284, wherein the sepsis is induced by or associated with the viral infection.

286. The method of paragraph 285, wherein the sepsis is induced by or associated with COVID-19.

287. The method of any one of paragraph 270-286, wherein the patient is receiving mechanical ventilation.

288. A method of treating or preventing cytokine release syndrome in a patient having a respiratory viral infection, comprising administering to a patient in need thereof a compound that is a HIF prolyl hydroxylase inhibitor or a HIF-alpha stabilizer, or a pharmaceutically acceptable salt thereof.

289. A method of reducing mortality and morbidity related to cytokine release syndrome in a patient having a respiratory viral infection, comprising administering to a patient in need thereof a compound that is a HIF prolyl hydroxylase inhibitor or a HIF-alpha stabilizer, or a pharmaceutically acceptable salt thereof.

290. A method of reducing incidence, severity, or risk of cytokine release syndrome in a patient having a respiratory viral infection, comprising administering to a patient in need thereof a compound that is a HIF prolyl hydroxylase inhibitor or a HIF-alpha stabilizer, or a pharmaceutically acceptable salt thereof.

291. The method of any one of paragraphs 288-291, wherein the patient has a lower respiratory infection.

292. The method of any one of paragraphs 288-291, wherein the patient has an upper respiratory infection.

293. A method of treating or preventing cytokine release syndrome in a patient having a pulmonary viral infection, comprising administering to a patient in need thereof a compound that is a HIF prolyl hydroxylase inhibitor or a HIF-alpha stabilizer, or a pharmaceutically acceptable salt thereof.

294. A method of reducing mortality and morbidity related to cytokine release syndrome in a patient having a pulmonary viral infection, comprising administering to a patient in need thereof a compound that is a HIF prolyl hydroxylase inhibitor or a HIF-alpha stabilizer, or a pharmaceutically acceptable salt thereof.

295. A method of reducing incidence, severity, or risk of cytokine release syndrome in a patient having a pulmonary viral infection, comprising administering to a patient in need thereof a compound that is a HIF prolyl hydroxylase inhibitor or a HIF-alpha stabilizer, or a pharmaceutically acceptable salt thereof.

296. The method of any one of paragraphs 288-295, wherein the viral infection is induced by or associated with a virus that could lead to viral pneumonia.

297. The method of any one of paragraphs 288-296, wherein the viral infection is induced by or associated with a coronavirus, an influenza A, an influenza B, a Rhinovirus, a respiratory syncytial virus (RSV), an adenovirus, a human parainfluenza virus (HPIV) or an enterovirus.

298. A method of treating or preventing cytokine release syndrome in a patient infected with a coronavirus, comprising administering to a patient in need thereof a compound that is a HIF prolyl hydroxylase inhibitor or a HIF-alpha stabilizer, or a pharmaceutically acceptable salt thereof.

299. A method of reducing mortality and morbidity related to cytokine release syndrome in a patient infected with a coronavirus, comprising administering to a patient in need thereof a compound that is a HIF prolyl hydroxylase inhibitor or a HIF-alpha stabilizer, or a pharmaceutically acceptable salt thereof.

300. A method of reducing incidence, severity, or risk of cytokine release syndrome in a patient infected with a coronavirus, comprising administering to a patient in need thereof a compound that is a HIF prolyl hydroxylase inhibitor or a HIF-alpha stabilizer, or a pharmaceutically acceptable salt thereof.

301. The method of any one of paragraphs 288-300, wherein the patient is infected by a coronavirus that is SARS-CoV, MERS-CoV, or SARS-CoV-2.

302. The method of any one of paragraphs 288-301, wherein the patient has COVID-19.

303. The method of any one of paragraphs 288-302, wherein the cytokine release syndrome is induced by or associated with the viral infection.
304. The method of paragraph 303, wherein the cytokine release syndrome is induced by or associated with COVID-19.
305. The method of any one of paragraphs 288-304, wherein the patient is receiving mechanical ventilation.
306. A method of treating or preventing neurological disorder in a patient having a respiratory viral infection, comprising administering to a patient in need thereof a compound that is a HIF prolyl hydroxylase inhibitor or a HIF-alpha stabilizer, or a pharmaceutically acceptable salt thereof.
307. A method of reducing mortality and morbidity related to neurological disorder in a patient having a respiratory viral infection, comprising administering to a patient in need thereof a compound that is a HIF prolyl hydroxylase inhibitor or a HIF-alpha stabilizer, or a pharmaceutically acceptable salt thereof.
308. A method of reducing incidence, severity, or risk of neurological disorder in a patient having a respiratory viral infection, comprising administering to a patient in need thereof a compound that is a HIF prolyl hydroxylase inhibitor or a HIF-alpha stabilizer, or a pharmaceutically acceptable salt thereof.
309. The method of any one of paragraphs 306-308, wherein the patient has a lower respiratory infection.
310. The method of any one of paragraphs 306-308, wherein the patient has an upper respiratory infection.
311. A method of treating or preventing neurological disorder in a patient having a pulmonary viral infection, comprising administering to a patient in need thereof a compound that is a HIF prolyl hydroxylase inhibitor or a HIF-alpha stabilizer, or a pharmaceutically acceptable salt thereof.
312. A method of reducing mortality and morbidity related to neurological disorder in a patient having a pulmonary viral infection, comprising administering to a patient in need thereof a compound that is a HIF prolyl hydroxylase inhibitor or a HIF-alpha stabilizer, or a pharmaceutically acceptable salt thereof.
313. A method of reducing incidence, severity, or risk of neurological disorder in a patient having a pulmonary viral infection, comprising administering to a patient in need thereof a compound that is a HIF prolyl hydroxylase inhibitor or a HIF-alpha stabilizer, or a pharmaceutically acceptable salt thereof.
314. The method of any one of paragraphs 306-313, wherein the viral infection is induced by or associated with a virus that could lead to viral pneumonia.
315. The method of any one of paragraphs 306-314, wherein the viral infection is induced by or associated with a coronavirus, an influenza A, an influenza B, a Rhinovirus, a respiratory syncytial virus (RSV), an adenovirus, a human parainfluenza virus (HPIV) or an enterovirus.
316. A method of treating or preventing neurological disorder in a patient infected with a coronavirus, comprising administering to a patient in need thereof a compound that is a HIF prolyl hydroxylase inhibitor or a HIF-alpha stabilizer, or a pharmaceutically acceptable salt thereof.
317. A method of reducing mortality and morbidity related to neurological disorder in a patient infected with a coronavirus, comprising administering to a patient in need thereof a compound that is a HIF prolyl hydroxylase inhibitor or a HIF-alpha stabilizer, or a pharmaceutically acceptable salt thereof.
318. A method of reducing incidence, severity, or risk of neurological disorder in a patient infected with a coronavirus, comprising administering to a patient in need thereof a compound that is a HIF prolyl hydroxylase inhibitor or a HIF-alpha stabilizer, or a pharmaceutically acceptable salt thereof.
319. The method of any one of paragraphs 306-318, wherein the patient is infected by a coronavirus that is SARS-CoV, MERS-CoV, or SARS-CoV-2.
320. The method of any one of paragraphs 306-319, wherein the patient has COVID-19.
321. The method of any one of paragraphs 306-320, wherein the neurological disorder is induced by or associated with the viral infection.
322. The method of paragraph 321, wherein the neurological disorder is induced by or associated with COVID-19.
323. The method of any one of paragraphs 306-322, wherein the patient is receiving mechanical ventilation.
324. A method of treating or preventing pulmonary barotrauma in a patient having a respiratory viral infection, comprising administering to a patient in need thereof a compound that is a HIF prolyl hydroxylase inhibitor or a HIF-alpha stabilizer, or a pharmaceutically acceptable salt thereof.
325. A method of reducing mortality and morbidity related to pulmonary barotrauma in a patient having a respiratory viral infection, comprising administering to a patient in need thereof a compound that is a HIF prolyl hydroxylase inhibitor or a HIF-alpha stabilizer, or a pharmaceutically acceptable salt thereof.
326. A method of reducing incidence, severity, or risk pulmonary barotrauma in a patient having a respiratory viral infection, comprising administering to a patient in need thereof a compound that is a HIF prolyl hydroxylase inhibitor or a HIF-alpha stabilizer, or a pharmaceutically acceptable salt thereof.
327. The method of any one of paragraphs 324-326, wherein the patient has a lower respiratory infection.
328. The method of any one of paragraphs 324-326, wherein the patient has an upper respiratory infection.
329. A method of treating or preventing pulmonary barotrauma in a patient having a pulmonary viral infection, comprising administering to a patient in need thereof a compound that is a HIF prolyl hydroxylase inhibitor or a HIF-alpha stabilizer, or a pharmaceutically acceptable salt thereof.
330. A method of reducing mortality and morbidity related to pulmonary barotrauma in a patient having a pulmonary viral infection, comprising administering to a patient in need thereof a compound that is a HIF prolyl hydroxylase inhibitor or a HIF-alpha stabilizer, or a pharmaceutically acceptable salt thereof.
331. A method of reducing incidence, severity, or risk of pulmonary barotrauma in a patient having a pulmonary viral infection, comprising administering to a patient in need thereof a compound that is a HIF prolyl hydroxylase inhibitor or a HIF-alpha stabilizer, or a pharmaceutically acceptable salt thereof.
332. The method of any one of paragraphs 324-331, wherein the viral infection is induced by or associated with a virus that could lead to viral pneumonia.
333. The method of any one of paragraphs 324-332, wherein the viral infection is induced by or associated with a coronavirus, an influenza A, an influenza B, a Rhinovirus, a respiratory syncytial virus (RSV), an adenovirus, a human parainfluenza virus (HPIV) or an enterovirus.

334. A method of treating or preventing pulmonary barotrauma in a patient infected with a coronavirus, comprising administering to a patient in need thereof a compound that is a HIF prolyl hydroxylase inhibitor or a HIF-alpha stabilizer, or a pharmaceutically acceptable salt thereof.

335. A method of reducing mortality and morbidity related to pulmonary barotrauma in a patient infected with a coronavirus, comprising administering to a patient in need thereof a compound that is a HIF prolyl hydroxylase inhibitor or a HIF-alpha stabilizer, or a pharmaceutically acceptable salt thereof.

336. A method of reducing incidence, severity, or risk of pulmonary barotrauma in a patient infected with a coronavirus, comprising administering to a patient in need thereof a compound that is a HIF prolyl hydroxylase inhibitor or a HIF-alpha stabilizer, or a pharmaceutically acceptable salt thereof.

337. The method of any one of paragraphs 324-336, wherein the patient is infected by a coronavirus that is SARS-CoV, MERS-CoV, or SARS-CoV-2.

338. The method of any one of paragraphs 324-337, wherein the patient has COVID-19.

339. The method of any one of paragraphs 324-338, wherein the pulmonary barotrauma is induced by or associated with the viral infection.

340. The method of paragraph 339, wherein the pulmonary barotrauma is induced by or associated with COVID-19.

341. The method of any one of paragraphs 324-340, wherein the patient is receiving mechanical ventilation.

342. A method of treating or preventing organ dysfunction induced by or associated with acute lung injury (ALI), acute respiratory distress syndrome (ARDS), pneumonia, lung inflammation, or any combination thereof, comprising administering to a patient in need thereof a compound that is a HIF prolyl hydroxylase inhibitor or a HIF-alpha stabilizer, or a pharmaceutically acceptable salt thereof.

343. The method of paragraph 342, wherein the patient is infected with coronavirus.

344. The method of paragraph 342 or 343, wherein the patient is infected by a coronavirus that is SARS-CoV, MERS-CoV, or SARS-CoV-2.

345. The method of any one of paragraphs 342-344, wherein the patient has COVID-19.

346. The method of any one of paragraphs 342-345, wherein the patient has a respiratory viral infection.

347. The method of paragraph 346, wherein the patient has a lower respiratory infection.

348. The method of paragraph 346, wherein the patient has an upper respiratory infection.

349. The method of paragraph 342, wherein the patient has a pulmonary viral infection.

350. A method for improving lung volumes in a patient in need thereof, comprising administering to a patient in need thereof a compound that is a HIF prolyl hydroxylase inhibitor or a HIF-alpha stabilizer, or a pharmaceutically acceptable salt thereof.

351. A method for improving pulmonary compliance in a patient in need thereof, comprising administering to a patient in need thereof a compound that is a HIF prolyl hydroxylase inhibitor or a HIF-alpha stabilizer, or a pharmaceutically acceptable salt thereof.

352. A method for promoting fibroproliferative repair in a patient in need thereof, comprising administering to a patient in need thereof a compound that is a HIF prolyl hydroxylase inhibitor or a HIF-alpha stabilizer, or a pharmaceutically acceptable salt thereof.

353. A method for regulating innate and adaptive immunity, comprising administering to a patient in need thereof a compound that is a HIF prolyl hydroxylase inhibitor or a HIF-alpha stabilizer, or a pharmaceutically acceptable salt thereof.

354. A method for promoting regulatory T-cells, lymphocytes and B cells, comprising administering to a patient in need thereof a compound that is a HIF prolyl hydroxylase inhibitor or a HIF-alpha stabilizer, or a pharmaceutically acceptable salt thereof.

355. A method for treating/preventing bronchial inflammation, comprising administering to a patient in need thereof a compound that is a HIF prolyl hydroxylase inhibitor or a HIF-alpha stabilizer, or a pharmaceutically acceptable salt thereof.

356. A method for reducing cytokine production, comprising administering to a patient in need thereof a compound that is a HIF prolyl hydroxylase inhibitor or a HIF-alpha stabilizer, or a pharmaceutically acceptable salt thereof.

357. A method for improving dyspnea, comprising administering to a patient in need thereof a compound that is a HIF prolyl hydroxylase inhibitor or a HIF-alpha stabilizer, or a pharmaceutically acceptable salt thereof.

358. A method for improving arterial $PaO_2$, comprising administering to a patient in need thereof a compound that is a HIF prolyl hydroxylase inhibitor or a HIF-alpha stabilizer, or a pharmaceutically acceptable salt thereof.

359. The method of any one of paragraphs 350-358, wherein the patient has a viral infection.

360. The method of paragraph 359, wherein the viral infection is induced by or associated with a coronavirus, an influenza A, an influenza B, a Rhinovirus, a respiratory syncytial virus (RSV), an adenovirus, a human parainfluenza virus (HPIV) or an enterovirus.

361. The method of paragraph 360, wherein the viral infection is induced by or associated with coronavirus.

362. The method of paragraph 361, wherein the coronavirus is the SARS-CoV, MERS-CoV, or SARS-CoV-2.

363. The method of any one of paragraphs 350-362, wherein the patient has COVID-19.

364. A method of treating or preventing acute respiratory distress syndrome (ARDS) in a hospitalized patient with COVID-19, the method comprising administering to said patient a compound that is a HIF prolyl hydroxylase inhibitor or a HIF-alpha stabilizer, or a pharmaceutically acceptable salt thereof.

365. The method of any one of paragraphs 101-364, wherein said patient is an adult.

366. The method of any one of paragraphs 101-365, wherein said patient exhibits one or more symptoms of hypoxia.

367. The method of paragraph 366, wherein the patient has a lower oxygen saturation of hemoglobin compared to normal oxygen saturation.

368. The method of any one of paragraphs 101-367, wherein the patient has an oxygen saturation of hemoglobin that is about 94% or less.

369. The method of any one of paragraphs 1-368, wherein the patient has a pre-existing respiratory or pulmonary disease.

370. The method of paragraph 369, wherein the pre-existing respiratory or pulmonary disease is acute lung injury, bronchitis, pneumonia, pulmonary fibrosis, asthma, and acute respiratory distress syndrome, or pulmonary hypertension.

371. The method of any one of paragraphs 1-368, wherein the patient does not have a pre-existing respiratory or pulmonary disease.

372. The method of any one of paragraphs 1-371, wherein the patient is an adult aged 45 years and above, aged 65 years and above, aged 80 years and above, over 80 years of age, aged 45-60 years, aged 60-80 years, or has underlying medical conditions.

373. The method of paragraph 372, wherein the underlying medical conditions comprise liver disease, heart conditions, kidney disease, obesity, diabetes, or being immunocompromised.

374. The method of paragraph 373, wherein the patient has a body mass index (BMI) that is 25 or above or is 30 or above.

375. The method of paragraphs 1-374, wherein the patient has one or more clinically-recognized symptoms associated with the respiratory viral infection or the coronavirus infection, wherein the respiratory viral infection or the coronavirus infection is COVID-19.

376. The method of paragraph 375, wherein the one or more symptoms associated with COVID-19 are fever, dry cough, fatigue, coughing up sputum from the lungs, bone or joint pain, sore throat, headache, chills, nausea or vomiting, stuffy nose, pressure or pain in the chest, shortness of breath, sudden confusion, digestive issues, conjunctivitis, bluish face or lips, or loss of smell or taste.

377. The method of any one of paragraphs 1-376, wherein the patient has decreased oxygen saturation relative to normal levels.

378. The method of paragraph 377, wherein the decreased oxygen saturation is an oxygen saturation of about 94% or less.

379. The method of any one of paragraphs 1-376, wherein the patient has an elevated level of an inflammation marker.

380. The method of paragraph 379, wherein the elevated level of an inflammation marker is detected in the serum of the patient.

381. The method of paragraph 380, wherein the elevated level of an inflammation marker is detected in the lung of the patient.

382. The method of paragraph 381, wherein the inflammation marker is a presence of ground-glass opacity.

383. The method of paragraphs 1-382, wherein the patient has a positive diagnostic test for SARS-CoV-2.

384. The method of any one of paragraphs 1-383, wherein the compound stabilizes HIFα.

385. The method of any one of paragraphs 1-384, wherein the compound inhibits hydroxylation of HIFα.

386. The method of any one of paragraphs 1-385, wherein the HIF prolyl hydroxylase inhibitor or the HIF-alpha stabilizer has a structure of Formula (I), Formula (II) or Formula (III)

Formula (I)

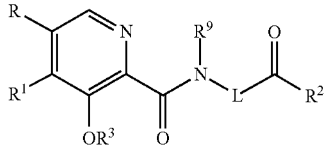

Formula (II)

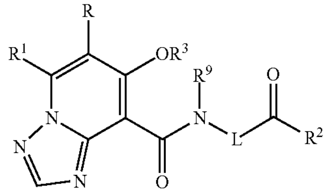

-continued

Formula (III)

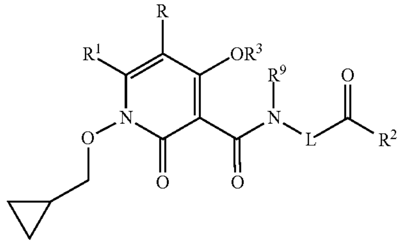

or a pharmaceutically acceptable salt thereof, wherein

R and $R^1$ are each independently:

(i) hydrogen (ii) substituted or unsubstituted phenyl;

(iii) substituted or unsubstituted heteroaryl; or (iv) substituted or unsubstituted alkyl;

said substitution selected from:

(i) $C_1$-$C_4$ alkyl;

(ii) $C_3$-$C_4$ cycloalkyl;

(iii) $C_1$-$C_4$ alkoxy;

(iv) $C_3$-$C_4$ cycloalkoxy;

(v) $C_1$-$C_4$ haloalkyl;

(vi) $C_3$-C4 halocycloalkyl;

(vii) halogen;

(viii) cyano;

(ix) $NHC(O)R^4$;

(x) $C(O)NR^{5a}R^{5b}$;

(xi) phenyl; and (xii) heteroaryl; or (xiii) two substituents are taken together to form a fused ring having from 5 to 7 atoms;

$R^4$ is a $C_1$-$C_4$ alkyl or $C_3$-$C_4$ cycloalkyl;

$R^{5a}$ and $R^{5b}$ are each independently selected from:

(i) hydrogen;

(ii) $C_1$-$C_4$ alkyl;

(iii) $C_3$-$C_4$ cycloalkyl; or (iv) $R^{5a}$ and $R^{5b}$ are taken together to form a ring having from 3 to 7 atoms;

$R^2$ is selected from:

(i) $OR^6$ (ii) $NR^{7a}R^{7b}$; and $R^6$ is selected from hydrogen and $C_1$-$C_4$ alkyl or $C_3$-$C_4$ cycloalkyl;

$R^{7a}$ and $R^{7b}$ are each independently selected from:

(i) hydrogen;

(ii) $C_1$-$C_4$ alkyl or $C_3$-$C_4$ cycloalkyl; or (iii) $R^{7a}$ and $R^{7b}$ are taken together to form a ring having from 3 to 7 atoms;

$R^3$ is selected from hydrogen, methyl, and ethyl;

L is a linking unit having a structure $—[C(R^{8a}R^{8b})]_n—$ $R^{8a}$ and $R^{8b}$ are each independently selected from hydrogen, methyl and ethyl;

n is an integer from 1 to 3; and $R^9$ is selected from hydrogen and methyl.

387. The method of any one of paragraphs 1-385, wherein the HIF prolyl hydroxylase inhibitor or the HIF-alpha stabilizer has a structure of Formula (IV)

Formula (IV)

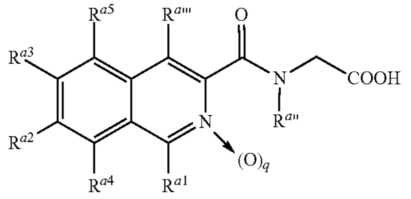

or a pharmaceutically acceptable salt thereof, wherein q is zero or one;

$R^{a1}$ is selected from the group consisting of hydrogen, alkyl, Substituted alkyl, alkoxy, substituted alkoxy, amino, substituted amino, aminoacyl, aryl, substituted aryl, halo, heteroaryl, substituted heteroaryl, heterocyclic, substituted heterocyclic, and —$XR^{a6}$ where X is oxygen, —$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted hetero cyclic, and $R^{a7}$ is hydrogen, alkyl or aryl or, when X is —$NR^{a7}$—, then $R^{a7}$ and $R^{a6}$, together with the nitrogen atom to which they are bound, can be joined to form a heterocyclic or substituted heterocyclic group;

$R^{a2}$ and $R^{a3}$ are independently selected from the group consisting of hydrogen, alkyl, substituted alkyl, aryl, substituted aryl, heteroaryl, substituted heteroaryl, halo, hydroxy, cyano. —$S(O)_n$—$N(R^{a6})$—$R^{a6}$ where n is 0, 1, or 2, —$NR^{a6}C(O)NR^{a6}R^{a6}$, —$XR^{a6}$ where X is oxygen, —$S(O)_n$—, or —$NR^{a7}$— where n is zero, one or two, each $R^{a6}$ is independently selected from the group consisting of hydrogen, alkyl, Substituted alkyl, aryl, substituted aryl, cycloalkyl, substituted cycloalkyl, heteroaryl, substituted heteroaryl, heterocyclic and substituted heterocyclic provided that when X is —SO— or —$SO_2$—, then $R^{a6}$ is not hydrogen, and $R^{a7}$ is selected from the group consisting of hydrogen, alkyl, aryl, or $R^{a2}$, $R^{a3}$ together with the carbon atom pendent thereto, form an aryl substituted aryl, heteroaryl, or substituted heteroaryl;

$R^{a4}$ and $R^{a5}$ are independently selected from the group consisting of hydrogen, halo, alkyl, substituted alkyl, alkoxy, Substituted alkoxy, aryl, substituted aryl, heteroaryl, substituted heteroaryl and —$XR^{a6}$ where X is oxygen, —$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl or, when X is —$NR^{a7}$—, then $R^{a7}$ and $R^{a6}$, together with the nitrogen atom to which they are bound, can be joined to form a heterocyclic or Substituted heterocyclic group;

$R^{a''}$ is selected from the group consisting of hydrogen, alkyl and substituted alkyl;

$R^{a'''}$ is selected from the group consisting of hydroxy, alkoxy, substituted alkoxy, acyloxy, cycloalkoxy, substituted cycloalkoxy, aryloxy, substituted aryloxy, heteroaryloxy, substituted heteroaryloxy, aryl, —S(O)—$R^{a10}$ wherein $R^{a10}$ is selected from the group consisting of alkyl, substituted alkyl, cycloalkyl, substituted cycloalkyl, aryl, substituted aryl, heteroaryl and substituted heteroaryl and n is zero, one or two;

or a pharmaceutically acceptable salt, ester, or prodrug thereof;

with the proviso that when $R^{a''}$ is hydrogen and q is zero, then at least one of the following occurs:

1) $R^{a1}$ is fluoro, bromo, iodo, alkyl, substituted alkyl, alkoxy, aminoacyl, Substituted alkoxy, aryl, substituted aryl, heteroaryl, substituted heteroaryl, heterocyclic, substituted heterocyclic, and —$XR^{a6}$ where X is oxygen, —$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl; or 2) $R^{a2}$ is substituted alkyl, aryl, substituted aryl, heteroaryl, substituted heteroaryl, fluoro, bromo, iodo, cyano, —$XR^{a6}$ where X is oxygen, —$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl provided that:

a) when $R^{a2}$ is substituted alkyl such a substituent does not include trifluoromethyl;

b) —$XR^{a6}$ is not alkoxy; and c) when —$XR^{a6}$ is substituted alkoxy such a substituent does not include benzyl or benzyl substituted by a substituent selected from the group consisting of ($C_1$-$C_5$) alkyl and ($C_1$-$C_5$) alkoxy or does not include a fluoroalkoxy substituent of the formula:

$$—O—[CH_2]_x—C_fH_{(2f+1-g)}F_g$$

where x is zero or one; f is an integer of from 1 to 5; and g is an integer of from 1 to (2f+1); or 3) $R^{a3}$ is substituted alkyl, aryl, substituted aryl, heteroaryl, substituted heteroaryl, bromo, iodo, —$XR^{a6}$ where X is oxygen —$S(O)_n$, —, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl provided that:

a) when $R^{a3}$ is substituted alkyl such a substituent does not include trifluoromethyl;

b) —$XR^{a6}$ is not alkoxy; and c) when $XR^{a6}$ is substituted alkoxy such a substituent does not include benzyl or benzyl substituted by a substituent selected from the group consisting of ($C_1$-$C_5$) alkyl and (C—C) alkoxy or does not include a fluoroalkoxy substituent of the formula:

$$—O—[CH_2]_x—C_fH_{(2f+1-g)}F_g$$

where x is zero or one; f is an integer of from 1 to 5; and g is an integer of from 1 to (2f+1); or 4) $R^{a4}$ is iodo, substituted alkyl, aryl, substituted aryl, heteroaryl, substituted heteroaryl, —$XR^{a6}$ where X is oxygen —$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl provided that:

a) when $R^{a4}$ is substituted alkyl such a substituent does not include trifluoromethyl;

b) —$XR^{a6}$ is not alkoxy; and c) when $XR^{a6}$ is substituted alkoxy such a substituent does not include benzyl or benzyl substituted by a substituent selected from the group consisting of ($C_1$-$C_5$) alkyl and (C—C) alkoxy or does not include a fluoroalkoxy substituent of the formula:

$$—O—[CH_2]_x—C_fH_{(2f+1-g)}F_g$$

where x is zero or one; f is an integer of from 1 to 5; and g is an integer of from 1 to (2f+1); or 5) $R^{a5}$ is iodo, substituted alkyl, aryl, substituted aryl, heteroaryl, substituted heteroaryl, —$XR^{a6}$ where X is oxygen, —$S(O)_n$—, or —$NR^{a7}$— where n is zero, one or two, $R^{a6}$ is selected from the group consisting of alkyl, substituted alkyl, aryl, substituted aryl, heteroaryl, substituted heteroaryl, heterocyclic and substituted heterocyclic, and $R^{a7}$ is hydrogen, alkyl or aryl provided that:

a) when $R^{a5}$ is substituted alkyl such a substituent does not include trifluoromethyl;

b) —$XR^{a6}$ is not alkoxy; and c) when $XR^{a6}$ is substituted alkoxy such a substituent does not include benzyl or benzyl substituted by a substituent selected from the group consisting of ($C_1$-$C_5$) alkyl and (C—C) alkoxy or does not include a fluoroalkoxy substituent of the formula:

$$—O—[CH_2]_x—C_fH_{(2f+1-g)}F_g$$

where x is zero or one; f is an integer of from 1 to 5; and g is an integer of from 1 to (2f+1);

and with the further following proviso:

that when $R^{a1}$, $R^{a3}$, $R^{a4}$, and $R^{a5}$ are hydrogen, then $R^{a2}$ is not bromo.

388. The method of any one of paragraphs 1-385, wherein the HIF prolyl hydroxylase inhibitor or the HIF-alpha stabilizer has a structure of Formula (V)

Formula (V)

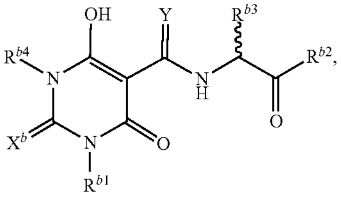

or a pharmaceutically acceptable salt thereof, wherein $R^{b1}$ and $R^{b4}$ are each independently selected from the group consisting of hydrogen, —$NR^{b5}R^{b6}$, $C_1$-$C_{10}$ alkyl, $C_2$-$C_{10}$ alkenyl, $C_2$-$C_{10}$ alkynyl, $C_3$-$C_8$ cycloalkyl, $C_3$-$C_8$ cycloalkyl-$C_1$-$C_{10}$ alkyl, $C_5$-$C_8$ cycloalkenyl, $C_5$-$C_8$ cycloalkenyl-$C_1$-$C_{10}$ alkyl, $C_3$-$C_8$ heterocycloalkyl, $C_3$-$C_8$ heterocycloalkyl-$C_1$-$C_{10}$ alkyl, aryl, aryl-$C_1$-$C_{10}$ alkyl, heteroaryl and heteroaryl-$C_1$-$C_{10}$ alkyl;

$R^{b2}$ is —$NR^{b7}R^{b8}$ or —$OR^{b9}$;

$R^{b3}$ is H or $C_1$-$C_4$ alkyl;

where $R^{b5}$ and $R^{b6}$ are each independently selected from the group consisting of hydrogen, $C_1$-$C_{10}$ alkyl, $C_3$-$C_8$ cycloalkyl, $C_3$-$C_8$ cycloalkyl-$C_1$-$C_{10}$ alkyl, $C_3$-$C_8$ heterocycloalkyl, $C_3$-$C_8$ heterocycloalkyl-$C_1$-$C_{10}$ alkyl, aryl, aryl-$C_1$-$C_{10}$ alkyl, heteroaryl and heteroaryl-$C_1$-$C_{10}$ alkyl, —$C(O)C_1$-$C_4$ alkyl, —$C(O)C_3$-$C_6$ cycloalkyl, —$C(O)C_3$-$C_6$ heterocycloalkyl, —C(O)aryl, —C(O)heteroaryl and $S(O)_2$ $C_1$-$C_4$ alkyl, or, when $R^{b5}$ and $R^{b6}$ are attached to the same nitrogen, $R^{b5}$ and $R^{b6}$ taken together with the nitrogen to which they are attached forma 5- or 6- or 7-membered saturated ring optionally containing one other heteroatom selected from oxygen, nitrogen and sulphur, $R^{b7}$ and $R^{b8}$ are each independently selected from the group consisting of hydrogen, $C_1$-$C_{10}$ alkyl, $C_2$-$C_{10}$ alkenyl, $C_3$-$C_8$ cycloalkyl, $C_3$-$C_8$ heterocycloalkyl, aryl, and heteroaryl, and $R^{b9}$ is H or a cation, or $C_1$-$C_{10}$ alkyl which is unsubstituted or substituted with one or more substituents independently selected from the group consisting of $C_3$-$C_6$ cycloalkyl, heterocycloalkyl, aryl and heteroaryl;

$X^b$ is O or S; and

Y is O or S;

where any carbon or heteroatom of $R^{b1}$, $R^{b2}$, $R^{b3}$, $R^{b4}$, $R^{b5}$, $R^{b6}$, $R^{b7}$, $R^{b8}$, $R^{b9}$ is unsubstituted or is substituted with one or more substituents independently selected from $C_1$-$C_6$ alkyl, $C_1$-$C_6$ haloalkyl, halogen, —$OR^{bm}$, —$NR^{b5}R^{b6}$, oxo, cyano, nitro, —$C(O)R^{b10}$, —C(O)$OR^{b10}$, —$SR^{b10}$, —$S(O)R^{b10}$, —$S(O)_2R^{b10}$, —$CONR^{b5}R^{b6}$, —$N(R^{b5})C(O)R^{b10}$, —$(R^{b5})C(O)OR^{b10}$, —$OC(O)NR^{b5}R^{b6}$', —$N(R^{b5})C(O)NR^{b5}R^{b6}$, —$SO_2NR^{b5}R^{b6}$, —$N(R^{b5})SO_2R^{b10}$, $C_2$-$C_{10}$ alkenyl, $C_2$-$C_{10}$ alkynyl, $C_3$-$C_6$ cycloalkyl, $C_3$-$C_6$ heterocycloalkyl, aryl, $C_1$-$C_6$ alkyl-aryl, heteroaryl and $C_1$-$C_6$ alkyl-heteroaryl, wherein $R^{b5}$ and $R^{b6}$ are the same as defined above and $R^{b10}$ is selected from hydrogen, $C_1$-$C_{10}$ alkyl, $C_2$-$C_{10}$ alkenyl, $C_2$-$C_{10}$ alkynyl. —$C(O)C_1$-$C_4$ alkyl, —C(O)aryl, —C(O)heteroaryl, —$C(O)C_3$-$C_6$ cycloalkyl, —$C(O)C_3$-$C_6$ heterocycloalkyl, —$S(O)_2C_1$-$C_4$ alkyl, $C_3$-$C_8$ cycloalkyl, $C_3$-$C_8$ heterocycloalkyl, $C_6$-$C_{14}$ aryl, aryl-$C_1$-$C_{10}$ alkyl, heteroaryl and heteroaryl-$C_1$-$C_{10}$ alkyl;

389. The method of any one of paragraphs 1-385, wherein the HIF prolyl hydroxylase inhibitor or the HIF-alpha stabilizer has a structure of Formula (VI)

Formula (VI)

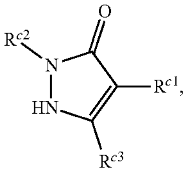

or a pharmaceutically acceptable salt thereof, wherein $R^{c1}$ represents a heteroaryl group of the formula

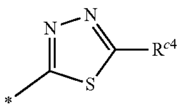

or

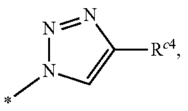

wherein

* denotes the linkage point with the dihydropyrazolone ring and $R^{c4}$ denotes hydrogen, fluorine, chlorine, bromine, cyano, $C_1$-$C_4$ alkyl, trifluoromethyl, hydroxymethyl, $C_1$-$C_4$ alkoxy, trifluoromethoxy, hydroxycarbonyl or $C_1$-$C_4$ alkoxycarbonyl;

$R^{c2}$ represents a heteroaryl group of the formula

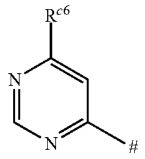

or

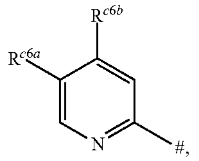

wherein denotes the linkage point with the dihydropyrazolone ring and $R^{c6}$, $R^{c6a}$ and $R^{c6b}$ are identical or different and independently of one another denote hydrogen or a substituent chosen from the group consisting of fluorine, chlorine, bromine, cyano, $C_1$-$C_6$ alkyl, trifluoromethyl, hydroxyl, $C_1$-$C_6$ alkoxy, trifluoromethoxy, amino, mono-$C_1$-$C_4$ alkylamino, di-$C_1$-$C_4$ alkylamino, hydroxycarbonyl, $C_1$-$C_4$ alkoxycarbonyl, 4- to 6-membered heterocycloalkyl, phenyl and 5- or 6-membered heteroaryl, wherein $C_1$-$C_6$ alkyl in its turn can be substituted by hydroxyl, $C_1$-$C_4$ alkoxy or amino and 4- to 6-membered heterocycloalkyl, phenyl and 5- or 6-membered heteroaryl in their turn can in each case be substituted once or twice in an identical or different manner by fluorine, chlorine, bromine, cyano, $C_1$-$C_4$ alkyl, trifluoromethyl, hydroxyl, $C_1$-$C_4$ alkoxy, trifluoromethoxy, oxo, amino, mono-$C_1$-$C_4$ alkylamino, di-$C_1$-$C_4$ alkylamino, hydroxycarbonyl or $C_1$-$C_4$ alkoxycarbonyl, and $R^{c3}$ represents hydrogen, or a salt thereof.

390. The method of any one of paragraphs 1-389, wherein the HIF prolyl hydroxylase inhibitor or a HIF-alpha stabilizer, or a pharmaceutically acceptable salt thereof, is administered orally, intravenously, intramuscularly, by inhalation or transdermally.

391. The method of paragraph 390, wherein the HIF prolyl hydroxylase inhibitor or a HIF-alpha stabilizer, or a pharmaceutically acceptable salt thereof, is administered orally.

392. The method of any one of paragraphs 1-391, wherein the HIF prolyl hydroxylase inhibitor or a HIF-alpha stabilizer, or a pharmaceutically acceptable salt thereof, is administered to a subject patient at a dose of about 100-1500, 100-1800, or 150-1800 mg per day.

393. The method of any one of paragraphs 1-389, wherein the HIF prolyl hydroxylase inhibitor or the HIF-alpha stabilizer is vadadustat (AKB-6548), roxadustat (FG-4592), daprodustat (GSK-12788363), molidustat (BAY 85-3934), enarodustat (JTZ-951) or desidustat (ZYAN1).

394. The method of paragraph 393, wherein the HIF prolyl hydroxylase inhibitor or the HIF-alpha stabilizer is vadadustat (AKB-6548).

395. The method of paragraph 394, wherein vadadustat (AKB-6548) is administered at a dose of 150 mg to 1000 mg or of 150 mg to 1800 mg per day.

396. The method of paragraph 395, wherein vadadustat (AKB-6548) is administered at an initial dose of 900 mg per day.

397. The method of paragraph 394 or 395, wherein vadadustat (AKB-6548) is administered at a dose of 900 mg per day throughout the treatment period.

398. The method of paragraph 394 or 395, comprising administration of vadadustat (AKB-6548) a dose of 900-1800 mg per day.

399. The method of paragraph 398, comprising administration of vadadustat (AKB-6548) at a dose of 900, 1050, 1200, 1350, 1500, 1650, or 1800 mg per day.

400. The method of any one of paragraphs 1-399, wherein the HIF prolyl hydroxylase inhibitor or the HIF-alpha stabilizer is administered to the patient for up to about one month.

401. The method of paragraph 400, wherein the HIF prolyl hydroxylase inhibitor or the HIF-alpha stabilizer is administered to the patient for up to about four weeks (about 28 days), three weeks (about 21 days), two weeks (about 14 days), or one week (about 7 days).

402. The method of any one of paragraphs 1-401, wherein the HIF prolyl hydroxylase inhibitor or the HIF-alpha stabilizer is administered in combination with another treatment.

403. The method of paragraph 402, wherein the treatment comprises an antiviral agent or oxygen therapy.

404. The method of paragraph 403, wherein oxygen therapy comprises mechanical ventilation.

405. The method of any one of paragraphs 1-404, wherein the severity of disease is maintained or reduced following commencement of administering the HIF prolyl hydroxylase inhibitor or the HIF-alpha stabilizer to the patient.

406. The method of paragraph 405, wherein the severity of disease is assessed according to the following ordinal scale where increasing numbers denote increased severity:

| Score | Descriptor | Patient State | |
|---|---|---|---|
| 0 | No clinical or virological evidence of infection | Uninfected | Uninfected/ Ambulatory |
| 1 | Not hospitalized, no limitation of patient's activities | Infected (Ambulatory) | |
| 2 | Not hospitalized, limitation of patient's activities and/or requiring home oxygen | | |
| 3 | Patient is hospitalized but does not receive oxygen therapy-no longer requires ongoing medical care | Infected-Hospitalized (Mild Disease) | Hospitalized but not intubated |
| 4 | Patient is hospitalized but does not require oxygen therapy-requiring ongoing care (COVID-19 related or otherwise) | | |
| 5 | Patient is hospitalized and requiring supplemental oxygen | Infected-Hospitalized (Severe Disease) | |
| 6 | Patient is hospitalized and receives oxygen therapy that is non-invasive ventilation or high flow oxygen devices | | Hospitalized and intubated |
| 7 | Patient is hospitalized and receives invasive mechanical ventilation and additional organ support such as pressors, renal replacement therapy (RRT), and/or extracorporeal membrane oxygenation (ECMO) | | |

407. The method of paragraph 405 or 406, wherein the severity of disease is maintained and the patient's condition stabilizes following commencement of administering the HIF prolyl hydroxylase inhibitor or the HIF-alpha stabilizer to the patient.

408. The method of paragraph 406, wherein the patient's score does not change and the patient's condition stabilizes following commencement of administering the HIF prolyl hydroxylase inhibitor or the HIF-alpha stabilizer to the patient.

409. The method of paragraph 405 or 406, wherein the severity of disease decreases following commencement of administering the HIF prolyl hydroxylase inhibitor or the HIF-alpha stabilizer to the patient.

410. The method of paragraph 406, wherein the patient's score decreases by at least one point following commencement of administering the HIF prolyl hydroxylase inhibitor or the HIF-alpha stabilizer to the patient.

411. The method of paragraph 406, wherein the patient's severity of disease is assessed as uninfected/ambulatory.

412. The method of paragraph 406, wherein the patient's severity of disease is assessed as hospitalized but not intubated.

413. The method of paragraph 406, wherein the patient's severity of disease is assessed as hospitalized and intubated.

414. The method of paragraph 406, wherein the patient's category decreases by at least one category following commencement of administering the HIF prolyl hydroxylase inhibitor or the HIF-alpha stabilizer to the patient.

415. The method of any one of paragraphs 405-410, wherein the patient is hypoxic.

416. The method of paragraph 415, wherein the patient has an oxygen saturation value that is about 94% or less.

417. The method of paragraph 415 or 416, wherein the patient's oxygen saturation value improves to a value of about 95% or greater following commencement of administering the HIF prolyl hydroxylase inhibitor or the HIF-alpha stabilizer to the patient.

418. The method of any one of paragraphs 405-417, wherein the patient has hypotension.

419. The method of paragraph 418, wherein the patient receives vasopressor therapy.

420. The method of paragraph 419, wherein vasopressor therapy is reduced or discontinued following commencement of administering the HIF prolyl hydroxylase inhibitor or the HIF-alpha stabilizer to the patient.

421. The method of any one of paragraphs 405-420, wherein the patient is hospitalized.

422. The method of paragraph 421, wherein the patient does not receive oxygen therapy.

423. The method of paragraph 421, wherein the patient has a score of 1, 2, and/or 3 according to the ordinal scale of paragraph 406.

424. The method of paragraph 421, wherein the patient receives oxygen therapy.

425. The method of paragraph 424, wherein the patient has a score of 4, 5, 6, or 7 according to the ordinal scale of paragraph 406.

426. The method of paragraph 424 or 425, wherein the patient receives oxygen therapy by mask or nasal prongs.

427. The method of paragraph 424 or 425, wherein the patient receives oxygen therapy by intubation and mechanical ventilation.

428. The method of paragraph 427, wherein the patient has multi-organ injuries and receives additional organ support therapy.

429. The method of paragraph 427, wherein the patient has any of a cardiovascular injury, a neurological injury, a liver injury, a pancreas injury, and/or a kidney disease.

430. The method of paragraph 429, wherein the patient has a heart injury and/or a lung injury.

431. The method of any one of paragraphs 427-430, wherein the patient receives organ support therapy that is vasopressor therapy, renal replacement therapy (RRT), and/or extracorporeal membrane oxygenation (ECMO).

432. The method of any one of paragraphs 427-431, wherein the organ support therapy received by the patient is discontinued following commencement of administering the HIF prolyl hydroxylase inhibitor or the HIF-alpha stabilizer to the patient.

433. The method of any one of paragraphs 424-432, wherein the oxygen therapy received by the patient is discontinued following commencement of administering the HIF prolyl hydroxylase inhibitor or the HIF-alpha stabilizer to the patient.

434. The method of any one of paragraphs 427-433, wherein the patient has increased ventilator-free survival following discontinuation of mechanical ventilation.

435. The method of any one of paragraphs 405-434, wherein the patient receives vadadustat, or a pharmaceutically acceptable salt thereof.

From the ongoing description, one skilled in the art can easily ascertain the essential characteristics of this invention, and without departing from the spirit and scope thereof, can make various changes and modifications of the invention to adapt it to various usages and conditions.

All references, patents or applications, U.S. or foreign, cited in the application are hereby incorporated by reference as if written herein in their entireties. Where any inconsistencies arise, material literally disclosed herein controls.

What is claimed is:

1. A method of treating or preventing a lung disease that is acute respiratory distress syndrome (ARDS) in a patient having a respiratory viral infection, comprising administering to the patient a compound that is a HIF prolyl hydroxylase inhibitor or a HIF-alpha stabilizer that is vadadustat (AKB-6548),

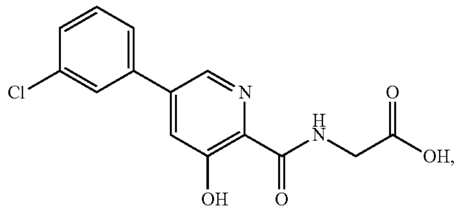 [SMILES: O=C(O)CNC(=O)c1ncc(-c2cccc(Cl)c2)cc1O]

or a pharmaceutically acceptable salt thereof.

2. The method of claim 1, wherein the respiratory viral infection is COVID-19.

3. The method of claim 1, wherein the ARDS is induced by or associated with the viral infection.

4. A method of treating or preventing a lung disease that is acute respiratory distress syndrome (ARDS) in a patient infected with a coronavirus, comprising administering to the patient a compound that is a HIF prolyl hydroxylase inhibitor or a HIF-alpha stabilizer that is vadadustat (AKB-6548),

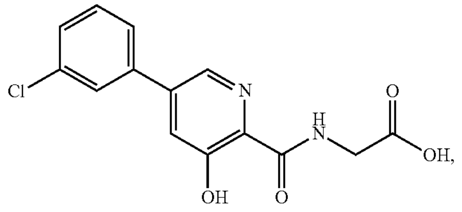

or a pharmaceutically acceptable salt thereof.

5. The method of claim 4, wherein the patient is infected with SARS-COV-2.

6. The method of claim 4, wherein the ARDS is induced by or associated with the viral infection.

7. The method of claim 1, wherein vadadustat (AKB-6548) is administered at a dose of 150 mg to 1000 mg, of 150 mg to 1800 mg per day, or of 900-1800 mg per day.

8. The method of claim 7, wherein vadadustat (AKB-6548) is administered at an initial dose of 900 mg per day.

9. The method of claim 7, comprising administration of vadadustat (AKB-6548) a dose of 900-1800 mg per day.

10. The method of claim 7, wherein vadadustat (AKB-6548) is administered to the patient for up to about one month.

11. The method of claim 4, wherein vadadustat (AKB-6548) is administered at a dose of 150 mg to 1000 mg, of 150 mg to 1800 mg per day, or of 900-1800 mg per day.

12. The method of claim 11, wherein vadadustat (AKB-6548) is administered at an initial dose of 900 mg per day.

13. The method of claim 11, comprising administration of vadadustat (AKB-6548) a dose of 900-1800 mg per day.

14. The method of claim 11, wherein vadadustat (AKB-6548) is administered to the patient for up to about one month.

15. A method for treating or preventing acute respiratory distress syndrome (ARDS) in a patient in need thereof, wherein the method comprises administering a compound that can stabilize HIF and inhibit HIF prolyl hydroxylase (HIF-PH) that is vadadustat,

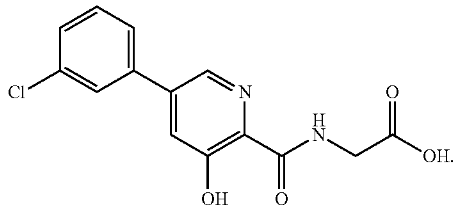 [SMILES: O=C(O)CNC(=O)c1ncc(-c2cccc(Cl)c2)cc1O]

16. The method of claim 15, wherein the acute respiratory distress syndrome (ARDS) is characterized by accumulation of inflammatory cells into the lungs, cytokine release, inflammatory activation of recruited or resident cells, disruption of the alveolar-capillary barrier function, pulmonary edema, attenuated gas exchange, or lung inflammation, or any combination thereof.

17. The method of claim 15, comprising administering to said patient a once daily dose of vadadustat that is between 900 mg to 1800 mg.

18. The method of claim 17, comprising administering to said patient an initial dose of 900 mg vadadustat.

19. The method of claim 17, comprising administering to said patient a once daily dose of 900 mg vadadustat.

20. The method of claim 19, comprising administering to said patient vadadustat for up to about one month.

21. The method of claim 20, wherein the patient receives a once daily dose of about 900 mg vadadustat throughout the period of treatment.

* * * * *